(12) United States Patent
Sudau et al.

(10) Patent No.: US 11,213,031 B2
(45) Date of Patent: Jan. 4, 2022

(54) TETRAZOLYLPROPYL DERIVATIVES AND THEIR USE AS FUNGICIDES

(71) Applicants: BAYER AKTIENGESELLSCHAFT, Leverkusen (DE); BAYER CROPSCIENCE AKTIENGESELLSCHAFT, Monheim am Rhein (DE)

(72) Inventors: Alexander Sudau, Langenfeld (DE); Sebastian Hoffmann, Neuss (DE); Peter Dahmen, Neuss (DE); Robert Alan Webster, Mettmann (DE); Ruth Meissner, Leverkusen (DE); Andreas Goertz, Dormagen (DE); Ricarda Miller, Duesseldorf (DE); Pierre-Yves Coqueron, Lyons (FR); David Bernier, Lyons (FR); Lionel Nicolas, Lyons (FR); Stephane Brunet, Saint Andre de Corcy (FR); Philippe Kennel, Biot (FR); Valerie Toquin, Davis, CA (US); Mathieu Gourgues, Lyons (FR); Dominique Loque, Vernier (CH); Vincent Thomas, Lyons (FR)

(73) Assignees: BAYER AKTIENGESELLSCHAFT, Leverkusen (DE); BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/762,615

(22) PCT Filed: Nov. 8, 2018

(86) PCT No.: PCT/EP2018/080574
§ 371 (c)(1),
(2) Date: May 8, 2020

(87) PCT Pub. No.: WO2019/092086
PCT Pub. Date: May 16, 2019

(65) Prior Publication Data
US 2020/0275660 A1    Sep. 3, 2020

(30) Foreign Application Priority Data
Nov. 13, 2017  (EP) .................... 17201420

(51) Int. Cl.
*A01N 43/713* (2006.01)
*C07D 257/04* (2006.01)

(52) U.S. Cl.
CPC ......... *A01N 43/713* (2013.01); *C07D 257/04* (2013.01)

(58) Field of Classification Search
CPC ........................... C07D 257/04; A01N 43/713
See application file for complete search history.

(56) References Cited

U.S. PATENT DOCUMENTS

| | | | |
|---|---|---|---|
| 8,809,378 B2 * | 8/2014 | Hoekstra | A61P 37/02 514/340 |
| 10,196,375 B2 * | 2/2019 | Hoekstra | A61K 31/4439 |
| 2017/0303540 A1 | 10/2017 | Coqueron et al. | |

FOREIGN PATENT DOCUMENTS

| | | |
|---|---|---|
| CN | 104557742 A | 4/2015 |
| DE | 3328273 A | 2/1985 |
| WO | 2012/177603 A2 | 12/2012 |
| WO | 2014/118170 A1 | 8/2014 |
| WO | 2016/050769 A1 | 4/2016 |

OTHER PUBLICATIONS

International Search Report of International Patent Application No. PCT/EP2018/080574 dated Jan. 4, 2019.

* cited by examiner

*Primary Examiner* — Kamal A Saeed
(74) *Attorney, Agent, or Firm* — McBee Moore & Vanik IP, LLC

(57) ABSTRACT

The present invention relates to tetrazolylpropyl derivatives of formula (I)

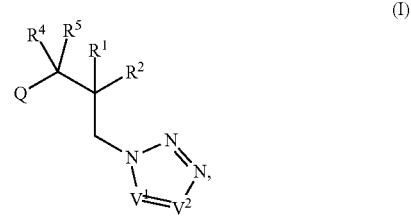

wherein one of $V^1$ and $V^2$ represents $CR^3$ and the other one of $V^1$ and $V^2$ represents N, Q represents a 6-membered aromatic cycle as defined in the specification, and $R^1$, $R^2$, $R^3$, $R^4$, and $R^5$ are defined as disclosed in the specification, to compositions comprising such compounds, to the use of said compounds as fungicides, as well as to particular intermediates useful in the synthesis of said tetrazolylpropyl derivatives.

15 Claims, No Drawings

TETRAZOLYLPROPYL DERIVATIVES AND THEIR USE AS FUNGICIDES

CROSS-REFERENCE TO RELATED APPLICATIONS

This application is a National Stage entry of International Application No. PCT/EP2018/080574, filed 8 Nov. 2018, which claims priority to European Patent Application No. 17201420.1, filed 13 Nov. 2017.

BACKGROUND

Field

The present invention relates to novel tetrazolylpropyl derivatives, to processes for preparing these compounds, to compositions comprising those, and to the use thereof as biologically active compounds and compositions, especially for control of harmful microorganisms in crop protection and in the protection of materials. The invention also relates to particular intermediates useful in the synthesis of said tetrazolylpropyl derivatives.

Description of Related Art

It is already known that certain tetrazolyl derivatives and salts thereof can be used in crop protection. DE 3328273 A1 discloses particular tetrazolyl-(alkylene)-oxime carbamates showing insecticidal properties. DE 3328273 A1 also mentions fungicidal efficacy of the tetrazolyl-(alkylene)-oxime carbamates. However, no examples actually showing such efficacy are given. WO 2014/118170 A1 discloses microbiocidally active, in particular fungicidally active, cycloalkyl-heteroaryl and cycloheteroalkyl-heteroaryl containing compounds comprising an azolyl group. The azolyl group, denominated MBG in WO 2014/118170 A1, is broadly defined and encompasses optionally substituted tetrazolyl, optionally substituted triazolyl, optionally substituted oxazolyl, optionally substituted thiazolyl, and optionally substituted imidazolyl. All compounds exemplified in WO 2014/118170 A1 comprise as azolyl group MBG either non-substituted triazolyl or non-substituted imidazolyl. Examples of compounds comprising a tetrazolyl group are not given.

Since the ecological and economic demands made on modern active ingredients, for example fungicides, are increasing constantly, for example with respect to activity spectrum, toxicity, selectivity, application rate, formation of residues and favourable manufacture, and there can also be problems, for example, with resistances, there is a constant need to develop novel fungicidal compounds and compositions which have advantages over the known compounds and compositions at least in some areas.

SUMMARY

Hence, object of the invention is to serve this need by providing novel compounds useful for control of harmful microorganisms in crop protection and in the protection of materials, in particular compounds showing fungicidal efficacy.

Surprisingly, it has been found that particular tetrazolylpropyl derivatives are valuable fungicides.

Accordingly, subject of this invention are compounds of formula (I)

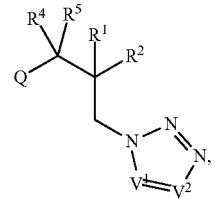

wherein $R^1$ represents hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, phenyl-$C_2$-$C_8$-alkynyl, [tri($C_1$-$C_8$-alkyl)silyl]phenyl-$C_2$-$C_8$-alkynyl, $C_3$-$C_7$-cycloalkyl, bicycloalkyl, $C_3$-$C_7$-cycloalkyl-$C_1$-$C_4$-alkyl, $C_3$-$C_7$-cycloalkyl-$C_3$-$C_7$-cycloalkyl, $C_3$-$C_7$-cycloalkenyl, tri($C_1$-$C_8$-alkyl)silyl-$C_1$-$C_4$-alkyl, or tri($C_1$-$C_8$-alkyl)silyl-$C_3$-$C_7$-cyclo alkyl, wherein the phenyl-$C_2$-$C_8$-alkynyl, [tri($C_1$-$C_8$-alkyl)silyl]phenyl-$C_2$-$C_8$-alkynyl, $C_3$-$C_7$-cycloalkyl, bicycloalkyl, $C_3$-$C_7$-cycloalkyl-$C_1$-$C_4$-alkyl, $C_3$-$C_7$-cycloalkyl-$C_3$-$C_7$-cyclo alkyl, $C_3$-$C_7$-cycloalkenyl, tri($C_1$-$C_8$-alkyl)silyl-$C_1$-$C_4$-alkyl, and tri($C_1$-$C_8$-alkyl)silyl-$C_3$-$C_7$-cycloalkyl is non-substituted or substituted by one or more group(s) selected from halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

$R^2$ represents hydrogen, halogen, cyano or —$OR^{2a}$, wherein $R^{2a}$ represents hydrogen, $C_1$-$C_8$-alkyl, —Si($R^{6a}$)($R^{6b}$)($R^{6c}$), —P(O)(OH)$_2$, —CH$_2$—O—P(0)(OH)$_2$, C(O)—$C_1$-$C_8$-alkyl, C(O)—$C_3$-$C_7$-cycloalkyl, C(O)NH—$C_1$-$C_8$-alkyl, C(O)N-di-$C_1$-$C_8$-alkyl, or C(O)O—$C_1$-$C_8$-alkyl, wherein the C(O)—$C_1$-$C_8$-alkyl, C(O)—$C_3$-$C_7$-cycloalkyl, C(O)NH—$C_1$-$C_8$-alkyl, C(O)N-di-$C_1$-$C_8$-alkyl and C(O)—$C_1$-$C_8$-alkyl is non-substituted or substituted by one or more group(s) selected from halogen and $C_1$-$C_8$-alkoxy, wherein $R^{6a}$, $R^{6b}$, $R^{6c}$ represent independently from each other phenyl or $C_1$-$C_8$-alkyl;

one of $V^1$ and $V^2$ represents $CR^3$ and the other one of $V^1$ and $V^2$ represents N, $R^3$ represents hydrogen, halogen, hydroxyl, cyano, sulfanyl, $C_1$-$C_8$-alkyl, or $C_1$-$C_8$-haloalkyl;

$R^4$ represents hydrogen, fluorine, $C_1$-$C_8$-alkyl, $C_1$-$C_8$-haloalkyl or $C_1$-$C_8$-alkyloxy;

$R^5$ represents hydrogen, fluorine, $C_1$-$C_8$-alkyl, $C_1$-$C_8$-haloalkyl or $C_1$-$C_8$-alkyloxy;

or $R^4$ and $R^5$ form together with the carbon atom to which they are attached $C_3$-$C_7$-cycloalkyl, wherein the $C_3$-$C_7$-cycloalkyl ring is non-substituted or substituted by one or more substituent(s) selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

or $R^4$ and $R^5$ form together with the carbon atom to which they are attached $C_2$-alkenyl, wherein the $C_2$-alkenyl is non-substituted or substituted by one or more substituent(s) selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

and
Q represents a 6-membered aromatic cycle of formula (Q-I)

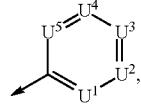

wherein
$U^1$ represents $CX^1$ or N;
$U^2$ represents $CX^2$ or N;
$U^3$ represents $CX^3$ or N;
$U^4$ represents $CX^4$ or N;
$U^5$ represents $CX^5$ or N;
wherein $X^1$, $X^2$, $X^3$, $X^4$, and $X^5$ independently from each other represent hydrogen, halogen, nitro, cyano, sulfanyl, pentafluoro-$\lambda^6$-sulfanyl, $C_1$-$C_8$-alkyl, $C_1$-$C_8$-haloalkyl having 1 to 5 halogen atoms, $C_3$-$C_8$-cycloalkyl, $C_3$-$C_8$-halocycloalkyl having 1 to 5 halogen atoms, $C_1$-$C_8$-haloalkyl-$C_3$-$C_7$-cycloalkyl, $C_3$-$C_7$-cycloalkenyl, $C_2$-$C_8$-alkenyl, $C_2$-$C_8$-alkynyl, $C_6$-$C_{12}$-bicycloalkyl, $C_3$-$C_8$-cycloalkyl-$C_2$-$C_8$-alkenyl, $C_3$-$C_8$-cycloalkyl-$C_2$-$C_8$-alkynyl, $C_1$-$C_8$-alkoxy, $C_1$-$C_8$-haloalkoxy having 1 to 5 halogen atoms, $C_1$-$C_8$-alkoxycarbonyl, $C_1$-$C_8$-haloalkoxycarbonyl, $C_1$-$C_8$-alkylsulfenyl, $C_2$-$C_8$-alkenyloxy, $C_3$-$C_8$-alkynyloxy, $C_3$-$C_6$-cycloalkoxy, $C_1$-$C_8$-alkylsulfinyl, $C_1$-$C_8$-alkylsulfonyl, tri($C_1$-$C_8$-alkyl)-silyloxy, tri($C_1$-$C_8$-alkyl)-silyl, tri($C_1$-$C_8$-alkyl)-silyl-$C_2$-$C_8$-alkynyl, tri($C_1$-$C_8$-alkyl)-silyl-$C_2$-$C_8$-alkynyloxy, $C_6$-$C_{14}$-aryl, $C_6$-$C_{14}$-aryloxy, $C_6$-$C_{14}$-arylsulfenyl, 5- or 6-membered heteroaryl, 5- or 6-membered heteroaryloxy,
wherein the $C_6$-$C_{14}$-aryl, $C_6$-$C_{14}$-aryloxy, $C_6$-$C_{14}$-arylsulfenyl, 5- or 6-membered heteroaryl, 5- or 6-membered heteroaryloxy is non-substituted or substituted by one or more group(s) selected from halogen, cyanosulfanyl, pentafluoro-$\lambda^6$-sulfanyl, $C_1$-$C_8$-alkyl, $C_1$-$C_8$-haloalkyl, $C_1$-$C_8$-cyanoalkyl, $C_1$-$C_8$-alkyloxy, $C_1$-$C_8$-haloalkyloxy, tri($C_1$-$C_8$-alkyl)silyl, tri($C_1$-$C_8$-alkyl)silyl-$C_1$-$C_8$-alkyl, $C_3$-$C_7$-cycloalkyl, $C_3$-$C_7$-halocycloalkyl, $C_3$-$C_7$-cycloalkenyl, $C_3$-$C_7$-halocycloalkenyl, $C_4$-$C_{10}$-cycloalkylalkyl, $C_4$-$C_{10}$-halocycloalkylalkyl, $C_6$-$C_{12}$-cycloalkylcycloalkyl, $C_1$-$C_8$-alkyl-$C_3$-$C_7$-cycloalkyl, $C_1$-$C_8$-alkoxy-$C_3$-$C_7$-cycloalkyl, tri($C_1$-$C_8$-alkyl)silyl-$C_3$-$C_7$-cycloalkyl, $C_2$-$C_8$-alkenyl, $C_2$-$C_8$-alkynyl, $C_2$-$C_8$-alkenyloxy, $C_2$-$C_8$-haloalkenyloxy, $C_3$-$C_8$-alkynyloxy, $C_3$-$C_8$-haloalkynyloxy, $C_1$-$C_8$-cyanoalkoxy, $C_4$-$C_8$-cycloalkylalkoxy, $C_3$-$C_6$-cycloalkoxy, $C_1$-$C_8$-alkylsulfanyl, $C_1$-$C_8$-haloalkylsulfanyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylsulfonyloxy, $C_1$-$C_8$-haloalkylsulfonyloxy, $C_1$-$C_8$-alkoxyalkyl, $C_1$-$C_8$-alkylthioalkyl, $C_1$-$C_8$-alkoxyalkyl, $C_1$-$C_8$-haloalkoxyalkyl, benzyl, phenyl, 5-membered heteroaryl, 6-membered heteroaryl, 6-membered heteroaryloxy, benzyloxy, phenyloxy, benzylsulfanyl, and phenylsulfanyl,
wherein the benzyl, phenyl, 5-membered heteroaryl, 6-membered heteroaryl, 6-membered heteroaryloxy, benzyloxy, phenyloxy, benzylsulfanyl and phenylsulfanyl is non-substituted or substituted by one or more group(s) selected from halogen, CN, nitro, $C_1$-$C_8$-alkyl, $C_1$-$C_4$-haloalkyl, $C_1$-$C_4$-alkoxy, $C_1$-$C_4$-haloalkoxy and pentafluoro-$\lambda^6$-sulfanyl;

and wherein at most two of $U^2$, $U^3$, $U^4$ and $U^5$ represent N;
or
$U^1$ and $U^2$ or $U^2$ and $U^3$ or $U^3$ and $U^4$ form together an additional saturated or unsaturated 4 to 6-membered halogen- or $C_1$-$C_8$-alkyl-substituted or non-substituted ring;
and its salts and N-oxides.

DETAILED DESCRIPTION OF A PREFERRED EMBODIMENT

An arrow, as in formula (Q-I), depicts the bonding position of the shown moiety to the remainder of the molecule.
Formula (I) provides a general definition of the tetrazolylpropyl derivatives according to the invention. Formula (I) encompasses tetrazol-1-yl derivatives of formula (Ia) and tetrazol-2-yl derivatives of formula (Ib)

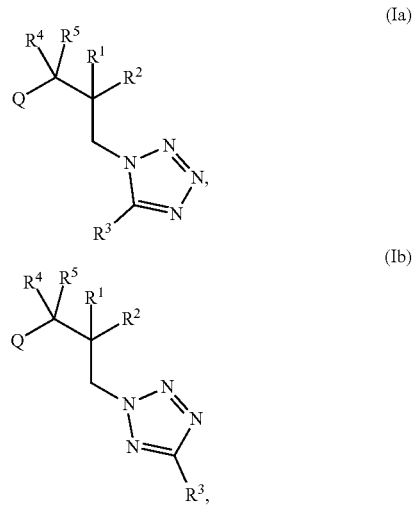

wherein Q, $R^1$, $R^2$, $R^3$, $R^4$, and $R^5$ are defined as in formula (I).
Preferred radical definitions for the formulae shown above and below are given below. These definitions apply to the end products of formula (I), (Ia), (Ib), (I-en), (Ia-en), (Ib-en) and likewise to all educts and intermediates.
$R^1$ preferably represents $C_1$-$C_8$-alkyl, $C_1$-$C_8$-haloalkyl, $C_2$-$C_7$-alkenyl, $C_2$-$C_7$-haloalkenyl, or optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl.
$R^1$ more preferably represents $C_1$-$C_8$-alkyl, $C_1$-$C_8$-haloalkyl, or optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-halo alkylthio-substituted $C_3$-$C_7$-cycloalkyl.
$R^1$ more preferably represents $C_1$-$C_8$-alkyl, or optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl.
$R^1$ more preferably represents $C_1$-$C_4$-alkyl, or optionally halogen-, cyano-, $C_1$-$C_4$-alkyl-, $C_1$-$C_4$-haloalkyl-, $C_1$-$C_4$-haloalkoxy-, $C_1$-$C_4$-alkoxy-, $C_1$-$C_4$-alkylthio- or $C_1$-$C_4$-haloalkylthio-substituted $C_3$-$C_6$-cycloalkyl.
$R^1$ more preferably represents methyl, ethyl, n-propyl, isopropyl, n-butyl, isobutyl, tert-butyl, 1-halocyclopropyl, or 1-($C_1$-$C_4$-alkyl)cyclopropyl.
$R^1$ more preferably represents isopropyl, isobutyl, tert-butyl, 1-chlorocyclopropyl, 1-fluorocyclopropyl or 1-methylcyclopropyl.

R¹ more preferably represents tert-butyl, 1-chlorocyclopropyl, 1-fluorocyclopropyl or 1-methylcyclopropyl.

R¹ also more preferably represents 1-halocyclopropyl or 1-($C_1$-$C_4$-alkyl)cyclopropyl.

R¹ most preferably represents 1-chlorocyclopropyl, 1-fluorocyclopropyl or 1-methylcyclopropyl.

R² preferably represents hydrogen, fluorine, chlorine, cyano or —OR$^{2a}$.

R² more preferably represents —OR$^{2a}$.

R$^{2a}$ preferably represents H, $C_1$-$C_8$-alkyl, or halogen- or $C_1$-$C_8$-alkoxy-substituted or non-substituted C(O)—$C_1$-$C_8$-alkyl.

R$^{2a}$ more preferably represents H or $C_1$-$C_8$-alkyl.

R$^{2a}$ more preferably represents H or $C_1$-$C_4$-alkyl.

R$^{2a}$ more preferably represents H or methyl.

R$^{2a}$ most preferably represents H.

R² most preferably represents —OH.

R³ preferably represents hydrogen, fluorine, chlorine, bromine, iodine, cyano, sulfanyl, $C_1$-$C_8$-alkyl, or $C_1$-$C_8$-haloalkyl.

R³ more preferably represents hydrogen, fluorine, chlorine, bromine, iodine, cyano, sulfanyl, $C_1$-$C_4$-alkyl, or $C_1$-$C_4$-haloalkyl.

R³ more preferably represents hydrogen, fluorine, chlorine, bromine, iodine, cyano, sulfanyl, methyl, ethyl, n-propyl, isopropyl, n-butyl, isobutyl, tert-butyl, or $CF_3$.

R³ more preferably represents hydrogen, fluorine, chlorine, bromine, iodine, methyl, or $CF_3$.

R³ more preferably represents hydrogen, fluorine, chlorine, bromine, or iodine.

R³ more preferably represents hydrogen, or fluorine.

R³ most preferably represents hydrogen.

R⁴ preferably represents hydrogen, fluorine, methyl, ethyl, n-propyl, isopropyl, n-butyl, isobutyl, or tert-butyl.

R⁴ more preferably represents hydrogen, fluorine, methyl or ethyl.

R⁴ more preferably represents hydrogen, fluorine or methyl.

R⁴ more preferably represents hydrogen or methyl.

R⁴ most preferably represents hydrogen.

R⁵ preferably represents hydrogen, fluorine, methyl, ethyl, n-propyl, isopropyl, n-butyl, isobutyl, or tert-butyl.

R⁵ more preferably represents hydrogen, fluorine, methyl or ethyl.

R⁵ more preferably represents hydrogen, or fluorine.

R⁵ most preferably represents hydrogen.

R⁴ and R⁵ may form together with the carbon atom to which they are attached a $C_3$-$C_7$-cycloalkyl ring, wherein the $C_3$-$C_7$-cycloalkyl ring is non-substituted or substituted by one or more substituent(s) selected from halogen, $C_1$-$C_4$-alkyl, $C_1$-$C_4$-halo alkyl, $C_1$-$C_4$-alkoxy, $C_1$-$C_4$-haloalkoxy, $C_1$-$C_4$-alkylthio and $C_1$-$C_4$-haloalkylthio.

In such embodiment R⁴ and R⁵ preferably form together with the carbon atom to which they are attached a non-substituted $C_3$-$C_6$-cycloalkyl ring, more preferably a non-substituted $C_3$-$C_5$-cycloalkyl ring, most preferably a cyclopropyl ring.

R⁴ and R⁵ may furthermore form together with the carbon atom to which they are attached $C_2$-alkenyl, wherein the $C_2$-alkenyl is non-substituted or substituted by one or more substituent(s) selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio.

The respective compounds are represented by formula (I-en)

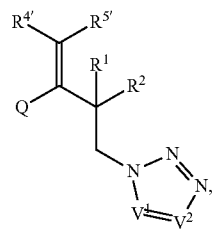

(I-en)

wherein Q, R¹, R², V', and V² are defined as in formula (I); and

R$^{4'}$ and R$^{5'}$ independently from each other represent hydrogen, halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio.

Formula (I-en) encompasses tetrazol-1-yl derivatives of formula (Ia-en) and tetrazol-2-yl derivatives of formula (Ib-en)

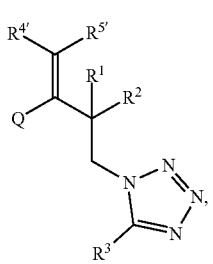

(Ia-en)

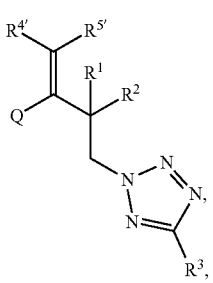

(Ib-en)

wherein Q, R¹, R² and R³ are defined as in formula (I), and R$^{4'}$ and R$^{5'}$ are defined as in formula (I-en).

The preferred, more preferred and most preferred definitions of Q, R¹, R², V¹, V², and R³ given with regard to formula (I) apply mutatis mutandis.

R$^{4'}$ and R$^{5'}$ independently from each other preferably represent hydrogen, fluorine, chlorine, bromine, iodine, methyl, ethyl, n-propyl, isopropyl, n-butyl, isobutyl, tert-butyl, $CF_3$, methoxy, or $OCF_3$.

R$^{4'}$ and R$^{5'}$ independently from each other more preferably represent hydrogen, fluorine, methyl, ethyl, n-propyl, isopropyl, n-butyl, isobutyl, or tert-butyl.

R$^{4'}$ and R$^{5'}$ independently from each other more preferably represent hydrogen or methyl.

R$^{4'}$ and R$^{5'}$ most preferably both represent hydrogen.

Q preferably represents a substituted 6-membered aromatic heterocycle containing one or two nitrogen atoms or a substituted 6-membered aromatic carbocycle. Substituted meaning that the cycle of the given formula comprises at least one of X¹, X², X³, X⁴ or X⁵ not being hydrogen.

Q more preferably represents a, preferably substituted, 6-membered aromatic cycle of formula (Q-I-1) to (Q-I-10)

(Q-I-1)
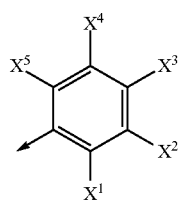

(Q-I-2)
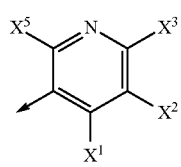

(Q-I-3)
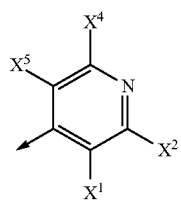

(Q-I-4)
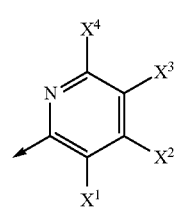

(Q-I-5)
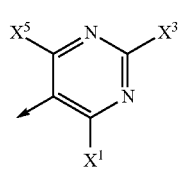

(Q-I-6)
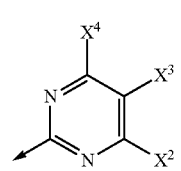

(Q-I-7)
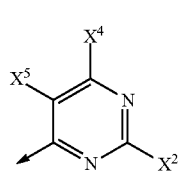

(Q-I-8)
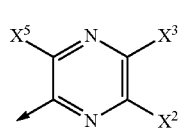

(Q-I-9)
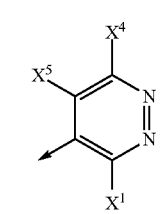

(Q-I-10)
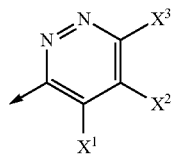

wherein $X^1$, $X^2$, $X^3$, $X^4$ and $X^5$ have the same definition as given for formula (I) above. Preferred definitions of $X^1$, $X^2$, $X^3$, $X^4$ and $X^5$ are given below.

Q more preferably represents a, preferably substituted, phenyl, 3-pyridyl or 4-pyridyl of formula (Q-I-1) to (Q-I-3)

(Q-I-1)
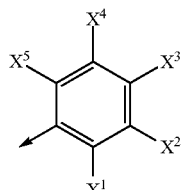

(Q-I-2)
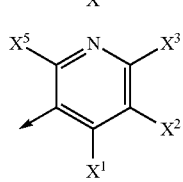

(Q-I-3)
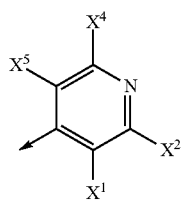

wherein $X^1$, $X^2$, $X^3$, $X^4$ and $X^5$ have the same definition as given for formula (I) above. Preferred definitions of $X^1$, $X^2$, $X^3$, $X^4$ and $X^5$ are given below.

Q more preferably represents a, preferably substituted, phenyl or 3-pyridyl of formula (Q-I-1) or (Q-I-2)

(Q-I-1)
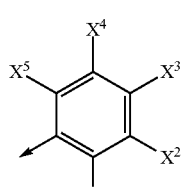

(Q-I-2)
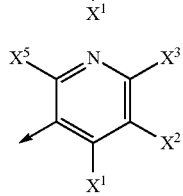

wherein $X^1$, $X^2$, $X^3$, $X^4$ and $X^5$ have the same definition as given for formula (I) above. Preferred definitions of $X^1$, $X^2$, $X^3$, $X^4$ and $X^5$ are given below.

Q most preferably represents a, preferably substituted, phenyl of formula (Q-I-1)

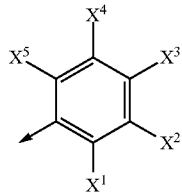
(Q-I-1)

wherein $X^1$, $X^2$, $X^3$, $X^4$ and $X^5$ have the same definition as given for formula (I) above. Preferred definitions of $X^1$, $X^2$, $X^3$, $X^4$ and $X^5$ are given below.

$X^1$, $X^2$, $X^3$, $X^4$, and $X^5$ independently from each other preferably represent hydrogen, halogen, nitro, cyano, sulfanyl, pentafluoro-$\lambda^6$-sulfanyl, $C_1$-$C_8$-alkyl, $C_1$-$C_8$-haloalkyl having 1 to 5 halogen atoms, $C_3$-$C_8$-cycloalkyl, $C_3$-$C_8$-halocycloalkyl having 1 to 5 halogen atoms, $C_1$-$C_8$-haloalkyl-$C_3$-$C_7$-cycloalkyl, $C_3$-$C_7$-cycloalkenyl, $C_2$-$C_8$-alkenyl, $C_2$-$C_8$-alkynyl, $C_6$-$C_{12}$-bicycloalkyl, $C_3$-$C_8$-cycloalkyl-$C_2$-$C_8$-alkenyl, $C_3$-$C_8$-cycloalkyl-$C_2$-$C_8$-alkynyl, $C_1$-$C_8$-alkoxy, $C_1$-$C_8$-haloalkoxy having 1 to 5 halogen atoms, $C_1$-$C_8$-alkoxycarbonyl, $C_1$-$C_8$-haloalkoxycarbonyl, $C_1$-$C_8$-alkylsulfenyl, $C_2$-$C_8$-alkenyloxy, $C_3$-$C_8$-alkynyloxy, $C_3$-$C_6$-cycloalkoxy, $C_1$-$C_8$-alkylsulfinyl, $C_1$-$C_8$-alkylsulfonyl, tri($C_1$-$C_8$-alkyl)-silyloxy, tri($C_1$-$C_8$-alkyl)-silyl, tri($C_1$-$C_8$-alkyl)-silyl-$C_2$-$C_8$-alkynyl, tri($C_1$-$C_8$-alkyl)-silyl-$C_2$-$C_8$-alkynyloxy, $C_6$-$C_{14}$-aryl, $C_6$-$C_{14}$-aryloxy, $C_6$-$C_{14}$-arylsulfenyl, 5- or 6-membered heteroaryl, or 5- or 6-membered heteroaryloxy, wherein the $C_6$-$C_{14}$-aryl, $C_6$-$C_{14}$-aryloxy, $C_6$-$C_{14}$-arylsulfenyl, 5- or 6-membered heteroaryl, and 5- or 6-membered heteroaryloxy is non-substituted or substituted by one or more group(s) selected from halogen, cyanosulfanyl, pentafluoro-$\lambda^6$-sulfanyl, $C_1$-$C_8$-alkyl, $C_1$-$C_8$-haloalkyl, $C_1$-$C_8$-cyano alkyl, $C_1$-$C_8$-alkyloxy, $C_1$-$C_8$-haloalkyloxy, tri($C_1$-$C_8$-alkyl)silyl, tri($C_1$-$C_8$-alkyl)silyl-$C_1$-$C_8$-alkyl, $C_3$-$C_7$-cycloalkyl, $C_3$-$C_7$-halocycloalkyl, $C_3$-$C_7$-cycloalkenyl, $C_3$-$C_7$-halocycloalkenyl, $C_4$-$C_{10}$-cycloalkylalkyl, $C_4$-$C_{10}$-halocycloalkylalkyl, $C_6$-$C_{12}$-cycloalkylcycloalkyl, $C_1$-$C_8$-alkyl-$C_3$-$C_7$-cycloalkyl, $C_1$-$C_8$-alkoxy-$C_3$-$C_7$-cyclo alkyl, tri($C_1$-$C_8$-alkyl)silyl-$C_3$-$C_7$-cycloalkyl, $C_2$-$C_8$-alkenyl, $C_2$-$C_8$-alkynyl, $C_2$-$C_8$-alkenyloxy, $C_2$-$C_8$-haloalkenyloxy, $C_3$-$C_8$-alkynyloxy, $C_3$-$C_8$-haloalkynyloxy, $C_1$-$C_8$-cyanoalkoxy, $C_4$-$C_8$-cycloalkylalkoxy, $C_3$-$C_6$-cycloalkoxy, $C_1$-$C_8$-alkylsulfanyl, $C_1$-$C_8$-haloalkylsulfanyl, $C_1$-$C_8$-alkyl sulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylsulfonyloxy, $C_1$-$C_8$-haloalkylsulfonyloxy, $C_1$-$C_8$-alkoxyalkyl, $C_1$-$C_8$-alkylthioalkyl, $C_1$-$C_8$-alkoxyalkoxyalkyl, $C_1$-$C_8$-haloalkoxyalkyl, benzyl, phenyl, 5-membered heteroaryl, 6-membered heteroaryl, 6-membered heteroaryloxy, benzyloxy, phenyloxy, benzylsulfanyl, and phenylsulfanyl.

$X^1$, $X^2$, $X^3$, $X^4$ and $X^5$ independently from each other more preferably represent hydrogen, halogen, cyano, $C_1$-$C_8$-alkyl, $C_1$-$C_8$-haloalkyl having 1 to 5 halogen atoms, $C_2$-$C_8$-alkenyl, $C_2$-$C_8$-alkynyl, $C_3$-$C_8$-cycloalkyl-$C_2$-$C_8$-alkenyl, $C_3$-$C_8$-cycloalkyl-$C_2$-$C_8$-alkynyl, $C_1$-$C_8$-alkoxy, $C_1$-$C_8$-haloalkoxy having 1 to 5 halogen atoms, $C_6$-$C_{14}$-aryl, or $C_6$-$C_{14}$-aryloxy, wherein the $C_6$-$C_{14}$-aryl and $C_6$-$C_{14}$-aryloxy is non-substituted or substituted by one or more group(s) selected from halogen, $C_1$-$C_8$-alkyl, $C_1$-$C_8$-haloalkyl, $C_1$-$C_8$-alkyloxy, and $C_1$-$C_8$-haloalkyloxy.

$X^1$, $X^2$, $X^3$, $X^4$ and $X^5$ independently from each other more preferably represent hydrogen, fluorine, chlorine, bromine, cyano, $C_1$-$C_4$-alkyl, $C_1$-$C_4$-haloalkyl having 1 to 5 halogen atoms, $C_2$-$C_4$-alkenyl, $C_2$-$C_4$-alkynyl, $C_3$-$C_6$-cycloalkyl-$C_2$-$C_4$-alkenyl, $C_3$-$C_6$-cycloalkyl-$C_2$-$C_4$-alkynyl, $C_1$-$C_4$-alkoxy, $C_1$-$C_4$-haloalkoxy having 1 to 5 halogen atoms, phenyl, or phenyloxy, wherein the phenyl and phenyloxy is non-substituted or substituted by one or more group(s) selected from fluorine, chlorine, bromine, $C_1$-$C_4$-alkyl, $C_1$-$C_4$-haloalkyl, $C_1$-$C_4$-alkyloxy, and $C_1$-$C_4$-haloalkyloxy.

$X^1$, $X^2$, $X^3$, $X^4$ and $X^5$ independently from each other more preferably represent hydrogen, fluorine, chlorine, bromine, cyano, methyl, ethyl, n-propyl, isopropyl, n-butyl, isobutyl, tert-butyl, $CF_3$, vinyl, cyclopropyl-$C_2$-$C_4$-alkynyl, methoxy, ethoxy, n-propoxy, isopropoxy, n-butoxy, isobutoxy, tert-butoxy, $OCF_3$, phenyl, or phenyloxy, wherein the phenyl and phenyloxy is non-substituted or substituted by one or more group(s) selected from fluorine, chlorine, bromine, methyl, ethyl, n-propyl, isopropyl, n-butyl, isobutyl, tert-butyl, and $CF_3$.

$X^1$, $X^2$, $X^3$, $X^4$ and $X^5$ independently from each other more preferably represent hydrogen, fluorine, chlorine, bromine, cyano, methyl, $CF_3$, vinyl, cyclopropyl-ethynyl, methoxy, $OCF_3$, phenyl, or phenyloxy, wherein the phenyl and phenyloxy is non-substituted or substituted by one or more group(s) selected from fluorine, and chlorine.

$X^1$, $X^2$, $X^3$, $X^4$ and $X^5$ independently from each other more preferably represent hydrogen, fluorine, chlorine, bromine, methyl, $CF_3$, methoxy or $OCF_3$.

$X^1$, $X^2$, $X^3$, $X^4$ and $X^5$ independently from each other more preferably represent hydrogen, fluorine, chlorine, bromine, methyl, $CF_3$, methoxy or $OCF_3$, wherein two, three, four or all five of $X^1$, $X^2$, $X^3$, $X^4$ and $X^5$ represent hydrogen.

$X^1$, $X^2$, $X^3$, $X^4$, and $X^5$ independently from each other more preferably represent hydrogen, fluorine, chlorine or bromine.

$X^1$, $X^2$, $X^3$, $X^4$, and $X^5$ independently from each other more preferably represent hydrogen, fluorine or chlorine.

$X^1$ more preferably represents hydrogen, fluorine or chlorine, most preferably fluorine or chlorine.

$X^2$ most preferably represents hydrogen, fluorine or chlorine.

$X^3$ more preferably represents hydrogen, fluorine or chlorine, most preferably hydrogen.

$X^4$ more preferably represents hydrogen, fluorine or chlorine, most preferably hydrogen.

$X^5$ more preferably represents hydrogen, fluorine or chlorine, most preferably hydrogen.

The radical definitions and explanations given above in general terms or stated within preferred ranges can be combined with one another as desired, i.e. including between the particular ranges and preferred ranges.

They apply both to the end products and correspondingly to educts and intermediates. In addition, individual definitions may not apply.

Preference is given to those cases in which each of the radicals have the abovementioned preferred definitions.

Particular preference is given to those cases in which each of the radicals have the abovementioned more and/or most preferred definitions.

Hence, particular preferred are for example compounds of formula (I)

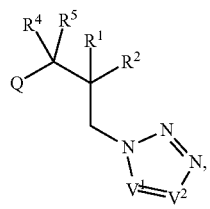

(I)

wherein

R¹ represents $C_1$-$C_8$-alkyl, or optionally halogen-, or $C_1$-$C_4$-alkyl-substituted $C_3$-$C_7$-cycloalkyl, preferably methyl, ethyl, n-propyl, isopropyl, n-butyl, isobutyl, tert-butyl, 1-halocyclopropyl, or 1-($C_1$-$C_4$-alkyl)cyclopropyl, more preferably isopropyl, isobutyl, tert-butyl, 1-chlorocyclopropyl, 1-fluorocyclopropyl or 1-methylcyclopropyl, more preferably tert-butyl, 1-chlorocyclopropyl, 1-fluorocyclopropyl or 1-methylcyclopropyl, and most preferably 1-chlorocyclopropyl, 1-fluorocyclopropyl or 1-methylcyclopropyl;

R² represents OH;

one of V¹ and V² represents CH, i.e. R³ represents hydrogen, and the other one of V¹ and V² represents N;

R⁴ represents hydrogen, fluorine or methyl, preferably hydrogen or methyl, more preferably hydrogen;

R⁵ represents hydrogen or fluorine, preferably hydrogen;

or R⁴ and R⁵ form together with the carbon atom to which they are attached $C_2$-alkenyl, wherein the $C_2$-alkenyl is substituted by methyl or non-substituted;

and

Q represents a 6-membered aromatic cycle of formula (Q-I-1) or (Q-I-2)

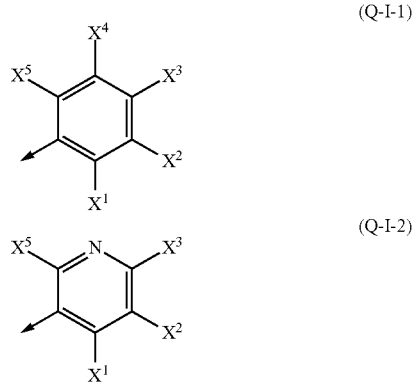

wherein

X¹, X², X³, X⁴, and X⁵ independently from each other represent hydrogen, halogen, cyano, $C_1$-$C_8$-alkyl, $C_1$-$C_8$-haloalkyl having 1 to 5 halogen atoms, $C_2$-$C_8$-alkenyl, $C_2$-$C_8$-alkynyl, $C_3$-$C_8$-cycloalkyl-$C_2$-$C_8$-alkenyl, $C_3$-$C_8$-cycloalkyl-$C_2$-$C_8$-alkynyl, $C_1$-$C_8$-alkoxy, $C_1$-$C_8$-haloalkoxy having 1 to 5 halogen atoms, $C_6$-$C_{14}$-aryl, or $C_6$-$C_{14}$-aryloxy, wherein the $C_6$-$C_{14}$-aryl and $C_6$-$C_{14}$-aryloxy is non-substituted or substituted by one or more group(s) selected from halogen, $C_1$-$C_8$-alkyl, $C_1$-$C_8$-haloalkyl, $C_1$-$C_8$-alkyloxy, and $C_1$-$C_8$-haloalkyloxy; preferably represent independently from each other hydrogen, fluorine, chlorine, bromine, cyano, methyl, $CF_3$, vinyl, cyclopropyl-ethynyl, methoxy, $OCF_3$, phenyl, or phenyloxy, wherein the phenyl and phenyloxy is non-substituted or substituted by one or more group(s) selected from fluorine, and chlorine; more preferably represent independently from each other hydrogen, fluorine, chlorine, bromine, methyl, $CF_3$, methoxy, or $OCF_3$; more preferably represent independently from each other hydrogen, fluorine, chlorine, or bromine; and most preferably represent independently from each other hydrogen, fluorine, or chlorine.

and its salts and N-oxides.

In the definitions of the symbols given in the above and below formulae, collective terms were used. Unless defined elsewhere those are generally representative of the following substituents:

Halogen: fluorine, chlorine, bromine or iodine, preferably fluorine, chlorine or bromine. Halogen-substitution is generally indicated by the prefix halo, halogen or halogeno.

Alkyl: saturated, straight-chain or branched hydrocarbyl radical having 1 to 8, preferably 1 to 6, and more preferably 1 to 4 carbon atoms, for example (but not limited to) $C_1$-$C_6$-alkyl such as methyl, ethyl, propyl (n-propyl), 1-methylethyl (iso-propyl), butyl (n-butyl), 1-methylpropyl (sec-butyl), 2-methylpropyl (iso-butyl), 1,1-dimethylethyl (tert-butyl), pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Particularly, said group is a $C_1$-$C_4$-alkyl group, e.g. a methyl, ethyl, propyl, 1-methylethyl (isopropyl), butyl, 1-methylpropyl (sec-butyl), 2-methylpropyl (iso-butyl) or 1,1-dimethylethyl (tert-butyl) group. This definition also applies to alkyl as part of a composite substituent, for example cycloalkylalkyl, hydroxyalkyl etc., unless defined elsewhere like, for example, alkylsulfanyl, alkylsulfinyl, alkylsulfonyl, haloalkyl or haloalkylsulfanyl.

Alkenyl: unsaturated, straight-chain or branched hydrocarbyl radicals having 2 to 8, preferably 2 to 6, and more preferably 2 to 4 carbon atoms and one double bond in any position, for example (but not limited to) $C_2$-$C_6$-alkenyl such as vinyl, allyl, (E)-2-methylvinyl, (Z)-2-methylvinyl, isopropenyl, homoallyl, (E)-but-2-enyl, (Z)-but-2-enyl, (E)-but-1-enyl, (Z)-but-1-enyl, 2-methylprop-2-enyl, 1-methylprop-2-enyl, 2-methylprop-1-enyl, (E)-1-methylprop-1-enyl, (Z)-1-methylprop-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, (E)-3,3-dimethylprop-1-enyl, (Z)-3,3-dimethylprop-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, 1-(1,1-dimethylethyl)ethenyl, buta-1,3-dienyl, penta-1,4-dienyl, hexa-1,5-dienyl or methylhexadienyl. Particularly, said group is vinyl or allyl. This definition also applies to alkenyl as part of a composite substituent, for example haloalkenyl etc., unless defined elsewhere.

Alkynyl: straight-chain or branched hydrocarbyl groups having 2 to 8, preferably 2 to 6, and more preferably 2 to 4 carbon atoms and one triple bond in any position, for example (but not limited to) $C_2$-$C_6$-alkynyl, such as ethynyl, prop-1-ynyl, prop-2-ynyl, but-1-ynyl, but-2-ynyl, but-3-ynyl, 1-methylprop-2-ynyl, pent-1-ynyl, pent-2-ynyl, pent-3-ynyl, pent-4-ynyl, 2-methylbut-3-ynyl, 1-methylbut-3-ynyl, 1-methylbut-2-ynyl, 3-methylbut-1-ynyl, 1-ethylprop-2-ynyl, hex-1-ynyl, hex-2-ynyl, hex-3-ynyl, hex-4-ynyl, hex-5-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl. This definition also applies to alkynyl as part of a composite substituent, for example haloalkynyl etc., unless defined elsewhere.

Alkoxy: saturated, straight-chain or branched alkoxy radicals having 1 to 8, preferably 1 to 6 and more preferably 1 to 4 carbon atoms, for example (but not limited to) $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, 1,1-dimethylpropoxy, 1,2-dimethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. This definition also applies to alkoxy as part of a composite substituent, for example haloalkoxy, alkynylalkoxy, etc., unless defined elsewhere.

Alkoxycarbonyl: an alkoxy group which has 1 to 8, preferably 1 to 6 and more preferably 1 to 4 carbon atoms (as specified above) and is bonded to the skeleton via a carbonyl group (—C(=O)—). This definition also applies to alkoxycarbonyl as part of a composite substituent, for example cycloalkylalkoxycarbonyl etc., unless defined elsewhere.

Alkylsulfanyl: saturated, straight-chain or branched alkylsulfanyl radicals having 1 to 8, preferably 1 to 6 and more preferably 1 to 4 carbon atoms, for example (but not limited to) $C_1$-$C_6$-alkylsulfanyl such as methylsulfanyl, ethylsulfanyl, propylsulfanyl, 1-methylethylsulfanyl, butylsulfanyl, 1-methylpropyl-sulfanyl, 2-methylpropylsulfanyl, 1,1-dimethylethylsulfanyl, pentylsulfanyl, 1-methylbutylsulfanyl, 2-methylbutylsulfanyl, 3-methylbutylsulfanyl, 2,2-dimethylpropylsulfanyl, 1-ethylpropylsulfanyl, 1,1-dimethylpropylsulfanyl, 1,2-dimethylpropylsulfanyl, hexylsulfanyl, 1-methylpentylsulfanyl, 2-methylpentylsulfanyl, 3-methylpentylsulfanyl, 4-methylpentylsulfanyl, 1,1-dimethylbutylsulfanyl, 1,2-dimethylbutylsulfanyl, 1,3-dimethylbutylsulfanyl, 2,2-dimethylbutylsulfanyl, 2,3-dimethylbutylsulfanyl, 3,3-dimethylbutylsulfanyl, 1-ethylbutylsulfanyl, 2-ethylbutylsulfanyl, 1,1,2-trimethylpropylsulfanyl, 1,2,2-trimethylpropylsulfanyl, 1-ethyl-1-methylpropylsulfanyl and 1-ethyl-2-methylpropylsulfanyl. This definition also applies to alkylsulfanyl as part of a composite substituent, for example haloalkylsulfanyl etc., unless defined elsewhere.

Alkylsulfinyl saturated, straight-chain or branched alkylsulfinyl radicals having 1 to 8, preferably 1 to 6 and more preferably 1 to 4 carbon atoms, for example (but not limited to) $C_1$-$C_6$-alkylsulfinyl such as methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentyl-sulfinyl, 3-methylpentylsulfinyl, 4-methylpentylsulfinyl, 1,1-dimethylbutylsulfinyl, 1,2-dimethyl-butylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl. This definition also applies to alkylsulfinyl as part of a composite substituent, for example haloalkylsulfinyl etc., unless defined elsewhere.

Alkylsulfonyl: saturated, straight-chain or branched alkylsulfonyl radicals having 1 to 8, preferably 1 to 6 and more preferably 1 to 4 carbon atoms, for example (but not limited to) $C_1$-$C_6$-alkylsulfonyl such as methylsulfonyl, ethylsulfonyl, propylsulfonyl, 1-methylethylsulfonyl, butylsulfonyl, 1-methylpropyl-sulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl. This definition also applies to alkylsulfonyl as part of a composite substituent, for example alkylsulfonylalkyl etc., unless defined elsewhere.

Monoalkylamino represents an amino radical having one alkyl residue with 1 to 4 carbon atoms attached to the nitrogen atom. Non-limiting examples include methylamino, ethylamino, n-propylamino, isopropyl-amino, n-butylamino and tert-butylamino.

Dialkylamino represents an amino radical having two independently selected alkyl residues with 1 to 4 carbon atoms each attached to the nitrogen atom. Non-limiting examples include N,N-dimethylamino, N,N-diethylamino, N,N-diisopropylamino, N-ethyl-N-methylamino, N-methyl-N-n-propylamino, N-iso-propyl-N-n-propylamino and N-tert-butyl-N-methylamino.

Cycloalkyl: monocyclic, saturated hydrocarbyl groups having 3 to 10, preferably 3 to 8 and more preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Cycloalkenyl: monocyclic, partially unsaturated hydrocarbyl groups having 3 to 10, preferably 3 to 8 and more preferably 3 to 6 carbon ring members, for example (but not limited to) cyclopropenyl, cyclopentenyl and cyclohexenyl. This definition also applies to cycloalkenyl as part of a composite substituent, for example cycloalkenylalkyl etc., unless defined elsewhere.

Cycloalkoxy: monocyclic, saturated cycloalkyloxy radicals having 3 to 10, preferably 3 to 8 and more preferably 3 to 6 carbon ring members, for example (but not limited to) cyclopropyloxy, cyclopentyloxy and cyclohexyloxy. This definition also applies to cycloalkoxy as part of a composite substituent, for example cycloalkoxyalkyl etc., unless defined elsewhere.

Haloalkyl: straight-chain or branched alkyl groups having 1 to 8, preferably 1 to 6 and more preferably 1 to 4 carbon atoms (as specified above), where some or all of the hydrogen atoms in these groups are replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere.

Haloalkenyl and haloalkynyl are defined analogously to haloalkyl except that, instead of alkyl groups, alkenyl and alkynyl groups are present as part of the substituent.

Haloalkoxy: straight-chain or branched alkoxy groups having 1 to 8, preferably 1 to 6 and more preferably 1 to 4 carbon atoms (as specified above), where some or all of the hydrogen atoms in these groups are replaced by halogen atoms as specified above, for example (but not limited to) $C_1$-$C_3$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoro-ethoxy and 1,1,1-trifluoroprop-2-oxy. This definition also applies to haloalkoxy as part of a composite substituent, for example haloalkoxyalkyl etc., unless defined elsewhere.

Haloalkylsulfanyl: straight-chain or branched alkylsulfanyl groups having 1 to 8, preferably 1 to 6 and more preferably 1 to 4 carbon atoms (as specified above), where some or all of the hydrogen atoms in these groups are replaced by halogen atoms as specified above, for example (but not limited to) $C_1$-$C_3$-haloalkylsulfanyl such as chloromethylsulfanyl, bromomethylsulfanyl, dichloromethylsulfanyl, trichloromethylsulfanyl, fluoromethylsulfanyl, difluoromethylsulfanyl, trifluoromethylsulfanyl, chlorofluoromethylsulfanyl, dichlorofluoromethylsulfanyl, chlorodifluoromethylsulfanyl, 1-chloroethylsulfanyl, 1-bromoethylsulfanyl, 1-fluoroethylsulfanyl, 2-fluoroethylsulfanyl, 2,2-difluoroethylsulfanyl, 2,2,2-trifluoroethylsulfanyl, 2-chloro-2-fluoroethylsulfanyl, 2-chloro-2,2-difluoroethylsulfanyl, 2,2-dichloro-2-fluoroethylsulfanyl, 2,2,2-trichloroethylsulfanyl, pentafluoroethylsulfanyl and 1,1,1-trifluoroprop-2-ylsulfanyl. This definition also applies to haloalkylsulfanyl as part of a composite substituent, for example haloalkylsulfanylalkyl etc., unless defined elsewhere.

Aryl: mono-, bi- or tricyclic aromatic or partially aromatic group having 6 to 14 carbon atoms, for example (but not limited to) phenyl, naphthyl, tetrahydronapthyl, indenyl and indanyl. The binding to the superordinate general structure can be carried out via any possible ring member of the aryl residue. Aryl is preferably selected from phenyl, 1-naphthyl and 2-naphthyl. Phenyl is particularly preferred.

Heteroaryl: 5 or 6-membered cyclic aromatic group containing at least 1, if appropriate also 2, 3, 4 or 5 heteroatoms, wherein the heteroatoms are each selected independently of one another from the group S, N and O, and which group can also be part of a bi- or tricyclic system having up to 14 ring members, wherein the ring system can be formed with one or two further cycloalkyl, cycloalkenyl, heterocyclyl, aryl and/or heteroaryl residues and wherein benzofused 5 or 6-membered heteroaryl groups are preferred. The binding to the superordinate general structure can be carried out via any possible ring member of the heteroaryl residue. Examples of 5-membered heteroaryl groups which are attached to the skeleton via one of the carbon ring members are fur-2-yl, fur-3-yl, thien-2-yl, thien-3-yl, pyrrol-2-yl, pyrrol-3-yl, isoxazol-3-yl, isoxazol-4-yl, isoxazol-5-yl, isothiazol-3-yl, isothiazol-4-yl, isothiazol-5-yl, pyrazol-3-yl, pyrazol-4-yl, pyrazol-5-yl, oxazol-2-yl, oxazol-4-yl, oxazol-5-yl, thiazol-2-yl, thiazol-4-yl, thiazol-5-yl, imidazol-2-yl, imidazole-4-yl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl. Examples of 5-membered heteroaryl groups which are attached to the skeleton via a nitrogen ring member are pyrrol-1-yl, pyrazol-1-yl, 1,2,4-triazol-1-yl, imidazol-1-yl, 1,2,3-triazol-1-yl and 1,3,4-triazol-1-yl. Examples of 6-membered heteroaryl groups are pyridine-2-yl, pyridine-3-yl, pyridine-4-yl, pyridazin-3-yl, pyridazin-4-yl, pyrimidin-2-yl, pyrimidin-4-yl, pyrimidin-5-yl, pyrazine-2-yl, 1,3,5-triazin-2-yl, 1,2,4-triazin-3-yl and 1,2,4,5-tetrazin-3-yl. Examples of benzofused 5-membered heteroaryl groups are indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl. Examples of benzofused 6-membered heteroaryl groups are quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl. Further examples of 5- or 6-membered heteroaryls which are part of a bicyclic ring system are 1,2,3,4-tetrahydroquinolin-1-yl, 1,2,3,4-tetrahydroquinolin-2-yl, 1,2,3,4-tetrahydroquinolin-7-yl, 1,2, 3,4-tetrahydroquinolin-8-yl, 1,2,3,4-tetrahydroisoquinolin-1-yl, 1,2,3,4-tetrahydroisoquinolin-2-yl, 1,2,3,4-tetrahydroisoquinolin-5-yl, 1,2,3,4-tetrahydroisoquinolin-6-yl and 1,2,3,4-tetrahydroisoquinolin-7-yl. This definition also applies to heteroaryl as part of a composite substituent, for example heteroarylalkyl etc., unless defined elsewhere.

Heterocyclyl: three- to seven-membered, saturated or partially unsaturated heterocyclic group containing at least one, if appropriate up to four heteroatoms and/or heterogroups independently selected from the group consisting of N, O, S, S($=$O), S($=$O)$_2$ and di-($C_1$-$C_4$)alkylsilyl, which group can be benzofused. The binding to the superordinate general structure can be carried out via a ring carbon atom or, if possible, via a ring nitrogen atom of the heterocyclic group. Saturated heterocyclic groups in this sense are for example (but not limited to) oxiranyl, aziridinyl, tetrahydrofuran-2-yl, tetrahydrofuran-3-yl, tetrahydrothien-2-yl, tetrahydrothien-3-yl, pyrrolidin-2-yl, pyrrolidin-3-yl, isoxazolidin-3-yl, isoxazolidin-4-yl, isoxazolidin-5-yl, isothiazolidin-3-yl, isothiazolidin-4-yl, isothiazolidin-5-yl, pyrazolidin-3-yl, pyrazolidin-4-yl, pyrazolidin-5-yl, oxazolidin-2-yl, oxazolidin-4-yl, oxazolidin-5-yl, thiazolidin-2-yl, thiazolidin-4-yl, thiazolidin-5-yl, imidazolidin-2-yl, imidazolidin-4-yl, 1,2,4-oxadiazolidin-3-yl, 1,2,4-oxadiazolidin-5-yl, 1,3,4-oxadiazolidin-2-yl, 1,2,4-thiadiazolidin-3-yl, 1,2,4-thiadiazolidin-5-yl, 1,3,4-thiadiazolidin-2-yl, 1,2,4-triazolidin-3-yl, 1,3,4-triazolidin-2-yl, piperidin-2-yl, piperidin-3-yl, piperidin-4-yl, 1,3-dioxan-5-yl, tetrahydropyran-2-yl, tetrahydropyran-4-yl, tetrahydrothien-2-yl, hexahydropyridazin-3-yl, hexa-hydropyridazin-4-yl, hexahydropyrimidin-2-yl, hexahydropyrimidin-4-yl, hexahydropyrimidin-5-yl, piperazin-2-yl, 1,3,5-hexahydrotriazin-2-yl and 1,2,4-hexahydrotriazin-3-yl. Partially unsaturated heterocyclic groups in this sense are for example (but not limited to) 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl. Examples of benzofused heterocyclic groups are indolin-1-yl, indolin-2-yl, indolin-3-yl, isoindolin-1-yl, isoindolin-2-yl, 2,3-dihydrobenzofuran-2-yl and 2,3-dihydrobenzofuran-3-yl. This definition also applies to heterocyclyl as part of a composite substituent, for example heterocyclylalkyl etc., unless defined elsewhere.

Oxo represents a doubly bonded oxygen atom.

Thiooxo represents a doubly bonded sulfur atom.

Optionally substituted groups may be mono- or polysubstituted, where the substituents in the case of polysubstitutions may be identical or different.

Not included are combinations which are against natural laws and which the person skilled in the art would therefore exclude based on his/her expert knowledge. Ring structures having three or more adjacent oxygen atoms, for example, are excluded.

Isomers

Depending on the nature of the substituents, the compounds of the invention may be present in the form of different stereoisomers. These stereoisomers are, for example, enantiomers, diastereomers, atropisomers or geometric isomers. Accordingly, the invention encompasses both pure stereoisomers and any mixture of these isomers. Where a compound can be present in two or more tautomer forms in equilibrium, reference to the compound by means of one tautomeric description is to be considered to include all tautomer forms.

Illustration of the Processes and Intermediates

The present invention furthermore relates to processes for preparing compounds of formula (I), including compounds of formulae (Ia), (Ib), (I-en), (Ia-en) and (Ib-en). The present invention furthermore relates to intermediates such as ketones of formula (XVI), epoxides of formula (XVII) and the preparation thereof.

The compounds (I) can be obtained by various routes in analogy to prior art processes known (see e.g. "Design and optimization of highly-selective fungal CYP51 inhibitors": Hoekstra, Garvey, Moore, Rafferty, Yates, Schotzinger, *Bioorg. Med. Chem. Lett.* 2014, 24(15), 3455-3458; "Design and optimization of highly-selective, broad spectrum fungal CYP51 inhibitors": Yates, Garvey, Shaver, Schotzinger, Hoekstra, *Bioorg. Med. Chem. Lett.* 2017, 27(15), 3243-3248; WO-A 2008/064311; WO-A 2011/133875; WO-A 2012/177603; WO-A 2012/177608; WO-A 2012/177635; WO-A 2012/177638; WO-A 2012/177725; WO-A 2012/177728; WO-A 2015/143154; WO-A 2015/143184; WO-A 2015/143188; WO-A 2015/143192; WO-A 2017/049080; WO-A 2017/049196 and references cited therein) and by synthesis routes shown schematically below and in the experimental part of this application. Unless indicated otherwise, the radicals Q, $V^1$, $V^2$, $R^1$, $R^2$, $R^{2a}$, $R^3$, $R^4$ and $R^5$ have the meanings given above for the compounds of formula (I). These definitions apply not only to the end products but likewise to all intermediates.

Process A (Scheme 1):

Scheme 1: Process A - Preparation of ketones (V).

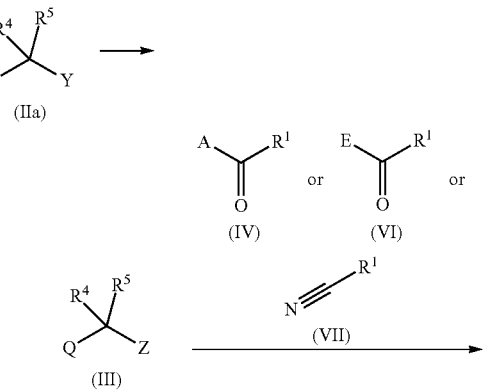

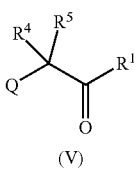

Y = —H or —OH
Z = halogen, —OSO$_2$—C$_1$—C$_8$—alkyl, —OSO$_2$—aryl, —OP(O)(O—C$_1$—C$_8$—alkyl)$_2$ or —OP(O)(O—aryl)$_2$, preferably —Cl or —Br
A = halogen, preferably Cl
E = —O—C$_1$—C$_8$—alkyl, preferably —O—methyl, —O—ethyl, —O—aryl; —S—C$_1$—C$_8$—alkyl; —S—aryl; —NHR$^a$, —NR$^a$R$^b$; R$^a$: is aryl, C$_1$—C$_8$—alkyl or C$_3$—C$_7$—cycloalkyl, R$^b$: is C$_1$—C$_8$—alkyl or C$_1$—C$_8$—alkyloxy, preferably —NMe$_2$, —NMeOMe; or cyano; or heterocyclic leaving groups, such as imidazole, triazole and hydroxybenzotriazole.

Compounds (IIa) and/or (III) are either commercially available or producible by processes described in the literature (see, for example, "Comprehensive Heterocyclic Chemistry III", Pergamon Press, 2008, vol. 7, pages 101-169 and 217-308 & vol. 7, pages 1-331 and references cited therein; "Comprehensive Heterocyclic Chemistry II", Pergamon Press, 1996, vol. 5, pages 37-243 & vol. 6, pages 1-278 and references cited therein; "Comprehensive Heterocyclic Chemistry I", Pergamon Press, 1984, vol. 2, pages 395-510 & vol. 3, pages 1-197 and references cited therein; "Comprehensive Heterocyclic Chemistry III", Pergamon Press, 2008, vol. 3, pages 45-388 & vol. 4, pages 1-364 and references cited therein; "Comprehensive Heterocyclic Chemistry II", Pergamon Press, 1996, vol. 2, pages 39-257 & vol. 3, pages 1-220 and references cited therein; "Comprehensive Heterocyclic Chemistry I", Pergamon Press, 1984, vol. 4, pages 155-376 & vol. 5, pages 167-498 and references cited therein).

The compounds (IIa) (Scheme 1) can be converted by means of methods described in the literature to the corresponding compounds (III) and subsequently to compounds (V). In a first process, for example, compounds (IIa) are halogenated.

In case Y stands for hydrogen, the compounds (IIa) can be halogenated e.g. with bromo- or chlorosuccinimide (see e.g. WO-A 2011/012622, WO-A 2008/003622, WO-A 2005/111003; Synthesis, 18, 2008, 2996 and references cited therein), preferably in the presence of a radical initiator such as azobisisobutyronitrile or dibenzoyl peroxide and in the presence of an organic solvent, e.g. a chlorinated organic solvent such as tetrachloromethane. Alternatively, compounds (IIa) undergo side-chain halogenation in the presence of bromine or chlorine (see e.g. EP 557967) to obtain compounds (III). Optionally, a radical initiator such as azobisisobutyronitrile or dibenzoyl peroxide can be used. Alternatively, compounds (IIa) are reacted with a base, e.g. methyl lithium, and subsequently with a halogen source such as magnesiumbromide to obtain compounds (III) (see e.g. WO-A 2012/087784).

Compounds (IIa), wherein Y stands for —OH, can be reacted with halogenating agents, such as PBr$_3$, PCl$_3$ or thionyl chloride, to obtain compounds (III) (see e.g. WO-A 2009/153554, Bioorganic & Medicinal Chemistry Letters, 22, 2012, 901-906; WO-A 2010/132999 and references cited therein). Alternatively, compounds (IIa) can be reacted with sulfonyl halides, such as e.g. mesylchloride or tosylchloride, or with phosphonic acid halides, such as e.g. diphenylphosphoryl chloride, to obtain the respective sulfonates and phosphates (see e.g. J. Org. Chem. 1992, 57, 5425-5431 and references cited therein).

The compounds (III) can subsequently be reacted with compounds (IV) or (VI) wherein A and E represent a replaceable group such as halide, —OR, NHR$^a$ or NR$^a$R$^b$, preferably chloro, —O-methyl, —O-ethyl, —NMe$_2$ or —NMeOMe. To obtain compounds (V), compounds (III) are, for example, reacted in a first step with e.g. zinc, magnesium or isopropylmagnesium chloride, followed by a carbonyl compound (IV) or (VI) preferably under anhydrous conditions and optionally in the presence of a metal catalyst, such as palladium- or nickel-based catalysts. Suitable metal catalysts are for example (Ph$_3$P)$_2$PdCl$_2$ (e.g. WO-A 2012/087784, EP-A 461 502) and PEPPSI-IPr (Chem. Eur. J. 2006, 12, 4743-4748). The metal catalyst can also be prepared in-situ by the mixing of a metals salt (e.g. Pd(OAc)$_2$) and a ligand (such as e.g. PPh$_3$, 2-dicyclohexylphosphino-2',6'-dimethoxybiphenyl (S-Phos)). The insertion of the metal can be enhanced by the addition of ionic salts, such as LiBr, LiCl, LiI, CuI, Zn(OPiv)$_2$, MgCl$_2$, CuCN (see e.g. Dissertation Albrecht Metzer 2010 (University Munich); Angew. Chem. Int. Ed. 2011, 50, 9205 9209), or by activation of the metal using halogenated alkanes (1,2-dibromoethane) or halogenated alkylsilanes (TMSCl). Alternatively this sequence may be carried out in a one-pot fashion (see e.g. Beller et al., Chem. Asian J., 2011, 7(1) 40-44).

In an alternative route compounds (III) are reacted with nitriles (VII) to obtain compounds (V) after hydrolysis of the intermediate imine or its salt (see e.g Wakefield, Basil J. "Addition to Carbon-Nitrogen Multiple Bonds." pp. 87-109 in *Organomagnesium Methods in Organic Synthesis*, Academic Press, 1995, and references cited therein).

The reaction is preferably performed at temperatures between room temperature and refluxing temperature of the solvent.

As the solvent, all common solvents inert under the reaction conditions, such as for example ethers (such as e.g. tetrahydrofurane, diethyl ether) can be used and the reaction can be effected in mixtures of two or more of these solvents.

Process B (Scheme 2):

Scheme 2: Process B-Preparation of ketones (V).

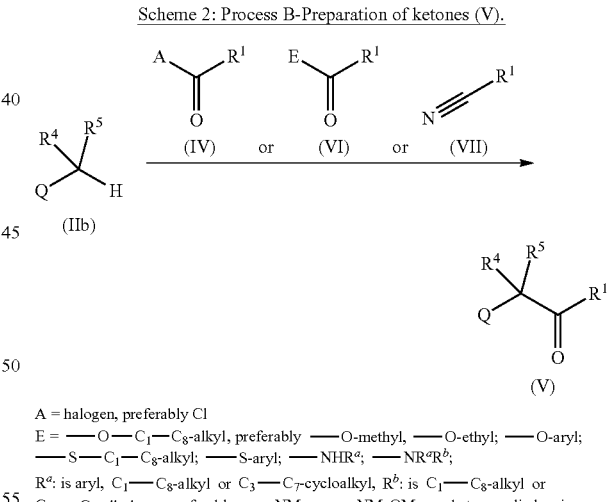

A = halogen, preferably Cl
E = —O—C$_1$—C$_8$-alkyl, preferably —O-methyl, —O-ethyl; —O-aryl; —S—C$_1$—C$_8$-alkyl; —S-aryl; —NHR$^a$; —NR$^a$R$^b$;
R$^a$: is aryl, C$_1$—C$_8$-alkyl or C$_3$—C$_7$-cycloalkyl, R$^b$: is C$_1$—C$_8$-alkyl or C$_1$—C$_8$-alkyloxy, preferably —NMe$_2$, —NMeOMe; or heterocyclic leaving groups, such as imidazole, triazole and hydroxybenzotriazole.

Compounds (IIb) are either commercially available or producible by processes described in the literature (see, for example, "Comprehensive Heterocyclic Chemistry III", Pergamon Press, 2008, vol. 7, pages 101-169 and 217-308 & vol. 7, pages 1-331 and references cited therein; "Comprehensive Heterocyclic Chemistry II", Pergamon Press, 1996, vol. 5, pages 37-243 & vol. 6, pages 1-278 and references cited therein; "Comprehensive Heterocyclic Chemistry I", Pergamon Press, 1984, vol. 2, pages 395-510 & vol. 3, pages 1-197 and references cited therein; "Comprehensive Heterocyclic Chemistry III", Pergamon Press, 2008, vol. 3, pages 45-388 & vol. 4, pages 1-364 and references cited therein; "Comprehensive Heterocyclic Chemistry II", Pergamon Press, 1996, vol. 2, pages 39-257 & vol. 3, pages 1-220 and references cited therein; "Comprehensive Heterocyclic Chemistry I", Pergamon Press, 1984, vol. 4, pages 155-376 & vol. 5, pages 167-498 and references cited therein).

There are numerous literature methods for the preparation of ketones (see e.g. WO-A 2012/055942, WO-A 2012/100342, WO-A 2012/087784, WO-A 2012/087833, US-A 2012/0010190, Dalton Transaction, 2011, 2366-2374, Journal of the American Chemical Society, 1955, 3858-3860, Journal of the American Chemical Society, 1937, 1494-1497, WO-A 2012/085815, WO-A 2011/042389, WO-A 2003/026663, Heterocycles, 1998, 2103-2109, Bioorganic & Medicinal Chemistry Letters, 2010, 2634-2640).

In general, it is possible to prepare compounds of the formula (V) from corresponding compounds (IIb) and (IV) and/or from corresponding compounds (IIb) and (VI) with suitable groups A and E (see Scheme 2, process B). Compounds (IIb) are optionally reacted sequentially with a base, e.g. n-butyllithium, lithium-diisopropylamide, lithium bis(trimethylsilyl)amide, sodium bis(trimethylsilyl)amide, potassium bis(trimethylsilyl)amide sodium amide, potassium amide, potassium tert-butoxide, methyl lithium, $TMP_2Zn.2MgCl_2.2LiCl$ (see e.g. Dissertation Albrecht Metzer 2010, University Munich), followed by compounds (IV) or (VI), preferably under anhydrous conditions. Optionally, the reaction of compounds (IIb) and compounds (IV) or (VI) is carried out in the presence of a base in a one-pot fashion. The possible groups for A and E are, for example, halide, —OR, $NHR^a$ or $NR^aR^b$, preferably chloro, —O-methyl, —O-ethyl, —$NMe_2$ or —NMeOMe, etc., which can act as appropriate leaving groups to form the desired ketones (V) under suitable reaction conditions (Scheme 2).

In an alternative route compounds (IIb) are reacted with compounds (VII) in the presence of a base, e.g. phenyl lithium or methyl lithium, to obtain compounds (V) (see e.g. (see e.g Wakefield, Basil J. "Addition to Carbon-Nitrogen Multiple Bonds." pp. 87-109 in *Organomagnesium Methods in Organic Synthesis*, Academic Press, 1995; *J. Amer. Chem. Soc.* 2011, 11194-11204; *J. Med. Chem.* 1963, 205-207 and references cited therein).

Process C (Scheme 3):

Scheme 3: Process C-Preparation of ketones (V).

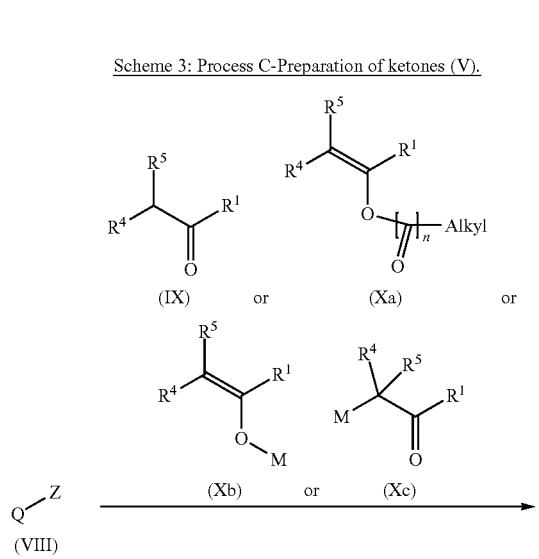

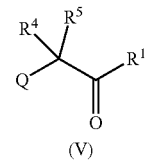

Z = halogen, preferably Cl or Br
n = 0 or 1
M = Li, $MgZ^M$, $ZnZ^M$, $Si(C_1\text{—}C_8\text{-alkyl})_3$, $Sn(C_1\text{—}C_8\text{-alkyl})_3$
$Z^M$ = halogen, hydroxyl, preferably Cl or Br One means of preparing compounds of the formula (V) from corresponding compounds (VIII) with the compounds (IX) or (X) is shown in Scheme 3 (Process C). Compounds (X) include compounds (Xa), (Xb) and (Xc).

Compounds (VIII) are either commercially available or producible by processes described in the literature (see, for example, "Comprehensive Heterocyclic Chemistry III", Pergamon Press, 2008, vol. 7, pages 101-169 and 217-308 & vol. 7, pages 1-331 and references cited therein; "Comprehensive Heterocyclic Chemistry II", Pergamon Press, 1996, vol. 5, pages 37-243 & vol. 6, pages 1-278 and references cited therein; "Comprehensive Heterocyclic Chemistry I", Pergamon Press, 1984, vol. 2, pages 395-510 & vol. 3, pages 1-197 and references cited therein; "Comprehensive Heterocyclic Chemistry III", Pergamon Press, 2008, vol. 3, pages 45-388 & vol. 4, pages 1-364 and references cited therein; "Comprehensive Heterocyclic Chemistry II", Pergamon Press, 1996, vol. 2, pages 39-257 & vol. 3, pages 1-220 and references cited therein; "Comprehensive Heterocyclic Chemistry I", Pergamon Press, 1984, vol. 4, pages 155-376 & vol. 5, pages 167-498 and references cited therein).

Compounds (IX) and (X) are either commercially available or producible by processes described in the literature (see, for example, WO-A 2010/029066; Chemische Berichte, 1986, 2995-3026 and references cited therein).

A compound having the general formula (V) can be synthesized analogously to methods described in the literature (see, for example Organic letters, 2009, 1773-1775; European Journal of Organic Chemistry, 2011, 1570-1574; Chemical & Pharmaceutical Bulletin, 1970, 1457-1464; Chemical & Pharmaceutical Bulletin, 1980, 337-342; WO-A 2005/044785), by a coupling reaction of a compound with the corresponding general formula (VIII) with a substrate of the general formula (IX) or (X), wherein Z is halogen, preferably chlorine or bromine. Those reactions can be optionally carried out in the presence of a catalyst and a base.

As catalysts various metal based catalysts can be used which are either used directly or being prepared in situ from a metal precursor (e.g. $Pd_2dba_3$, $Pd(OAc)_2$) and a ligand (e.g. phosphine based ligands like Xanthphos, 2-(dicyclohexylphosphino)-2'-methylbiphenyl, 2-diphenylphosphino-2'-(N,N-dimethylamino)-biphenyl, tri-t-butylphosphine, tri-o-tolylphosphine) (see e.g. WO-A 2008/147544, WO-A 2005/027837).

As bases various organic and inorganic bases can be used such as potassium phosphate, or a sodium base, e.g. sodium amide, sodium hydride or sodium tert-butoxide. Alternatively, silicon containing bases can be used, e.g. NaHMDS, KHMDS, LiHMDS.

Process D (Scheme 4):

Scheme 4: Process D-Preparation of epoxides (XI).

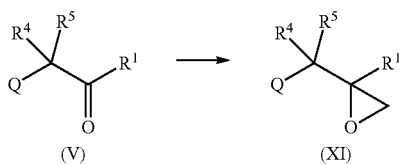

The ketones (V) (Scheme 4) can be converted by means of methods described in the literature to the corresponding epoxides (XI) (see e.g. Gololobov, Nesmeyanov, Lysenko, Boldeskul, *Tetrahedron* 1987, 43(12), 2609-2651; H. Adolfsson "Product Class 2: Epoxides (Oxiranes). Category 5, Compounds with One Saturated Carbon Heteroatom Bond" in *Science of Synthesis*, Forsyth (Ed.), Thieme: Stuttgart, 2008, Vol. 2008, Section 37. 2, p. 227; EP-A 461 502, DE-A 33 15 681, EP-A 291 797, Bioorganic & Medicinal Chemistry Letters (1996), 6(16), 2031-2036). Intermediates (V) are preferably reacted with trimethylsulfoxonium- or trimethylsulfonium-salts, preferably trimethylsulfoxonium halides, trimethylsulfonium halides, trimethylsulfoxonium methylsulfates or trimethylsulfonium methylsulfates, preferably in the presence of a base such as sodium hydride.

Process E (Scheme 5):

Scheme 5: Process E-Preparation of epoxides (XI).

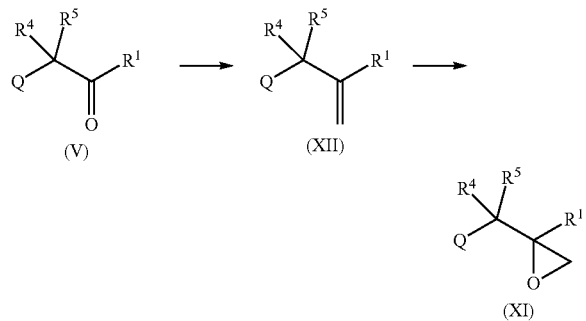

Alternatively, compounds (V) can be first converted to the corresponding olefins (XII), followed by an epoxidation to obtain epoxides (XI) (see e.g. EP-A 291 797).

Process F (Scheme 6):

Scheme 6: Process F-Preparation of epoxides (XI).

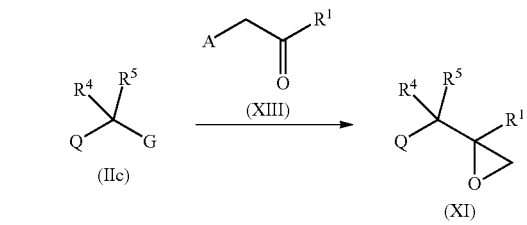

G = halogen or hydrogen
A = halogen, O—$SO_2$—$C_1$—$C_8$-alkyl or O—$SO_2$-aryl, preferably Cl or Br Alternatively, epoxides (XI) can be synthesized analogously to methods described in the literature by a coupling reaction of a compound having the corresponding general formula (IIc) with a substrate of the general formula (XIII) (see e.g. DE-A 40 27 608, WO-A 93/02086, WO-A 93/12121, Journal of Organic Chemistry, 2001, 2149-2153 and references cited therein).

Compounds (IIc) are either commercially available or producible by processes described in the literature (see, for example, "Comprehensive Heterocyclic Chemistry III", Pergamon Press, 2008, vol. 7, pages 101-169 and 217-308 & vol. 7, pages 1-331 and references cited therein; "Comprehensive Heterocyclic Chemistry II", Pergamon Press, 1996, vol. 5, pages 37-243 & vol. 6, pages 1-278 and references cited therein;

"Comprehensive Heterocyclic Chemistry I", Pergamon Press, 1984, vol. 2, pages 395-510 & vol. 3, pages 1-197 and references cited therein; "Comprehensive Heterocyclic Chemistry III", Pergamon Press, 2008, vol. 3, pages 45-388 & vol. 4, pages 1-364 and references cited therein; "Comprehensive Heterocyclic Chemistry II", Pergamon Press, 1996, vol. 2, pages 39-257 & vol. 3, pages 1-220 and references cited therein; "Comprehensive Heterocyclic Chemistry I", Pergamon Press, 1984, vol. 4, pages 155-376 & vol. 5, pages 167-498 and references cited therein).

If G stands for halogen, preferably chloride or bromide, compounds (IIc) are first transformed into Grignard reagents by the reaction with magnesium or with halogen/metal exchange reagents such as isopropylmagnesium halides and subsequently reacted with ketones (XIII), preferably under anhydrous conditions, to obtain compounds of the general formula (XI) (see e.g. DE4027608). Alternatively, if G stands for halogen, the halides (IIc) can be converted to the corresponding zinc reagents and subsequently reacted with ketones (XIII) (e.g. ChemComm, 2008, 5824-5826; Journal of Organic Chemistry, 2004, 908-914 and references cited therein).

In an alternative route compounds (IIc) (G=hydrogen) are reacted with compounds (XIII) preferably in the presence of a base. Compounds (IIc) (G=hydrogen) are optionally reacted with a base upfront, e.g. n-butyllithium, lithiumdiisopropylamide, lithium bis(trimethylsilyl)amide, sodium bis(trimethylsilyl)amide, potassium bis(trimethylsilyl)amide, sodium amide, potassium amide, potassium tert-butoxide, methyl lithium, $TMP_2Zn.2MgCl_2.2LiCl$ (see e.g. Dissertation Albrecht Metzer 2010, University Munich), followed by compounds of the general structure (XIII), preferably under anhydrous conditions. The possible groups for A are, for example, halides which can act as appropriate leaving groups to form the desired compounds (XI) under suitable reaction conditions.

Process G (Scheme 7):

Scheme 7: Process G-Preparation of alcohol (XIV).

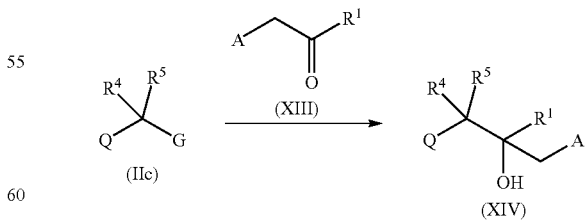

G = halogen or hydrogen
A = halogen, O—$SO_2$—$C_1$—$C_8$-alkyl or O—$SO_2$-aryl, preferably Cl or Br A compound having the general formula (XIV) can be synthesized analogously to methods described in the literature by a coupling reaction of a compound having the corresponding general formula (IIc) with a substrate of the general formula (XIII) (see e.g. DE-A 40 27 608, WO-A 93/02086, WO-A 93/12121, Journal of Organic Chemistry, 2001, 2149-2153).

If G stands for halogen, preferably chloride or bromide, compounds (IIc) are first transformed into Grignard reagents by the reaction with magnesium or with halogen/metal exchange reagents, such as isopropylmagnesium halides, and subsequently reacted with ketones (XIII) preferably under anhydrous conditions to obtain compounds of the general formula (XIV) (see e.g. DE-A 4027608). Alternatively, if G stands for halogen, the halides (IIc) can be converted to the corresponding zinc reagents and subsequently reacted with ketones (XIII) (e.g. ChemComm, 2008, 5824-5826; Journal of Organic Chemistry, 2004, 908-914 and references cited therein).

In an alternative route compounds (IIc) (G=hydrogen) are reacted with compounds (XIII), preferably in the presence of a base. Compounds (IIc) (G=hydrogen) are optionally reacted with a base upfront, e.g. n-butyllithium, lithium-diisopropylamide, lithium bis(trimethylsilyl)amide, methyl lithium, followed by compounds of the general structure (XIII), preferably under anhydrous conditions. The possible groups for A are, for example, halides which can act as appropriate leaving groups to form the desired compounds (XIV) under suitable reaction conditions.

According to the specific educts (IIc) and (XIII) and/or the specific reaction conditions either the epoxide (XI) (cf. process F) or the alcohol (XIV) or a mixture thereof is formed. Generally, at low reaction temperatures formation of alcohols (XIV) is promoted, while higher reaction temperatures favor formation of epoxides (XI).

Process H (Scheme 8):

Scheme 8: Process H-Preparation of compounds (Ia-OH) and/or (Ib-OH).

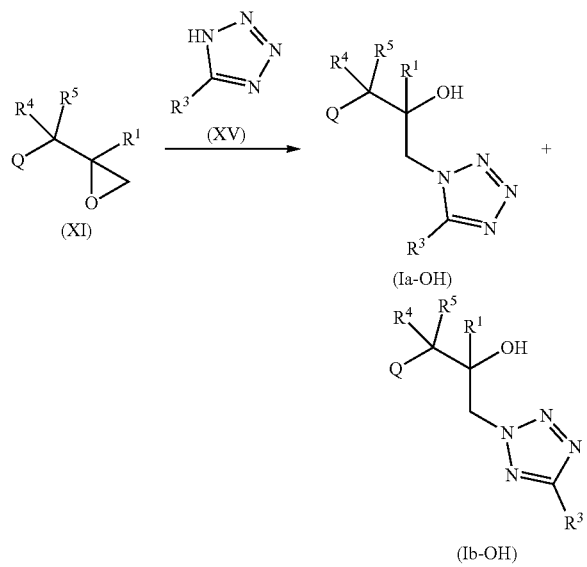

Epoxides (XI) obtainable according to process D, E or F can be converted in analogy to methods described in the literature to the corresponding compounds (Ia-OH) and/or (Ib-OH) (see e.g. DE-A 40 27 608, EP-A 461 502, DE-A 33 15 681, EP-A 291 797, WO-A 95/29901). For example, the starting materials (XI) can be reacted with tetrazoles of formula (XV) which are commercially available or can be obtained by means of methods described in the literature, optionally in the presence of a base, such as potassium carbonate and/or potassium tert-butoxide, optionally in the presence of a Lewis acid, such as magnesium dichloride or $BF_3/Et_2O$.

Preferably the reaction is performed in the presence of a solvent. As the solvent, all common solvents inert under the reaction conditions, such as for example nitriles (such as e.g. acetonitrile, propionitrile) or amides (such as e.g. DMF, DMAc, NMP) can be used and the reaction can be effected in mixtures of two or more of these solvents.

Process I (Scheme 9):

Scheme 9: Process I-Preparation of compounds (Ia-OH) and/or (Ib-OH).

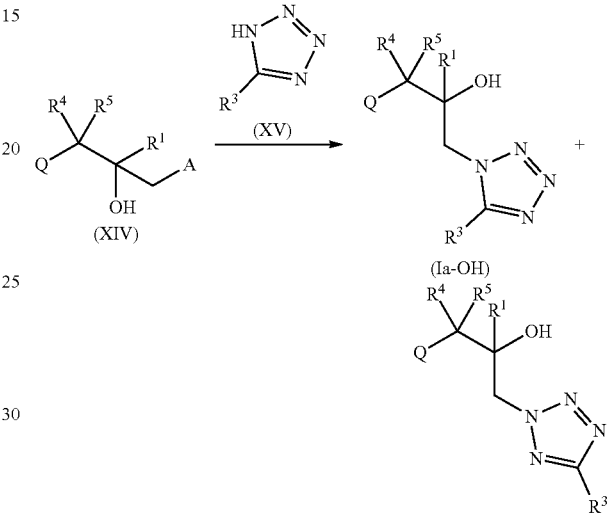

A = halogen, $O-SO_2-C_1-C_8$-alkyl or $O-SO_2$-aryl, preferably Cl or Br

Also alcohols (XIV) obtainable according to process G can be converted in analogy to methods described in the literature to the corresponding compounds (Ia-OH) and/or (Ib-OH) (see e.g. DE-A 40 27 608). The starting materials (XIV) can be reacted with tetrazoles of formula (XV) which are commercially available or can be obtained by means of methods described in the literature, optionally in the presence of a base, such as potassium carbonate and/or potassium tert-butoxide, optionally in the presence of a Lewis acid, such as magnesium dichloride or $BF_3/Et_2O$.

Preferably the reaction is performed in the presence of a solvent. As the solvent, all common solvents inert under the reaction conditions, such as for example nitriles (such as e.g. acetonitrile, propionitrile) or amides (such as e.g. DMF, DMAc, NMP) can be used and the reaction can be effected in mixtures of two or more of these solvents.

Process J (Scheme 10):

Scheme 10: Process J-Preparation of ketones (XVIa/XVIb)

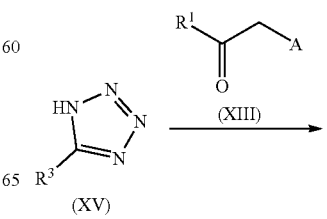

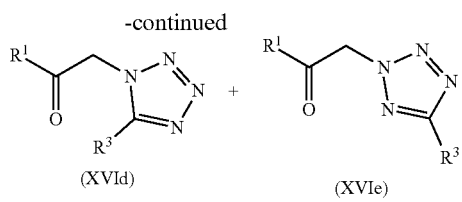

A = halogen, O—SO$_2$—C$_1$–C$_8$-alkyl or O—SO$_2$-aryl, preferably Cl or Br

The tetrazoles of formula (XV), which are commercially available or can be obtained by means of methods described in the literature, can be alkylated by compounds of formula (XIII) by means of methods described in the literature to the corresponding ketones (XVId) or (XVIe) (see e.g DE-A 33 28 273; *J. Chem. Soc. Perkin Trans.* 1 2001, (7), 720-728; *J. Med. Chem.* 1994, 37(1), 201-205; *Chemical Biology & Drug Design* 2010, 75(1), 68-90). The reaction is optionally performed in the presence of a base, such as potassium carbonate, triethylamine, and/or potassium tert-butoxide, optionally in the presence of a Lewis acid, such as magnesium dichloride or BF$_3$/Et$_2$O, optionally in the presence of a metal oxide, such as zinc oxide or barium oxide.

Preferably the reaction is performed in the presence of a solvent. As the solvent, all common solvents inert under the reaction conditions, such as for example nitriles (such as e.g. acetonitrile, propionitrile) or amides (such as e.g. DMF, DMAc, NMP) can be used and the reaction can be effected in mixtures of two or more of these solvents.

Process K (Scheme 11):

Scheme 11: Process K-Preparation of compounds (Ia-OH) and/or (Ib-OH)

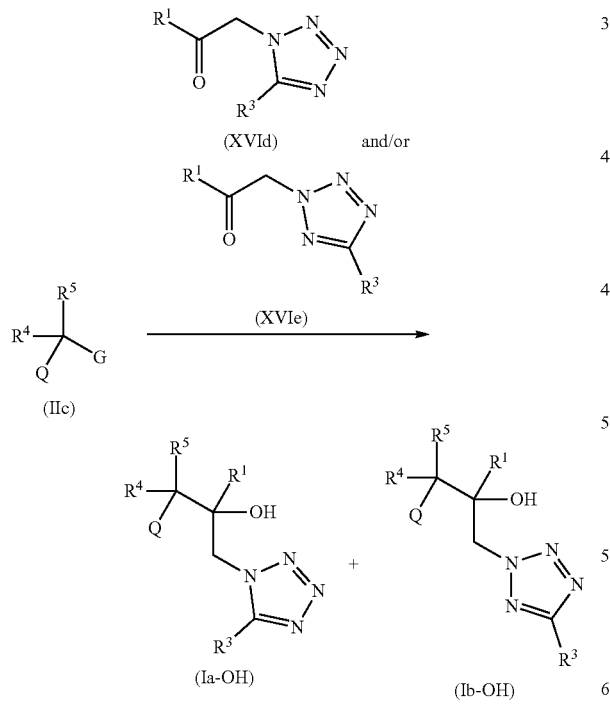

G = halogen or hydrogen

According to process K, the ketones of formula (XVId) and/or (XVIe) obtainable according to process J, either isolated or as a mixture, are reacted with derivatives (IIc), wherein G stands for halogen or hydrogen. If G stands for halogen, compounds (IIc) can first be transformed into an organometallic reagent, preferably an organomagnesium, organomanganese or organozinc reagent, optionally in presence of a Lewis acid, preferably a lanthanide halide such as cerium chloride or lanthanum chloride, which may be in complex with lithium chloride (Synlett 2009, 1433-1436, Angew. Chem. Int. Ed. 2006, 45, 497 500), or a titanium salt such as titanium(IV) chloride. This reaction is preferably run in an aprotic solvent such as diethyl ether, tetrahydrofuran or dichloromethane, preferably tetrahydrofuran or dichloromethane or in a mixture of these solvents. The reaction mixture is subsequently reacted with ketone (XVId) and/or (XVIe), either isolated or as a mixture, preferably under anhydrous conditions, to obtain compounds (Ia-OH) and/or (Ib-OH), either isolated or as a mixture (see e.g. WO-A 2008/064311).

In case G stands for hydrogen, compounds (IIc) can be reacted with an organolithium reagent such as methyllithium or n-butyllithium preferably under anhydrous conditions to obtain a lithiated species. Optionally, a base such as lithiumdiisopropylamide or lithium bis(trimethylsilyl)amide, can be used. The obtained intermediates are subsequently reacted with ketones (XVId) and/or (XVIe), either isolated or as a mixture, preferably under anhydrous conditions to obtain compounds of the general formula (Ia-OH) and/or (Ib-OH).

Preferably the reaction is performed in the presence of a solvent. As the solvent, all common solvents inert under the reaction conditions, such as for example ethers (such as e.g. THF, Et$_2$O, dioxane), toluene, alkanes or dichloromethane can be used and the reaction can be effected in mixtures of two or more of these solvents.

Process L (Scheme 12):

Scheme 12: Process L-Preparation of compounds (Ic-OH) and/or (Id-OH)

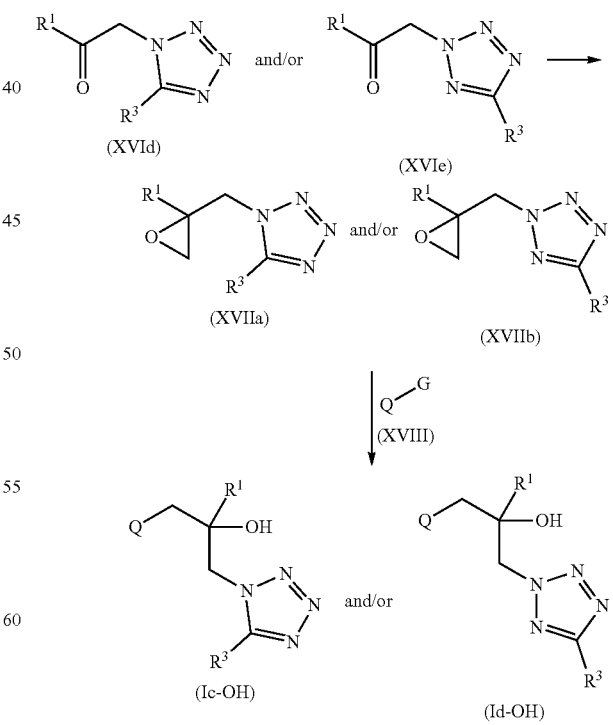

G = halogen or hydrogen

The compounds (XVId) and/or (XVIe) obtainable according to process J, either isolated or as a mixture, can be converted by means of methods described in the literature to the corresponding oxiranes (XVIIa) and/or (XVIIb) (see e.g. Gololobov, Nesmeyanov, Lysenko, Boldeskul, *Tetrahedron* 1987, 43(12), 2609-2651; H. Adolfsson "Product Class 2: Epoxides (Oxiranes). Category 5, Compounds with One Saturated Carbon Heteroatom Bond" in *Science of Synthesis*, Forsyth (Ed.), Thieme: Stuttgart, 2008, vol. 2008, Section 37.2, p. 227; WO-A 2008/078720). Compounds of the general formula (XVId) and/or (XVIe) are preferably reacted with trimethylsulfoxonium halides, trimethylsulfonium halides, trimethylsulfoxonium methylsulfates or trimethylsulfonium methylsulfates, preferably in the presence of a base, such as sodium hydroxide, to obtain compounds (XVIIa) and/or (XVIIb).

Compounds (XVIII) are either commercially available or producible by processes described in the literature (see, for example, "Comprehensive Heterocyclic Chemistry III", Pergamon Press, 2008, vol. 7, pages 101-169 and 217-308 & vol. 7, pages 1-331 and references cited therein; "Comprehensive Heterocyclic Chemistry II", Pergamon Press, 1996, vol. 5, pages 37-243 & vol. 6, pages 1-278 and references cited therein; "Comprehensive Heterocyclic Chemistry I", Pergamon Press, 1984, vol. 2, pages 395-510 & vol. 3, pages 1-197 and references cited therein; "Comprehensive Heterocyclic Chemistry III", Pergamon Press, 2008, vol. 3, pages 45-388 & vol. 4, pages 1-364 and references cited therein; "Comprehensive Heterocyclic Chemistry II", Pergamon Press, 1996, vol. 2, pages 39-257 & vol. 3, pages 1-220 and references cited therein; "Comprehensive Heterocyclic Chemistry I", Pergamon Press, 1984, vol. 4, pages 155-376 & vol. 5, pages 167-498 and references cited therein).

Subsequently, compounds (Ic-OH) and/or (Id-OH) can be obtained by the reaction of epoxide (XVIIa) and/or (XVIIb) with compound (XVIII). If G stands for halogen, preferably chloride or bromide, compounds (XVIII) are preferably first transformed into Grignard reagents by the reaction with magnesium or with transmetallation reagents such as isopropylmagnesium halides and subsequently reacted with epoxides (XVIIa) and/or (XVIIb), preferably under anhydrous conditions. As the solvent, all common solvents inert under the reaction conditions can be used and the reaction can be effected in mixtures of two or more of these solvents.

In an alternative route compounds (XVIII) (G=hydrogen or halogen) are directly reacted with compounds (XVIIa) and/or (XVIIb), preferably in the presence of a base. Compounds (XVIII) (G=hydrogen or halogen) are optionally reacted with a base upfront, e.g. n-butyllithium, lithium-diisopropylamide, lithium bis(trimethylsilyl)amide, methyl lithium, followed by compounds of the general structure (XVIIa) and/or (XVIIb), preferably under anhydrous conditions, to form the desired compounds (Ic-OH) and/or (Id-OH). As the solvent, all common solvents inert under the reaction conditions can be used and the reaction can be effected in mixtures of two or more of these solvents.

Process M (Scheme 13):

Scheme 13: Process M-Preparation of compounds (Ia-OH)

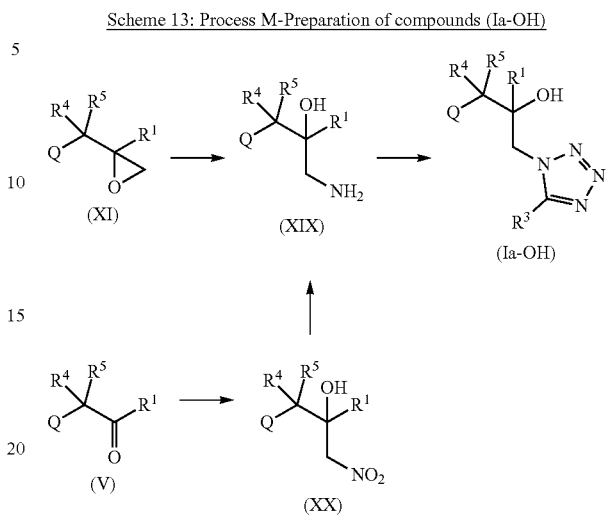

According to process M, α-aminoalcohols (XIX) can be converted into tetrazoles (Ia-OH) by reaction with either:
An acyl chloride or ester, in the presence of an activating reagent (such as e.g. phosphoryl trichloride), a suitable azide source (such as e.g. sodium azide or azidotrimethylsilane), in analogy to methods known in the literature (see e.g. *Eur. J. Org. Chem.* 2016, 2016(14), 2383-2387). As the solvent, all common solvents inert under the reaction conditions, such as for example nitriles (such as e.g. acetonitrile) can be used and the reaction can be effected in mixtures of two or more of these solvents.
In case $R^3$ stands for H: a trialkylorthoformate (e.g. trimethyl orthoformate or triethyl orthoformate) or formic acid or an ester thereof, in the presence of a suitable azide source, such as e.g. sodium azide or azidotrimethylsilane (see e.g. Benson, "Tetrazoles" in *Heterocyclic Compounds*, 1967, vol. 8, p. 1-104; Nishiyama, Oba, Watanabe, *Tetrahedron* 1987, 43(4), 693-700; Jin, Kamijo, Yamamoto, *Tetrahedron Lett.* 2004, 45(51), 9435-9437; WO-A 2015/143154; WO-A 2015/143166; WO-A 2015/143172; WO-A 2015/143184; WO-A 2017/049080). As the solvent, all common solvents inert under the reaction conditions, such as for example carboxylic acids (such as e.g. acetic acid) can be used and the reaction can be effected in mixtures of two or more of these solvents.

α-Aminoalcohols (XIX) can be obtained from aminolysis of epoxides (XI), e.g. by treatment with ammonia or alkali amides (such as e.g. lithium or sodium amide), or ammonium salts (such as e.g. ammonium chloride or ammonium acetate) in a suitable solvent. As the solvent, all common solvents inert under the reaction conditions, such as for example alcohols (such as e.g. methanol, ethanol) can be used and the reaction can be effected in mixtures of two or more of these solvents.

α-Aminoalcohols (XIX) can also be obtained by reduction of the corresponding nitro-derivatives (XX), e.g. by treatment with a metal (such as e.g. zinc, magnesium or iron) in the presence of a protic solvent or an acid (such as e.g. acetic acid or aqueous hydrochloric acid) in a suitable solvent. Alternatively, hydrogenation in the presence of a suitable catalyst can also effect this conversion. (see e.g. Burke, Danheiser, "Handbook of Reagents for Organic Synthesis, Oxidizing and Reducing Agents" 1999, Wiley;

Smith "March's Advanced Organic Chemistry, 6th Edition" John Wiley & Sons 2007; Hartman, Silloway, *Org. Synth.* 1945, 25, 5). As the solvent, all common solvents inert under the reaction conditions can be used and the reaction can be effected in mixtures of two or more of these solvents.

The nitro-derivatives (XX) can be conveniently accessed by addition of nitromethane or a synthetic equivalent to a ketone (V) in a Henry reaction (see e.g. Smith "March's Advanced Organic Chemistry, 6th Edition" John Wiley & Sons 2007; also WO-A 2015/143192 or WO-A 2017/049096). The reaction is preferably conducted in the presence of a suitable base (such as e.g. alkali carbonates, alkali phosphates, or organic amines including quinine derivatives such as 0-demethyl quinine). As the solvent, all common solvents inert under the reaction conditions can be used, preferably nitromethane, and the reaction can be effected in mixtures of two or more of these solvents.

Process N (Scheme 14):

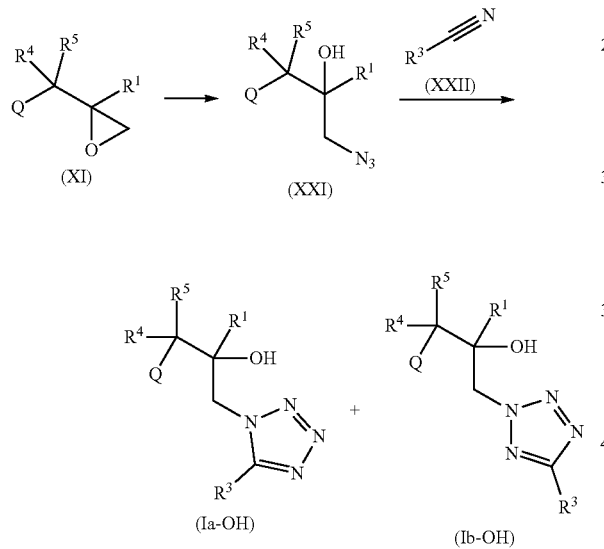

According to process N, α-hydroxyazides (XXI) can be converted into tetrazoles (Ia-OH) and/or (Ib-OH) by reaction with a nitrile (XXII) (see e.g. Benson, "Tetrazoles" in *Heterocyclic Compounds,* 1967, vol. 8, p. 1-104; WO-A 2015/143188). The nitrile (XXII) can be an organic nitrile (in case $R^3$ stands for an organic rest), or a source of cyanide or of cyanhydric acid, such as e.g. a combination of alkali cyanide, TMS-CN or tetraalkylammonium cyanide with a protic solvent of an acid (in case $R^3$ stands for a proton). As the solvent, all common solvents inert under the reaction conditions (such as e.g. DMF, dichloromethane, isopropanol) can be used and the reaction can be effected in mixtures of two or more of these solvents.

α-hydroxyazides (XXI) can be prepared by reaction of an epoxide (XI) with a suitable azide source, such as e.g. sodium azide or azidotrimethylsilane in a suitable solvent. As the solvent, all common solvents inert under the reaction conditions can be used, and the reaction can be effected in mixtures of two or more of these solvents.

Process O (Scheme 15):

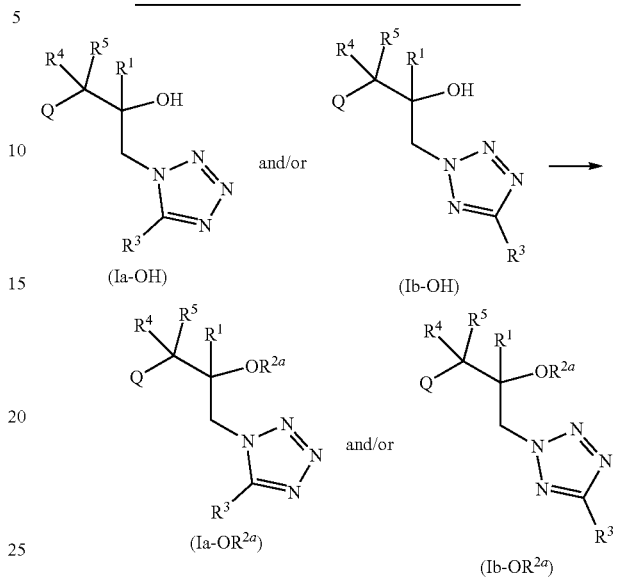

The compounds (Ia-OH) and/or (Ib-OH) obtainable according to processes H, I, K, M or N or (Ic-OH/Id-OH) obtainable according to process L can be converted in analogy to methods described in the literature to the corresponding compounds (Ia-OR$^{2a}$) and/or (Ib-OR$^2$a), wherein $R^{2a}$ is different from hydrogen (see e.g. DE-A 3202604, JP-A 02101067, EP-A 225 739, CN-A 101824002, FR-A 2802772; WO-A 2012/175119, Bioorganic & Medicinal Chemistry Letters, 2012, p. 7207-7213; Journal of the American Chemical Society, 2012, p. 19358-19361; Journal of Organic Chemistry, 2012, p. 9458-9472; Organic Letters, 2013, p. 554-557; Journal of the American Chemical Society, 2012, p. 15556). Compounds of the general structure (Ia-OH) and/or (Ia-OH) are preferably reacted with alkylhalides, dialkylsulfates, anhydrides, acid chlorides, phosphorylchloride, alkylisocyanate, carbamoyl chlorides, carbono chloridates or imidocarbonates, preferably in the presence of a base to obtain compounds (Ia-OR$^{2a}$) and/or (Ib-OR$^{2a}$), wherein $R^{2a}$ is different from hydrogen. Preferably the reaction is performed in the presence of a solvent. As the solvent, all common solvents inert under the reaction conditions, such as for example nitriles (such as e.g. acetonitrile, propionitrile), ketones (such as e.g. acetone) or amides (such as e.g. DMF, DMAc, NMP) can be used and the reaction can be effected in mixtures of two or more of these solvents.

Process P (Scheme 16):

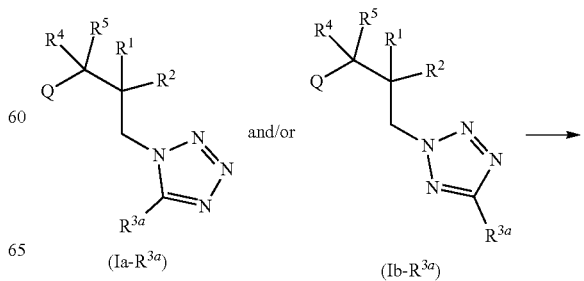

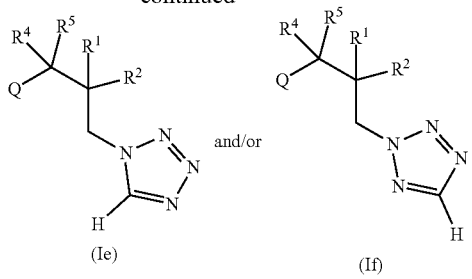

$R^{3a} = C_1-C_8$-acyl, $C_1-C_8$-alkoxycarbonyl, sulfonyl

The $R^{3a}$ group of the 5-substituted tetrazoles (Ia-$R^{3a}$) and/or (Ib-$R^{3a}$) can be cleaved to obtain the corresponding tetrazole derivatives (Ie) and/or (If).

This transformation can be effected:
In case $R^{3a}$ stands for an acyl or alkoxycarbonyl group: by treatment with a base or a nucleophile, such as e.g. sodium hydroxide in a suitable solvent. As the solvent, all common solvents inert under the reaction conditions can be used and the reaction can be effected in mixtures of two or more of these solvents.
In case $R^{3a}$ stands for a sulfonyl group (such as e.g. p-tolylsulfonyl): by treatment with a metal (such as e.g. zinc, magnesium or iron) in the presence of a protic solvent or an acid (such as e.g. acetic acid or aqueous hydrochloric acid) in a suitable solvent. As the solvent, all common solvents inert under the reaction conditions can be used and the reaction can be effected in mixtures of two or more of these solvents.

Examples of similar conversions can be found in WO-A 2015/143188.

Process Q (Scheme 17):

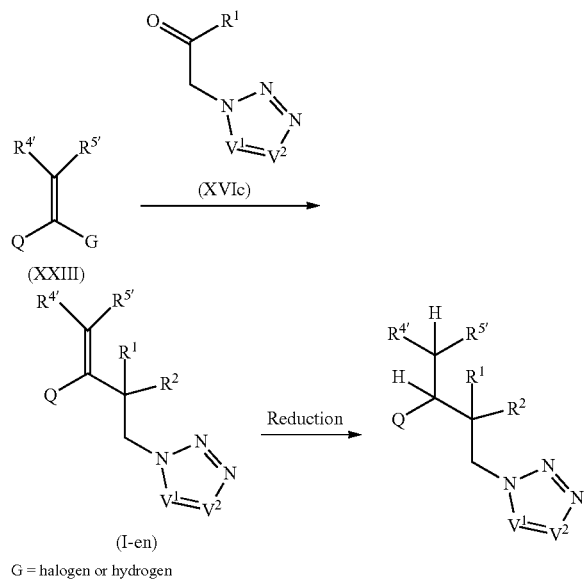

G = halogen or hydrogen

In a process according to Scheme 17, ketones of formula (XVIc), which can be obtained as described in this application (cf. process J), are reacted with derivatives (XXIII), wherein G stands for halogen.

Compounds (XXIII), wherein G stands for halogen, are either commercially available or can be prepared by literature-known methods, e.g. by dibromination of the corresponding styrenes followed by base-promoted elimination as described in US2009/30238 or by Piou & Rovis, J. Am. Chem. Soc. 2014, 136(32), 11292-11295. Those are first reacted either with metals (e.g. lithium, magnesium or zinc, in an appropriate form such as metallic powder or turnings) or with alkylmetal reagents (such as e.g. solutions of methyllithium, n-butyllithium, phenyllithium or isopropylmagnesium halide, with or without added salts such as lithium chloride) and subsequently reacted with ketones (XVIc), optionally in the presence of added salts such as lithium chloride preferably under anhydrous conditions to obtain compounds of the general formula (I-en). Depending on the carbonyl substrate, it can be advantageous to perform an intermediate transmetalation step with e.g. trialkoxyzirconium(IV) or trialkoxytitanium(IV) chloride [see e.g. Weidmann, Seebach, Angew. Chem. Int. Ed. 1983, 22(1), 31-45], cerium(III) trichloride [see e.g. Imamoto et al., J. Am. Chem. Soc. 1989, 111 (12), pp 4392-4398], lanthanum (III) trichloride [see e.g. Krasovskiy et al., Angew. Chem. Int. Ed. 2006, 45(3), 497-500], magnesium(II) dichloride [see e.g. Metzger et al., Angew. Chem. Int. Ed. 2010, 49(27), 4665-4668], zinc(II) dichloride [see e.g. Hatano et al., J. Org. Chem. 2010, 75(15), 5008-5016], or manganese(II) dichloride [see e.g. Quinio et al., Synlett 2015, 26(04), 514-518].

As the solvent, all common solvents inert under the reaction conditions, such as for example ethers (such as e.g. diethyl ether, tetrahydrofurane, 2-methyl tetrahydrofurane), dichloromethane, or mixtures thereof can be used and the reaction can be effected in mixtures of two or more of these solvents.

The reaction is preferably performed at temperatures between −78° C. and refluxing temperature of the solvent, more preferably between −50° C. and 25° C.

As described in Scheme 17, the compounds of the general formula (I-en), can optionally be reduced using methods known to a person skilled in the art for carbon-carbon double bond reduction, such as hydrogenation using a metal catalyst, including palladium, platinum, rhodium, iridium, cobalt metals or salts thereof, optionally under pressure of hydrogen, or using a transfer hydrogenation reagent, such as cyclohexadiene or formic acid or salts thereof, an alkyl silane such as triethylsilane or polymethylhydrosiloxane or similar, or by reaction with diimide (see: J. Org. Chem. 2009, 74, 3186-3188; Org. Lett. 2010, 12, 5418-5421).

As the solvent, all common solvents inert under the conditions of said reduction, such as for example alcohols (such as e.g. methanol, ethanol, isopropanol), ethers (such as e.g. diethyl ether, tetrahydrofuran, 2-methyl tetrahydrofuran), ethyl acetate, or mixtures thereof can be used and the reduction can be effected in mixtures of two or more of these solvents.

The reduction step is preferably performed at temperatures between 0° C. and refluxing temperature of the solvent, more preferably between 25° C. and 100° C.

General

The processes A to Q according to the invention for preparing compounds of formula (I) are optionally performed using one or more reaction auxiliaries.

Useful reaction auxiliaries are, as appropriate, inorganic or organic bases or acid acceptors. These preferably include alkali metal or alkaline earth metal acetates, amides, carbonates, hydrogencarbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, n-butyllithium, sec-butyllithium, tert-butyllithium, lithium diisopropylamide, lithium bis(trimethylsilyl)amide, sodium methoxide, ethoxide, n- or i-propoxide, n-, i-, s- or t-butoxide or potassium methoxide, ethoxide, n- or i-propoxide, n-, i-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]-octane (DABCO), 1,5-diazabicyclo[4.3.0]-non-5-ene (DBN) or 1,8-diazabicyclo[5.4.0]-undec-7-ene (DBU).

Useful reaction auxiliaries are, as appropriate, inorganic or organic acids. These preferably include inorganic acids, for example hydrogen fluoride, hydrogen chloride, hydrogen bromide and hydrogen iodide, sulphuric acid, phosphoric acid and nitric acid, and acidic salts such as $NaHSO_4$ and $KHSO_4$, or organic acids, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$ fatty acids, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulphonic acid, salicylic acid, p-aminosalicylic acid, 2-phenoxybenzoic acid, 2-acetoxybenzoic acid, etc.

The processes A to Q are optionally performed using one or more diluents. Useful diluents are virtually all inert organic solvents. Unless otherwise indicated for the above described processes, these preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, dibutyl ether and methyl tert-butyl ether, glycol dimethyl ether and diglycol dimethyl ether, tetrahydrofuran and dioxane, ketones such as acetone, methyl ethyl ketone, methyl isopropyl ketone and methyl isobutyl ketone, esters, such as methyl acetate and ethyl acetate, nitriles, for example acetonitrile and propionitrile, amides, for example dimethylformamide, dimethylacetamide and N-methylpyrrolidone, and also dimethyl sulphoxide, tetramethylenesulphone and hexamethylphosphoramide and DMPU.

In the processes outlined above, the reaction temperatures can be varied within a relatively wide range. In general, the temperatures employed are between −78° C. and 250° C., preferably temperatures between −78° C. and 150° C.

The reaction time varies as a function of the scale of the reaction and of the reaction temperature, but is generally between a few minutes and 48 hours.

The processes are generally performed under standard pressure. However, it is also possible to work under elevated or reduced pressure.

For performance of the processes, the starting materials required in each case are generally used in approximately equimolar amounts. However, it is also possible to use one of the components used in each case in a relatively large excess.

After a reaction has ended, the compounds are optionally separated from the reaction mixture by one of the customary separation techniques. If necessary, the compounds are purified by recrystallization or chromatography.

If appropriate, in the processes A to Q also salts and/or N-oxides of the starting compounds can be used.

The invention further relates to novel intermediates useful in the synthesis of compounds of formula (I), which form part of the invention.

Novel intermediates according to the present invention are ketones of formula (XVI)

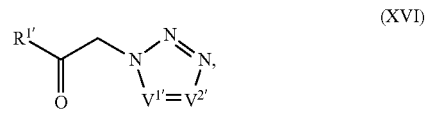

(XVI)

wherein $R^{1'}$ represents $C_3$-$C_7$-cycloalkyl, wherein the $C_3$-$C_7$-cycloalkyl is non-substituted or substituted by one or more group(s) selected from halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio; and one of $V^{1'}$ and $V^{2'}$ represents CH and the other one of $V^{1'}$ and $V^{2'}$ represents N;

and its salts and N-oxides.

Formula (XVI) encompasses ketones of formula (XVIa) and ketones of formula (XVIb)

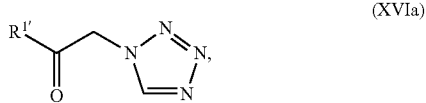

(XVIa)

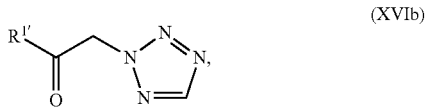

(XVIb)

wherein $R^{1'}$ is defined as in formula (XVI).

$R^{1'}$ preferably represents optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_6$-cycloalkyl.

$R^{1'}$ more preferably represents optionally halogen- or $C_1$-$C_4$-alkyl-substituted $C_3$-$C_6$-cycloalkyl.

$R^{1'}$ more preferably represents 1-halocyclopropyl or 1-($C_1$-$C_4$-alkyl)cyclopropyl.

$R^{1'}$ most preferably represents 1-chlorocyclopropyl, 1-fluorocyclopropyl or 1-methylcyclopropyl.

The ketones of formula (XVI) can be obtained as outlined above in the description of the synthesis of compounds of formula (I) as well as in analogy to the synthesis of ketones of formula (VIII) disclosed in DE 3328273 A1.

Further novel intermediates according to the present invention are epoxides of formula (XVII)

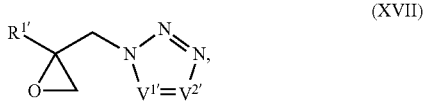

wherein
R$^{1'}$ represents C$_3$-C$_7$-cycloalkyl, wherein the C$_3$-C$_7$-cycloalkyl is non-substituted or substituted by one or more group(s) selected from halogen, cyano, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio and C$_1$-C$_4$-haloalkylthio; and
one of V$^{1'}$ and V$^{2'}$ represents CH and the other one of V$^{1'}$ and V$^{2'}$ represents N;
and its salts and N-oxides.
R$^{1'}$ preferably represents optionally halogen-, cyano-, C$_1$-C$_4$-alkyl-, C$_1$-C$_4$-haloalkyl-, C$_1$-C$_4$-alkoxy-, C$_1$-C$_4$-haloalkoxy-, C$_1$-C$_4$-alkylthio- or C$_1$-C$_4$-haloalkylthio-substituted C$_3$-C$_6$-cycloalkyl.
R$^{1'}$ more preferably represents optionally halogen- or C$_1$-C$_4$-alkyl-substituted C$_3$-C$_6$-cycloalkyl.
R$^{1'}$ more preferably represents 1-halocyclopropyl or 1-(C$_1$-C$_4$-alkyl)cyclopropyl.
R$^{1'}$ more preferably represents 1-chlorocyclopropyl, 1-fluorocyclopropyl or 1-methylcyclopropyl.
R$^{1'}$ most preferably represents 1-chlorocyclopropyl or 1-fluorocyclopropyl.

The epoxides of formula (XVII) can be obtained as outlined above in the description of the synthesis of compounds of formula (I).

Salts

Depending on the nature of the substituents, the compounds of the invention may be present in the form of the free compound and/or an agriculturally acceptable salt thereof. The term "agriculturally acceptable salt" refers to a salt of a compound of the invention with acids or bases which are agriculturally acceptable.

Depending on the nature of the substituents defined above, the compounds of formula (I) may have acidic or basic properties and can form salts, if appropriate also inner salts, or adducts with inorganic or organic acids or with bases or with metal ions. If the compounds carry amino, alkylamino or other groups which induce basic properties, these compounds can be reacted with acids to give salts, or they are directly obtained as salts in the synthesis. If the compound carries hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having (C$_1$-C$_4$)-alkyl groups, mono-, di- and trialkanolamines of (C$_1$-C$_4$)-alkanols, choline and also chlorocholine.

The salts obtainable in this manner also have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as NaHSO$_4$ and KHSO$_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, maleic acid, fumaric acid, tartaric acid, sorbic acid oxalic acid, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, 1,5-naphthalenedisulphonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals can be present in various valencies that they can assume.

The acid addition salts of the compounds of the formula (I) can be obtained in a simple manner by customary methods for forming salts, for example by dissolving a compound of the formula (I) in a suitable inert solvent and adding the acid, for example hydrochloric acid, and be isolated in a known manner, for example by filtration, and, if required, be purified by washing with an inert organic solvent.

Suitable anions of the salts are those which are preferably derived from the following acids: hydrohalic acids, such as, for example, hydrochloric acid and hydrobromic acid, furthermore phosphoric acid, nitric acid and sulphuric acid.

The metal salt complexes of compounds of the formula (I) can be obtained in a simple manner by customary processes, for example by dissolving the metal salt in alcohol, for example ethanol, and adding the solution to the compound of the formula (I). Metal salt complexes can be isolated in a known manner, for example by filtration, and, if required, be purified by recrystallization.

Salts of the intermediates can also be prepared according to the processes mentioned above for the salts of compounds of formula (I).

N-oxides of compounds of the formula (I) or intermediates thereof can be obtained in a simple manner by customary processes, for example by N-oxidation with hydrogen peroxide (H$_2$O$_2$), peracids, for example peroxy sulfuric acid or peroxy carboxylic acids, such as meta-chloroperoxybenzoic acid or peroxymonosulfuric acid (Caro's acid).

Crystalline Form

The compound of the invention may exist in multiple crystalline and/or amorphous forms. Crystalline forms include unsolvated crystalline forms, solvates and hydrates.

Compositions/Formulations

The present invention further relates to a composition for controlling harmful microorganisms, preferably for controlling phytopathogenic harmful fungi, comprising at least one compound of formula (I) and at least one carrier and/or surfactant. The compositions may be applied to the microorganisms and/or in their habitat.

A carrier is a solid or liquid, natural or synthetic, organic or inorganic substance that is generally inert. The carrier generally improves the application of the compounds, for instance, to plants, plants parts or seeds. Examples of suitable solid carriers include, but are not limited to, ammonium salts, natural rock flours, such as kaolins, clays, talc, chalk, quartz, attapulgite, montmorillonite and diatomaceous earth, and synthetic rock flours, such as finely divided silica, alumina and silicates. Examples of typically useful solid carriers for preparing granules include, but are not limited to crushed and fractionated natural rocks such as calcite, marble, pumice, sepiolite and dolomite, synthetic granules of inorganic and organic flours and granules of organic material such as paper, sawdust, coconut shells, maize cobs and tobacco stalks. Examples of suitable liquid carriers include, but are not limited to, water, organic solvents and combinations thereof. Examples of suitable solvents include polar and nonpolar organic chemical liquids, for example from the classes of aromatic and nonaromatic hydrocarbons (such as cyclohexane, paraffins, alkylbenzenes, xylene, toluene alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as butanol or glycol), ketones (such as acetone, methyl ethyl ketone, methyl isobutyl ketone or cyclohexanone), esters (including fats and oils) and (poly)ethers, unsubstituted and substituted amines, amides (such as dimethylformamide), lactams (such as N-alkylpyrrolidones) and lactones, sulfones and sulfoxides (such as dimethyl sulfoxide). The carrier may also be a liquefied gaseous extender, i.e. liquid which is gaseous at standard temperature and under standard pressure, for example aerosol propellants such as halohydrocarbons, butane, propane, nitrogen and carbon dioxide. The amount of carrier typically ranges from 1 to 99.99%, preferably from 5 to 99.9%, more preferably from 10 to 99.5%, and most preferably from 20 to 99% by weight of the composition.

The surfactant can be an ionic (cationic or anionic) or non-ionic surfactant, such as ionic or non-ionic emulsifier(s), foam former(s), dispersant(s), wetting agent(s) and any mixtures thereof. Examples of suitable surfactants include, but are not limited to, salts of polyacrylic acid, salts of lignosulfonic acid, salts of phenolsulfonic acid or naphthalenesulfonic acid, polycondensates of ethylene and/or propylene oxide with fatty alcohols, fatty acids or fatty amines (polyoxyethylene fatty acid esters, polyoxyethylene fatty alcohol ethers, for example alkylaryl polyglycol ethers), substituted phenols (preferably alkylphenols or arylphenols), salts of sulfosuccinic esters, taurine derivatives (preferably alkyl taurates), phosphoric esters of polyethoxylated alcohols or phenols, fatty esters of polyols and derivatives of compounds containing sulfates, sulfonates, phosphates (for example, alkylsulfonates, alkyl sulfates, arylsulfonates) and protein hydrolysates, lignosulfite waste liquors and methylcellulose. A surfactant is typically used when the compound of the invention and/or the carrier is insoluble in water and the application is made with water. Then, the amount of surfactants typically ranges from 5 to 40% by weight of the composition.

The composition may comprise at least one other suitable auxiliary.

Further examples of suitable auxiliaries include water repellents, siccatives, binders (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone and tylose), thickeners, stabilizers (e.g. cold stabilizers, preservatives, antioxidants, light stabilizers, or other agents which improve chemical and/or physical stability), dyes or pigments (such as inorganic pigments, e.g. iron oxide, titanium oxide and Prussian Blue; organic dyes, e.g. alizarin, azo and metal phthalocyanine dyes), antifoams (e.g. silicone antifoams and magnesium stearate), preservatives (e.g. dichlorophene and benzyl alcohol hemiformal), secondary thickeners (cellulose derivatives, acrylic acid derivatives, xanthan, modified clays and finely divided silica), stickers, gibberellins and processing auxiliaries, mineral and vegetable oils, perfumes, waxes, nutrients (including trace nutrients, such as salts of iron, manganese, boron, copper, cobalt, molybdenum and zinc), protective colloids, thixotropic substances, penetrants, sequestering agents and complex formers.

The choice of the auxiliaries is related to the intended mode of application of the compound of the invention and/or on the physical properties. Furthermore, the auxiliaries may be chosen to impart particular properties (technical, physical and/or biological properties) to the compositions or use forms prepared therefrom. The choice of auxiliaries may allow customizing the compositions to specific needs.

The composition of the invention may be in any customary form, such as solutions (e.g aqueous solutions), emulsions, wettable powders, water- and oil-based suspensions, powders, dusts, pastes, soluble powders, soluble granules, granules for broadcasting, suspoemulsion concentrates, natural or synthetic products impregnated with the compound of the invention, fertilizers and also microencapsulations in polymeric substances. The compound of the invention may be present in a suspended, emulsified or dissolved form.

The composition of the invention may be provided to the end user as ready-for-use formulation, i.e. the compositions may be directly applied to the plants or seeds by a suitable device, such as a spraying or dusting device. Alternatively, the compositions may be provided to the end user in the form of concentrates which have to be diluted, preferably with water, prior to use.

The composition of the invention can be prepared in conventional manners, for example by mixing the compound of the invention with one or more suitable auxiliaries, such as disclosed herein above.

The composition according to the invention contains generally from 0.01 to 99% by weight, from 0.05 to 98% by weight, preferably from 0.1 to 95% by weight, more preferably from 0.5 to 90% by weight, most preferably from 1 to 80% by weight of the compound of the invention. It is possible that a composition comprises two or more compounds of the invention. In such case the outlined ranges refer to the total amount of compounds of the present invention.

Mixtures/Combinations

The compound and the composition of the invention can be mixed with other active ingredients like fungicides, bactericides, acaricides, nematicides, insecticides, herbicides, fertilizers, growth regulators, safeners or semiochemicals. This may allow to broaden the activity spectrum or to prevent development of resistance. Examples of known fungicides, insecticides, acaricides, nematicides and bactericides are disclosed in the Pesticide Manual, 17th Edition.

Examples of especially preferred fungicides which could be mixed with the compound and the composition of the invention are:

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) Pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl]-1H-1,2,4-triazol-5-yl thiocyanate, (1.040) 1-{[rel(2R,3R)-3-(2-chlorophenyl)-2-(2,4-difluoro-phenyl)oxiran-2-yl]methyl]-1H-1,2,4-triazol-5-yl thiocyanate, (1.041) 1-{[rel(2R,3S)-3-(2-chlorophenyl)-2-(2,4-difluorophenyl)oxiran-2-yl]methyl]-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)propan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl]-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl]-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl]-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl]-1H-1,2,4-triazole, (1.061) 5-(allylsulfanyl)-1-{[rel(2R,3R)-3-(2-chlorophenyl)-2-(2,4-difluorophenyl)oxiran-2-yl]methyl]-1H-1,2,4-triazole, (1.062) 5-(allylsulfanyl)-1-{[rel(2R,3S)-3-(2-chlorophenyl)-2-(2,4-difluorophenyl)oxiran-2-yl]methyl]-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Mefentrifluconazole, (1.082) Ipfentrifluconazole.

2) Inhibitors of the respiratory chain at complex I or II, for example (2.001) benzovindiflupyr, (2.002) bixafen, (2.003) boscalid, (2.004) carboxin, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbo-thioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide 3) Inhibitors of the respiratory chain at complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy) methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl{5-[3-(2,4-dimethylphenyl)-1H-pyrazol-1-yl]-2-methylbenzyl}carbamate.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4- fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine 5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper(2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable to induce a host defense, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.001) propamocarb, (10.002) propamocarb hydrochloride, (10.003) tolclofos-methyl.

11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).

13) Inhibitors of the signal transduction, for example (13.001) fludioxonil, (13.002) iprodione, (13.003) procymidone, (13.004) proquinazid, (13.005) quinoxyfen, (13.006) vinclozolin.

14) Compounds capable to act as an uncoupler, for example (14.001) fluazinam, (14.002) meptyldinocap.

15) Further compounds, for example (15.001) Abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) Oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5 S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methane-sulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl{6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl{6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one.

All named mixing partners of the classes (1) to (15) as described here above can be present in the form of the free compound and/or, if their functional groups enable this, an agriculturally acceptable salt thereof.

The compound and the composition of the invention may also be combined with one or more biological control agents.

Examples of biological control agents which may be combined with the compound and the composition of the invention are:

(A) Antibacterial agents selected from the group of:

(A1) bacteria, such as (A1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (A1.2) *Bacillus amyloliquefaciens*, in particular strain D747 (available as Double Nickel™ from Certis, US, having accession number FERM BP-8234 and disclosed in U.S. Pat. No. 7,094,592); (A1.3) *Bacillus pumilus*, in particular strain BU F-33 (having NRRL Accession No. 50185); (A1.4) *Bacillus subtilis* var. *amyloliquefaciens* strain FZB24 (available as Taegro® from Novozymes, US); (A1.5) a *Paenibacillus* sp. strain having Accession No. NRRL B-50972 or Accession No. NRRL B-67129 and described in International Patent Publication No. WO 2016/154297; and (A2) fungi, such as (A2.1) *Aureobasidium pullulans*, in particular blastospores of strain DSM14940; (A2.2) *Aureobasidium pullulans* blastospores of strain DSM 14941; (A2.3) *Aureobasidium pullulans*, in particular mixtures of blastospores of strains DSM14940 and DSM14941;

(B) Fungicides selected from the group of:

(B1) bacteria, for example (B1.1) *Bacillus subtilis*, in particular strain QST713/AQ713 (available as SERENADE OPTI or SERENADE ASO from Bayer CropScience LP, US, having NRRL Accession No. B21661 and described in U.S. Pat. No. 6,060,051); (B1.2) *Bacillus pumilus*, in particular strain QST2808 (available as SONATA® from Bayer CropScience LP, US, having Accession No. NRRL B-30087 and described in U.S. Pat. No. 6,245,551); (B1.3) *Bacillus pumilus*, in particular strain GB34 (available as Yield Shield® from Bayer AG, DE); (B1.4) *Bacillus pumilus*, in particular strain BU F-33 (having NRRL Accession No. 50185); (B1.5) *Bacillus amyloliquefaciens*, in particular strain D747 (available as Double Nickel™ from Certis, US, having accession number FERM BP-8234 and disclosed in U.S. Pat. No. 7,094,592); (B1.6) *Bacillus subtilis* Y1336 (available as BIOBAC® WP from Bion-Tech, Taiwan, registered as a biological fungicide in Taiwan under Registration Nos. 4764, 5454, 5096 and 5277); (B1.7) *Bacillus amyloliquefaciens* strain MBI 600 (available as SUBTILEX from BASF SE); (B1.8) *Bacillus subtilis* strain GB03 (available as Kodiak® from Bayer AG, DE); (B1.9) *Bacillus subtilis* var. *amyloliquefaciens* strain FZB24 (available from Novozymes Biologicals Inc., Salem, Va. or Syngenta Crop Protection, LLC, Greensboro, N.C. as the fungicide TAEGRO® or TAEGRO® ECO (EPA Registration No. 70127-5); (B1.10) *Bacillus mycoides*, isolate J (available as BmJ TGAI or WG from Certis USA); (B1.11) *Bacillus licheniformis*, in particular strain SB3086 (available as EcoGuard™ Biofungicide and Green Releaf from Novozymes); (B1.12) a *Paenibacillus* sp. strain having Accession No. NRRL B-50972 or Accession No. NRRL B-67129 and described in International Patent Publication No. WO 2016/154297.

In some embodiments, the biological control agent is a *Bacillus subtilis* or *Bacillus amyloliquefaciens* strain that produces a fengycin or plipastatin-type compound, an iturin-type compound, and/or a surfactin-type compound. For background, see the following review article: Ongena, M., et al., "*Bacillus* Lipopeptides: Versatile Weapons for Plant Disease Biocontrol," Trends in Microbiology, Vol 16, No. 3, March 2008, pp. 115-125. *Bacillus* strains capable of producing lipopeptides include *Bacillus subtilis* QST713 (available as SERENADE OPTI or SERENADE ASO from Bayer CropScience LP, US, having NRRL Accession No. B21661 and described in U.S. Pat. No. 6,060,051), *Bacillus amyloliquefaciens* strain D747 (available as Double Nickel™ from Certis, US, having accession number FERM BP-8234 and disclosed in U.S. Pat. No. 7,094,592); *Bacillus subtilis* MBI600 (available as SUBTILEX® from Becker Underwood, US EPA Reg. No. 71840-8); *Bacillus subtilis* Y1336 (available as BIOBAC® WP from Bion-Tech, Taiwan, registered as a biological fungicide in Taiwan under Registration Nos. 4764, 5454, 5096 and 5277); *Bacillus amyloliquefaciens*, in particular strain FZB42 (available as RHIZOVITAL® from ABiTEP, DE); and *Bacillus subtilis* var. *amyloliquefaciens* FZB24 (available from Novozymes Biologicals Inc., Salem, Va. or Syngenta Crop Protection, LLC, Greensboro, N.C. as the fungicide TAEGRO® or TAEGRO® ECO (EPA Registration No. 70127-5); and (B2) fungi, for example: (B2.1) *Coniothyrium minitans*, in particular strain CON/M/91-8 (Accession No. DSM-9660; e.g. Contans® from Bayer); (B2.2) *Metschnikowia fructicola*, in particular strain NRRL Y-30752 (e.g. Shemer®); (B2.3) *Microsphaeropsis ochracea* (e.g. Microx® from Prophyta); (B2.5) *Trichoderma* spp., including *Trichoderma atroviride*, strain SCl described in International Application No. PCT/IT2008/000196); (B2.6) *Trichoderma harzianum rifai* strain KRL-AG2 (also known as strain T-22, /ATCC 208479, e.g. PLANTSHIELD T-22G, Rootshield®, and TurfShield from BioWorks, US); (B2.14) *Gliocladium roseum*, strain 321U from W.F. Stoneman Company LLC; (B2.35) *Talaromyces flavus*, strain V117b; (B2.36) *Trichoderma asperellum*, strain ICC 012 from Isagro; (B2.37) *Trichoderma asperellum*, strain SKT-1 (e.g. ECO-HOPE® from Kumiai Chemical Industry); (B2.38) *Trichoderma atroviride*, strain CNCM 1-1237 (e.g. Esquive® WP from Agrauxine, FR); (B2.39) *Trichoderma atroviride*, strain no. V08/002387; (B2.40) *Trichoderma atroviride*, strain NMI no. V08/002388; (B2.41) *Trichoderma atroviride*, strain NMI no. V08/002389; (B2.42) *Trichoderma atroviride*, strain NMI no. V08/002390; (B2.43) *Trichoderma atroviride*, strain LC52 (e.g. Tenet by Agrimm Technologies Limited); (B2.44) *Trichoderma atroviride*, strain ATCC 20476 (IMI 206040); (B2.45) *Trichoderma atroviride*, strain T11 (IMI352941/CECT20498); (B2.46) *Trichoderma hamatum*; (B2.47) *Trichoderma harzianum*; (B2.48) *Trichoderma harzianum rifai* T39 (e.g. Trichodex® from Makhteshim, US); (B2.49) *Trichoderma harzianum*, in particular, strain KD (e.g. Trichoplus from Biological Control Products, SA (acquired by Becker Underwood)); (B2.50) *Trichoderma harzianum*, strain ITEM 908 (e.g. Trianum-P from Koppert); (B2.51) *Trichoderma harzianum*, strain TH35 (e.g. Root-Pro by Mycontrol); (B2.52) *Trichoderma virens* (also known as *Gliocladium virens*), in particular strain GL-21 (e.g. SoilGard 12G by Certis, US); (B2.53) *Trichoderma viride*, strain TV1 (e.g. Trianum-P by Koppert); (B2.54) *Ampelomyces quisqualis*, in particular strain AQ 10 (e.g. AQ 10® by IntrachemBio Italia); (B2.56) *Aureobasidium pullulans*, in particular blastospores of strain DSM14940; (B2.57) *Aureobasidium pullulans*, in particular blastospores of strain DSM 14941; (B2.58) *Aureobasidium pullulans*, in particular mixtures of blastospores of strains DSM14940 and DSM 14941 (e.g. Botector® by bio-ferm, CH); (B2.64) *Cladosporium cladosporioides*, strain H39 (by Stichting Dienst Landbouwkundig Onderzoek); (B2.69) *Gliocladium catenulatum* (Synonym: *Clonostachys rosea f. catenulate*) strain J1446 (e.g. Prestop by AgBio Inc. and also e.g. Primastop® by Kemira Agro Oy); (B2.70) *Lecanicillium lecanii* (formerly known as *Verticillium lecanii*) conidia of strain KV01 (e.g. Vertalec® by Koppert/Arysta); (B2.71) *Penicillium vermiculatum*; (B2.72) *Pichia anomala*, strain WRL-076 (NRRL Y-30842); (B2.75) *Trichoderma atroviride*, strain SKT-1 (FERM P-16510); (B2.76) *Trichoderma atroviride*, strain SKT-2 (FERM P-16511); (B2.77) *Trichoderma atroviride*, strain SKT-3 (FERM P-17021); (B2.78) *Trichoderma gamsii* (formerly *T. viride*), strain ICC080 (IMI CC 392151 CABI, e.g. BioDerma by AGROBIOSOL DE MEXICO, S.A. DE C.V.); (B2.79) *Trichoderma harzianum*, strain DB 103 (e.g., T-Gro 7456 by Dagutat Biolab); (B2.80) *Trichoderma polysporum*, strain IMI 206039 (e.g. Binab TF WP by BINAB Bio-Innovation AB, Sweden); (B2.81) *Trichoderma stromaticum* (e.g. Tricovab by Ceplac, Brazil); (B2.83) *Ulocladium oudemansii*, in particular strain HRU3 (e.g. Botry-Zen® by Botry-Zen Ltd, NZ); (B2.84) *Verticillium albo-atrum* (formerly *V. dahliae*), strain WCS850 (CBS 276.92; e.g. Dutch Trig by Tree Care Innovations); (B2.86) *Verticillium chlamydosporium*; (B2.87) mixtures of *Trichoderma asperellum* strain ICC 012 and *Trichoderma gamsii* strain ICC 080 (product known as e.g. BIO-TAM™ from Bayer CropScience LP, US).

Further examples of biological control agents which may be combined with the compound and the composition of the invention are:

bacteria selected from the group consisting of *Bacillus cereus*, in particular *B. cereus* strain CNCM 1-1562 and *Bacillus firmus*, strain 1-1582 (Accession number CNCM I-1582), *Bacillus subtilis* strain OST 30002 (Accession No. NRRL B-50421), *Bacillus thuringiensis*, in particular *B. thuringiensis* subspecies *israelensis* (serotype H-14), strain AM65-52 (Accession No. ATCC 1276), *B. thuringiensis* subsp. *aizawai*, in particular strain ABTS-1857 (SD-1372), *B. thuringiensis* subsp. *kurstaki* strain HD-1, *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), and *Streptomyces galbus* strain AQ 6047 (Accession Number NRRL 30232); fungi and yeasts selected from the group consisting of *Beauveria bassiana*, in particular strain ATCC 74040, *Lecanicillium* spp., in particular strain HRO LEC 12, *Metarhizium anisopliae*, in particular strain F52 (DSM3884 or ATCC 90448), *Paecilomyces fumosoroseus* (now: *Isaria fumosorosea*), in particular strain IFPC 200613, or strain Apopka 97 (Accession No. ATCC 20874), and *Paecilomyces lilacinus*, in particular *P. lilacinus* strain 251 (AGAL 89/030550);

viruses selected from the group consisting of *Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, and *Spodoptera littoralis* (African cotton leafworm) NPV.

bacteria and fungi which can be added as 'inoculant' to plants or plant parts or plant organs and which, by virtue of their particular properties, promote plant growth and plant health. Examples are: *Agrobacterium* spp., *Azorhizobium caulinodans, Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum, Glomus* spp., *Zaccaria* spp., *Lactobacillus buchneri, Paraglomus* spp., *Pisolithus tinctorus, Pseudomonas* spp., *Rhizobium* spp., in particular *Rhizobium trifolii, Rhizopogon* spp., *Scleroderma* spp., *Suillus* spp., and *Streptomyces* spp.

plant extracts and products formed by microorganisms including proteins and secondary metabolites which can be used as biological control agents, such as *Allium sativum, Artemisia absinthium*, azadirachtin, Biokeeper WP, *Cassia nigricans, Celastrus angulatus, Chenopodium anthelminticum*, chitin, Armour-Zen, *Diyopteris filix-mas, Equisetum arvense*, Fortune Aza, Fungastop, Heads Up (*Chenopodium quinoa* saponin extract), *Pyrethrum/Pyrethrins, Quassia amara, Quercus, Quillaja*, Regalia, "Requiem™ Insecticide", rotenone, iyania/ryanodine, *Symphytum officinale, Tanacetum vulgare*, thymol, Triact 70, TriCon, *Tropaeulum majus, Urtica dioica*, Veratrin, *Viscum album, Brassicaceae* extract, in particular oilseed rape powder or mustard powder.

Examples of insecticides, acaricides and nematicides, respectively, which could be mixed with the compound and the composition of the invention, are:

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, such as, for example, cyclodiene-organochlorines, for example chlordane and endosulfan or phenylpyrazoles (fiproles), for example ethiprole and fipronil.

(3) Sodium channel modulators, such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinic acetylcholine receptor (nAChR) competitive modulators, such as, for example, neonicotinoids, e.g. acetamiprid, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as, for example, spinosyns, e.g. spinetoram and spinosad.

(6) Glutamate-gated chloride channel (GluCl) allosteric modulators, such as, for example, avermectins/milbemycins, for example abamectin, emamectin benzoate, lepimectin and milbemectin.

(7) Juvenile hormone mimics, such as, for example, juvenile hormone analogues, e.g. hydroprene, kinoprene and methoprene or fenoxycarb or pyriproxyfen.

(8) Miscellaneous non-specific (multi-site) inhibitors, such as, for example, alkyl halides, e.g. methyl bromide and other alkyl halides; or chloropicrine or sulphuryl fluoride or borax or tartar emetic or methyl isocyanate generators, e.g. diazomet and metam.

(9) Modulators of Chordotonal Organs, such as, for example pymetrozine or flonicamid.

(10) Mite growth inhibitors, such as, for example clofentezine, hexythiazox and diflovidazin or etoxazole.

(11) Microbial disruptors of the insect gut membrane, such as, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and B.t. plant proteins: Cry1Ab, Cry1Ac, Cry1Fa, Cry1A.105, Cry2Ab, Vip3A, mCry3A, Cry3Ab, Cry3Bb, Cry34Ab1/35Ab1.

(12) Inhibitors of mitochondrial ATP synthase, such as, ATP disruptors such as, for example, diafenthiuron or organotin compounds, for example azocyclotin, cyhexatin and fenbutatin oxide or propargite or tetradifon.

(13) Uncouplers of oxidative phosphorylation via disruption of the proton gradient, such as, for example, chlorfenapyr, DNOC and sulfluramid.

(14) Nicotinic acetylcholine receptor channel blockers, such as, for example, bensultap, cartap hydrochloride, thiocylam, and thiosultap-sodium.

(15) Inhibitors of chitin biosynthesis, type 0, such as, for example, bistrifluron, chlorfluazuron, diflubenzuron, flucycloxuron, flufenoxuron, hexaflumuron, lufenuron, novaluron, novifluron, teflubenzuron and triflumuron.

(16) Inhibitors of chitin biosynthesis, type 1, for example buprofezin.

(17) Moulting disruptor (in particular for Diptera, i.e. dipterans), such as, for example, cyromazine

(18) Ecdysone receptor agonists, such as, for example, chromafenozide, halofenozide, methoxyfenozide and tebufenozide.

(19) Octopamine receptor agonists, such as, for example, amitraz.

(20) Mitochondrial complex III electron transport inhibitors, such as, for example, hydramethylnone or acequinocyl or fluacrypyrim.

(21) Mitochondrial complex I electron transport inhibitors, such as, for example from the group of the METI acaricides, e.g. fenazaquin, fenpyroximate, pyrimidifen, pyridaben, tebufenpyrad and tolfenpyrad or rotenone (Derris).

(22) Voltage-dependent sodium channel blockers, such as, for example indoxacarb or metaflumizone.

(23) Inhibitors of acetyl CoA carboxylase, such as, for example, tetronic and tetramic acid derivatives, e.g. spirodiclofen, spiromesifen and spirotetramat.

(24) Mitochondrial complex IV electron transport inhibitors, such as, for example, phosphines, e.g. aluminium phosphide, calcium phosphide, phosphine and zinc phosphide or cyanides, e.g. calcium cyanide, potassium cyanide and sodium cyanide.

(25) Mitochondrial complex II electron transport inhibitors, such as, for example, beta-ketonitrile derivatives, e.g. cyenopyrafen and cyflumetofen and carboxanilides, such as, for example, pyflubumide.

(28) Ryanodine receptor modulators, such as, for example, diamides, e.g. chlorantraniliprole, cyantraniliprole and flubendiamide, further active compounds such as, for example, Afidopyropen, Afoxolaner, Azadirachtin, Benclothiaz, Benzoximate, Bifenazate, Broflanilide, Bromopropylate, Chinomethionat, Chloroprallethrin, Cryolite, Cyclaniliprole, Cycloxaprid, Cyhalodiamide, Dicloromezotiaz, Dicofol, epsilon-Metofluthrin, epsilon-Momfluthrin, Flometoquin, Fluazaindolizine, Fluensulfone, Flufenerim, Flufenoxystrobin, Flufiprole, Fluhexafon, Fluralaner, Fluxametamide, Fufenozide, Guadipyr, Heptafluthrin, Imidaclothiz, Iprodione, kappa-Bifenthrin, kappa-Tefluthrin, Lotilaner, Meperfluthrin, Paichongding, Pyridalyl, Pyrifluquinazon, Pyriminostrobin, Spirobudiclofen, Tetramethylfluthrin, Tetraniliprole, Tetrachlorantraniliprole, Tigolaner, Tioxazafen, Thiofluoximate, Triflumezopyrim and iodomethane; furthermore preparations based on *Bacillus firmus* (1-1582, BioNeem, Votivo), and also the following compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethyl carbonate (known from EP2647626) (CAS 1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoro-propan-2-one (known from WO2013/144213) (CAS 1461743-15-6) N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)-benzamide, 4-[5-(3,5-dichlorophenyl)-4,5-dihydro-5-(trifluoromethyl)-3-ioxazolyl]-2-methyl-N-(trans-1-oxido-3-thietanyl)-benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]-propanamide, (+)-N-[3-chloro-1-(3-pyridinyl)-1H-pyrazol-4-yl]-N-ethyl-3-[(3,3,3-trifluoropropyl)sulfinyl]-propanamide and (−)-N-[3-chloro-1-(3-pyridinyl)-1H-pyrazol-4-yl]-N-ethyl-3-[(3,3,3-trifluoropropyl) sulfinyl]-propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-

(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methyl amino)thioxomethyl]phenyl]-1-(3-chloro-2-pyridinyl)-1H-pyrazole-5-carboxamide, (Liudaibenjiaxuanan, known from CN 103109816 A) (CAS 1232543-85-9); N-[4-chloro-2-[[(1,1-dimethylethyl) amino]carbonyl]-6-methylphenyl]-1-(3-chloro-2-pyridinyl)-3-(fluoromethoxy)-1H-Pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)-pyrimidine (known from CN 101337940 A) (CAS 1108184-52-6); (2E)- and 2(Z)-2-[2-(4-cyanophenyl)-1-[3-(trifluoromethyl) phenyl]ethylidene]-N-[4-(difluoromethoxy)phenyl]-hydrazinecarboxamide (known from CN 101715774 A) (CAS 1232543-85-9); 3-(2,2-dichloroethenyl)-2,2-dimethyl-4-(1H-benzimidazol-2-yl) phenyl-cyclopropanecarboxylic acid ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]-indeno[1,2-e][1,3,4]oxadiazine-4a(3H)-carboxylic acid methyl ester (known from CN 102391261 A) (CAS 1370358-69-2); 6-deoxy-3-O-ethyl-2,4-di-O-methyl-, 1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethyl-phenoxy)-3-(6-trifluoromethyl-pyridazin-3-yl)-3-aza-bicyclo[3.2.1]octane (CAS 1253850-56-4), (8-anti)-8-(2-cyclopropylmethoxy-4-trifluoromethyl-phenoxy)-3-(6-trifluoromethyl-pyridazin-3-yl)-3-aza-bicyclo[3.2.1]octane (CAS 933798-27-7), (8-syn)-8-(2-cyclopropylmethoxy-4-trifluoromethyl-phenoxy)-3-(6-trifluoromethyl-pyridazin-3-yl)-3-aza-bicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]-propanamide (known from WO 2015/058021 A1, WO 2015/058028 A1) (CAS 1477919-27-9) and N-[4-(aminothioxomethyl)-2-methyl-6-[(methylamino) carbonyl]phenyl]-3-bromo-1-(3-chloro-2-pyridinyl)-1H-pyrazole-5-carboxamide (known from CN 103265527 A) (CAS 1452877-50-7), 5-(1,3-dioxan-2-yl)-4-[[4-(trifluoromethyl)phenyl]methoxy]-pyrimidine (known from WO 2013/115391 A1) (CAS 1449021-97-9), 3-(4-chloro-2,6-dimethylphenyl)-4-hydroxy-8-methoxy-1-methyl-1,8-diazaspiro[4.5]dec-3-en-2-one (known from WO 2010/066780 A1, WO 2011/151146 A1) (CAS 1229023-34-0), 3-(4-chloro-2,6-dimethylphenyl)-8-methoxy-1-methyl-1,8-diazaspiro[4.5]decane-2,4-dione (known from WO 2014/187846 A1) (CAS 1638765-58-8), 3-(4-chloro-2, 6-dimethylphenyl)-8-methoxy-1-methyl-2-oxo-1,8-diazaspiro[4.5]dec-3-en-4-yl-carbonic acid ethyl ester (known from WO 2010/066780 A1, WO 2011151146 A1) (CAS 1229023-00-0), N-[1-[(6-chloro-3-pyridinyl)methyl]-2(1H)-pyridinylidene]-2,2,2-trifluoro-acetamide (known from DE 3639877 A1, WO 2012029672 A1) (CAS 1363400-41-2), [N(E)]-N-[1-[(6-chloro-3-pyridinyl)methyl]-2(1H)-pyridinylidene]-2,2,2-trifluoro-acetamide, (known from WO 2016005276 A1) (CAS 1689566-03-7), [N(Z)]—N-[1-[(6-chloro-3-pyridinyl)methyl]-2(1H)-pyridinylidene]-2,2,2-trifluoro-acetamide, (CAS 1702305-40-5), 3-endo-3-[2-propoxy-4-(trifluoromethyl)phenoxy]-9-[[5-(trifluoromethyl)-2-pyridinyl]oxy]-9-azabicyclo[3.3.1] nonane (known from WO 2011/105506 A1, WO 2016/133011 A1) (CAS 1332838-17-1).

Examples of safeners which could be mixed with the compound and the composition of the invention are, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[methylcarbamoyl)amino]phenyl}-sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Examples of herbicides which could be mixed with the compound and the composition of the invention are:

Acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate, and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, -2-ethylhexyl, -isobutyl, -isooctyl, -isopropylammonium, -potassium, -triisopropanolammonium, and -trolamine, 2,4-DB, 2,4-DB-butyl, -dimethylammonium, -isooctyl, -potassium, and -sodium, daimuron (dymron), dalapon, dazomet, n-decanol, desmedipham, detosyl-pyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-9600, F-5231, i.e. N-{2-chloro-4-fluoro-5-[4-(3-fluoropropyl)-5-oxo-4,5-dihydro-1H-tetrazol-1-yl]phenyl}ethanesulfonamide, F-7967, i. e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyrethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glyphosate, glyphosate-ammonium, -isopropylammonium, -diammonium, -dimethylammonium, -potassium, -sodium, and -trimesium, H-9201, i.e. O-(2,4-dimethyl-6-nitrophenyl) O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl-(2,4-dichlorophenoxy) acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and -sodium, ipfencarbazone, iso-proturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium, and -sodium, MCPB, MCPB-methyl, -ethyl, and -sodium, mecoprop, mecoprop-sodium, and -butotyl, mecoprop-P, mecoprop-P-butotyl, -dimethylammonium, -2-ethylhexyl, and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-(3-chloro-4-isopropylphenyl)-2-methylpentan amide, NGGC-011, napropamide, NC-310, i.e. [5-(benzyloxy)-1-methyl-1H-pyrazol-4-yl](2,4-dichlorophenyl)-methanone, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxo-imidazolidine-4,5-dione, 2,3,6-TBA, TCA (trichloroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflu-sulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy]benzyl}aniline, and the following compounds:

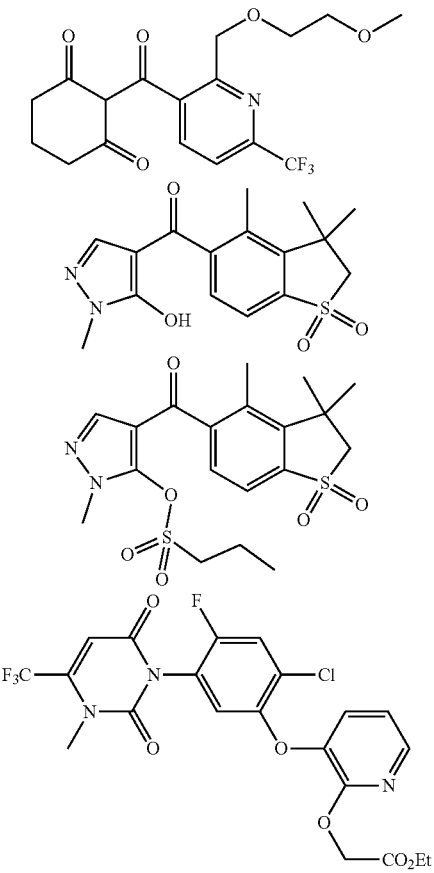

Examples for plant growth regulators are:
Acibenzolar, acibenzolar-S-methyl, 5-aminolevulinic acid, ancymidol, 6-benzylaminopurine, Brassinolid, catechine, chlormequat chloride, cloprop, cyclanilide, 3-(cycloprop-1-enyl) propionic acid, daminozide, dazomet, n-decanol, dikegulac, dikegulac-sodium, endothal, endothal-dipotassium, -disodium, and -mono(N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, maleic hydrazide, mepiquat chloride, 1-methylcyclopropene, methyl jasmonate, 2-(1-naphthyl)acetamide, 1-naphthylacetic acid, 2-naphthyloxyacetic acid, nitrophenolate-mixture, paclobutrazol, N-(2-phenylethyl)-beta-alanine, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Methods and Uses

The compounds and compositions of the invention have potent microbicidal activity and/or plant defense modulating potential. They can be used for controlling unwanted microorganisms, such as unwanted fungi and bacteria. They can be particularly useful in crop protection (they control microorganisms that cause plants diseases) or for protecting materials (e.g. industrial materials, timber, storage goods) as described in more details herein below. More specifically, the compounds and compositions of the invention can be used to protect seeds, germinating seeds, emerged seedlings, plants, plant parts, fruits, harvest goods and/or the soil in which the plants grow from unwanted microorganisms.

Hence, the invention further relates to a method for controlling harmful microorganisms, preferably phytopathogenic harmful fungi, in crop protection and in the protection of materials, wherein at least one compound of formula (I) or a composition comprising such compound is applied to the harmful microorganisms and/or their habitat.

The invention further relates to the use of at least one compound of formula (I) or a composition comprising such compound for control of harmful microorganisms, preferably phytopathogenic harmful fungi, in crop protection and in the protection of materials.

The invention also relates to the use of at least one compound of formula (I) or a composition comprising such compound for treatment of a transgenic plant or for treatment of seed, preferably seed of a transgenic plant.

Control or controlling as used herein encompasses protective, curative and eradicative treatment of unwanted microorganisms. Unwanted microorganisms may be pathogenic bacteria, pathogenic virus, pathogenic oomycetes or pathogenic fungi, more specifically phytopathogenic bacteria, phytopathogenic virus, phytopathogenic oomycetes or phytopathogenic fungi. As detailed herein below, these phytopathogenic microorganisms are the causal agents of a broad spectrum of plants diseases.

More specifically, the compound and the composition of the invention can be used as fungicides. For the purpose of the specification, the term "fungicide" refers to a compound or composition that can be used in crop protection for the control of unwanted fungi, such as Plasmodiophoromycetes, Chytridiomycetes, Zygomycetes, Ascomycetes, Basidiomycetes and Deuteromycetes and/or for the control of Oomycetes.

The compound and the composition of the invention may also be used as antibacterial agent. In particular, they may be used in crop protection, for example for the control of unwanted bacteria, such as Pseudomonadaceae, Rhizobiaceae, Xanthomonadaceae, Enterobacteriaceae, Corynebacteriaceae and Streptomycetaceae.

The compound and the composition of the invention may also be used as antiviral agent in crop protection. For example the compound and the composition of the invention may have effects on diseases from plant viruses, such as the tobacco mosaic virus (TMV), tobacco rattle virus, tobacco stunt virus (TStuV), tobacco leaf curl virus (VLCV), tobacco nervilia mosaic virus (TVBMV), tobacco necrotic dwarf virus (TNDV), tobacco streak virus (TSV), potato virus X (PVX), potato viruses Y, S, M, and A, potato acuba mosaic virus (PAMV), potato mop-top virus (PMTV), potato leaf-roll virus (PLRV), alfalfa mosaic virus (AMV), cucumber mosaic virus (CMV), cucumber green mottlemosaic virus (CGMMV), cucumber yellows virus (CuYV), watermelon mosaic virus (WMV), tomato spotted wilt virus (TSWV), tomato ringspot virus (TomRSV), sugarcane mosaic virus (SCMV), rice drawf virus, rice stripe virus, rice black-streaked drawf virus, strawberry mottle virus (SMoV), strawberry vein banding virus (SVBV), strawberry mild yellow edge virus (SMYEV), strawberry crinkle virus (SCrV), broad beanwilt virus (BBWV), and melon necrotic spot virus (MNSV).

The present invention also relates to a method for controlling unwanted microorganisms, such as unwanted fungi, oomycetes and bacteria, comprising the step of applying at least one compound of the invention or at least one composition of the invention to the microorganisms and/or their habitat (to the plants, plant parts, seeds, fruits or to the soil in which the plants grow).

Typically, when the compound and the composition of the invention are used in curative or protective methods for controlling phytopathogenic fungi and/or phytopathogenic oomycetes, an effective and plant-compatible amount thereof is applied to the plants, plant parts, fruits, seeds or to the soil or substrates in which the plants grow. Suitable substrates that may be used for cultivating plants include inorganic based substrates, such as mineral wool, in particular stone wool, perlite, sand or gravel; organic substrates, such as peat, pine bark or sawdust; and petroleum based substrates such as polymeric foams or plastic beads. Effective and plant-compatible amount means an amount that is sufficient to control or destroy the fungi present or liable to appear on the cropland and that does not entail any appreciable symptom of phytotoxicity for said crops. Such an amount can vary within a wide range depending on the fungus to be controlled, the type of crop, the crop growth stage, the climatic conditions and the respective compound or composition of the invention used. This amount can be determined by systematic field trials that are within the capabilities of a person skilled in the art.

Plants and Plant Parts

The compound and the composition of the invention may be applied to any plants or plant parts.

Plants mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the genetically modified plants (GMO or transgenic plants) and the plant cultivars which are protectable and non-protectable by plant breeders' rights.

Genetically Modified Plants (GMO)

Genetically modified plants (GMO or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome. This gene gives the transformed plant new or improved agronomic or other properties by expressing a protein or polypeptide of interest or by downregulating or silencing other gene(s) which are present in the plant (using for example, antisense technology, cosuppression technology, RNA interference-RNAi-technology or microRNA-miRNA-technology). A heterologous gene that is located in the genome is also called a transgene. A transgene that is defined by its particular location in the plant genome is called a transformation or transgenic event.

Plant cultivars are understood to mean plants which have new properties ("traits") and have been obtained by conventional breeding, by mutagenesis or by recombinant DNA techniques. They can be cultivars, varieties, bio- or genotypes.

Plant parts are understood to mean all parts and organs of plants above and below the ground, such as shoots, leaves, needles, stalks, stems, flowers, fruit bodies, fruits, seeds, roots, tubers and rhizomes. The plant parts also include harvested material and vegetative and generative propagation material, for example cuttings, tubers, rhizomes, slips and seeds.

Plants which may be treated in accordance with the methods of the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

Plants and plant cultivars which may be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may be treated by the above disclosed methods include those plants characterized by enhanced yield characteristics. Increased yield in said plants may be the result of, for example, improved plant physiology, growth and development, such as water use efficiency, water retention efficiency, improved nitrogen use, enhanced carbon assimilation, improved photosynthesis, increased germination efficiency and accelerated maturation. Yield may furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants and plant cultivars which may be treated by the above disclosed methods include plants and plant cultivars which are hybrid plants that already express the characteristic of heterosis or hybrid vigor which results in generally higher yield, vigor, health and resistance towards biotic and abiotic stresses.

Plants and plant cultivars (obtained by plant biotechnology methods such as genetic engineering) which may be treated by the above disclosed methods include plants and plant cultivars which are herbicide-tolerant plants, i.e. plants made tolerant to one or more given herbicides. Such plants can be obtained either by genetic transformation, or by selection of plants containing a mutation imparting such herbicide tolerance.

Plants and plant cultivars (obtained by plant biotechnology methods such as genetic engineering) which may be treated by the above disclosed methods include plants and plant cultivars which are insect-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which may be treated by the above disclosed methods include plants and plant cultivars which are disease-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which may be treated by the above disclosed methods include plants and plant cultivars which are tolerant to abiotic stresses. Such plants can be obtained by genetic transformation, or by selection of plants containing a mutation imparting such stress resistance.

Plants and plant cultivars (obtained by plant biotechnology methods such as genetic engineering) which may be treated by the above disclosed methods include plants and plant cultivars which show altered quantity, quality and/or storage-stability of the harvested product and/or altered properties of specific ingredients of the harvested product.

Plants and plant cultivars (obtained by plant biotechnology methods such as genetic engineering) which may be treated by the above disclosed methods include plants and plant cultivars, such as cotton plants, with altered fiber characteristics. Such plants can be obtained by genetic transformation, or by selection of plants contain a mutation imparting such altered fiber characteristics.

Plants and plant cultivars (obtained by plant biotechnology methods such as genetic engineering) which may be treated by the above disclosed methods include plants and plant cultivars, such as oilseed rape or related Brassica plants, with altered oil profile characteristics. Such plants can be obtained by genetic transformation, or by selection of plants contain a mutation imparting such altered oil profile characteristics.

Plants and plant cultivars (obtained by plant biotechnology methods such as genetic engineering) which may be treated by the above disclosed methods include plants and plant cultivars, such as oilseed rape or related Brassica plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants and plant cultivars (obtained by plant biotechnology methods such as genetic engineering) which may be treated by the above disclosed methods include plants and plant cultivars, such as Tobacco plants, with altered post-translational protein modification patterns.

Pathogens

Non-limiting examples of pathogens of fungal diseases which may be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* or *Phakopsora meibomiae*; *Puccinia* species, for example *Puccinia recondita, Puccinia graminis* oder *Puccinia striiformis*; *Uromyces* species, for example *Uromyces appendiculatus*;

diseases caused by pathogens from the group of the Oomycetes, for example *Albugo* species, for example *Albugo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidial form: *Drechslera*, syn: *Helminthosporium*) or *Cochliobolus miyabeanus*; *Colletotrichum* species, for example *Colletotrichum lindemuthanium*; *Corynespora* species, for example *Corynespora cassiicola*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola, Mycosphaerella arachidicola* or *Mycosphaerella fijiensis*; *Phaeosphaeria* species, for example *Phaeosphaeria nodorum*; *Pyrenophora* species, for example *Pyrenophora teres* or *Pyrenophora tritici repentis*; *Ramularia* species, for example *Ramularia collo-cygni* or *Ramularia areola*; *Rhynchosporium* species, for example *Rhynchosporium secalis*; *Septoria* species, for example *Septoria apii* or *Septoria lycopersici*; *Stagonospora* species, for example *Stagonospora nodorum*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Plasmodiophora* species, for example *Plasmodiophora brassicae*; *Rhizoctonia* species, for example *Rhizoctonia solani*; *Sarocladium* species, for example *Sarocladium oryzae*; *Sclerotium* species, for example *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Stagnospora* species, for example *Stagnospora nodorum*;

diseases caused by smut fungi, for example *Sphacelotheca* species, for example *Sphacelotheca reiliana*; *Tilletia* species, for example *Tilletia caries* or *Tilletia controversa*; *Urocystis* species, for example *Urocystis occulta*; *Ustilago* species, for example *Ustilago nuda*;

fruit rot caused, for example, by *Aspergillus* species, for example *Aspergillus flavus*; *Botrytis* species, for example *Botrytis cinerea*; *Monilinia* species, for example *Monilinia laxa*; *Penicillium* species, for example *Penicillium expansum* or *Penicillium purpurogenum*; *Rhizopus* species, for example *Rhizopus stolonifer*; *Sclerotinia* species, for example *Sclerotinia sclerotiorum*; *Verticilium* species, for example *Verticilium alboatrum*;

seed- and soil-borne rot and wilt diseases, and also diseases of seedlings, caused, for example, by *Alternaria* species, for example *Alternaria brassicicola*; *Aphanomyces* species, for example *Aphanomyces euteiches*; *Ascochyta* species, for example *Ascochyta lentis*; *Aspergillus* species, for example *Aspergillus flavus*; *Cladosporium* species, for example *Cladosporium herbarum*; *Cochliobolus* species, for example *Cochliobolus sativus* (conidial form: *Drechslera, Bipolaris* Syn: *Helminthosporium*); *Colletotrichum* species, for example *Colletotrichum coccodes*; *Fusarium* species, for example *Fusarium culmorum*; *Gibberella* species, for example *Gibberella zeae*; *Macrophomina* species, for example *Macrophomina phaseolina*; *Microdochium* species, for example *Microdochium nivale*; *Monographella* species, for example *Monographella nivalis*; *Penicillium* species, for example *Penicillium expansum*; *Phoma* species, for example *Phoma lingam*; *Phomopsis* species, for example *Phomopsis sojae*; *Phytophthora* species, for example *Phytophthora cactorum*; *Pyrenophora* species, for example *Pyrenophora graminea*; *Pyricularia* species, for example *Pyricularia oryzae*; *Pythium* species, for example *Pythium ultimum*; *Rhizoctonia* species, for example *Rhizoctonia solani*; *Rhizopus* species, for example *Rhizopus oryzae*; *Sclerotium* species, for example *Sclerotium rolfsii*; *Septoria* species, for example *Septoria nodorum*; *Typhula* species, for example *Typhula incarnata*; *Verticillium* species, for example *Verticillium dahliae*;

cancers, galls and witches' broom caused, for example, by *Nectria* species, for example *Nectria galligena*;

wilt diseases caused, for example, by *Verticillium* species, for example *Verticillium longisporum; Fusarium* species, for example *Fusarium oxysporum;* deformations of leaves, flowers and fruits caused, for example, by *Exobasidium* species, for example *Exobasidium vexans; Taphrina* species, for example *Taphrina deformans;* degenerative diseases in woody plants, caused, for example, by *Esca* species, for example *Phaeomoniella chlamydospora, Phaeoacremonium aleophilum* or *Fomitiporia mediterranea; Ganoderma* species, for example *Ganoderma boninense;* diseases of plant tubers caused, for example, by *Rhizoctonia* species, for example *Rhizoctonia solani; Helminthosporium* species, for example *Helminthosporium solani;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora; Liberibacter* species, for example *Liberibacter asiaticus; Xyella* species, for example *Xylella fastidiosa; Ralstonia* species, for example *Ralstonia solanacearum; Dickeya* species, for example *Dickeya solani; Clavibacter* species, for example *Clavibacter michiganensis; Streptomyces* species, for example *Streptomyces scabies.* diseases of soya beans:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), sudden death syndrome (*Fusarium virgulifomie*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megaspemia*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Mycotoxins

In addition, the compound and the composition of the invention may reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. clavifomie, P. roqueforti, Claviceps* spec., such as *C. purpurea, C. fusifomis, C. paspali, C. africana, Stachybotrys* spec. and others.

Material Protection

The compound and the composition of the invention may also be used in the protection of materials, especially for the protection of industrial materials against attack and destruction by phytopathogenic fungi.

In addition, the compound and the composition of the invention may be used as antifouling compositions, alone or in combinations with other active ingredients.

Industrial materials in the present context are understood to mean inanimate materials which have been prepared for use in industry. For example, industrial materials which are to be protected from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compound and the composition of the invention may prevent adverse effects, such as rotting, decay, discoloration, decoloration or formation of mould.

In the case of treatment of wood the compound and the composition of the invention may also be used against fungal diseases liable to grow on or inside timber.

Timber means all types of species of wood, and all types of working of this wood intended for construction, for example solid wood, high-density wood, laminated wood, and plywood. In addition, the compound and the composition of the invention may be used to protect objects which come into contact with saltwater or brackish water, especially hulls, screens, nets, buildings, moorings and signalling systems, from fouling.

The compound and the composition of the invention may also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, may be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The compound and the composition of the invention may prevent adverse effects, such as rotting, decay, discoloration, decoloration or formation of mould.

Microorganisms capable of degrading or altering industrial materials include, for example, bacteria, fungi, yeasts, algae and slime organisms. The compound and the composition of the invention preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

Seed Treatment

The compound and the composition of the invention may also be used to protect seeds from unwanted microorganisms, such as phytopathogenic microorganisms, for instance phytopathogenic fungi or phytopathogenic oomycetes. The term seed(s) as used herein include dormant seeds, primed seeds, pregerminated seeds and seeds with emerged roots and leaves.

Thus, the present invention also relates to a method for protecting seeds from unwanted microorganisms which comprises the step of treating the seeds with the compound or the composition of the invention.

The treatment of seeds with the compound or the composition of the invention protects the seeds from phytopathogenic microorganisms, but also protects the germinating seeds, the emerging seedlings and the plants after emergence from the treated seeds. Therefore, the present invention also relates to a method for protecting seeds, germinating seeds and emerging seedlings.

The seeds treatment may be performed prior to sowing, at the time of sowing or shortly thereafter.

When the seeds treatment is performed prior to sowing (e.g. so-called on-seed applications), the seeds treatment may be performed as follows: the seeds may be placed into a mixer with a desired amount of the compound or the composition of the invention, the seeds and the compound or the composition of the invention are mixed until an homogeneous distribution on seeds is achieved. If appropriate, the seeds may then be dried.

The invention also relates to seeds coated with the compound or the composition of the invention.

Preferably, the seeds are treated in a state in which it is sufficiently stable for no damage to occur in the course of treatment. In general, seeds can be treated at any time between harvest and shortly after sowing. It is customary to use seeds which have been separated from the plant and freed from cobs, shells, stalks, coats, hairs or the flesh of the fruits. For example, it is possible to use seeds which have been harvested, cleaned and dried down to a moisture content of less than 15% by weight. Alternatively, it is also possible to use seeds which, after drying, for example, have been treated with water and then dried again, or seeds just after priming, or seeds stored in primed conditions or pre-germinated seeds, or seeds sown on nursery trays, tapes or paper.

The amount of the compound or the composition of the invention applied to the seeds is typically such that the germination of the seed is not impaired, or that the resulting plant is not damaged. This must be ensured particularly in case the compound of the invention would exhibit phytotoxic effects at certain application rates. The intrinsic phenotypes of transgenic plants should also be taken into consideration when determining the amount of the compound of the invention to be applied to the seed in order to achieve optimum seed and germinating plant protection with a minimum amount of compound being employed.

The compound of the invention can be applied as such, directly to the seeds, i.e. without the use of any other components and without having been diluted. Also the composition of the invention can be applied to the seeds.

The compound and the composition of the invention are suitable for protecting seeds of any plant variety. Preferred seeds are that of cereals (such as wheat, barley, rye, millet, triticale, and oats), oilseed rape, maize, cotton, soybean, rice, potatoes, sunflower, beans, coffee, peas, beet (e.g. sugar beet and fodder beet), peanut, vegetables (such as tomato, cucumber, onions and lettuce), lawns and ornamental plants. More preferred are seeds of wheat, soybean, oilseed rape, maize and rice.

The compound and the composition of the invention may be used for treating transgenic seeds, in particular seeds of plants capable of expressing a polypeptide or protein which acts against pests, herbicidal damage or abiotic stress, thereby increasing the protective effect. Seeds of plants capable of expressing a polypeptide or protein which acts against pests, herbicidal damage or abiotic stress may contain at least one heterologous gene which allows the expression of said polypeptide or protein. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originate from *Bacillus* sp., in which case the gene product is effective against the European corn borer and/or the Western corn rootworm. Particularly preferably, the heterologous genes originate from *Bacillus thuringiensis*.

Antimycotic Effects

The compound and the composition of the invention may also have very good antimycotic effects. They have a very broad antimycotic activity spectrum, especially against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The enumeration of these fungi by no means constitutes a restriction of the mycotic spectrum covered, and is merely of illustrative character.

The compound and the composition of the invention may also be used to control important fungal pathogens in fish and crustacea farming, e.g. saprolegnia diclina in trouts, saprolegnia parasitica in crayfish.

The compound and the composition of the invention may therefore be used both in medical and in non-medical applications.

Plant Growth Regulation

The compound and the composition of the invention may, at particular concentrations or application rates, also be used as herbicides, safeners, growth regulators or agents to improve plant properties, or as microbicides, for example as bactericides, viricides (including compositions against viroids) or as compositions against MLO (Mycoplasma-like organisms) and RLO (Rickettsia-like organisms).

The compound and the composition of the invention may intervene in physiological processes of plants and may therefore also be used as plant growth regulators. Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Growth regulating effects, comprise earlier germination, better emergence, more developed root system and/or improved root growth, increased ability of tittering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased or improved yield is referring to total biomass per hectare, yield per hectare, kernel/fruit weight, seed size and/or hectolitre weight as well as to improved product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaptation to cooking and frying;

improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

decreased undesired ingredients such as e.g. less mycotoxines, less aflatoxins, geosmin level, phenolic aromas, lacchase, polyphenol oxidases and peroxidases, nitrate content etc.

Plant growth-regulating compounds can be used, for example, to slow down the vegetative growth of the plants. Such growth depression is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, vegetative growth depression allows denser planting, and it is thus possible to achieve higher yields based on the soil surface. Another advantage of the smaller plants obtained in this way is that the crop is easier to cultivate and harvest.

Reduction of the vegetative plant growth may also lead to increased or improved yields because the nutrients and assimilates are of more benefit to flower and fruit formation than to the vegetative parts of the plants.

Alternatively, growth regulators can also be used to promote vegetative growth. This is of great benefit when harvesting the vegetative plant parts. However, promoting vegetative growth may also promote generative growth in that more assimilates are formed, resulting in more or larger fruits.

Furthermore, beneficial effects on growth or yield can be achieved through improved nutrient use efficiency, especially nitrogen (N)-use efficiency, phosphorous (P)-use efficiency, water use efficiency, improved transpiration, respiration and/or $CO_2$ assimilation rate, better nodulation, improved Ca-metabolism etc.

Likewise, growth regulators can be used to alter the composition of the plants, which in turn may result in an improvement in quality of the harvested products. Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Furthermore, growth regulators can modulate plant senescence, which may result in prolonged green leaf area duration, a longer grain filling phase, improved yield quality, etc.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"). In addition it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to synchronize maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Plant Defense Modulators

The compound and the composition of the invention may also exhibit a potent strengthening effect in plants. Accordingly, they may be used for mobilizing the defenses of the plant against attack by undesirable microorganisms.

Plant-strengthening (resistance-inducing) substances in the present context are substances capable of stimulating the defense system of plants in such a way that the treated plants, when subsequently inoculated with undesirable microorganisms, develop a high degree of resistance to these microorganisms.

Further, in context with the present invention plant physiology effects comprise the following:

Abiotic stress tolerance, comprising tolerance to high or low temperatures, drought tolerance and recovery after drought stress, water use efficiency (correlating to reduced water consumption), flood tolerance, ozone stress and UV tolerance, tolerance towards chemicals like heavy metals, salts, pesticides etc.

Biotic stress tolerance, comprising increased fungal resistance and increased resistance against nematodes, viruses and bacteria. In context with the present invention, biotic stress tolerance preferably comprises increased fungal resistance and increased resistance against nematodes and bacteria Increased plant vigor, comprising plant health/plant quality and seed vigor, reduced stand failure, improved appearance, increased recovery after periods of stress, improved pigmentation (e.g. chlorophyll content, stay-green effects, etc.) and improved photosynthetic efficiency.

Application

The compounds of the invention can be applied as such, or for example in the form of as ready-to-use solutions, emulsions, water- or oil-based suspensions, powders, wettable powders, pastes, soluble powders, dusts, soluble granules, granules for broadcasting, suspoemulsion concentrates, natural products impregnated with the compound of the invention, synthetic substances impregnated with the compound of the invention, fertilizers or microencapsulations in polymeric substances.

Application is accomplished in a customary manner, for example by watering, spraying, atomizing, broadcasting, dusting, foaming, spreading-on and the like. It is also possible to deploy the compound of the invention by the ultra-low volume method, via a drip irrigation system or drench application, to apply it in-furrow or to inject it into the soil stem or trunk. It is further possible to apply the compound of the invention by means of a wound seal, paint or other wound dressing.

The effective and plant-compatible amount of the compound of the invention which is applied to the plants, plant parts, fruits, seeds or soil will depend on various factors, such as the compound/composition employed, the subject of the treatment (plant, plant part, fruit, seed or soil), the type of treatment (dusting, spraying, seed dressing), the purpose of the treatment (curative and protective), the type of microorganisms, the development stage of the microorganisms, the sensitivity of the microorganisms, the crop growth stage and the environmental conditions.

When the compound of the invention is used as a fungicide, the application rates can vary within a relatively wide range, depending on the kind of application. For the treatment of plant parts, such as leaves, the application rate may range from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used). For the treatment of seeds, the application rate may range from 0.1 to 200 g per 100 kg of seeds, preferably from 1 to 150 g per 100 kg of seeds, more preferably from 2.5 to 25 g per 100 kg of seeds, even more preferably from 2.5 to 12.5 g per 100 kg of seeds. For the treatment of soil, the application rate may range from 0.1 to 10 000 g/ha, preferably from 1 to 5000 g/ha.

These application rates are merely examples and are not intended to limit the scope of the present invention.

The invention is illustrated by the examples below. However, the invention is not limited to the examples.

PREPARATION EXAMPLES

Preparation of 2-(1-chlorocyclopropyl)-1-(2-chlorophenyl)-3-(tetrazol-1-yl)propan-2-ol (Ia-05) and 2-(1-chlorocyclopropyl)-1-(2-chlorophenyl)-3-(tetrazol-2-yl)propan-2-ol (Ib-04)

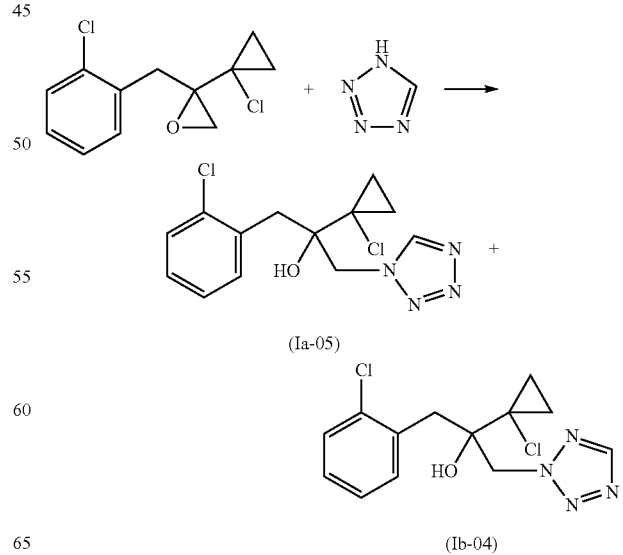

In a 50 mL 2-neck round bottom flask, equipped with a magnetic stirrer and condenser, tetrazole (761 mg, 10.8 mmol) was dissolved in 8 ml DMF (dimethylformamide). K$_2$CO$_3$ (1500 mg, 10.8 mmol) was added and the reaction mixture was then stirred for 15 minutes at room temperature (21° C.), before 2-(1-chlorocyclopropyl)-2-[(2-chlorophenyl)methyl]oxirane (2000 mg, 7.23 mmol) in DMF (2 ml) was added in one portion. The reaction mixture was heated to 70° C. and maintained for 22 hours during which time the reaction mixture became deep orange in colour.

The reaction mixture was cooled, added to ice/water, stirred vigorously for 1 hour, at which point a precipitate had formed. The solid was filtered, washed with water and dried.

Purification by flash chromatography, using a 40 g silica cartridge and 0-5% ethyl acetate/dichloromethane as eluent afforded 200 mg (8.3%) of 2-(1-chlorocyclopropyl)-1-(2-chlorophenyl)-3-(tetrazol-1-yl)propan-2-ol as a colourless solid {MS (ESI): 313.2 ([M+H]$^+$)} and 190 mg of 2-(1-chlorocyclopropyl)-1-(2-chlorophenyl)-3-(tetrazol-2-yl)propan-2-ol as a colourless solid {MS (ESI): 313.2 ([M+H]$^+$)}.

Preparation of 2-(1-chlorocyclopropyl)-1-(2-fluorophenyl)-3-(tetrazol-1-yl)propan-2-ol (Ia-04) and 2-(1-chlorocyclopropyl)-1-(2-fluorophenyl)-3-(tetrazol-2-yl)propan-2-ol (Ib-02)

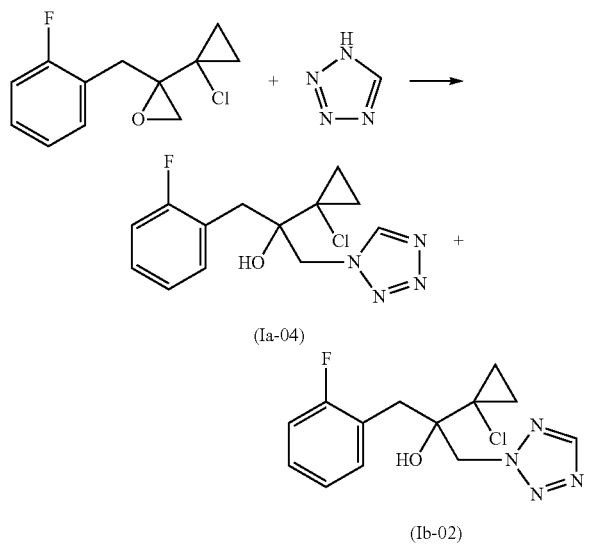

In a 50 mL 2-neck round bottom flask, equipped with a magnetic stirrer and condenser, tetrazole (816 mg, 11.5 mmol) was dissolved in 8 ml DMF (dimethylformamide). K$_2$CO$_3$ (1609 mg, 11.6 mmol) was added and the reaction mixture was then stirred for 15 minutes at room temperature, before 2-(1-chlorocyclopropyl)-2-[(2-fluorophenyl)methyl]oxirane (2000 mg, 7.76 mmol) in DMF (2 ml) was added in one portion. The reaction mixture was stirred at room temperature for 15 hours, then heated to 70° C. and further stirred for 22 hours at that temperature during which time the reaction mixture became deep orange in colour.

The reaction mixture was cooled, added to ice/water, stirred vigorously for 1 hour, at which point a precipitate had formed. The solid was filtered, washed with water and dried.

Purification by reverse phase preparative HPLC, afforded 460 mg (19%) of 2-(1-chlorocyclopropyl)-1-(2-fluorophenyl)-3-(tetrazol-1-yl)propan-2-ol as a colourless solid {MS (ESI): 297.2 ([M+H]$^+$)} and 450 mg (18%) of 2-(1-chlorocyclopropyl)-1-(2-fluorophenyl)-3-(tetrazol-2-yl)propan-2-ol as a colourless solid {MS (ESI): 297.2 ([M+H]$^+$)}.

Preparation of 2-(1-chlorocyclopropyl)-1-(2-chloro-3-pyridyl)-3-(tetrazol-1-yl)propan-2-ol (Ia-03) and 2-(1-chlorocyclopropyl)-1-(2-chloro-3-pyridyl)-3-(tetrazol-2-yl)propan-2-ol (Ib-05)

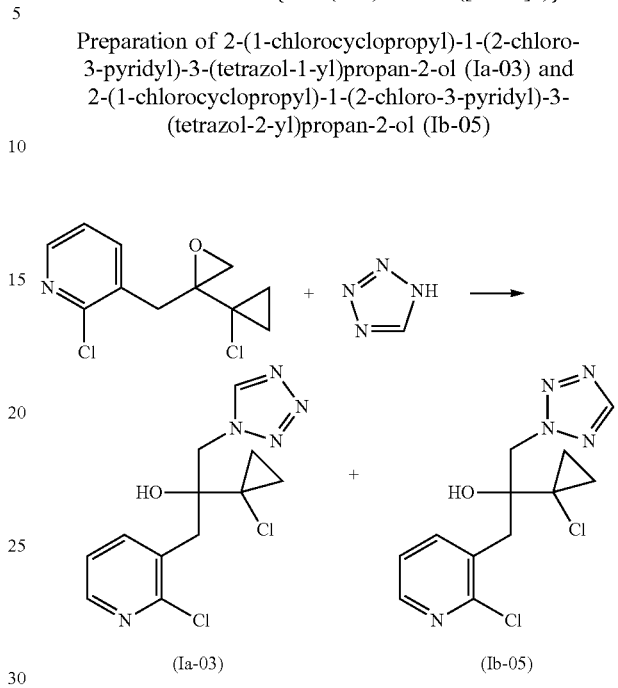

A solution of tetrazole (0.45 M solution in acetonitrile, 5.56 mL, 2.5 mmol) was diluted further with acetonitrile (6.0 mL), then potassium carbonate (2.5 mmol, 345 mg) was added and the suspension was stirred for 10 minutes at room temperature before 2-chloro-3-[[2-(1-chlorocyclopropyl)oxiran-2-yl]methyl]pyridine (2.5 mmol, 642 mg) dissolved in acetonitrile (2.0 mL) was added. The reaction mixture was heated to 75° C. and stirred for 18 h. The reaction mixture was cooled to room temperature, then quenched with water, extracted with ethyl acetate, dried over Na$_2$SO$_4$, and concentrated. Flash column chromatography yielded 60 g of (Ia-03) (97% pure, 7% yield) {MS (ESI): 314.05 ([M]$^+$)} and 50 mg of (Ib-05) (94% pure, 6% yield) {MS (ESI): 314.05 ([M]$^+$)}.

Preparation of 2-(1-chlorocyclopropyl)-1-phenyl-3-(tetrazol-1-yl)propan-2-ol (Ia-01)

Step 1: Preparation of 1-(1-chlorocyclopropyl)-2-(tetrazol-1-yl)ethanone and 1-(1-chlorocyclopropyl)-2-(tetrazol-2-yl)ethanone

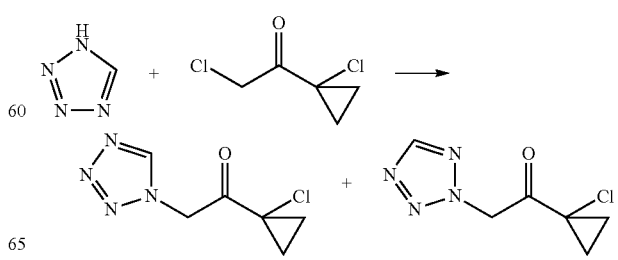

To a solution of tetrazole (360 mg, 5.13 mmol) in acetonitrile (10.3 ml) under argon, in a 20 ml micro-wave tube, equipped with a magnetic stirrer, DBU (1,8-diazabicyclo[5.4.0]undec-7-ene) (861 mg, 5.65 mmol) was added. The reaction mixture was stirred at room temperature for 5 minutes, then 2-chloro-1-(1-chlorocyclopropyl)ethanone (786 mg, 5.13 mmol) in acetonitrile (1 ml) was added dropwise. The resulting reaction mixture was stirred at room temperature for 1 hour, then heated to 40° C. and stirred for a further 1 hour. The reaction mixture was cooled, concentrated to about 5 ml of solvent, diluted with ethyl acetate (15 ml), washed sequentially with 10% $Na_2CO_3$ solution, brine, and dried over $MgSO_4$ and finally the solvent was evaporated.

Purification by reverse phase preparative HPLC afforded 350 mg (34.7%) of 1-(1-chlorocyclopropyl)-2-(tetrazol-1-yl)ethanone as a colourless solid {MS (ESI): 187.2 ([M+H]$^+$)} and 100 mg (10.4%) of 1-(1-chlorocyclopropyl)-2-(tetrazol-2-yl)ethanone as a colourless solid {MS (ESI): 187.2 ([M+H]$^+$)}.

Step 2: Preparation of 2-(1-chlorocyclopropyl)-1-phenyl-3-(tetrazol-1-yl)propan-2-ol (Ia-01)

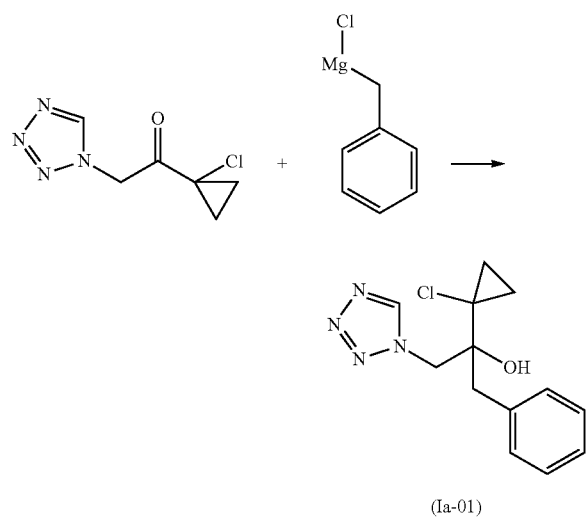

(Ia-01)

A THF (tetrahydrofuran) solution of benzylmagnesium chloride (1.38 ml, 1.01 mmol) was furnished under argon in an oven-dried 20 ml microwave tube, equipped with a magnetic stirrer and fitted with a rubber septum, and cooled to 0° C. A THF solution of manganese chloride bis(lithium chloride) complex (2.46 ml, 1.23 mmol) was added dropwise slowly over a period of 10 minutes. The reaction mixture was stirred at 0° C. for 10 minutes, then 1-(1-chlorocyclopropyl)-2-(tetrazol-1-yl)ethanone (135 mg, 0.72 mmol) in dichloromethane (3 ml) was added and the reaction mixture stirred at 0° C. for 2 hours. The reaction mixture was quenched by dropwise addition of saturated $NH_4Cl$ solution, partitioned between water and dichloromethane, the organic layer was separated, washed with brine, dried over $MgSO_4$ and the solvent was evaporated.

Purification by reverse phase preparative HPLC, afforded 95 mg (44.8%) of compound (Ia-01) as a colourless solid {MS (ESI): 279.2 ([M+H]$^+$)}.

Preparation of 2-(1-chlorocyclopropyl)-3-(2-fluorophenyl)-1-(tetrazol-1-yl)but-3-en-2-ol (Ia-en-02)

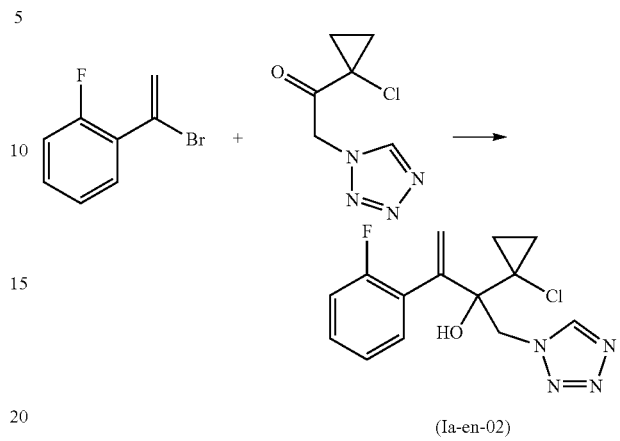

(Ia-en-02)

Magnesium turnings (163.2 mg, 6.71 mmol, 1.5 equivalents) were first stirred 1 h at room temperature under argon, then covered with $Et_2O$ (2 mL) and 1,2-dibromoethane (2 drops) was added under continuous stirring. The resulting suspension was stirred at room temperature for 20 min. A few drops of 1-(1-bromovinyl)-2-fluoro-benzene were added, then the resulting mixture was cooled down to 0-5° C., and the remaining amount of 1-(1-bromovinyl)-4-chloro-benzene (total amount: 1.00 g, 4.47 mmol) [as a solution in $Et_2O$ (6 mL)] was added dropwise over a period of 30 min. After addition, the reaction mixture was stirred for 10 min at 0-5° C. Rapid titration of the resulting solution using iodine as an indicator gave a concentration of 0.44 M.

The obtained Grignard solution (6.84 mL, 0.44 M, 3.00 mmol) was added dropwise at 5° C. to a solution of 1-(1-chlorocyclopropyl)-2-(tetrazol-1-yl)ethanone (XVIa-01) (461 mg, 2.38 mmol, 1.0 equivalent) in a mixture of THF and dichloromethane (50:50, 5 mL). The reaction mixture was further stirred at 0-5° C. for 50 min, and then quenched by addition of saturated aqueous $NH_4Cl$ at 0-5° C. The resulting mixture was diluted with water, and then extracted with ethyl acetate (3×20 mL). The combined organic layers were washed with brine, dried (ChemElut), and then concentrated to dryness in vacuo. The oily residue was purified by preparative HPLC to afford 235 mg (36%) of 2-(1-chlorocyclopropyl)-3-(2-fluorophenyl)-1-(tetrazol-1-yl)but-3-en-2-ol as a colourless solid.

MS (ESI): 309 ([M+H]$^+$)

Preparation of 2-(1-chlorocyclopropyl)-3-(2-fluorophenyl)-1-(tetrazol-1-yl)butan-2-ol, diastereoisomer 1 and diastereoisomer 2 (Ia-20 & Ia-22)

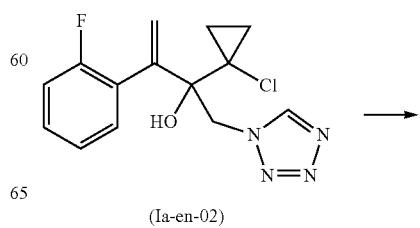

(Ia-en-02)

-continued

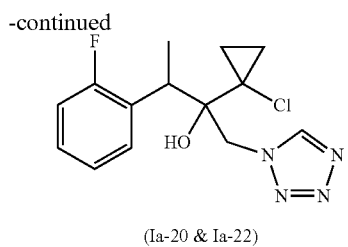

(Ia-20 & Ia-22)

A solution of 2-(1-chlorocyclopropyl)-3-(2-fluorophenyl)-1-(tetrazol-1-yl)but-3-en-2-ol (160 mg, 0.51 mmol) in methanol (25 mL) was hydrogenated in an H-Cube apparatus (full $H_2$) over a Pd/C cartridge (flow: 1 mL/min) at room temperature. The resulting solution was concentrated to dryness in vacuo. The oily residue was purified by preparative HPLC to afford respectively 125 mg (74%) and 14 mg (8%) of each diastereoisomer (as a racemate) as a colourless solid.

MS (ESI): 311 ([M+H]$^+$)

The following tables illustrate in a non-limiting manner examples of compounds according to the invention. The compounds have been prepared according to the preparation examples outlined above or in analogy thereto.

TABLE 1

Compounds according to formula (Ia)

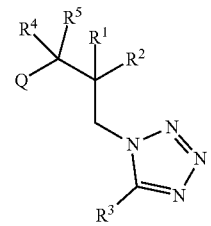

(Ia)

| Ex N° | R$^1$ | R$^2$ | R$^3$ | R$^4$ | R$^5$ | Q | LogP |
|---|---|---|---|---|---|---|---|
| Ia-01 | 1-chlorocyclopropyl | OH | H | H | H | phenyl | 2.41[a] |
| Ia-02 | 1-chlorocyclopropyl | OH | H | H | H | 3-chloro-2-fluorophenyl | 2.72[a] |
| Ia-03 | 1-chlorocyclopropyl | OH | H | H | H | 2-chloropyridin-3-yl | 1.72[a];1.68[b] |
| Ia-04 | 1-chlorocyclopropyl | OH | H | H | H | 2-fluorophenyl | 2.46[a] |
| Ia-05 | 1-chlorocyclopropyl | OH | H | H | H | 2-chlorophenyl | 2.65[a] |
| Ia-06 | 1-chlorocyclopropyl | OH | H | H | H | 2,3-difluorophenyl | 2.46[a] |
| Ia-07 | 1-chlorocyclopropyl | OH | H | H | H | 2-(trifluoromethyl)phenyl | 3.02[a] |
| Ia-08 | 1-methylcyclopropyl | OH | H | H | H | 2-chlorophenyl | 2.80[a] |
| Ia-09 | 1-methylcyclopropyl | OH | H | H | H | 2-bromophenyl | 2.92[a] |
| Ia-10 | 1-methylcyclopropyl | OH | H | H | H | phenyl | 2.35[a] |
| Ia-11 | 1-methylcyclopropyl | OH | H | H | H | 2-(trifluoromethyl)phenyl | 2.94[a] |
| Ia-12 | 1-methylcyclopropyl | OH | H | H | H | 2-methylphenyl | 2.75[a] |
| Ia-13 | 1-chlorocyclopropyl | OH | H | H | H | 2,6-difluorophenyl | 2.52[a] |
| Ia-14 | 1-chlorocyclopropyl | OH | H | H | H | 2-methoxyphenyl | 2.73[a] |
| Ia-15 | 1-chlorocyclopropyl | OH | H | H | H | 2,3-dichlorophenyl | 3.19[a] |
| Ia-16* | 1-chlorocyclopropyl | OH | H | CH$_3$ | H | 2,5-difluorophenyl | 2.66[a] |
| Ia-17 | 1-fluorocyclopropyl | OH | H | H | H | phenyl | 2.08[a] |
| Ia-18* | 1-chlorocyclopropyl | OH | H | CH$_3$ | H | 2,5-difluorophenyl | 2.92[a] |
| Ia-19 | 1-fluorocyclopropyl | OH | H | H | H | 2-chlorophenyl | 2.40[a] |
| Ia-20*1 | 1-chlorocyclopropyl | OH | H | CH$_3$ | H | 2-fluorophenyl | 2.61[a] |
| Ia-21 | 1-fluorocyclopropyl | OH | H | H | H | 2-bromophenyl | 2.49[a] |
| Ia-22*1 | 1-chlorocyclopropyl | OH | H | CH$_3$ | H | 2-fluorophenyl | 2.80[a] |
| Ia-23 | 1-fluorocyclopropyl | OH | H | H | H | 3-bromophenyl | 2.59[a] |
| Ia-24 | 1-chlorocyclopropyl | OH | H | H | H | 2-bromophenyl | 2.88[a] |
| Ia-25 | 1-chlorocyclopropyl | OH | H | CH$_3$ | H | 2,3-difluorophenyl | 2.96[a] |
| Ia-26 | 1-fluorocyclopropyl | OH | H | H | H | 3-methoxyphenyl | 2.11[a] |
| Ia-27 | 1-fluorocyclopropyl | OH | H | H | H | 4-methoxyphenyl | 2.08[a] |
| Ia-28 | 1-fluorocyclopropyl | OH | H | H | H | 3-methylphenyl | 2.42[a] |
| Ia-29 | 1-chlorocyclopropyl | OH | H | H | H | 5-chloro-2-fluorophenyl | 2.86[a] |
| Ia-30 | 1-methylcyclopropyl | OH | H | H | H | 4-methylphenyl | 2.73[a] |
| Ia-31 | 1-chlorocyclopropyl | OH | H | H | H | 3,5-difluorophenyl | 2.63[a] |
| Ia-32 | 1-chlorocyclopropyl | OH | H | H | H | 2-(trifluoromethoxy)phenyl | 3.06[a] |
| Ia-33 | 1-fluorocyclopropyl | OH | H | H | H | 4-methylphenyl | 2.44[a] |
| Ia-34 | 1-methylcyclopropyl | OH | H | H | H | 4-methoxyphenyl | 2.35[a] |
| Ia-35 | 1-chlorocyclopropyl | OH | H | H | H | 2,4,6-trifluorophenyl | 2.64[a] |
| Ia-36 | 1-chlorocyclopropyl | OH | H | H | H | 2,6-difluoro-3-methylphenyl | 2.90[a] |
| Ia-37 | 1-chlorocyclopropyl | OCH$_3$ | H | H | H | 2-chlorophenyl | 3.19[a] |
| Ia-38 | 1-chlorocyclopropyl | OH | H | H | H | 3-chloro-2,4-difluorophenyl | 2.94[a] |
| Ia-39 | 1-chlorocyclopropyl | OH | H | H | H | 2-chloro-4-fluorophenyl | 2.90[a] |
| Ia-40 | 1-chlorocyclopropyl | OH | H | H | H | 4-chloro-2-fluorophenyl | 2.90[a] |
| Ia-41 | 1-chlorocyclopropyl | OH | H | H | H | 3-bromo-2-fluorophenyl | 2.92[a] |
| Ia-42 | 1-chlorocyclopropyl | OH | H | H | H | 2,5-difluorophenyl | 2.52[a] |
| Ia-43 | 1-chlorocyclopropyl | OH | H | H | H | 2,3,5-trifluorophenyl | 2.66[a] |
| Ia-44 | 1-chlorocyclopropyl | OH | H | H | H | 2,3,4-trifluorophenyl | 2.71[a] |
| Ia-45 | 1-chlorocyclopropyl | OH | H | H | H | 2-chloro-6-fluoro-3-methylphenyl | 3.23[a] |

TABLE 1-continued

Compounds according to formula (Ia)

(Ia)

| Ex N° | R¹ | R² | R³ | R⁴ | R⁵ | Q | LogP |
|---|---|---|---|---|---|---|---|
| Ia-46 | 1-chlorocyclopropyl | OH | H | H | H | 2,6-difluoro-3-methoxyphenyl | 2.51[a] |
| Ia-47 | 1-chlorocyclopropyl | OH | H | H | H | 3-chlorophenyl | 2.82[a] |
| Ia-48 | 1-chlorocyclopropyl | OH | H | H | H | 2,3-difluoro-4-methoxyphenyl | 2.59[a] |
| Ia-49 | 1-chlorocyclopropyl | OH | H | H | H | 2,6-difluoro-4-methoxyphenyl | 2.69[a] |
| Ia-50 | 1-chlorocyclopropyl | OH | H | H | H | 2,4-difluoro-3-methoxyphenyl | 2.62[a] |
| Ia-51 | 1-chlorocyclopropyl | OH | H | H | H | 2,4,5-trifluorophenyl | 2.66[a] |
| Ia-52 | 1-chlorocyclopropyl | OH | H | H | H | 3-chloro-4-fluorophenyl | 2.90[a] |
| Ia-53 | 1-chlorocyclopropyl | OH | H | H | H | 2,4-difluorophenyl | 2.57[a] |
| Ia-54 | 1-chlorocyclopropyl | OH | H | H | H | 2,3,6-trifluorophenyl | 2.60[a] |
| Ia-55 | 1-chlorocyclopropyl | OH | H | H | H | 2,3-difluoro-4-methylphenyl | 2.92[a] |
| Ia-56 | 1-chlorocyclopropyl | OH | H | H | H | 3,4-difluorophenyl | 2.64[a] |
| Ia-57 | 1-chlorocyclopropyl | OH | H | H | H | 4-methylphenyl | 2.78[a] |
| Ia-58 | 1-chlorocyclopropyl | OH | H | H | H | 4-methoxyphenyl | 2.40[a] |
| Ia-59 | 1-chlorocyclopropyl | OH | H | H | H | 5-fluoropyridin-3-yl | 1.53[a] |
| Ia-60 | 1-chlorocyclopropyl | OH | H | H | H | 3-methoxyphenyl | 2.42[a] |
| Ia-61 | 1-methylcyclopropyl | OH | H | H | H | 3-methoxyphenyl | 2.37[a] |
| Ia-62 | 1-chlorocyclopropyl | OH | H | H | H | 3-bromophenyl | 2.92[a] |
| Ia-63 | 1-methylcyclopropyl | OH | H | H | H | 3-bromophenyl | 2.84[a] |
| Ia-64 | 1-chlorocyclopropyl | OH | H | H | H | 3-methylphenyl | 2.78[a] |
| Ia-65 | 1-methylcyclopropyl | OH | H | H | H | 3-methylphenyl | 2.73[a] |
| Ia-66 | 1-chlorocyclopropyl | OH | H | H | H | 2-methylphenyl | 2.77[a] |
| Ia-67 | 1-chlorocyclopropyl | OH | H | H | H | 4-bromo-2-fluorophenyl | 3.23[a] |
| Ia-68 | 1-methylcyclopropyl | OH | H | H | H | 2-fluorophenyl | 2.45[a] |
| Ia-69 | 1-chlorocyclopropyl | OH | H | H | H | 3-fluorophenyl | 2.54[a] |
| Ia-70 | 1-chlorocyclopropyl | OCH₃ | H | H | H | 2-bromophenyl | 3.23[a] |
| Ia-71 | 1-chlorocyclopropyl | OH | H | H | H | 2-fluoro-3-(trifluoromethyl)phenyl | 3.04[a] |
| Ia-72 | 1-chlorocyclopropyl | OH | H | H | H | 2-chloro-6-fluorophenyl | 2.90[a] |
| Ia-73 | 1-chlorocyclopropyl | OH | H | H | H | 3-chloropyridin-4-yl | 1.65[a] |
| Ia-74 | 1-chlorocyclopropyl | OH | H | H | H | 5-chloropyridin-3-yl | 1.86[a] |
| Ia-75 | 1-chlorocyclopropyl | OH | H | H | H | 4-chloro-2,6-difluorophenyl | 2.98[a] |
| Ia-76 | 1-fluorocyclopropyl | OH | H | H | H | 2-(trifluoromethyl)phenyl | 2.71[a] |

*: Compounds Ia-16 and Ia-18 are diastereoisomers
*¹: Compounds Ia-20 and Ia-22 are diastereoisomers

TABLE 2

Compounds according to formula (Ib)

(Ib)

| Ex N° | R¹ | R² | R³ | R⁴ | R⁵ | Q | LogP |
|---|---|---|---|---|---|---|---|
| Ib-01 | 1-chlorocyclopropyl | OH | H | H | H | 5-chloropyridin-3-yl | 2.13[a] |
| Ib-02 | 1-chlorocyclopropyl | OH | H | H | H | 2-fluorophenyl | 2.86[a] |
| Ib-03 | 1-chlorocyclopropyl | OH | H | H | H | 2,3-difluorophenyl | 2.82[a] |

TABLE 2-continued

Compounds according to formula (Ib)

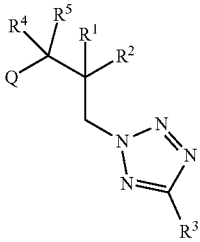

(Ib)

| Ex N° | R¹ | R² | R³ | R⁴ | R⁵ | Q | LogP |
|---|---|---|---|---|---|---|---|
| Ib-04 | 1-chlorocyclopropyl | OH | H | H | H | 2-chlorophenyl | 3.20[a] |
| Ib-05 | 1-chlorocyclopropyl | OH | H | H | H | 2-chloropyridin-3-yl | 2.03[a] |
| Ib-06 | 1-chlorocyclopropyl | OH | H | H | H | 3-chloro-2-fluorophenyl | 3.19[a] |
| Ib-07 | 1-chlorocyclopropyl | OH | H | H | H | 2,4,6-trifluorophenyl | 3.09[a] |
| Ib-08 | 1-chlorocyclopropyl | OH | H | H | H | 4-chloro-2-fluorophenyl | 3.37[a] |
| Ib-09 | 1-chlorocyclopropyl | OH | H | H | H | 2,6-difluoro-3-methylphenyl | 3.37[a] |
| Ib-10 | 1-chlorocyclopropyl | OH | H | H | H | 2,3,4-trifluorophenyl | 3.11[a] |
| Ib-11 | 1-chlorocyclopropyl | OH | H | H | H | 2,3,5-trifluorophenyl | 3.06[a] |
| Ib-12 | 1-chlorocyclopropyl | OH | H | H | H | 3-chloro-2,4-difluorophenyl | 3.37[a] |
| Ib-13 | 1-chlorocyclopropyl | OH | H | H | H | 2,3-difluoro-4-methoxyphenyl | 2.94[a] |
| Ib-14 | 1-chlorocyclopropyl | OH | H | H | H | 2,4-difluoro-3-methoxyphenyl | 3.00[a] |
| Ib-15 | 1-chlorocyclopropyl | OH | H | H | H | 2,6-difluoro-4-methoxyphenyl | 3.11[a] |
| Ib-16 | 1-chlorocyclopropyl | OH | H | H | H | 2,4,5-trifluorophenyl | 3.09[a] |
| Ib-17 | 1-chlorocyclopropyl | OH | H | H | H | 2,4-difluorophenyl | 2.96[a] |
| Ib-18 | 1-chlorocyclopropyl | OH | H | H | H | 3-chloro-4-fluorophenyl | 3.33[a] |
| Ib-19 | 1-chlorocyclopropyl | OH | H | H | H | 2,3,6-trifluorophenyl | 3.02[a] |
| Ib-20 | 1-chlorocyclopropyl | OH | H | H | H | 2,6-difluoro-3-methoxyphenyl | 2.86[a] |
| Ib-21 | 1-chlorocyclopropyl | OH | H | H | H | 2,3-difluoro-4-methylphenyl | 3.33[a] |
| Ib-22 | 1-chlorocyclopropyl | OH | H | H | H | 3-chloropyridin-4-yl | 1.96[b] |
| Ib-23 | 1-chlorocyclopropyl | OH | H | H | H | 5-fluoropyridin-3-yl | 1.76[a] |
| Ib-24 | 1-chlorocyclopropyl | OH | H | H | H | 3,4-difluorophenyl | 3.04[a] |
| Ib-25 | 1-chlorocyclopropyl | OH | H | H | H | 2-fluoropyridin-3-yl | 1.91[a] |

TABLE 3

Compounds according to formula (Ia-en), wherein R³ is hydrogen

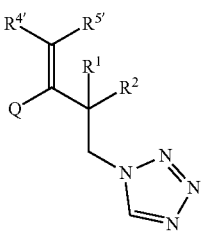

| Ex N° | R¹ | R² | R⁴' | R⁵' | Q | LogP |
|---|---|---|---|---|---|---|
| Ia-en-01 | 1-chlorocyclopropyl | OH | H | H | 2,5-difluorophenyl | 2.54[a] |
| Ia-en-02 | 1-chlorocyclopropyl | OH | H | H | 2-fluorophenyl | 2.46[a] |
| Ia-en-03 | 1-chlorocyclopropyl | OH | H | H | phenyl | 2.46[a] |
| Ia-en-04 | 1-chlorocyclopropyl | OH | CH₃ | H | 2-fluorophenyl | 2.66[a] |
| Ia-en-05 | 1-chlorocyclopropyl | OH | CH₃ | H | 3-chloro-2-fluorophenyl | 3.00[a] |
| Ia-en-06 | 1-chlorocyclopropyl | OH | CH₃ | H | 2,3-difluorophenyl | 2.82[a] |
| Ia-en-07 | 1-chlorocyclopropyl | OH | H | CH₃ | 2,3-difluorophenyl | 2.75[a] |
| Ia-en-08 | 1-chlorocyclopropyl | OH | H | H | 2,3-difluorophenyl | 2.57[a] |
| Ia-en-09 | 1-chlorocyclopropyl | OH | H | H | 2-chlorophenyl | 2.71[a] |
| Ia-en-10 | 1-chlorocyclopropyl | OH | H | H | 3-chloro-2-fluorophenyl | 2.82[a] |
| Ia-en-11* | 1-chlorocyclopropyl | OH | CH₃ | H | phenyl | 2.73 + 2.80[a] |

*: mixture of isomer E-Z 70-30

TABLE 4

Compounds according to formula (Ib-en), wherein $R^3$ is hydrogen

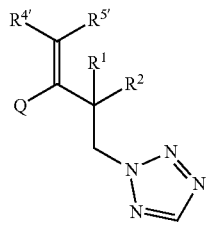

| Ex N° | $R^1$ | $R^2$ | $R^{4'}$ | $R^{5'}$ | Q | LogP |
|---|---|---|---|---|---|---|
| Ib-en-01 | 1-chlorocyclopropyl | OH | H | H | 2-fluorophenyl | 2.96[a] |

TABLE 5

Compounds according to formula (XVIa)

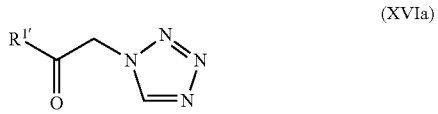

| Ex N° | $R^{1'}$ | LogP |
|---|---|---|
| XVIa-01 | 1-chlorocyclopropyl | 0.99[a] |
| XVIa-02 | 1-methylcyclopropyl | 0.79[a] |
| XVIa-03 | 1-fluorocyclopropyl | 0.59[a] |

TABLE 6

Compounds according to formula (XVIb)

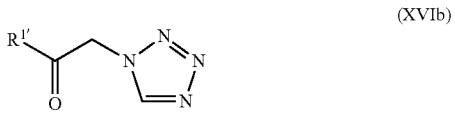

| Ex N° | $R^{1'}$ | LogP |
|---|---|---|
| XVIb-01 | 1-chlorocyclopropyl | 1.30[a] |
| XVIb-02 | 1-methylcyclopropyl | 1.05[a] |
| XVIb-03 | 1-fluorocyclopropyl | 0.86[a] |

Log P Values:

Measurement of Log P values was performed according to EEC directive 79/831 Annex V.A8 by HPLC (High Performance Liquid Chromatography) on reversed phase columns with the following methods:

[a] Log P value is determined by measurement of LC-UV, in an acidic range, with 0.1% formic acid in water and acetonitrile as eluent (linear gradient from 10% acetonitrile to 95% acetonitrile).

[b] Log P value is determined by measurement of LC-UV, in a neutral range, with 0.001 molar ammonium acetate solution in water and acetonitrile as eluent (linear gradient from 10% acetonitrile to 95% acetonitrile).

[c] Log P value is determined by measurement of LC-UV, in an acidic range, with 0.1% phosphoric acid and acetonitrile as eluent (linear gradient from 10% acetonitrile to 95% acetonitrile).

If more than one Log P value is available within the same method, all the values are given and separated by "+".

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

NMR-Peak Lists $^1$H-NMR data of selected examples are written in form of $^1$H-NMR-peak lists. To each signal peak are listed the δ-value in ppm and the signal intensity in round brackets. Between the δ-value signal intensity pairs are semicolons as delimiters.

The peak list of an example has therefore the form:

$\delta_1$ (intensity$_1$); . . . $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

One skilled in the art, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

Ia-01: $^1$H-NMR (300.2 MHz, CDCl$_3$):

δ=8.8124 (3.1); 7.4263 (0.4); 7.4142 (0.3); 7.4078 (1.4); 7.4019 (0.8); 7.3962 (0.6); 7.3899 (1.5); 7.3828 (3.5); 7.3757 (1.6); 7.3635 (1.0); 7.3445 (2.3); 7.3373 (1.8); 7.3189 (1.1); 7.3131 (0.9); 7.2988 (10.7); 5.0090 (1.8); 4.9612 (2.4); 4.6641 (1.9); 4.6163 (1.5); 3.4710 (1.5); 3.4247 (1.8); 2.9562 (1.7); 2.9099 (1.5); 2.3696 (3.5); 1.5931 (16.0); 0.8136 (0.5); 0.8083 (0.5); 0.7975 (0.6); 0.7900 (0.8); 0.7739 (0.6); 0.7561 (0.7); 0.6362 (0.5); 0.6198 (0.5); 0.6136 (0.7); 0.5971 (0.9); 0.5793 (0.7); 0.5739 (1.1); 0.5686 (1.1); 0.5614 (0.6); 0.5453 (0.9);

0.5267 (0.8); 0.5222 (0.6); 0.5041 (0.6); 0.4497 (0.8); 0.4437 (0.4); 0.4335 (0.6); 0.4151 (0.8); 0.4096 (0.6); 0.3989 (0.4); 0.3918 (0.4); 0.0485 (0.4); 0.0376 (10.8); 0.0267 (0.4)

Ia-02: $^{1}$H-NMR (300.2 MHz, CDCl$_{3}$):
δ=8.9425 (1.6); 8.8963 (16.0); 7.4294 (0.6); 7.3966 (1.9); 7.3914 (3.1); 7.3833 (3.0); 7.3655 (6.2); 7.3572 (5.7); 7.3473 (2.7); 7.3415 (4.6); 7.3353 (4.4); 7.3129 (0.6); 7.3070 (0.6); 7.2989 (2.4); 7.1309 (3.6); 7.1285 (3.6); 7.1047 (5.7); 7.1023 (5.6); 7.0901 (0.9); 7.0870 (0.9); 7.0786 (2.6); 7.0762 (2.5); 7.0636 (0.9); 7.0610 (0.8); 7.0368 (0.5); 5.3237 (2.0); 5.2297 (0.8); 5.1772 (6.8); 5.1293 (7.7); 4.8871 (0.8); 4.8395 (0.6); 4.5683 (7.2); 4.5204 (6.2); 3.4400 (3.4); 3.4370 (3.3); 3.3892 (6.2); 3.3428 (7.1); 3.3351 (7.1); 3.2726 (5.1); 3.2668 (5.0); 3.2252 (3.0); 3.2193 (3.0); 2.0353 (1.0); 1.9878 (0.7); 1.5532 (1.7); 1.5293 (1.6); 1.2733 (0.6); 0.8244 (4.5); 0.7934 (9.8); 0.7632 (8.0); 0.5824 (2.3); 0.5626 (3.0); 0.5567 (2.6); 0.5478 (1.9); 0 5333 (3.5); 0.5221 (1.6); 0.5022 (1.7); 0.4006 (2.4); 0.3808 (2.5); 0.3708 (3.7); 0.3492 (2.8); 0.3399 (2.3); 0.3202 (1.6); 0.1512 (0.5); 0.0171 (2.0)

Ia-03: $^{1}$H-NMR (601.6 MHz, CD$_{3}$CN):
δ=8.9133 (1.0); 8.8488 (10.2); 8.3200 (5.6); 8.3138 (5.2); 8.2702 (1.0); 7.9249 (5.9); 7.9129 (5.3); 7.6749 (0.8); 7.6629 (0.8); 7.5475 (0.4); 7.5357 (0.4); 7.3484 (4.6); 7.3406 (5.0); 7.3367 (4.7); 7.3288 (3.6); 7.2820 (0.8); 7.2740 (0.9); 7.2624 (0.6); 6.8752 (0.4); 5.1587 (6.1); 5.1345 (6.3); 5.1194 (1.2); 4.9922 (0.6); 4.9675 (0.5); 4.8816 (3.6); 4.4961 (6.4); 4.4719 (5.8); 3.6531 (0.5); 3.6246 (0.6); 3.5196 (6.4); 3.4961 (16.0); 3.4383 (1.0); 3.4097 (0.8); 3.3264 (6.5); 3.3202 (8.3); 3.2957 (8.9); 3.2822 (16.0); 3.2750 (14.8); 3.1644 (0.4); 2.2519 (35.2); 2.1248 (0.4); 2.0570 (0.3); 1.9489 (7.0); 1.9458 (7.7); 1.2840 (0.6); 1.2673 (0.6); 0.9540 (0.5); 0.9450 (0.4); 0.9150 (0.6); 0.9036 (0.6); 0.8884 (0.7); 0.8723 (0.8); 0.8619 (0.9); 0.8183 (6.0); 0.8116 (6.8); 0.8008 (8.6); 0.7888 (6.3); 0.7835 (5.6); 0.7467 (1.5); 0.7288 (1.0); 0.6228 (0.6); 0.6044 (1.1); 0.5948 (1.8); 0.5910 (2.0); 0.5765 (1.4); 0.5628 (3.0); 0.5523 (4.0); 0.5492 (4.1); 0.5399 (3.9); 0.5361 (3.8); 0.5234 (2.4); 0.3664 (2.7); 0.3556 (4.1); 0.3489 (3.8); 0.3440 (3.8); 0.3391 (3.7); 0.3272 (2.3); −0.0002 (1.0)

Ia-04: $^{1}$H-NMR (499.9 MHz, CDCl$_{3}$):
δ=8.7891 (16.0); 7.4087 (2.3); 7.4054 (2.5); 7.3935 (4.5); 7.3902 (4.7); 7.3783 (2.5); 7.3749 (2.6); 7.3397 (1.5); 7.3361 (1.5); 7.3288 (1.7); 7.3248 (3.1); 7.3212 (2.4); 7.3128 (2.5); 7.3087 (3.3); 7.3048 (1.8); 7.2974 (1.9); 7.2939 (1.6); 7.2628 (17.7); 7.1923 (0.4); 7.1804 (3.6); 7.1783 (3.9); 7.1654 (5.7); 7.1633 (6.0); 7.1504 (2.7); 7.1483 (2.7); 7.1421 (0.4); 7.1179 (3.1); 7.1163 (3.0); 7.1013 (3.0); 7.0980 (3.9); 7.0808 (2.6); 7.0791 (2.5); 5.0851 (8.6); 5.0563 (9.3); 4.5071 (8.3); 4.4783 (7.5); 3.3756 (4.5); 3.3469 (6.0); 3.2027 (5.1); 3.2000 (5.2); 3.1741 (3.8); 3.1712 (3.8); 2.7319 (8.9); 2.7220 (8.8); 1.5881 (24.9); 0.8046 (1.5); 0.7923 (3.5); 0.7899 (2.4); 0.7831 (2.0); 0.7774 (3.8); 0.7711 (5.3); 0.7683 (3.1); 0.7578 (5.2); 0.7561 (5.2); 0.7513 (4.0); 0.7458 (1.9); 0.7388 (2.5); 0.7365 (4.3); 0.7243 (2.1); 0.5739 (2.9); 0.5619 (3.5); 0.5592 (3.1); 0.5523 (2.7); 0.5470 (3.3); 0.5404 (3.0); 0.5376 (2.5); 0.5255 (2.4); 0.4039 (2.9); 0.3918 (2.9); 0.3889 (3.2); 0.3825 (3.0); 0.3770 (2.7); 0.3703 (2.7); 0.3675 (2.8); 0.3554 (2.1); 0.0063 (0.7); −0.0002 (16.0); −0.0067 (0.7)

Ia-05: $^{1}$H-NMR (400.0 MHz, d$_{6}$-DMSO):
δ=9.1370 (16.0); 7.6228 (3.2); 7.6167 (3.3); 7.6042 (2.6); 7.5993 (3.6); 7.4764 (3.3); 7.4721 (2.4); 7.4700 (2.0); 7.4586 (4.1); 7.4531 (4.4); 7.3562 (0.9); 7.3515 (1.4); 7.3378 (4.0); 7.3332 (3.9); 7.3268 (4.1); 7.3207 (6.4); 7.3148 (3.3); 7.3082 (3.6); 7.3028 (3.1); 7.2897 (1.1); 7.2845 (0.8); 5.4601 (10.3); 5.1144 (4.6); 5.0786 (4.9); 4.2995 (5.9); 4.2637 (5.5); 3.5789 (5.1); 3.5435 (5.9); 3.3255 (31.5); 3.1369 (5.4); 3.1015 (4.6); 2.6711 (0.3); 2.5416 (3.0); 2.5246 (0.7); 2.5111 (19.4); 2.5067 (39.1); 2.5022 (51.0); 2.4977 (36.1); 2.4932 (16.9); 2.3290 (0.3); 0.9531 (1.1); 0.9380 (1.7); 0.9348 (1.7); 0.9262 (1.7); 0.9197 (1.8); 0.9112 (1.9); 0.9078 (1.8); 0.8928 (1.5); 0.7414 (1.2); 0.7260 (1.6); 0.7232 (1.8); 0.7147 (2.0); 0.7082 (1.6); 0.6995 (1.9); 0.6965 (2.1); 0.6816 (1.4); 0.4594 (1.4); 0.4454 (1.9); 0.4410 (1.8); 0.4328 (1.7); 0.4270 (2.0); 0.4188 (1.7); 0.4144 (1.4); 0.4003 (1.3); 0.2570 (1.4); 0.2427 (1.6); 0.2388 (1.8); 0.2301 (1.8); 0.2247 (1.7); 0.2159 (1.6); 0.2119 (1.6); 0.1977 (1.1); 0.0079 (2.4); −0.0002 (70.1); −0.0086 (2.3)

Ia-06: $^{1}$H-NMR (300.2 MHz, CDCl$_{3}$):
δ=8.9198 (0.4); 8.8717 (16.0); 7.2987 (4.2); 7.2356 (1.0); 7.2298 (1.5); 7.2252 (1.3); 7.2036 (3.9); 7.1806 (4.5); 7.1697 (1.3); 7.1579 (3.0); 7.1483 (4.4); 7.1450 (5.4); 7.1264 (6.5); 7.1185 (3.7); 7.1041 (2.2); 7.0916 (0.9); 7.0747 (0.8); 5.1789 (0.4); 5.1636 (7.4); 5.1157 (8.6); 4.5609 (7.7); 4.5130 (6.6); 3.4456 (3.1); 3.4417 (3.2); 3.3981 (5.6); 3.3942 (5.7); 3.2857 (5.0); 3.2795 (5.0); 3.2383 (2.8); 3.2320 (2.9); 3.0673 (6.6); 3.0593 (6.7); 1.7784 (1.6); 1.5673 (0.4); 1.5433 (0.4); 1.2809 (0.8); 0.8655 (0.5); 0.8453 (3.3); 0.8366 (3.7); 0.8187 (4.0); 0.8105 (8.9); 0.8022 (4.9); 0.7827 (5.5); 0.7773 (5.1); 0.7571 (1.0); 0.5990 (2.6); 0.5791 (3.3); 0.5745 (2.8); 0.5632 (2.1); 0.5530 (3.1); 0.5448 (2.6); 0.5386 (1.8); 0.5186 (2.0); 0.4141 (2.7); 0.3942 (2.5); 0.3861 (2.7); 0.3813 (3.0); 0.3678 (2.2); 0.3599 (2.5); 0.3534 (2.4); 0.3334 (1.7); 0.0262 (3.3)

Ia-07: $^{1}$H-NMR (400.1 MHz, d$_{6}$-DMSO):
δ=8.9930 (3.2); 7.7323 (0.5); 7.5146 (1.4); 7.4597 (0.7); 7.4407 (0.9); 7.4077 (0.6); 7.3880 (1.0); 7.3397 (0.8); 7.3206 (1.0); 7.3013 (0.4); 5.4561 (2.9); 4.8215 (1.1); 4.7855 (1.3); 4.3194 (1.3); 4.2833 (1.1); 3.1066 (16.0); 3.0769 (1.1); 3.0423 (1.3); 2.8498 (1.2); 2.8152 (0.9); 2.6700 (3.2); 2.5105 (3.0); 2.2855 (3.2); 2.2814 (4.2); 2.2772 (3.3); 0.1929 (0.4); 0.1839 (0.7); 0.1755 (1.0); 0.1666 (3.6); −0.0002 (0.7); −0.0180 (0.4); −0.0269 (0.3)

Ia-08: $^{1}$H-NMR (400.1 MHz, d$_{6}$-DMSO):
δ=9.1781 (7.4); 7.6898 (1.6); 7.6839 (1.7); 7.6714 (1.6); 7.6665 (2.0); 7.5719 (1.7); 7.5675 (1.5); 7.5541 (2.1); 7.5489 (2.3); 7.4418 (0.5); 7.4375 (0.7); 7.4235 (2.0); 7.4192 (2.0); 7.4122 (2.2); 7.4064 (3.4); 7.4011 (1.9); 7.3936 (1.9); 7.3885 (1.7); 7.3752 (0.6); 7.3702 (0.5); 5.0967 (2.6); 5.0610 (2.8); 4.7673 (6.1); 4.3159 (2.9); 4.2802 (2.7); 3.4396 (31.0); 3.4115 (3.2); 3.1453 (2.9); 3.1101 (2.4); 3.0028 (1.0); 2.8433 (0.9); 2.6181 (5.8); 2.6141 (7.6); 2.6100 (5.9); 1.3648 (16.0); 0.5424 (0.5); 0.5288 (0.9); 0.5183 (1.4); 0.5078 (1.0); 0.4942 (0.7); 0.0230 (0.6); 0.0092 (1.0); −0.0002 (1.5); −0.0135 (1.1); −0.0234 (0.9); −0.0993 (0.7); −0.1093 (0.9); −0.1228 (1.4); −0.1329 (0.9); −0.1462 (0.6); −0.2979 (0.8); −0.3074 (0.9); −0.3122 (1.0); −0.3211 (1.5); −0.3300 (0.9); −0.3349 (0.9); −0.3444 (0.7)

Ia-09: $^{1}$H-NMR (400.1 MHz, d$_{6}$-DMSO):
δ=9.1390 (7.5); 7.7165 (2.3); 7.6966 (2.7); 7.6792 (1.9); 7.6757 (1.9); 7.6600 (2.2); 7.6564 (2.2); 7.4587 (1.2); 7.4398 (2.4); 7.4214 (1.4); 7.3038 (1.3); 7.3000 (1.3); 7.2841 (2.0); 7.2812 (2.0); 7.2655 (1.0); 7.2617 (0.9); 5.0872 (2.5); 5.0516 (2.7); 4.7390 (5.8); 4.2521 (2.9); 4.2165 (2.7); 3.4727 (2.4); 3.4374 (2.9); 3.4083 (34.5); 3.1255 (2.8); 3.0902 (2.3); 2.9716 (1.5); 2.8122 (1.3);

2.5870 (7.0); 2.5830 (9.2); 2.5789 (7.1); 1.3418 (16.0);
1.2891 (0.5); 0.5755 (0.5); 0.5620 (0.9); 0.5515 (1.4);
0.5402 (1.0); 0.5278 (0.7); 0.0232 (0.6); 0.0094 (1.0);
−0.0002 (1.4); −0.0135 (1.1); −0.0235 (0.8); −0.1160 (0.6);
−0.1262 (0.9); −0.1396 (1.4); −0.1497 (0.9); −0.1631 (0.6);
−0.3111 (0.7); −0.3208 (0.9); −0.3254 (1.0); −0.3344 (1.5);
−0.3433 (0.9); −0.3483 (0.9); −0.3576 (0.7)

Ia-10: $^1$H-NMR (400.1 MHz, $d_6$-DMSO):

δ=8.8636 (4.8); 7.1477 (1.9); 7.1300 (3.3); 7.0877 (1.5);
7.0699 (3.1); 7.0511 (1.8); 7.0222 (1.2); 7.0044 (1.4);
6.9864 (0.5); 4.7262 (1.7); 4.6905 (1.9); 4.4121 (4.1);
4.0267 (1.9); 3.9910 (1.8); 3.1141 (16.0); 2.7907 (1.0);
2.7563 (2.2); 2.7078 (2.2); 2.6754 (1.6); 2.5168 (0.9);
2.2916 (3.2); 2.2877 (4.2); 2.2835 (3.2); 0.9939 (10.7);
0.0148 (0.6); −0.0002 (1.0); −0.4875 (0.8); −0.4969 (1.9);
−0.5090 (2.0); −0.5195 (0.9); −0.5336 (0.4); −0.7077 (0.7);
−0.7148 (0.8); −0.7208 (1.1); −0.7354 (0.7); −0.7419 (0.4)

Ia-11: $^1$H-NMR (400.1 MHz, $d_6$-DMSO):

δ=9.0018 (7.6); 7.8580 (1.1); 7.6330 (3.3); 7.5654 (1.6);
7.5465 (2.1); 7.4949 (1.3); 7.4754 (2.4); 7.4393 (1.9);
7.4202 (2.4); 7.4011 (0.9); 4.8719 (2.6); 4.8362 (2.8);
4.7197 (6.5); 4.1919 (2.9); 4.1561 (2.6); 3.2321 (37.1);
2.9602 (8.7); 2.7956 (6.7); 2.6361 (6.0); 2.4111 (6.9);
2.4070 (9.2); 2.4028 (7.0); 1.1316 (16.0); 0.0223 (0.5);
0.0100 (0.8); −0.0002 (1.4); −0.0084 (0.9); −0.0140 (1.9);
−0.0239 (0.7); −0.3467 (0.5); −0.3602 (0.9); −0.3692 (1.3);
−0.3843 (0.9); −0.3911 (1.0); −0.4024 (1.1); −0.4106 (0.9);
−0.4239 (1.5); −0.4333 (1.1); −0.4471 (0.7); −0.5619 (0.8);
−0.5704 (0.9); −0.5776 (1.0); −0.5845 (1.5); −0.5925 (0.9);
−0.5985 (0.8); −0.6057 (0.6)

Ia-12: $^1$H-NMR (400.1 MHz, $d_6$-DMSO):

δ=9.1510 (7.5); 8.0396 (0.4); 7.4486 (1.4); 7.4394 (1.7);
7.4264 (1.8); 7.2757 (0.7); 7.2625 (1.5); 7.2526 (2.7);
7.2455 (1.8); 7.2369 (5.0); 7.2281 (3.7); 7.2232 (3.1);
7.2142 (2.6); 5.0925 (2.7); 5.0568 (3.0); 4.4902 (6.9);
4.3394 (2.9); 4.3036 (2.7); 3.4145 (27.7); 3.2055 (2.2);
3.1704 (3.1); 3.0258 (3.1); 2.9907 (2.2); 2.9778 (2.7);
2.8184 (2.3); 2.5930 (5.5); 2.5891 (7.3); 2.5850 (5.7);
2.4088 (17.8); 2.3772 (0.5); 1.3293 (16.0); 1.2920 (0.5);
0.5385 (0.6); 0.5251 (0.9); 0.5148 (1.4); 0.5044 (0.9);
0.4913 (0.7); 0.0228 (0.6); 0.0090 (1.0); −0.0002 (1.5);
−0.0134 (1.1); −0.0233 (0.8); −0.1395 (0.7); −0.1502 (1.0);
−0.1629 (1.4); −0.1731 (1.0); −0.1860 (0.7); −0.3276 (0.8);
−0.3372 (0.9); −0.3419 (1.0); −0.3507 (1.5); −0.3597 (0.9);
−0.3645 (0.9); −0.3739 (0.7)

Ia-13: $^1$H-NMR (300.2 MHz, $CDCl_3$):

δ=8.8147 (16.0); 7.3931 (1.0); 7.3711 (2.2); 7.3652 (2.2);
7.3432 (4.6); 7.3375 (1.9); 7.3209 (2.2); 7.3153 (3.0);
7.2984 (9.8); 7.0492 (0.7); 7.0438 (1.1); 7.0314 (7.1);
7.0211 (1.2); 7.0052 (10.4); 6.9882 (1.2); 6.9783 (5.8);
6.9656 (0.9); 5.2615 (7.5); 5.2135 (8.4); 4.4717 (7.0);
4.4238 (6.2); 3.5303 (3.8); 3.4818 (6.3); 3.3387 (5.8);
3.2902 (3.6); 2.7543 (3.9); 2.0765 (0.4); 2.0422 (0.6);
1.2909 (0.4); 1.0026 (1.1); 0.9824 (3.4); 0.9769 (2.0);
0.9663 (1.5); 0.9601 (4.0); 0.9567 (4.5); 0.9465 (4.5);
0.9400 (3.7); 0.9357 (4.6); 0.9258 (4.4); 0.9201 (4.6);
0.9017 (4.5); 0.8815 (1.6); 0.6358 (2.7); 0.6158 (3.4);
0.6094 (2.6); 0.6019 (2.6); 0.5899 (3.0); 0.5813 (3.0);
0.5755 (2.2); 0.5553 (2.3); 0.4248 (2.8); 0.4045 (3.0);
0.4007 (3.3); 0.3884 (2.8); 0.3799 (2.6); 0.3687 (2.5);
0.3641 (2.8); 0.3439 (2.0); 0.0429 (0.4); 0.0321 (9.7);
0.0215 (0.4)

Ia-14: $^1$H-NMR (400.1 MHz, $d_6$-DMSO):

δ=8.9811 (5.9); 7.8289 (0.6); 7.2702 (1.4); 7.2671 (1.6);
7.2517 (1.6); 7.2484 (1.7); 7.1687 (0.7); 7.1649 (0.7);
7.1482 (1.6); 7.1297 (1.0); 7.1259 (1.0); 6.9041 (2.2);
6.8838 (1.9); 6.8292 (1.2); 6.8108 (2.1); 6.7924 (1.0);
5.0384 (4.2); 4.9483 (1.9); 4.9122 (2.0); 4.0527 (2.4);
4.0167 (2.2); 3.6979 (16.0); 3.6653 (0.3); 3.4290 (2.0);
3.3944 (2.2); 3.2037 (25.6); 2.7668 (3.6); 2.7108 (2.1);
2.6711 (1.9); 2.6073 (3.4); 2.3820 (5.0); 2.3781 (6.7);
2.3741 (5.2); 0.8333 (0.4); 0.8158 (0.8); 0.8065 (0.7);
0.8001 (0.8); 0.7907 (0.9); 0.7734 (0.6); 0.5683 (0.5);
0.5507 (0.8); 0.5417 (0.8); 0.5354 (0.7); 0.5241 (1.0);
0.5087 (0.6); 0.2777 (0.6); 0.2637 (0.8); 0.2598 (0.8);
0.2510 (0.8); 0.2458 (0.8); 0.2373 (0.8); 0.2333 (0.7);
0.2192 (0.6); 0.0268 (0.6); 0.0122 (0.7); 0.0088 (0.8);
−0.0002 (0.8); −0.0050 (0.8); −0.0141 (0.8); −0.0179 (0.8);
−0.0321 (0.5)

Ia-15: $^1$H-NMR (300.2 MHz, $CDCl_3$):

δ=8.8413 (13.9); 7.4846 (11.9); 7.4584 (16.0); 7.2986
(5.3); 7.2790 (5.5); 7.2542 (5.3); 7.2515 (5.0); 7.2267 (3.5);
5.2157 (8.1); 5.1678 (9.2); 4.4632 (7.5); 4.4153 (6.7);
3.7664 (6.7); 3.7186 (8.2); 3.3348 (7.1); 3.2870 (5.8);
3.0126 (2.2); 2.0722 (1.1); 2.0401 (4.9); 1.3115 (0.3);
1.2878 (0.7); 0.9231 (3.7); 0.9193 (3.8); 0.8944 (5.1);
0.8908 (8.1); 0.8875 (5.5); 0.8606 (8.3); 0.6246 (2.2);
0.6146 (0.4); 0.6047 (2.7); 0.5951 (2.8); 0.5760 (2.6);
0.5726 (2.9); 0.5640 (1.6); 0.5440 (1.8); 0.4424 (2.3);
0.4224 (2.2); 0.4164 (2.7); 0.4077 (2.1); 0.3933 (2.4);
0.3912 (2.2); 0.3817 (2.0); 0.3617 (1.5); 0.0293 (5.4)

Ia-16: $^1$H-NMR (499.9 MHz, $CDCl_3$):

δ=8.7162 (10.7); 7.0953 (2.0); 7.0544 (1.9); 7.0480 (2.4);
7.0436 (2.4); 7.0366 (3.3); 7.0294 (2.4); 7.0251 (2.3);
7.0187 (1.9); 6.8545 (1.4); 6.8451 (1.6); 6.8361 (3.2);
6.8268 (3.2); 6.8173 (2.4); 6.8080 (2.2); 6.7809 (1.4);
6.7740 (2.2); 6.7665 (2.7); 6.7588 (2.9); 6.7417 (1.4);
6.7350 (0.8); 4.9992 (6.2); 4.9706 (7.3); 4.6638 (6.3);
4.6353 (5.4); 3.8060 (1.4); 3.0425 (4.3); 1.8675 (0.4);
1.3364 (16.0); 1.3221 (15.9); 1.0787 (0.8); 0.1952 (1.4);
0.1886 (1.8); 0.1790 (3.0); 0.1734 (3.0); 0.1652 (2.4);
0.1453 (0.8); 0.0224 (1.5); −0.0002 (5.7); −0.0100 (5.5);
−0.0297 (1.6); −0.1050 (0.6); −0.1789 (2.6); −0.2830 (2.6);
−0.2953 (1.6)

Ia-17: $^1$H-NMR (300.2 MHz, $CDCl_3$):

δ=8.7337 (16.0); 7.4468 (0.4); 7.4346 (1.4); 7.4243 (2.0);
7.4187 (1.5); 7.4055 (7.9); 7.3999 (4.8); 7.3940 (3.5);
7.3877 (8.3); 7.3807 (18.7); 7.3739 (7.2); 7.3616 (3.9);
7.3415 (1.3); 7.3355 (1.3); 7.3282 (0.9); 7.3101 (10.4);
7.2984 (36.3); 7.2844 (6.9); 7.2790 (5.3); 7.2319 (0.3);
5.3373 (2.0); 4.8846 (4.6); 4.8790 (4.7); 4.8369 (6.8);
4.8314 (6.9); 4.6474 (6.2); 4.6426 (6.3); 4.5998 (4.3);
4.5950 (4.2); 3.3368 (4.1); 3.3311 (4.2); 3.2905 (5.0);
3.2847 (5.2); 2.9134 (5.3); 2.9085 (5.4); 2.8670 (4.3);
2.8622 (4.4); 2.2992 (7.9); 1.5990 (1.2); 1.2904 (0.6);
0.8935 (1.0); 0.8711 (1.4); 0.8681 (1.4); 0.8527 (1.6);
0.8463 (1.3); 0.8312 (2.0); 0.8276 (2.3); 0.8066 (2.1);
0.8002 (1.5); 0.7848 (1.6); 0.7784 (1.3); 0.7634 (1.9);
0.7600 (2.0); 0.7389 (1.7); 0.7046 (1.4); 0.6848 (1.8);
0.6808 (1.9); 0.6606 (1.9); 0.6397 (2.4); 0.6194 (2.9);
0.6152 (2.1); 0.5992 (1.1); 0.5949 (1.9); 0.5792 (1.1);
0.5749 (1.3); 0.5542 (1.3); 0.4170 (1.2); 0.3922 (1.3);
0.3788 (2.2); 0.3707 (0.9); 0.3570 (3.2); 0.3441 (2.1);
0.3329 (2.0); 0.3221 (2.4); 0.2984 (1.7); 0.2803 (1.9);
0.2605 (1.9); 0.2557 (2.0); 0.2453 (2.3); 0.2353 (1.8);
0.2255 (2.2); 0.2209 (2.8); 0.2076 (1.1); 0.2003 (1.9);
0.1875 (1.2); 0.1828 (1.2); 0.1621 (1.0); 0.1034 (0.5);
0.0479 (1.6); 0.0371 (43.3); 0.0262 (1.9); −0.0291 (0.4)

Ia-18: $^1$H-NMR (499.9 MHz, $CDCl_3$):

δ=8.7699 (16.0); 7.2697 (6.3); 7.0708 (1.9); 7.0616 (2.1);
7.0526 (4.6); 7.0434 (4.7); 7.0343 (3.2); 7.0251 (3.0);
6.9897 (1.7); 6.9825 (2.7); 6.9751 (3.5); 6.9671 (3.6);
6.9606 (2.6); 6.9574 (2.6); 6.9499 (1.9); 6.9427 (1.2);
5.0710 (7.7); 5.0419 (8.3); 4.0819 (9.7); 4.0528 (8.3);

2.9483 (9.3); 2.0108 (0.5); 1.4709 (20.2); 1.4566 (20.7); 1.2609 (2.3); 1.2481 (3.3); 1.2460 (3.3); 1.2386 (3.0); 1.2333 (3.2); 1.2260 (3.6); 1.2239 (3.4); 1.2111 (2.7); 1.0129 (2.5); 0.9990 (3.8); 0.9910 (3.4); 0.9860 (3.1); 0.9775 (4.1); 0.9642 (2.7); 0.3433 (2.0); 0.3298 (3.2); 0.3215 (2.7); 0.3156 (2.8); 0.3084 (3.2); 0.2938 (2.1); −0.0002 (4.8); −0.1048 (1.6); −0.1185 (3.0); −0.1273 (2.5); −0.1314 (2.5); −0.1403 (3.0); −0.1539 (1.6)

Ia-19: $^1$H-NMR (400.1 MHz, d$_6$-DMSO):

δ=9.1792 (16.0); 7.5901 (3.6); 7.5823 (3.6); 7.5669 (4.7); 7.4813 (3.7); 7.4644 (3.9); 7.4582 (5.1); 7.3477 (1.4); 7.3298 (8.6); 7.3206 (9.1); 7.3118 (7.4); 7.2935 (1.3); 5.5194 (10.8); 4.9831 (4.5); 4.9474 (5.2); 4.4727 (5.8); 4.4369 (5.1); 3.3378 (249.1); 3.2925 (8.2); 3.2473 (8.4); 3.2122 (3.6); 2.9111 (1.5); 2.7519 (1.4); 2.5220 (20.2); 0.7199 (0.6); 0.7041 (0.9); 0.6900 (1.1); 0.6851 (1.1); 0.6708 (1.8); 0.6560 (1.4); 0.6345 (1.3); 0.6211 (1.5); 0.6043 (1.0); 0.5515 (0.6); 0.5320 (1.4); 0.5250 (1.6); 0.5156 (1.4); 0.5051 (2.5); 0.4895 (3.6); 0.4771 (2.6); 0.4620 (2.2); 0.4416 (2.1); 0.4266 (1.9); 0.4085 (1.3); 0.3961 (1.1); 0.3770 (0.6); 0.0375 (0.8); 0.0208 (1.4); 0.0132 (1.9); −0.0002 (2.2); −0.0209 (1.8); −0.0475 (0.8)

Ia-20: $^1$H-NMR (499.9 MHz, CDCl$_3$):

δ=8.8645 (8.0); 7.4856 (2.3); 7.4826 (2.4); 7.4703 (4.4); 7.4675 (4.3); 7.4553 (2.4); 7.4526 (2.2); 7.2836 (1.3); 7.2807 (1.5); 7.2672 (9.6); 7.2540 (2.8); 7.2422 (1.4); 7.2393 (1.3); 7.1275 (3.2); 7.1131 (5.1); 7.0984 (2.4); 7.0719 (3.1); 7.0553 (3.0); 7.0540 (3.0); 7.0499 (3.3); 7.0333 (2.5); 5.1838 (6.8); 5.1554 (7.8); 4.8265 (5.8); 4.7981 (4.9); 4.1286 (0.5); 4.1143 (0.5); 3.9795 (0.9); 3.2614 (2.7); 3.2495 (3.7); 3.2375 (2.6); 3.0482 (1.7); 2.9224 (16.0); 2.0446 (2.0); 1.9994 (0.4); 1.9874 (1.0); 1.9755 (1.4); 1.9636 (0.9); 1.9517 (0.4); 1.5317 (15.8); 1.5172 (15.2); 1.2733 (0.8); 1.2589 (1.8); 1.2448 (0.7); 0.3270 (0.9); 0.3138 (1.7); 0.3065 (1.7); 0.2943 (2.0); 0.2806 (1.2); 0.1922 (1.8); 0.1805 (1.7); 0.1605 (1.0); 0.1185 (1.3); 0.1050 (1.7); 0.0975 (1.8); 0.0847 (1.9); 0.0715 (0.9); −0.0002 (6.1); −0.0636 (1.2); −0.0759 (1.9); −0.0835 (1.7); −0.0950 (1.5)

Ia-21: $^1$H-NMR (300.2 MHz, CDCl$_3$):

δ=8.7403 (16.0); 7.6467 (5.2); 7.6432 (5.2); 7.6202 (5.9); 7.6164 (5.8); 7.5123 (3.8); 7.5068 (4.1); 7.4868 (5.6); 7.4813 (5.8); 7.3885 (3.0); 7.3845 (3.0); 7.3637 (5.8); 7.3598 (5.5); 7.3385 (3.1); 7.3345 (2.8); 7.2985 (18.9); 7.2511 (3.4); 7.2453 (3.4); 7.2253 (4.5); 7.2200 (4.4); 7.1999 (2.4); 7.1941 (2.2); 5.3360 (0.7); 5.0391 (4.9); 5.0327 (4.9); 4.9914 (6.0); 4.9850 (6.0); 4.5810 (5.6); 4.5758 (5.6); 4.5333 (4.6); 4.5281 (4.6); 3.4960 (3.2); 3.4914 (3.2); 3.4480 (7.0); 3.4435 (6.9); 3.3665 (7.9); 3.3183 (3.7); 2.9938 (1.3); 2.9169 (1.2); 2.8843 (0.7); 2.7854 (9.2); 1.6239 (6.1); 0.9493 (0.8); 0.9339 (1.2); 0.9291 (1.2); 0.9159 (1.4); 0.9082 (1.4); 0.9010 (1.7); 0.8899 (1.5); 0.8684 (2.8); 0.8605 (1.3); 0.8485 (2.0); 0.8409 (1.3); 0.8224 (1.4); 0.8145 (0.9); 0.8031 (1.5); 0.7091 (1.1); 0.6884 (1.3); 0.6831 (1.7); 0.6700 (0.7); 0.6625 (2.0); 0.6439 (2.5); 0.6291 (2.6); 0.6232 (3.3); 0.6178 (2.2); 0.6075 (2.0); 0.5980 (2.5); 0.5912 (2.3); 0.5800 (4.6); 0.5716 (5.4); 0.5552 (2.3); 0.5451 (1.7); 0.5357 (1.8); 0.5294 (1.0); 0.5097 (1.1); 0.3056 (1.7); 0.2850 (1.4); 0.2696 (2.6); 0.2591 (2.2); 0.2500 (2.0); 0.2426 (1.4); 0.2338 (1.5); 0.2250 (2.3); 0.2142 (1.3); 0.2081 (1.8); 0.1741 (0.4); 0.0460 (0.8); 0.0354 (22.6); 0.0244 (0.8)

Ia-22: $^1$H-NMR (499.9 MHz, CDCl$_3$):

δ=8.8447 (16.0); 7.7614 (0.3); 7.7432 (0.3); 7.6133 (3.1); 7.3974 (1.6); 7.3946 (1.7); 7.3825 (4.6); 7.3682 (8.4); 7.3557 (2.8); 7.3529 (2.5); 7.2972 (6.0); 7.2826 (9.5); 7.2679 (4.1); 7.1931 (4.9); 7.1735 (6.6); 7.1560 (4.2); 5.5773 (1.2); 5.1868 (9.1); 5.1576 (9.7); 4.2271 (1.2); 4.2129 (3.0); 4.1987 (3.6); 4.1845 (2.3); 4.1602 (11.4); 4.1309 (10.6); 2.9888 (1.3); 2.1318 (6.3); 2.1006 (1.7); 1.9156 (0.5); 1.9085 (0.5); 1.6526 (0.6); 1.6455 (0.6); 1.5866 (22.1); 1.5722 (22.2); 1.3631 (1.7); 1.3491 (5.4); 1.3350 (5.5); 1.3283 (3.8); 1.3230 (4.0); 1.3157 (4.7); 1.3138 (4.4); 1.3009 (3.4); 1.0954 (3.5); 1.0812 (5.1); 1.0736 (4.5); 1.0685 (4.0); 1.0595 (5.4); 1.0467 (3.6); 0.4461 (2.4); 0.4326 (4.0); 0.4243 (3.2); 0.4186 (3.3); 0.4114 (3.8); 0.3969 (2.4); 0.0926 (3.0); 0.0134 (1.9); −0.0002 (3.4); −0.0094 (3.0); −0.0217 (3.3); −0.0352 (1.7)

Ia-23: $^1$H-NMR (300.2 MHz, CDCl$_3$):

δ=8.7375 (13.6); 8.0412 (1.4); 7.5255 (0.4); 7.5170 (1.4); 7.5105 (3.2); 7.4965 (11.2); 7.4853 (4.4); 7.4787 (1.5); 7.2987 (39.5); 7.2716 (8.2); 7.2658 (6.0); 7.2606 (6.8); 7.2505 (11.5); 7.2411 (1.1); 4.8678 (3.7); 4.8620 (3.8); 4.8201 (5.4); 4.8143 (5.5); 4.6224 (5.0); 4.6176 (5.2); 4.5747 (3.5); 4.5699 (3.5); 3.2828 (3.4); 3.2773 (3.5); 3.2363 (4.3); 3.2308 (4.4); 2.9962 (11.9); 2.9188 (10.2); 2.9025 (4.5); 2.8975 (4.6); 2.8559 (3.5); 2.8511 (3.6); 2.5205 (4.6); 1.6161 (16.0); 0.9021 (0.8); 0.8770 (1.1); 0.8622 (1.2); 0.8546 (1.0); 0.8359 (1.8); 0.8141 (1.8); 0.7941 (1.2); 0.7865 (1.0); 0.7721 (1.5); 0.7685 (1.5); 0.7466 (1.3); 0.6946 (1.1); 0.6734 (1.4); 0.6696 (1.5); 0.6545 (0.8); 0.6481 (1.5); 0.6291 (2.1); 0.6079 (2.4); 0.6041 (1.8); 0.5888 (0.7); 0.5824 (1.5); 0.5682 (0.8); 0.5638 (1.1); 0.5427 (1.1); 0.4635 (1.0); 0.4413 (1.1); 0.4254 (1.9); 0.4158 (0.8); 0.4029 (2.6); 0.3902 (1.6); 0.3783 (1.4); 0.3679 (1.6); 0.3431 (1.1); 0.2702 (1.3); 0.2491 (1.3); 0.2446 (1.5); 0.2349 (1.7); 0.2236 (1.3); 0.2100 (2.3); 0.1975 (1.1); 0.1885 (1.4); 0.1760 (1.1); 0.1718 (1.0); 0.1509 (0.8); 0.0472 (1.3); 0.0364 (45.7); 0.0255 (1.8)

Ia-24: $^1$H-NMR (300.2 MHz, CDCl$_3$):

δ=8.8251 (14.9); 7.6460 (4.7); 7.6424 (5.0); 7.6195 (5.3); 7.6157 (5.6); 7.5759 (3.7); 7.5705 (4.1); 7.5505 (5.0); 7.5451 (5.2); 7.3991 (2.6); 7.3951 (2.7); 7.3741 (5.2); 7.3703 (5.2); 7.3491 (2.9); 7.3451 (2.8); 7.2990 (38.6); 7.2548 (3.0); 7.2491 (3.2); 7.2286 (4.2); 7.2232 (4.1); 7.2035 (2.0); 7.1979 (1.9); 5.2076 (9.3); 5.1598 (10.6); 4.5091 (9.1); 4.4613 (8.0); 3.6882 (6.1); 3.6402 (8.1); 3.3676 (8.5); 3.3195 (6.4); 2.8204 (15.4); 2.0454 (1.1); 1.5862 (16.0); 1.2910 (1.2); 0.9459 (0.5); 0.9256 (3.5); 0.9167 (4.0); 0.8992 (4.0); 0.8908 (9.2); 0.8824 (5.0); 0.8634 (5.5); 0.8575 (5.3); 0.8373 (1.0); 0.6570 (2.6); 0.6372 (3.3); 0.6324 (2.9); 0.6214 (2.1); 0.6112 (3.0); 0.6030 (2.7); 0.5968 (2.0); 0.5769 (2.1); 0.4912 (2.8); 0.4715 (2.5); 0.4635 (2.7); 0.4584 (3.2); 0.4452 (2.2); 0.4372 (2.5); 0.4307 (2.5); 0.4107 (1.8); 0.0488 (1.6); 0.0380 (50.9); 0.0273 (2.1)

Ia-25: $^1$H-NMR (300.2 MHz, CDCl$_3$):

δ=8.8260 (0.7); 8.7932 (12.7); 7.3574 (1.8); 7.3322 (1.4); 7.3103 (0.5); 7.3088 (0.5); 7.2983 (22.0); 7.2216 (0.6); 7.2030 (1.2); 7.1949 (6.6); 7.1807 (3.1); 7.1760 (6.6); 7.1670 (4.4); 7.1539 (4.6); 7.1440 (2.1); 7.1371 (2.0); 7.1165 (0.7); 7.1095 (0.5); 7.0355 (0.4); 5.1070 (5.5); 5.1039 (5.5); 5.0585 (6.2); 5.0554 (5.9); 4.9303 (0.5); 4.7467 (0.4); 4.1617 (1.6); 4.1382 (1.6); 4.1137 (6.0); 4.0654 (4.9); 2.8821 (0.4); 2.8422 (0.4); 2.8038 (0.3); 2.7762 (0.7); 2.0803 (0.7); 2.0440 (1.8); 1.6194 (0.7); 1.5731 (0.5); 1.5313 (16.0); 1.5075 (15.9); 1.3184 (0.4); 1.3104 (2.0); 1.2902 (3.0); 1.2849 (2.6); 1.2734 (2.4); 1.2646 (2.7); 1.2531 (2.7); 1.2479 (2.5); 1.2276 (2.5); 1.0719 (2.2); 1.0514 (2.4); 1.0476 (2.8); 1.0357 (2.9); 1.0273 (2.4); 1.0152 (2.8); 1.0114 (3.1); 0.9910 (2.3); 0.4010 (1.9); 0.3803 (2.4); 0.3756 (2.2); 0.3648 (2.0);

Ia-26: ¹H-NMR (400.1 MHz, d₆-DMSO):

δ=9.1840 (5.3); 7.9739 (0.7); 7.2541 (1.1); 7.2349 (2.0); 7.2152 (1.2); 6.9614 (4.1); 6.9423 (1.6); 6.8521 (1.2); 6.8490 (1.2); 6.8328 (1.2); 6.8275 (1.1); 5.4451 (2.9); 4.9197 (1.3); 4.8840 (1.5); 4.4374 (1.7); 4.4015 (1.5); 3.7625 (16.0); 3.3404 (87.2); 3.0066 (4.3); 2.9122 (4.2); 2.7532 (3.9); 2.5269 (4.8); 2.5228 (6.4); 2.5188 (4.9); 0.6057 (0.4); 0.6009 (0.4); 0.5941 (0.4); 0.5866 (0.5); 0.5544 (0.4); 0.5354 (0.4); 0.4848 (0.4); 0.4727 (1.2); 0.4572 (1.2); 0.4443 (0.8); 0.4278 (1.4); 0.4094 (0.5); 0.3959 (0.3); 0.0318 (0.4); 0.0190 (0.5); 0.0122 (0.5); 0.0069 (0.5); −0.0002 (0.6); −0.0060 (0.6); −0.0112 (0.6); −0.0265 (0.4)

Ia-27: ¹H-NMR (400.1 MHz, d₆-DMSO):

δ=9.1780 (5.5); 7.9749 (0.8); 7.2905 (3.6); 7.2694 (4.0); 6.8965 (4.2); 6.8754 (3.8); 5.3904 (3.4); 4.8853 (1.6); 4.8495 (1.8); 4.4299 (1.9); 4.3941 (1.7); 3.7574 (16.0); 3.3389 (97.6); 3.0063 (0.5); 2.9713 (2.7); 2.9566 (2.6); 2.9132 (4.6); 2.7542 (4.3); 2.5235 (6.7); 0.5851 (0.4); 0.5614 (0.5); 0.5544 (0.5); 0.5315 (0.5); 0.5137 (0.4); 0.4631 (0.5); 0.4481 (0.9); 0.4318 (1.1); 0.4091 (1.4); 0.3950 (1.2); 0.0252 (0.4); −0.0002 (0.8); −0.0110 (0.7); −0.0186 (0.5); −0.0323 (0.4)

Ia-28: ¹H-NMR (400.1 MHz, d₆-DMSO):

δ=9.1898 (7.0); 7.9830 (1.0); 7.2342 (0.8); 7.2156 (2.7); 7.1965 (5.0); 7.1806 (3.1); 7.1619 (1.2); 7.0966 (2.1); 7.0787 (1.6); 5.4282 (4.2); 4.9160 (1.9); 4.8802 (2.2); 4.4492 (2.4); 4.4135 (2.1); 3.3483 (108.4); 3.0413 (0.6); 3.0070 (3.4); 2.9932 (3.2); 2.9587 (0.6); 2.9215 (5.6); 2.7623 (5.2); 2.5321 (7.8); 2.3224 (16.0); 0.6140 (0.4); 0.5950 (0.6); 0.5748 (0.7); 0.5626 (0.4); 0.5476 (0.6); 0.5426 (0.5); 0.5341 (0.7); 0.5052 (0.3); 0.4913 (0.3); 0.4719 (0.6); 0.4611 (1.6); 0.4464 (1.5); 0.4234 (1.8); 0.4134 (1.2); 0.3933 (0.6); 0.0436 (0.4); 0.0330 (0.5); 0.0188 (0.6); 0.0084 (0.8); −0.0002 (1.0); −0.0111 (0.6); −0.0256 (0.6)

Ia-29: ¹H-NMR (300.2 MHz, CDCl₃):

δ=8.8582 (16.0); 7.4632 (4.8); 7.4544 (5.5); 7.4419 (4.9); 7.4331 (5.3); 7.3212 (1.8); 7.3146 (2.1); 7.3072 (2.7); 7.2982 (8.0); 7.2854 (2.7); 7.2784 (3.2); 7.2704 (2.4); 7.0974 (4.3); 7.0671 (7.2); 7.0369 (3.4); 5.1457 (8.8); 5.0978 (10.2); 4.5378 (8.5); 4.4899 (7.3); 3.4102 (5.2); 3.3626 (7.8); 3.1847 (6.5); 3.1793 (6.6); 3.1372 (4.6); 3.1317 (4.7); 3.0483 (1.8); 2.0408 (0.4); 0.8811 (0.4); 0.8600 (3.4); 0.8546 (4.6); 0.8269 (9.2); 0.7958 (7.4); 0.7743 (0.9); 0.6037 (2.6); 0.5811 (3.7); 0.5682 (2.2); 0.5570 (3.0); 0.5501 (2.9); 0.5445 (2.1); 0.5233 (2.1); 0.4183 (3.1); 0.3983 (3.0); 0.3867 (4.1); 0.3715 (2.6); 0.3644 (3.1); 0.3577 (2.8); 0.3375 (2.1); 0.0286 (4.3)

Ia-30: ¹H-NMR (400.1 MHz, d₆-DMSO):

δ=9.0667 (6.8); 7.9605 (1.0); 7.2486 (4.0); 7.2290 (5.4); 7.1099 (5.0); 7.0904 (3.9); 4.9231 (2.6); 4.8874 (2.8); 4.5366 (6.0); 4.2227 (2.7); 4.1869 (2.5); 3.3278 (109.4); 2.9765 (1.6); 2.9420 (3.0); 2.8986 (5.7); 2.8689 (3.1); 2.8344 (1.7); 2.7396 (5.4); 2.5091 (8.2); 2.2865 (15.2); 1.2020 (16.0); 0.2794 (0.8); 0.2650 (1.5); 0.2507 (1.1); −0.2287 (0.4); −0.2430 (0.9); −0.2515 (1.5); −0.2691 (3.5); −0.2869 (1.4); −0.2954 (1.0); −0.3087 (0.6); −0.4797 (1.0); −0.4864 (1.0); −0.4946 (1.7); −0.5088 (0.9); −0.5168 (0.7)

Ia-31: ¹H-NMR (300.2 MHz, CDCl₃):

δ=8.8515 (16.0); 7.2983 (7.3); 7.2933 (2.8); 6.9631 (8.3); 6.9562 (10.1); 6.9362 (9.9); 6.8371 (2.2); 6.8296 (3.0); 6.8224 (2.1); 6.8073 (4.3); 6.7998 (5.8); 6.7938 (3.6); 6.7775 (2.3); 6.7700 (2.9); 6.7641 (1.8); 5.0232 (8.6); 5.0186 (4.2); 4.9753 (10.8); 4.9708 (5.2); 4.6349 (9.6); 4.5871 (7.6); 4.1862 (0.4); 4.1624 (1.2); 4.1574 (0.6); 4.1385 (1.2); 4.1334 (0.6); 4.1146 (0.4); 3.3962 (7.2); 3.3500 (9.0); 3.0204 (9.6); 2.9741 (7.8); 2.9099 (0.6); 2.8057 (0.4); 2.0766 (5.4); 2.0715 (2.3); 2.0433 (1.2); 2.0384 (0.6); 1.3147 (1.6); 1.3097 (0.8); 1.2909 (3.2); 1.2859 (1.6); 1.2670 (1.7); 1.2620 (0.8); 0.8243 (1.7); 0.8040 (3.1); 0.7980 (3.3); 0.7884 (3.5); 0.7797 (3.7); 0.7683 (4.5); 0.7640 (4.3); 0.7460 (3.2); 0.7154 (0.4); 0.6862 (2.1); 0.6618 (3.9); 0.6569 (2.8); 0.6500 (3.6); 0.6419 (3.5); 0.6365 (2.5); 0.6316 (2.8); 0.6259 (4.5); 0.6209 (2.7); 0.6077 (6.0); 0.6018 (6.2); 0.5841 (4.4); 0.5784 (3.0); 0.5676 (3.6); 0.5599 (3.6); 0.5547 (2.7); 0.5484 (3.5); 0.5436 (2.7); 0.5241 (1.9); 0.4151 (3.0); 0.4101 (2.0); 0.3975 (4.0); 0.3927 (4.5); 0.3810 (3.8); 0.3734 (3.7); 0.3679 (2.6); 0.3636 (3.1); 0.3569 (3.0); 0.3372 (1.8); 0.0311 (7.4); 0.0261 (2.9)

Ia-32: ¹H-NMR (400.1 MHz, d₆-DMSO):

δ=8.9258 (0.8); 7.1126 (0.6); 5.2743 (0.6); 4.7317 (0.4); 4.1829 (0.4); 4.1470 (0.3); 3.0785 (16.0); 2.9966 (0.4); 2.9290 (0.4); 2.6507 (0.5); 2.4914 (0.5); 2.2615 (1.5); 2.2578 (1.4)

Ia-33: ¹H-NMR (400.1 MHz, d₆-DMSO):

δ=9.1899 (6.9); 7.9873 (0.8); 7.2763 (4.1); 7.2570 (5.8); 7.1505 (5.3); 7.1312 (4.2); 5.4164 (4.8); 4.9026 (2.1); 4.8669 (2.5); 4.4428 (2.6); 4.4070 (2.3); 3.3539 (105.0); 3.0361 (0.7); 3.0016 (3.7); 2.9873 (3.6); 2.9523 (0.7); 2.9260 (4.4); 2.7667 (4.0); 2.5370 (8.8); 2.5334 (8.1); 2.3189 (16.0); 0.6157 (0.4); 0.5976 (0.7); 0.5774 (0.7); 0.5650 (0.5); 0.5458 (0.6); 0.5359 (0.7); 0.5070 (0.3); 0.4936 (0.4); 0.4861 (0.3); 0.4746 (0.6); 0.4634 (1.7); 0.4461 (1.7); 0.4249 (2.0); 0.4128 (1.3); 0.3956 (0.6); 0.0431 (0.4); 0.0328 (0.5); 0.0099 (1.0); −0.0002 (1.1); −0.0242 (0.6); −0.0344 (0.4)

Ia-34: ¹H-NMR (400.1 MHz, d₆-DMSO):

δ=8.8291 (1.0); 7.0373 (0.6); 7.0159 (0.7); 6.6302 (0.7); 6.6088 (0.7); 4.6774 (0.4); 4.6417 (0.4); 4.2890 (0.8); 3.9810 (0.4); 3.9453 (0.4); 3.4996 (3.0); 3.0891 (16.0); 2.6826 (0.4); 2.6594 (1.0); 2.6132 (0.4); 2.5004 (0.9); 2.2701 (1.3); 2.2662 (1.0); 0.9597 (2.2); −0.5092 (0.5)

Ia-35: ¹H-NMR (400.1 MHz, d₆-DMSO):

δ=8.9567 (2.2); 6.9765 (0.7); 6.9544 (1.1); 6.9336 (0.7); 5.2074 (1.8); 4.8455 (0.8); 4.8095 (0.9); 4.3293 (0.8); 4.2932 (0.8); 3.1013 (16.0); 2.9949 (0.4); 2.9593 (0.7); 2.8834 (0.7); 2.8479 (0.4); 2.6742 (0.3); 2.2849 (2.4); 2.2810 (1.9); 0.5560 (0.3); 0.5529 (0.3); 0.4633 (0.3); 0.4456 (0.4); 0.1730 (0.3); 0.0267 (0.3)

Ia-36: ¹H-NMR (400.1 MHz, d₆-DMSO):

δ=8.9404 (1.1); 6.7651 (0.3); 5.1418 (0.9); 4.8611 (0.4); 4.8251 (0.4); 4.2631 (0.4); 4.2271 (0.4); 3.0983 (16.0); 2.9619 (1.0); 2.6701 (1.3); 2.5108 (1.2); 2.2848 (1.0); 2.2806 (1.3); 2.2764 (1.0); 1.9941 (1.4)

Ia-37: ¹H-NMR (499.9 MHz, CDCl₃):

δ=8.7792 (4.2); 7.4743 (1.0); 7.4671 (1.0); 7.4627 (1.0); 7.4554 (1.2); 7.4101 (1.1); 7.4030 (1.0); 7.3986 (1.1); 7.3913 (1.3); 7.2619 (4.8); 7.2414 (0.6); 7.2340 (2.9); 7.2270 (2.4); 7.2222 (2.4); 7.2151 (2.5); 7.2076 (0.4); 5.2994 (1.4); 4.9454 (2.0); 4.9155 (2.9); 4.7902 (2.5); 4.7602 (1.8); 3.6313 (16.0); 3.5279 (0.5); 3.3315 (1.6); 3.3223 (1.4); 3.3016 (2.4); 3.2116 (0.3); 3.1822 (2.3); 3.1522 (2.2); 3.0866 (0.6); 3.0227 (1.3); 1.5695 (2.3); 0.8168 (0.8); 0.8128 (0.5); 0.8070 (0.9); 0.7997 (1.2); 0.7962 (1.4); 0.7920 (1.5); 0.7864 (1.1); 0.7789 (1.3); 0.7720 (1.3); 0.7595 (0.4); 0.6764 (0.4); 0.6645 (0.9);

0.6552 (0.5); 0.6499 (0.9); 0.6453 (1.4); 0.6344 (0.6); 0.6288 (1.4); 0.6176 (0.4); 0.6138 (0.4); 0.6087 (0.6); −0.0002 (5.6)

Ia-38: $^1$H-NMR (400.1 MHz, $d_6$-DMSO):

δ=8.9360 (2.2); 7.7118 (0.5); 7.2690 (0.4); 7.2527 (0.4); 7.0732 (0.4); 7.0547 (0.6); 7.0513 (0.6); 5.3300 (1.8); 4.7934 (0.8); 4.7573 (0.9); 4.3086 (0.9); 4.2725 (0.8); 3.0767 (16.0); 2.9798 (0.4); 2.9440 (0.8); 2.8935 (0.8); 2.8581 (0.4); 2.6505 (3.0); 2.4909 (2.8); 2.2653 (2.1); 2.2611 (2.9); 2.2570 (2.3); 0.4004 (0.3); 0.3922 (0.4); 0.3738 (0.4); 0.3607 (0.4); 0.3527 (0.4); 0.3347 (0.4); 0.1862 (0.3); −0.0002 (0.3)

Ia-39: $^1$H-NMR (300.2 MHz, CDCl$_3$):

δ=8.8402 (16.0); 7.5669 (4.1); 7.5463 (4.7); 7.5382 (5.0); 7.5177 (4.6); 7.2984 (6.1); 7.2149 (4.5); 7.2062 (5.0); 7.1870 (4.6); 7.1782 (4.9); 7.0838 (2.9); 7.0750 (2.7); 7.0564 (4.4); 7.0481 (4.0); 7.0289 (2.6); 7.0201 (2.3); 5.1826 (9.1); 5.1348 (10.4); 4.4749 (9.2); 4.4271 (8.1); 3.6360 (7.0); 3.5876 (8.9); 3.2639 (8.2); 3.2155 (6.4); 2.9348 (5.7); 2.0411 (2.2); 0.9208 (0.5); 0.9008 (4.6); 0.8954 (5.1); 0.8737 (6.0); 0.8679 (11.0); 0.8619 (6.3); 0.8378 (8.4); 0.8165 (1.0); 0.6234 (2.7); 0.6034 (3.8); 0.5985 (3.3); 0.5882 (2.5); 0.5762 (3.5); 0.5704 (3.2); 0.5631 (2.2); 0.5430 (2.2); 0.4442 (2.9); 0.4353 (0.9); 0.4242 (2.9); 0.4134 (4.2); 0.3972 (2.7); 0.3907 (3.0); 0.3837 (2.8); 0.3637 (2.0); 0.0309 (6.4)

Ia-40: $^1$H-NMR (400.1 MHz, $d_6$-DMSO):

δ=8.9562 (2.6); 7.7373 (0.6); 7.3142 (0.5); 7.2936 (1.0); 7.2730 (0.6); 7.1940 (0.6); 7.1890 (0.7); 7.1694 (0.6); 7.1644 (0.7); 7.0645 (0.7); 7.0599 (0.7); 7.0438 (0.6); 7.0392 (0.6); 5.3308 (2.0); 4.8135 (0.9); 4.7775 (1.0); 4.2748 (1.0); 4.2388 (0.9); 3.1054 (16.0); 2.9114 (2.4); 2.6756 (3.3); 2.5162 (3.1); 2.2905 (2.3); 2.2865 (3.1); 2.2825 (2.4); 0.4499 (0.4); 0.4415 (0.4); 0.3868 (0.4); 0.3785 (0.4); 0.3607 (0.4); 0.1930 (0.4); 0.1749 (0.4); 0.1668 (0.3); −0.0002 (0.4); −0.0104 (0.3); −0.0146 (0.3); −0.0262 (0.3)

Ia-41: $^1$H-NMR (400.1 MHz, $d_6$-DMSO):

δ=8.9558 (1.1); 6.9037 (0.4); 5.3412 (0.8); 4.8319 (0.4); 4.7959 (0.4); 4.2936 (0.4); 4.2575 (0.4); 3.1025 (16.0); 2.9693 (0.5); 2.9625 (0.6); 2.6717 (1.6); 2.5123 (1.5); 2.2865 (1.0); 2.2824 (1.4); 2.2783 (1.1)

Ia-42: $^1$H-NMR (300.2 MHz, CDCl$_3$):

δ=8.8681 (16.0); 7.2983 (3.0); 7.2160 (1.8); 7.2059 (2.2); 7.1966 (2.1); 7.1871 (3.8); 7.1770 (2.3); 7.1680 (2.0); 7.1579 (2.0); 7.1138 (1.3); 7.0985 (1.5); 7.0839 (3.8); 7.0684 (4.0); 7.0541 (3.2); 7.0458 (2.3); 7.0380 (3.8); 7.0317 (2.6); 7.0212 (3.4); 7.0158 (1.6); 7.0102 (2.3); 7.0068 (2.8); 7.0015 (1.4); 6.9968 (1.9); 6.9912 (1.6); 6.9803 (1.0); 6.9772 (0.9); 6.9667 (0.7); 5.1444 (7.2); 5.0965 (8.4); 4.5628 (7.7); 4.5149 (6.6); 3.4093 (3.7); 3.3614 (5.6); 3.1988 (5.6); 3.1933 (5.8); 3.1672 (2.5); 3.1515 (4.5); 3.1459 (4.2); 2.0379 (0.7); 0.8447 (3.9); 0.8392 (4.2); 0.8173 (5.0); 0.8118 (9.8); 0.8059 (5.2); 0.7814 (8.4); 0.7607 (0.7); 0.6022 (2.6); 0.5824 (3.3); 0.5773 (2.8); 0.5669 (2.1); 0.5551 (3.2); 0.5494 (2.7); 0.5419 (1.8); 0.5220 (2.0); 0.4269 (2.7); 0.4175 (0.6); 0.4071 (2.5); 0.3963 (4.1); 0.3798 (2.3); 0.3738 (2.5); 0.3662 (2.4); 0.3464 (1.7); 0.0235 (2.8)

Ia-43: $^1$H-NMR (400.1 MHz, $d_6$-DMSO):

δ=8.9510 (3.0); 7.2207 (0.4); 7.2154 (0.4); 7.2074 (0.4); 7.1991 (0.4); 7.1947 (0.4); 6.9408 (0.4); 6.9295 (0.4); 6.9178 (0.4); 5.4033 (2.6); 4.7982 (1.1); 4.7621 (1.3); 4.3148 (1.2); 4.2787 (1.0); 3.0769 (16.0); 2.9976 (0.6); 2.9621 (1.2); 2.9368 (1.3); 2.9015 (0.8); 2.6523 (0.6); 2.4930 (0.5); 2.2627 (3.6); 0.4704 (0.5); 0.4589 (0.4); 0.4530 (0.4); 0.4442 (0.5); 0.4262 (0.4); 0.3923 (0.4); 0.3840 (0.5); 0.3777 (0.3); 0.3663 (0.5); 0.3513 (0.3); 0.2208 (0.3); 0.2061 (0.4); 0.1942 (0.4); 0.1882 (0.4); 0.1802 (0.4); 0.0261 (0.4); 0.0153 (0.4); −0.0002 (0.4)

Ia-44: $^1$H-NMR (400.1 MHz, $d_6$-DMSO):

δ=8.9397 (1.1); 7.0692 (0.5); 7.0525 (0.3); 5.3392 (0.8); 4.7874 (0.4); 4.7513 (0.5); 4.3202 (0.5); 4.2840 (0.4); 3.0804 (16.0); 2.9403 (0.4); 2.8785 (0.4); 2.6495 (1.2); 2.4899 (1.2); 2.2603 (1.5)

Ia-45: $^1$H-NMR (400.1 MHz, $d_6$-DMSO):

δ=8.9002 (2.1); 7.7161 (0.4); 7.1316 (0.3); 7.1108 (0.5); 7.0951 (0.4); 6.9436 (0.5); 6.9210 (0.7); 6.8990 (0.4); 5.0078 (1.6); 4.8967 (0.7); 4.8608 (0.8); 4.2072 (0.7); 4.1714 (0.7); 3.2342 (0.3); 3.2043 (0.5); 3.1988 (0.6); 3.1160 (0.6); 3.1102 (0.6); 3.0812 (16.0); 2.6547 (2.3); 2.4952 (2.1); 2.2694 (1.7); 2.2653 (2.4); 2.2612 (1.9); 2.0974 (4.0); 0.5329 (0.3)

Ia-46: $^1$H-NMR (400.1 MHz, $d_6$-DMSO):

δ=8.9466 (1.2); 7.7408 (0.3); 5.1863 (0.7); 4.8661 (0.4); 4.8301 (0.5); 4.2677 (0.4); 4.2317 (0.4); 3.6127 (3.4); 3.1102 (16.0); 2.9780 (1.1); 2.6794 (1.9); 2.5200 (1.8); 2.2942 (1.1); 2.2901 (1.5); 2.2859 (1.2)

Ia-47: $^1$H-NMR (400.1 MHz, $d_6$-DMSO):

δ=8.9799 (2.1); 7.2264 (1.1); 7.1369 (0.6); 7.1218 (1.9); 7.1107 (0.8); 7.1062 (0.6); 5.3680 (1.8); 4.8108 (0.8); 4.7748 (0.9); 4.2737 (0.8); 4.2377 (0.8); 3.1034 (16.0); 2.9604 (0.6); 2.9258 (0.9); 2.8040 (0.9); 2.7695 (0.6); 2.6785 (1.8); 2.5195 (1.6); 2.2929 (1.7); 2.2890 (2.2); 0.2546 (0.3); 0.2374 (0.4); 0.1867 (0.4); −0.0002 (0.3)

Ia-48: $^1$H-NMR (400.1 MHz, $d_6$-DMSO):

δ=8.9515 (1.1); 5.2688 (0.9); 4.8160 (0.4); 4.7801 (0.4); 4.2769 (0.4); 4.2409 (0.4); 3.6579 (3.1); 3.1130 (16.0); 2.8967 (1.1); 2.6827 (1.8); 2.5232 (1.7); 2.2935 (1.3); 2.2896 (1.1)

Ia-49: $^1$H-NMR (400.1 MHz, $d_6$-DMSO):

δ=8.9527 (1.9); 7.7474 (0.4); 6.5422 (1.1); 6.5180 (1.1); 5.1221 (1.3); 4.8529 (0.6); 4.8170 (0.7); 4.2729 (0.7); 4.2369 (0.6); 3.5764 (5.5); 3.1107 (16.0); 2.8914 (1.1); 2.6859 (2.1); 2.5267 (1.9); 2.3006 (1.7); 2.2964 (2.3); 2.2922 (1.8)

Ia-50: $^1$H-NMR (400.1 MHz, $d_6$-DMSO):

δ=8.9430 (1.1); 5.2744 (0.8); 4.8012 (0.4); 4.7653 (0.4); 4.2713 (0.4); 4.2353 (0.4); 3.6803 (2.5); 3.0966 (16.0); 2.8893 (1.0); 2.6672 (1.0); 2.5079 (0.9); 2.2820 (1.0); 2.2778 (1.2); 2.2737 (1.1)

Ia-51: $^1$H-NMR (400.1 MHz, $d_6$-DMSO):

δ=8.9420 (2.3); 7.7154 (0.4); 7.2945 (0.6); 7.2882 (0.4); 7.2808 (0.6); 7.2705 (0.6); 7.2594 (0.4); 5.3449 (1.8); 4.7826 (0.8); 4.7466 (0.9); 4.2614 (0.9); 4.2254 (0.8); 3.0802 (16.0); 2.8787 (2.1); 2.6540 (2.1); 2.4947 (1.9); 2.2686 (2.0); 2.2645 (2.7); 2.2605 (2.1); 0.4528 (0.3); 0.4442 (0.4); 0.3898 (0.3); 0.3815 (0.4); 0.3636 (0.4); 0.1958 (0.3); 0.1920 (0.3); 0.1776 (0.3); 0.0094 (0.3)

Ia-52: $^1$H-NMR (400.1 MHz, $d_6$-DMSO):

δ=8.9672 (1.0); 7.1424 (0.5); 7.1201 (0.4); 5.3604 (0.8); 4.7870 (0.4); 4.7509 (0.4); 4.2742 (0.4); 4.2382 (0.4); 3.0961 (16.0); 2.9084 (0.4); 2.7732 (0.4); 2.6660 (1.2); 2.5067 (1.1); 2.2809 (1.1); 2.2768 (1.4); 2.2726 (1.1)

Ia-53: $^1$H-NMR (400.1 MHz, $d_6$-DMSO):

δ=8.9710 (2.1); 7.3273 (0.4); 7.3098 (0.5); 7.0036 (0.4); 6.9979 (0.4); 6.8648 (0.5); 6.8591 (0.4); 5.3259 (1.7); 4.8292 (0.7); 4.7932 (0.8); 4.2744 (0.8); 4.2384 (0.7); 3.1280 (16.0); 2.9166 (2.1); 2.6888 (1.5); 2.5292 (1.4); 2.3003 (2.1); 0.3636 (0.4)

Ia-54: $^1$H-NMR (400.1 MHz, $d_6$-DMSO):

δ=8.9445 (2.1); 7.1978 (0.3); 6.8932 (0.4); 5.2688 (1.6); 4.8448 (0.8); 4.8087 (0.9); 4.3351 (0.8); 4.2990 (0.8); 3.0872 (16.0); 3.0577 (0.6); 3.0221 (0.8); 2.9462 (0.7);

2.9110 (0.4); 2.6551 (0.5); 2.4955 (0.5); 2.2659 (1.4); 0.5401 (0.4); 0.4656 (0.3); 0.4566 (0.3); 0.4395 (0.4); 0.1867 (0.3); 0.0262 (0.3)

Ia-55: $^1$H-NMR (400.1 MHz, d$_6$-DMSO):

δ=8.9523 (1.1); 5.2942 (0.9); 4.8183 (0.4); 4.7823 (0.4); 4.2863 (0.4); 4.2503 (0.4); 3.1063 (16.0); 2.9234 (1.1); 2.6767 (1.3); 2.5173 (1.2); 2.2912 (1.1); 2.2874 (1.4); 2.2833 (1.1); 2.0546 (1.5); 2.0514 (1.5)

Ia-56: $^1$H-NMR (400.1 MHz, d$_6$-DMSO):

δ=8.9482 (3.6); 7.1654 (0.4); 7.1608 (0.4); 7.1523 (0.4); 7.1456 (0.5); 7.1405 (0.6); 7.1309 (1.2); 7.1098 (0.9); 7.1038 (0.8); 7.0822 (0.4); 6.9817 (0.5); 6.9710 (0.5); 6.9612 (0.4); 6.9504 (0.4); 5.5086 (1.3); 5.3303 (3.1); 4.7631 (1.3); 4.7270 (1.5); 4.2629 (1.5); 4.2268 (1.3); 3.0674 (16.0); 2.9251 (1.0); 2.8902 (1.4); 2.7526 (1.4); 2.7177 (0.9); 2.2641 (1.9); 2.2599 (2.5); 2.2558 (1.9); 0.3105 (0.4); 0.3065 (0.4); 0.2978 (0.3); 0.2920 (0.5); 0.2842 (0.5); 0.2795 (0.5); 0.2724 (0.4); 0.2658 (0.6); 0.2544 (0.5); 0.2467 (0.6); 0.2290 (0.7); 0.2151 (0.4); 0.1842 (0.5); 0.1711 (0.6); 0.1658 (0.5); 0.1586 (0.4); 0.1524 (0.5); 0.1454 (0.4); 0.0169 (0.4); 0.0035 (0.5); −0.0002 (0.5); −0.0097 (0.5); −0.0135 (0.5); −0.0228 (0.4); −0.0271 (0.4)

Ia-57: $^1$H-NMR (400.1 MHz, d$_6$-DMSO):

δ=8.9997 (8.0); 7.7879 (1.4); 7.1011 (4.3); 7.0814 (5.7); 6.9512 (5.1); 6.9318 (4.1); 5.2562 (6.7); 4.8382 (2.8); 4.8024 (3.2); 4.2549 (3.1); 4.2189 (2.9); 3.1591 (14.0); 2.9275 (1.8); 2.8927 (3.3); 2.8243 (3.2); 2.7896 (1.8); 2.7256 (8.4); 2.5663 (7.8); 2.3409 (6.9); 2.3368 (9.3); 2.3326 (7.0); 2.1185 (16.0); 0.4520 (0.5); 0.4353 (0.9); 0.4253 (0.9); 0.4192 (1.1); 0.4077 (1.1); 0.3925 (0.9); 0.3400 (0.6); 0.3221 (1.0); 0.3137 (1.2); 0.3076 (0.8); 0.2%1 (1.4); 0.2813 (0.9); 0.2141 (0.9); 0.2003 (1.2); 0.1961 (1.1); 0.1878 (0.9); 0.1821 (1.1); 0.1743 (0.9); 0.1557 (0.6); 0.0264 (0.8); 0.0087 (1.1); −0.0002 (1.1); −0.0047 (1.0); −0.0139 (0.9); −0.0179 (0.9); −0.0318 (0.6)

Ia-58: $^1$H-NMR (400.1 MHz, d$_6$-DMSO):

δ=8.9996 (5.4); 7.7859 (0.9); 7.1259 (3.3); 7.1045 (3.7); 6.7085 (3.8); 6.6870 (3.6); 5.2435 (4.7); 4.8298 (1.9); 4.7939 (2.1); 4.2548 (2.1); 4.2190 (1.9); 3.5668 (16.0); 3.1574 (9.6); 2.9091 (1.3); 2.8739 (2.3); 2.7990 (2.2); 2.7640 (1.2); 2.7236 (5.0); 2.5643 (4.7); 2.3389 (4.6); 2.3349 (6.1); 2.3308 (4.6); 0.4386 (0.3); 0.4211 (0.6); 0.4121 (0.6); 0.4058 (0.7); 0.3973 (0.8); 0.3795 (0.6); 0.3364 (0.4); 0.3179 (0.7); 0.3098 (0.8); 0.3034 (0.5); 0.2919 (0.9); 0.2771 (0.6); 0.2121 (0.6); 0.1985 (0.8); 0.1855 (0.6); 0.1802 (0.8); 0.1723 (0.6); 0.1538 (0.4); 0.0266 (0.6); 0.0091 (0.7); −0.0002 (0.7); −0.0047 (0.7); −0.0142 (0.6); −0.0176 (0.6); −0.0318 (0.4)

Ia-59: $^1$H-NMR (300.2 MHz, CDCl$_3$):

δ=8.8560 (16.0); 8.4551 (8.3); 8.4456 (12.3); 8.4396 (9.0); 7.5781 (2.4); 7.5704 (3.1); 7.5635 (2.4); 7.5472 (2.4); 7.5402 (3.1); 7.5326 (2.3); 7.2988 (19.1); 5.0719 (8.3); 5.0241 (10.1); 4.6298 (9.0); 4.5820 (7.4); 3.4329 (5.6); 3.3861 (7.4); 3.3457 (12.0); 3.1140 (7.0); 3.0672 (5.3); 2.0445 (0.7); 1.6677 (7.5); 1.2899 (0.6); 0.7894 (1.5); 0.7697 (2.1); 0.7614 (1.7); 0.7537 (2.5); 0.7455 (2.5); 0.7338 (3.2); 0.7297 (3.0); 0.7137 (2.6); 0.6898 (0.6); 0.6494 (1.7); 0.6251 (3.0); 0.6134 (2.4); 0.6053 (2.6); 0.5891 (3.7); 0.5736 (9.0); 0.5583 (3.7); 0.5419 (2.6); 0.5339 (2.4); 0.5224 (2.7); 0.4980 (1.6); 0.3788 (0.5); 0.3552 (2.4); 0.3394 (2.8); 0.3351 (3.1); 0.3232 (2.6); 0.3155 (2.5); 0.3075 (1.9); 0.2990 (2.2); 0.2794 (1.7); 0.0454 (0.8); 0.0346 (24.8); 0.0238 (1.1)

Ia-60: $^1$H-NMR (400.1 MHz, d$_6$-DMSO):

δ=8.9956 (5.5); 7.7750 (0.8); 7.0546 (1.0); 7.0355 (2.0); 7.0151 (1.2); 6.7876 (4.2); 6.7703 (1.6); 6.6526 (1.2); 6.6351 (1.1); 6.6294 (1.1); 5.2813 (4.7); 4.8482 (1.9); 4.8123 (2.1); 4.2499 (2.1); 4.2139 (1.9); 3.5619 (16.0); 3.1463 (11.4); 2.9265 (1.1); 2.8920 (2.5); 2.8479 (2.4); 2.8133 (1.1); 2.7126 (4.9); 2.5532 (4.5); 2.3279 (5.4); 2.3238 (7.2); 2.3197 (5.5); 0.4707 (0.4); 0.4529 (0.7); 0.4439 (0.6); 0.4376 (0.7); 0.4288 (0.8); 0.4112 (0.6); 0.3496 (0.4); 0.3316 (0.7); 0.3232 (0.8); 0.3170 (0.6); 0.3052 (0.9); 0.2907 (0.6); 0.2142 (0.6); 0.2005 (0.8); 0.1961 (0.7); 0.1879 (0.6); 0.1821 (0.8); 0.1742 (0.7); 0.1558 (0.4); 0.0267 (0.6); 0.0091 (0.7); −0.0002 (0.7); −0.0048 (0.7); −0.0138 (0.6); −0.0177 (0.6); −0.0317 (0.4)

Ia-61: $^1$H-NMR (400.1 MHz, d$_6$-DMSO):

δ=9.3091 (5.4); 8.1908 (0.8); 7.4557 (1.1); 7.4362 (2.1); 7.4166 (1.4); 7.1921 (2.1); 7.1873 (2.0); 7.1778 (1.8); 7.1588 (1.5); 7.0454 (1.2); 7.0399 (1.2); 7.0252 (1.1); 7.0194 (1.1); 5.1863 (1.8); 5.1504 (2.0); 4.8257 (4.5); 4.4532 (2.0); 4.4174 (1.9); 3.9779 (16.0); 3.5628 (7.7); 3.2472 (1.3); 3.2129 (2.1); 3.1285 (4.8); 3.1061 (2.2); 3.0719 (1.4); 2.9693 (4.4); 2.7438 (3.7); 2.7397 (4.9); 2.7356 (3.7); 1.4440 (11.5); 0.5482 (0.4); 0.5383 (0.5); 0.5247 (1.0); 0.5145 (0.7); 0.5030 (0.5); 0.0228 (0.3); 0.0087 (0.6); −0.0002 (1.0); −0.0140 (0.8); −0.0225 (1.2); −0.0330 (0.8); −0.0482 (1.0); −0.0574 (0.7); −0.0712 (0.4); −0.2350 (0.5); −0.2424 (0.6); −0.2478 (0.7); −0.2562 (1.1); −0.2625 (0.6); −0.2700 (0.6); −0.2787 (0.5)

Ia-62: $^1$H-NMR (400.1 MHz, d$_6$-DMSO):

δ=8.9922 (7.6); 7.7488 (1.8); 7.3830 (3.6); 7.2611 (1.6); 7.2412 (2.0); 7.1926 (1.7); 7.1735 (2.5); 7.0893 (2.3); 7.0698 (3.4); 7.0504 (1.4); 5.3806 (6.8); 4.8207 (2.7); 4.7846 (3.0); 4.2743 (3.0); 4.2382 (2.7); 3.1198 (16.0); 2.9569 (2.0); 2.9224 (3.0); 2.8065 (2.9); 2.7718 (2.0); 2.6866 (10.9); 2.5271 (10.1); 2.3018 (8.1); 2.2978 (10.8); 2.2937 (8.2); 0.3570 (0.4); 0.3427 (0.8); 0.3391 (0.8); 0.3298 (0.8); 0.3249 (1.1); 0.3163 (1.0); 0.3126 (1.0); 0.2985 (1.0); 0.2879 (0.7); 0.2699 (0.9); 0.2618 (1.2); 0.2442 (1.4); 0.2305 (1.0); 0.2057 (1.1); 0.1927 (1.2); 0.1883 (1.0); 0.1795 (0.8); 0.1745 (1.1); 0.1670 (0.8); 0.1485 (0.5); 0.0262 (0.8); 0.0128 (1.0); 0.0095 (1.0); −0.0002 (1.1); −0.0135 (0.9); −0.0175 (0.9); −0.0311 (0.6)

Ia-63: $^1$H-NMR (400.1 MHz, d$_6$-DMSO):

δ=8.8860 (7.3); 7.7532 (1.6); 7.3848 (3.5); 7.2319 (1.5); 7.2120 (2.0); 7.1734 (1.7); 7.1541 (2.4); 7.0724 (2.3); 7.0529 (3.3); 7.0335 (1.4); 4.7482 (2.4); 4.7124 (2.7); 4.5231 (6.2); 4.0387 (2.8); 4.0029 (2.6); 3.1238 (16.0); 2.8083 (1.4); 2.7740 (3.2); 2.7311 (3.3); 2.6910 (9.7); 2.5316 (8.7); 2.3062 (8.1); 2.3022 (10.8); 2.2981 (8.2); 1.0101 (15.9); 0.0150 (0.9); −0.0002 (1.6); −0.0144 (1.1); −0.0302 (0.4); −0.4544 (0.5); −0.4700 (3.6); −0.4844 (3.7); −0.4992 (0.8); −0.6564 (0.3); −0.6721 (1.1); −0.6862 (1.8); −0.7006 (1.0)

Ia-64: $^1$H-NMR (400.1 MHz, d$_6$-DMSO):

δ=8.9924 (7.3); 7.7781 (1.0); 7.0322 (0.5); 7.0136 (6.0); 6.9983 (6.1); 6.8916 (1.7); 6.8771 (1.3); 5.2575 (6.4); 4.8421 (2.6); 4.8062 (2.9); 4.2468 (2.9); 4.2109 (2.6); 3.1501 (10.2); 2.9196 (1.6); 2.8851 (3.4); 2.8343 (3.4); 2.7998 (1.6); 2.7156 (6.0); 2.5564 (5.5); 2.3310 (5.0); 2.3269 (6.6); 2.3228 (5.0); 2.1162 (16.0); 0.4570 (0.5); 0.4391 (0.9); 0.4303 (0.8); 0.4238 (1.0); 0.4152 (1.0); 0.3974 (0.8); 0.3406 (0.6); 0.3225 (0.9); 0.3141 (1.0); 0.3079 (0.7); 0.2964 (1.2); 0.2815 (0.8); 0.2091 (0.8); 0.1954 (1.1); 0.1910 (1.0); 0.1826 (0.8); 0.1771 (1.0); 0.1692 (0.9); 0.1507 (0.6); 0.0265 (0.8); 0.0124 (0.9); 0.0088 (1.0); −0.0002 (1.0); −0.0049 (0.9); −0.0140 (0.9); −0.0177 (0.9); −0.0318 (0.6)

Ia-65: $^1$H-NMR (400.1 MHz, d$_6$-DMSO):

δ=9.3170 (7.3); 8.2029 (1.1); 7.4429 (0.7); 7.4231 (3.6); 7.4174 (3.7); 7.4065 (4.4); 7.4001 (3.4); 7.3820 (0.9);

7.2933 (2.0); 7.2758 (1.5); 5.1871 (2.5); 5.1514 (2.8); 4.8058 (6.3); 4.4644 (2.8); 4.4286 (2.6); 3.5740 (11.9); 3.2404 (1.8); 3.2062 (3.0); 3.1406 (6.3); 3.1099 (3.1); 3.0756 (1.9); 2.9813 (5.8); 2.7557 (6.4); 2.7518 (8.5); 2.7478 (6.6); 2.5399 (16.0); 1.4543 (16.0); 0.5451 (0.6); 0.5361 (0.7); 0.5217 (1.4); 0.5081 (1.0); 0.0226 (0.5); 0.0085 (1.0); −0.0002 (1.4); −0.0143 (1.3); −0.0210 (2.7); −0.0423 (1.4); −0.0507 (1.0); −0.0649 (0.6); −0.2312 (0.7); −0.2371 (0.9); −0.2428 (1.0); −0.2510 (1.6); −0.2652 (0.8); −0.2735 (0.7)

Ia-66: $^1$H-NMR (400.1 MHz, $d_6$-DMSO):

δ=9.1775 (6.7); 7.9607 (1.3); 7.4355 (1.2); 7.4233 (1.6); 7.4138 (1.5); 7.1945 (0.4); 7.1824 (1.0); 7.1701 (3.5); 7.1631 (5.6); 7.1558 (2.9); 7.1488 (2.4); 7.1399 (1.9); 7.1316 (0.5); 5.2956 (5.8); 5.0457 (2.4); 5.0099 (2.7); 4.4154 (2.7); 4.3795 (2.4); 3.3321 (15.7); 3.2260 (1.8); 3.1903 (3.0); 3.1007 (3.0); 3.0651 (1.8); 2.8985 (7.8); 2.7391 (7.2); 2.5136 (6.4); 2.5096 (8.5); 2.5056 (6.6); 2.3174 (16.0); 0.8448 (0.5); 0.8266 (0.8); 0.8178 (0.8); 0.8113 (0.9); 0.8027 (1.0); 0.7846 (0.8); 0.7084 (0.6); 0.6906 (0.9); 0.6819 (0.9); 0.6754 (0.8); 0.6641 (1.1); 0.6490 (0.7); 0.4657 (0.7); 0.4515 (1.0); 0.4475 (0.9); 0.4392 (0.8); 0.4331 (0.9); 0.4251 (0.9); 0.4067 (0.6); 0.3092 (0.7); 0.2913 (0.9); 0.2824 (0.9); 0.2771 (0.8); 0.2679 (0.8); 0.2647 (0.9); 0.2503 (0.6)

Ia-67: $^1$H-NMR (300.2 MHz, CDCl$_3$):

δ=8.8395 (16.0); 7.3752 (0.9); 7.3646 (1.2); 7.3597 (1.1); 7.3463 (17.5); 7.3323 (21.4); 7.3048 (7.9); 7.2984 (21.9); 7.2741 (0.5); 7.2388 (0.4); 5.1197 (9.6); 5.0718 (11.2); 4.5284 (8.4); 4.4806 (7.2); 3.9167 (0.3); 3.3706 (5.3); 3.3670 (5.9); 3.3230 (9.2); 3.3193 (10.2); 3.1972 (8.3); 3.1923 (7.6); 3.1496 (4.9); 3.1444 (4.5); 2.9015 (1.2); 0.8616 (0.6); 0.8408 (3.7); 0.8297 (4.7); 0.8146 (4.2); 0.8049 (10.6); 0.7953 (6.3); 0.7787 (5.6); 0.7706 (7.1); 0.7505 (1.9); 0.6007 (3.8); 0.5807 (4.8); 0.5765 (4.5); 0.5648 (3.1); 0.5552 (4.5); 0.5459 (4.0); 0.5405 (3.1); 0.5202 (3.1); 0.4134 (4.2); 0.3935 (3.8); 0.3864 (4.1); 0.3798 (4.7); 0.3675 (3.5); 0.3587 (3.9); 0.3527 (4.0); 0.3327 (2.8); 0.0450 (0.4); 0.0340 (18.0); 0.0232 (0.9)

Ia-68: $^1$H-NMR (400.1 MHz, $d_6$-DMSO):

δ=9.3417 (7.5); 7.7171 (0.8); 7.7135 (0.9); 7.6981 (1.6); 7.6943 (1.9); 7.6751 (1.0); 7.5635 (0.4); 7.5594 (0.4); 7.5451 (1.1); 7.5303 (1.0); 7.5253 (1.3); 7.5113 (0.7); 7.5074 (0.6); 7.4210 (1.4); 7.3971 (3.5); 7.3775 (3.2); 7.3614 (1.2); 5.1816 (2.5); 5.1459 (2.8); 4.9439 (6.8); 4.5716 (2.8); 4.5358 (2.5); 3.5714 (9.7); 3.2479 (6.0); 3.1384 (0.5); 2.9791 (0.5); 2.7538 (5.5); 2.74% (7.3); 2.7454 (5.5); 1.4694 (16.0); 0.4444 (0.6); 0.4349 (0.7); 0.4277 (0.8); 0.4208 (1.4); 0.4110 (0.9); 0.4068 (0.9); 0.3994 (0.7); 0.0228 (0.5); 0.0087 (0.9); −0.0002 (1.5); −0.0140 (1.2); −0.0222 (2.0); −0.0311 (1.1); −0.0462 (1.4); −0.0553 (0.9); −0.0693 (0.5); −0.2310 (0.8); −0.2380 (0.9); −0.2436 (1.0); −0.2519 (1.6); −0.2581 (0.8); −0.2660 (0.8); −0.2748 (0.7)

Ia-69: $^1$H-NMR (300.2 MHz, CDCl$_3$):

δ=8.8257 (9.8); 7.3963 (1.2); 7.3712 (2.6); 7.3485 (2.6); 7.3242 (1.8); 7.2992 (19.7); 7.1279 (6.8); 7.1035 (5.4); 7.0987 (6.0); 7.0674 (2.7); 7.0611 (2.1); 7.0418 (1.1); 7.0358 (1.1); 7.0303 (0.9); 5.3384 (4.5); 5.0096 (5.6); 4.9617 (7.2); 4.6334 (6.2); 4.5855 (4.8); 3.4356 (4.6); 3.3892 (5.5); 2.9866 (5.3); 2.9402 (4.3); 2.5564 (11.1); 1.5998 (16.0); 1.2889 (1.1); 0.8293 (1.0); 0.8232 (0.8); 0.8154 (1.5); 0.7995 (2.1); 0.7912 (2.0); 0.7861 (1.9); 0.7757 (2.0); 0.7696 (1.4); 0.7608 (0.6); 0.7438 (1.1); 0.6287 (1.0); 0.6202 (1.3); 0.6046 (2.4); 0.5964 (3.2); 0.5897 (6.2); 0.5734 (6.0); 0.5665 (3.6); 0.5599 (2.7); 0.5426 (1.3); 0.5357 (1.2); 0.4335 (1.1); 0.4166 (0.6); 0.4078 (1.3); 0.4025 (2.1); 0.3915 (1.8); 0.3856 (2.0); 0.3785 (2.6); 0.3612 (1.5); 0.3544 (0.8); 0.3479 (1.1); 0.0476 (1.2); 0.0369 (25.8); 0.0262 (1.7)

Ia-70: $^1$H-NMR (300.2 MHz, CDCl$_3$):

δ=8.7821 (4.1); 7.6375 (1.2); 7.6337 (1.4); 7.6109 (1.4); 7.6071 (1.6); 7.4840 (1.0); 7.4790 (1.2); 7.4582 (1.4); 7.4531 (1.5); 7.3263 (0.7); 7.3222 (0.8); 7.2996 (2.6); 7.2761 (0.8); 7.2720 (0.8); 7.1970 (0.8); 7.1915 (0.9); 7.1705 (1.2); 7.1656 (1.2); 7.1459 (0.5); 7.1405 (0.6); 5.0026 (1.8); 4.9529 (2.9); 4.7822 (2.7); 4.7325 (1.7); 3.6505 (16.0); 3.3884 (1.5); 3.3381 (2.4); 3.1839 (2.4); 3.1337 (1.5); 1.6923 (0.8); 0.9510 (0.6); 0.9437 (0.5); 0.9364 (0.4); 0.9229 (0.9); 0.9167 (1.6); 0.9087 (0.8); 0.8927 (1.2); 0.8889 (1.5); 0.8815 (1.1); 0.8739 (0.4); 0.8587 (1.4); 0.8387 (0.7); 0.7928 (0.6); 0.7740 (1.1); 0.7523 (1.8); 0.7398 (1.0); 0.7354 (1.0); 0.7252 (1.0); 0.7178 (1.3); 0.7069 (0.4); 0.6995 (0.4); 0.6907 (0.6); 0.0302 (1-5)

Ia-71: $^1$H-NMR (300.2 MHz, CDCl$_3$):

δ=8.8877 (6.1); 7.9951 (2.0); 7.7140 (0.8); 7.6910 (1.6); 7.6658 (0.9); 7.6197 (0.8); 7.5945 (1.6); 7.5711 (0.9); 7.2987 (4.0); 7.2725 (2.0); 7.2467 (0.9); 5.1869 (3.0); 5.1392 (3.5); 4.5522 (2.5); 4.5044 (2.2); 3.5584 (0.4); 3.4698 (1.4); 3.4225 (2.3); 3.2984 (2.0); 3.2919 (2.1); 3.2511 (1.2); 3.2445 (1.2); 2.9913 (16.0); 2.8944 (12.0); 0.8177 (1.2); 0.8113 (1.4); 0.7842 (3.1); 0.7774 (1.8); 0.7549 (2.3); 0.5807 (1.0); 0.5607 (1.3); 0.5561 (1.1); 0.5450 (0.8); 0.5340 (1.1); 0.5271 (1.0); 0.5204 (0.7); 0.5003 (0.7); 0.3906 (1.1); 0.3708 (1.0); 0.3588 (1.4); 0.3439 (0.9); 0.3369 (1.0); 0.3300 (1.0); 0.3099 (0.7); 0.0242 (2.7)

Ia-72: $^1$H-NMR (300.2 MHz, CDCl$_3$):

δ=8.7836 (16.0); 7.3657 (0.5); 7.3386 (4.6); 7.3317 (5.3); 7.3268 (11.5); 7.3192 (13.8); 7.3050 (5.8); 7.2983 (12.2); 7.2779 (1.1); 7.1709 (0.5); 7.1561 (2.6); 7.1433 (2.6); 7.1371 (1.8); 7.1245 (4.4); 7.1145 (2.0); 7.1029 (2.2); 7.0928 (1.9); 5.3527 (6.5); 5.3049 (7.2); 4.4365 (5.9); 4.3889 (5.3); 3.7761 (3.9); 3.7692 (4.0); 3.7272 (5.3); 3.7202 (5.5); 3.4713 (5.1); 3.4626 (5.1); 3.4224 (3.7); 3.4137 (3.8); 2.7707 (7.4); 2.7600 (7.4); 2.0416 (0.4); 1.6411 (2.7); 1.2878 (1.7); 1.0521 (1.1); 1.0319 (3.5); 1.0263 (2.0); 1.0160 (1.5); 1.0109 (3.6); 1.0060 (4.2); 0.9961 (4.5); 0.9899 (3.4); 0.9859 (4.5); 0.9764 (4.1); 0.9696 (4.4); 0.9557 (2.4); 0.9520 (4.3); 0.9318 (1.6); 0.6725 (2.8); 0.6525 (3.3); 0.6460 (2.6); 0.6385 (2.7); 0.6266 (3.0); 0.6179 (3.0); 0.6120 (2.2); 0.5920 (2.3); 0.4277 (2.8); 0.4075 (2.8); 0.4033 (3.2); 0.3913 (2.8); 0.3826 (2.7); 0.3718 (2.4); 0.3669 (2.7); 0.3468 (2.0); 0.0435 (0.4); 0.0327 (11.2); 0.0218 (0.4)

Ia-73: $^1$H-NMR (400.0 MHz, CD$_3$CN):

δ=8.8434 (9.3); 8.5811 (16.0); 8.4363 (9.2); 8.4239 (9.4); 7.5201 (7.4); 7.5077 (7.2); 5.4476 (1.0); 5.1436 (10.9); 5.1072 (12.2); 4.4898 (9.7); 4.4534 (8.7); 3.5309 (8.6); 3.4957 (11.2); 3.3315 (10.4); 3.2963 (7.4); 2.1487 (15.2); 2.1204 (0.9); 2.1142 (0.8); 2.1080 (0.8); 2.1018 (0.6); 2.0956 (0.4); 2.0866 (0.5); 1.9648 (2.6); 1.9587 (6.3); 1.9529 (32.1); 1.9467 (57.6); 1.9406 (76.1); 1.9344 (52.4); 1.9282 (26.9); 1.7751 (0.3); 1.7690 (0.5); 0.8591 (1.4); 0.8437 (4.2); 0.8397 (2.4); 0.8322 (1.7); 0.8243 (7.3); 0.8168 (5.2); 0.8124 (2.8); 0.8057 (4.2); 0.7973 (7.6); 0.7903 (1.4); 0.7799 (4.5); 0.7643 (1.6); 0.5756 (2.8); 0.5609 (3.3); 0.5559 (2.8); 0.5499 (2.6); 0.5415 (3.0); 0.5348 (2.9); 0.5302 (2.3); 0.5153 (2.3); 0.3820 (3.2); 0.3672 (3.7); 0.3634 (3.5); 0.3548 (3.3); 0.3483 (3.0);

Ia-74: ¹H-NMR (300.2 MHz, CDCl₃):

δ=8.8556 (12.3); 8.5503 (6.3); 8.5426 (6.5); 8.5059 (6.2); 8.5000 (6.3); 7.8026 (3.6); 7.7958 (6.0); 7.7888 (3.5); 7.2984 (17.2); 5.0733 (6.3); 5.0256 (7.6); 4.6177 (6.4); 4.5699 (5.3); 3.5240 (16.0); 3.3990 (4.5); 3.3523 (6.1); 3.3251 (2.4); 3.0788 (5.8); 3.0320 (4.4); 1.6646 (1.8); 1.3018 (0.4); 1.2890 (0.8); 1.2786 (0.6); 1.2552 (0.3); 1.0800 (0.6); 0.7941 (1.2); 0.7741 (1.7); 0.7675 (1.4); 0.7581 (1.9); 0.7499 (1.9); 0.7381 (2.5); 0.7340 (2.2); 0.7165 (2.1); 0.6516 (1.4); 0.6271 (2.2); 0.6154 (1.8); 0.6072 (2.0); 0.5910 (2.8); 0.5733 (3.7); 0.5695 (3.7); 0.5520 (2.6); 0.5451 (0.8); 0.5358 (1.9); 0.5275 (1.8); 0.5161 (2.0); 0.4917 (1.2); 0.3427 (1.8); 0.3251 (2.1); 0.3213 (2.1); 0.3092 (1.8); 0.3013 (1.8); 0.2916 (1.4); 0.2849 (1.5); 0.2650 (1.2); 0.0450 (0.7); 0.0342 (19.8); 0.0233 (0.7)

Ia-75: ¹H-NMR (300.2 MHz, CDCl₃):

δ=8.8447 (16.0); 7.2984 (3.2); 7.0606 (0.9); 7.0509 (1.7); 7.0394 (11.6); 7.0151 (11.5); 7.0038 (1.8); 6.9941 (1.0); 5.3287 (0.5); 5.2434 (6.7); 5.1955 (7.6); 4.4937 (6.3); 4.4458 (5.6); 3.4322 (2.5); 3.3838 (6.2); 3.3214 (6.0); 3.2730 (2.5); 3.0113 (5.3); 2.0368 (1.4); 0.9924 (1.1); 0.9722 (2.8); 0.9669 (1.9); 0.9561 (1.4); 0.9461 (4.0); 0.9435 (3.6); 0.9360 (3.8); 0.9302 (2.2); 0.9183 (3.6); 0.9090 (5.6); 0.8982 (1.3); 0.8838 (3.7); 0.8636 (1.5); 0.6038 (2.3); 0.5836 (3.0); 0.5779 (2.4); 0.5693 (2.3); 0.5579 (2.7); 0.5487 (2.7); 0.5433 (2.0); 0.5230 (2.0); 0.3928 (2.4); 0.3722 (2.7); 0.3687 (3.0); 0.3561 (2.5); 0.3480 (2.4); 0.3359 (2.3); 0.3320 (2.5); 0.3117 (1.7); 0.0244 (2.6

Ia-76: ¹H-NMR (400.1 MHz, d₆-DMSO):

δ=8.9687 (3.2); 7.4527 (1.4); 7.4064 (0.7); 7.3861 (1.4); 7.3636 (1.0); 7.3163 (0.8); 7.2972 (1.0); 7.2780 (0.4); 5.3877 (1.5); 5.3836 (1.6); 4.6878 (0.8); 4.6521 (1.0); 4.2636 (1.0); 4.2277 (0.9); 3.0866 (16.0); 2.9401 (0.5); 2.9056 (1.0); 2.8309 (1.0); 2.7965 (0.6); 2.6498 (1.2); 2.4903 (1.1); 2.2653 (2.9); 2.2613 (3.9); 2.2571 (3.0); 0.2323 (0.9); 0.2206 (0.4); 0.1817 (1.0); 0.1709 (0.3); −0.0002 (0.5); −0.0255 (0.4); −0.2131 (0.4); −0.2395 (0.5)

Ib-01: ¹H-NMR (300.2 MHz, CDCl₃):

δ=8.6492 (16.0); 8.5475 (0.4); 8.5293 (8.7); 8.5214 (9.2); 8.5124 (8.6); 8.5064 (8.3); 7.7704 (4.9); 7.7638 (8.0); 7.7564 (4.7); 7.2985 (12.7); 5.3745 (8.5); 5.3278 (10.0); 4.8517 (10.7); 4.8049 (9.1); 3.7676 (0.4); 3.7442 (0.6); 3.7065 (1.1); 3.5228 (3.0); 3.3920 (6.7); 3.3453 (8.3); 2.9531 (7.9); 2.9065 (6.5); 2.7212 (0.4); 2.7174 (0.4); 1.3004 (0.3); 1.2771 (0.7); 1.2537 (0.3); 0.7413 (0.6); 0.7220 (2.8); 0.7158 (1.4); 0.7046 (3.6); 0.6968 (3.4); 0.6861 (5.5); 0.6799 (6.7); 0.6693 (4.0); 0.6606 (5.6); 0.6459 (5.0); 0.6271 (2.1); 0.5797 (3.6); 0.5607 (3.9); 0.5567 (2.8); 0.5434 (2.1); 0.5365 (3.2); 0.5249 (2.6); 0.5203 (1.7); 0.5006 (1.9); 0.3933 (3.1); 0.3743 (2.8); 0.3677 (2.9); 0.3596 (3.0); 0.3491 (2.5); 0.3397 (2.5); 0.3336 (2.6); 0.3140 (1.8); 0.0435 (0.4); 0.0328 (15.8); 0.0219 (0.7)

Ib-02: ¹H-NMR (300.2 MHz, CDCl₃):

δ=8.6050 (16.0); 7.4814 (2.2); 7.4757 (2.3); 7.4562 (4.6); 7.4504 (4.8); 7.4310 (2.6); 7.4252 (2.7); 7.3507 (1.2); 7.3447 (1.2); 7.3328 (1.3); 7.3259 (3.0); 7.3191 (2.4); 7.3070 (2.6); 7.2988 (9.4); 7.2929 (2.2); 7.2810 (2.1); 7.2749 (1.8); 7.1868 (3.8); 7.1829 (4.2); 7.1619 (5.8); 7.1580 (6.3); 7.1366 (3.0); 7.1322 (5.3); 7.1037 (3.0); 7.0985 (4.5); 7.0943 (3.3); 7.0702 (2.6); 7.0668 (2.4); 5.4574 (8.2); 5.4106 (9.3); 5.3334 (0.5); 4.7282 (9.2); 4.6814 (8.1); 3.4287 (4.4); 3.3814 (6.8); 3.2993 (7.4); 3.2928 (7.6); 3.2178 (5.9); 3.2128 (5.7); 3.1706 (3.8); 3.1654 (3.8); 1.6758 (2.0); 1.5284 (0.4); 1.5046 (0.4); 1.2889 (0.6); 0.9275 (1.8); 0.9081 (3.2); 0.9023 (2.6); 0.8911 (2.5); 0.8829 (3.7); 0.8717 (3.9); 0.8658 (3.0); 0.8463 (6.5); 0.8262 (2.3); 0.8220 (3.6); 0.8112 (3.8); 0.8027 (2.1); 0.7915 (3.1); 0.7873 (4.2); 0.7680 (2.6); 0.6057 (3.0); 0.5862 (4.0); 0.5804 (3.0); 0.5710 (2.6); 0.5610 (3.5); 0.5514 (3.3); 0.5457 (2.2); 0.5261 (2.5); 0.4565 (3.4); 0.4369 (3.4); 0.4328 (3.7); 0.4201 (3.4); 0.4131 (2.9); 0.4005 (2.9); 0.3963 (3.1); 0.3767 (2.1); 0.0337 (5.3)

Ib-03: ¹H-NMR (300.2 MHz, CDCl₃):

δ=8.6538 (0.3); 8.6261 (16.0); 7.2987 (8.1); 7.2425 (2.0); 7.2229 (2.9); 7.2176 (4.2); 7.2060 (1.8); 7.1976 (2.5); 7.1924 (2.1); 7.1841 (1.1); 7.1776 (1.2); 7.1561 (2.6); 7.1510 (2.6); 7.1448 (1.4); 7.1331 (2.8); 7.1242 (3.7); 7.1164 (5.1); 7.1023 (3.5); 7.0966 (5.9); 7.0885 (3.3); 7.0744 (2.5); 7.0712 (2.6); 7.0607 (1.1); 7.0439 (0.9); 5.4444 (8.2); 5.3977 (9.4); 4.7669 (9.2); 4.7202 (8.1); 3.4183 (11.7); 3.3683 (2.8); 3.3210 (7.3); 3.2700 (6.6); 3.2639 (6.6); 3.2229 (2.5); 3.2166 (2.5); 1.6516 (3.0); 1.5305 (0.5); 1.5069 (0.5); 1.2878 (1.6); 0.9252 (1.7); 0.9058 (3.2); 0.8999 (2.5); 0.8887 (2.4); 0.8804 (3.7); 0.8694 (3.9); 0.8633 (3.0); 0.8516 (3.2); 0.8440 (4.1); 0.8317 (2.3); 0.8276 (3.8); 0.8168 (3.8); 0.8083 (2.0); 0.7971 (3.0); 0.7930 (4.3); 0.7736 (2.5); 0.6108 (2.9); 0.5912 (3.9); 0.5854 (3.0); 0.5762 (2.5); 0.5658 (3.4); 0.5564 (3.3); 0.5508 (2.2); 0.5310 (2.4); 0.4606 (3.3); 0.4408 (3.3); 0.4369 (3.7); 0.4240 (3.2); 04170 (2.8); 0.4043 (2.9); 0.4003 (3.1); 0.3805 (2.0); 0.0331 (6.9)

Ib-04: ¹H-NMR (400.0 MHz, d₆-DMSO):

δ=8.9539 (16.0); 8.3162 (0.4); 7.6642 (0.3); 7.6544 (3.5); 7.6462 (2.8); 7.6404 (2.1); 7.6361 (2.6); 7.6308 (4.1); 7.6225 (0.4); 7.4588 (3.6); 7.4539 (2.4); 7.4497 (2.0); 7.4433 (2.9); 7.4416 (3.2); 7.4355 (5.0); 7.4253 (0.5); 7.3365 (0.6); 7.3310 (1.4); 7.3180 (5.0); 7.3127 (8.8); 7.3036 (10.1); 7.2947 (7.4); 7.2889 (3.9); 7.2763 (1.1); 7.2705 (0.6); 5.3482 (13.6); 5.2297 (5.9); 5.1947 (6.6); 4.5963 (6.7); 4.5614 (6.1); 3.5174 (5.7); 3.4819 (7.1); 3.3239 (63.3); 3.2275 (6.5); 3.1921 (5.2); 2.6755 (0.5); 2.6709 (0.7); 2.6666 (0.5); 2.5414 (4.3); 2.5244 (1.6); 2.5109 (39.6); 2.5065 (81.7); 2.5020 (109.0); 2.4974 (79.3); 2.4930 (38.5); 2.3333 (0.5); 2.3287 (0.7); 2.3242 (0.5); 0.9165 (1.2); 0.9017 (1.8); 0.8980 (2.0); 0.8897 (2.0); 0.8833 (2.1); 0.8750 (2.3); 0.8712 (2.1); 0.8565 (1.8); 0.7233 (1.3); 0.7085 (1.5); 0.7048 (2.1); 0.6971 (2.2); 0.6902 (1.9); 0.6823 (2.0); 0.6786 (2.5); 0.6639 (1.8); 0.5263 (1.6); 0.5120 (2.4); 0.5080 (2.0); 0.5001 (1.6); 0.4935 (2.4); 0.4859 (2.1); 0.4818 (1.5); 0.4672 (1.5); 0.4527 (1.8); 0.4343 (2.2); 0.4260 (2.1); 0.4201 (1.6); 0.4112 (1.6); 0.4076 (1.9); 0.3931 (1.0); 0.1460 (0.6); 0.0079 (5.5); −0.0002 (153.3); −0.0085 (5.7); −0.1497 (0.7)

Ib-05: ¹H-NMR (601.6 MHz, CD₃CN):

δ=8.6518 (16.0); 8.6276 (1.4); 8.5220 (7.2); 8.3069 (5.6); 8.3037 (5.9); 8.2991 (5.8); 8.2959 (5.8); 8.2521 (0.6); 8.2490 (0.6); 8.2443 (0.6); 8.2412 (0.6); 7.9456 (5.8); 7.9424 (5.8); 7.9329 (6.1); 7.9297 (5.9); 7.8957 (2.1); 7.8947 (2.1); 7.8873 (2.1); 7.6440 (0.5); 7.6409 (0.6); 7.6315 (0.6); 7.6283 (0.6); 7.5107 (1.0); 7.5085 (2.4); 7.5061 (2.4); 7.5039 (1.1); 7.4987 (1.1); 7.4965 (2.4); 7.4940 (2.4); 7.4918 (1.1); 7.3304 (6.4); 7.3227 (6.4); 7.3178 (6.3); 7.3100 (6.1); 7.2578 (0.8); 7.2501 (0.7); 7.2454 (0.6); 7.2375 (0.6); 6.8458 (3.1); 6.8373 (3.1); 6.8338 (3.1); 6.8253 (2.9); 5.3811 (12.1); 5.3574 (13.0); 5.3187 (4.8); 5.2946 (8.1); 5.2264 (8.0); 5.2023 (4.8); 5.0782 (0.9); 5.0540 (1.8); 5.0183 (1.9); 4.9941 (0.8); 4.7277 (13.2); 4.7039 (12.4); 3.6345 (2.4); 3.6060 (4.4);

3.5390 (4.7); 3.5171 (13.6); 3.5127 (11.2); 3.4887 (12.0); 3.3644 (11.9); 3.3405 (8.8); 3.3025 (3.6); 3.2759 (0.7); 3.0856 (0.4); 2.7714 (0.4); 2.7431 (0.3); 2.6879 (0.4); 2.6317 (0.4); 2.5284 (0.7); 2.2392 (0.4); 2.1954 (1.1); 2.1664 (26.4); 2.1413 (1.4); 2.1270 (0.4); 1.9876 (1.1); 1.9661 (1.0); 1.9580 (2.4); 1.9539 (2.8); 1.9500 (15.7); 1.9459 (27.4); 1.9418 (40.5); 1.9377 (27.9); 1.9336 (14.2); 1.9250 (1.0); 1.9226 (0.9); 1.6708 (1.9); 1.6210 (0.3); 1.6088 (0.3); 1.4350 (0.6); 1.4245 (1.0); 1.3404 (1.2); 1.3090 (1.0); 1.2969 (0.3); 1.2848 (1.7); 1.2682 (2.9); 1.0314 (0.9); 1.0216 (1.4); 1.0177 (1.4); 1.0144 (1.5); 1.0075 (2.3); 1.0060 (2.3); 1.0015 (2.0); 0.9929 (2.7); 0.9837 (1.4); 0.9780 (0.4); 0.9722 (1.9); 0.9687 (0.4); 0.9656 (2.4); 0.9623 (0.8); 0.9544 (3.8); 0.9506 (0.6); 0.9456 (3.7); 0.9436 (2.8); 0.9395 (0.7); 0.9348 (4.1); 0.9302 (4.4); 0.9248 (2.8); 0.9215 (2.0); 0.9191 (4.0); 0.9173 (4.4); 0.9121 (2.0); 0.9077 (2.4); 0.9033 (0.8); 0.8993 (1.8); 0.8897 (0.5); 0.8809 (0.6); 0.8692 (0.4); 0.8656 (0.4); 0.8546 (0.7); 0.8440 (0.7); 0.8374 (1.2); 0.8333 (2.9); 0.8236 (4.3); 0.8208 (3.2); 0.8154 (3.0); 0.8109 (4.6); 0.8056 (5.0); 0.8027 (3.6); 0.8004 (4.3); 0.7928 (5.0); 0.7905 (3.1); 0.7881 (4.9); 0.7827 (4.6); 0.7782 (2.4); 0.7727 (3.1); 0.7706 (5.1); 0.7606 (2.7); 0.6725 (0.4); 0.6622 (0.4); 0.6551 (0.4); 0.6508 (0.5); 0.6437 (0.6); 0.5527 (3.4); 0.5427 (4.1); 0.5400 (3.6); 0.5352 (3.4); 0.5300 (3.9); 0.5251 (3.9); 0.5225 (3.2); 0.5124 (3.2); 0.4189 (3.8); 0.4088 (3.8); 0.4068 (4.3); 0.4008 (3.8); 0.3966 (3.6); 0.3907 (3.6); 0.3887 (3.9); 0.3786 (2.9); −0.0002 (9.2); −0.0057 (0.4)

Ib-06: $^1$H-NMR (300.2 MHz, CDCl$_3$):
δ=8.6552 (1.0); 8.6261 (16.0); 7.4803 (0.4); 7.4006 (1.6); 7.3947 (4.9); 7.3867 (1.9); 7.3700 (9.8); 7.3455 (7.2); 7.3121 (0.4); 7.2990 (19.4); 7.1242 (3.8); 7.1209 (3.8); 7.0980 (5.5); 7.0948 (6.0); 7.0719 (2.6); 7.0685 (2.7); 7.0551 (0.5); 7.0514 (0.5); 5.6332 (0.4); 5.5867 (0.4); 5.4441 (7.6); 5.3974 (8.6); 5.3373 (0.4); 4.9682 (0.6); 4.9219 (0.5); 4.7579 (8.6); 4.7112 (7.6); 3.5877 (0.4); 3.4269 (11.2); 3.3743 (3.0); 3.3273 (6.4); 3.2509 (6.0); 3.2444 (6.1); 3.2037 (2.9); 3.1972 (3.0); 1.6196 (12.1); 1.5277 (1.2); 1.5037 (1.2); 1.2896 (0.7); 0.9321 (1.6); 0.9127 (3.0); 0.9067 (2.4); 0.8955 (2.2); 0.8873 (3.6); 0.8762 (3.8); 0.8701 (2.9); 0.8579 (3.0); 0.8508 (4.0); 0.8384 (2.0); 0.8339 (3.7); 0.8231 (3.8); 0.8147 (2.0); 0.8036 (2.8); 0.7992 (4.2); 0.7800 (2.5); 0.6153 (2.0); 0.5958 (3.7); 0.5899 (2.8); 0.5807 (2.5); 0.5704 (3.4); 0.5610 (3.2); 0.5553 (2.2); 0.5355 (2.4); 0.4666 (3.2); 0.4469 (3.1); 0.4428 (3.6); 0.4301 (3.2); 0.4231 (2.9); 0.4105 (2.7); 0.4062 (3.1); 0.3865 (2.1); 0.0463 (0.6); 0.0354 (20.3); 0.0245 (0.8)

Ib-07: $^1$H-NMR (400.1 MHz, d$_6$-DMSO):
δ=8.9873 (16.0); 7.9603 (0.4); 7.1788 (0.5); 7.1610 (5.0); 7.1394 (7.8); 7.1181 (5.1); 5.3429 (13.1); 5.2065 (5.8); 5.1712 (7.0); 4.8454 (6.6); 4.8102 (5.6); 3.3248 (120.1); 3.2514 (2.9); 3.2159 (5.5); 3.1505 (5.2); 3.1151 (2.7); 2.8986 (2.2); 2.7392 (2.0); 2.5132 (13.6); 2.5092 (18 0); 2.5051 (13.8); 0 8217 (1.1); 0.8075 (1.6); 0.7994 (2.3); 0.7849 (3.4); 0.7763 (1.9); 0.7621 (1.9); 0.7244 (1.4); 0.7100 (1.4); 0.7015 (2.8); 0.6914 (1.7); 0.6844 (2.3); 0.6803 (2.5); 0.6660 (1.7); 0.4801 (6.0); 0.4571 (8.0); 0.4348 (3.8)

Ib-08: $^1$H-NMR (400.1 MHz, d$_6$-DMSO):
δ=8.9825 (16.0); 7.5560 (3.0); 7.5355 (6.4); 7.5149 (3.7); 7.3865 (4.0); 7.3818 (4.4); 7.3620 (4.2); 7.3572 (4.6); 7.2598 (4.4); 7.2553 (4.4); 7.2391 (4.1); 7.2345 (3.9); 5.5342 (13.1); 5.1837 (5.9); 5.1485 (7.1); 4.8139 (6.6); 4.7787 (5.7); 3.3241 (124.8); 3.2704 (4.8); 3.2352 (6.0); 3.0699 (5.4); 3.0348 (3.9); 2.8982 (0.8); 2.7390 (0.7); 2.5090 (18.2); 0.6367 (0.7); 0.6215 (1.8); 0.6034 (2.3); 0.5946 (2.8); 0.5898 (2.8); 0.5764 (2.8); 0.5683 (2.8); 0.5616 (2.8); 0.5544 (1.7); 0.5433 (3.0); 0.5292 (1.8); 0.4611 (1.7); 0.4470 (2.7); 0.4362 (1.6); 0.4282 (2.6); 0.4223 (2.5); 0.4057 (3.0); 0.3906 (2.7); 0.3797 (2.4); 0.3645 (2.1); 0.3479 (1.0)

Ib-09: $^1$H-NMR (400.1 MHz, CDCl$_3$):
δ=8.5910 (7.9); 7.2863 (9.9); 7.1503 (0.9); 7.1299 (2.4); 7.1126 (3.0); 7.0927 (2.0); 6.8750 (1.7); 6.8533 (3.6); 6.8332 (2.5); 5.5539 (3.7); 5.5189 (4.6); 4.6816 (3.6); 4.6466 (3.9); 3.4246 (1.5); 3.3888 (4.5); 3.3503 (4.8); 3.3150 (2.5); 3.2669 (6.5); 2.2821 (16.0); 1.5748 (8.6); 1.0649 (0.9); 1.0504 (1.7); 1.0464 (1.8); 1.0372 (2.2); 1.0316 (2.3); 1.0232 (2.7); 1.0043 (2.3); 0.9287 (1.1); 0.9108 (2.0); 0.9021 (2.4); 0.8963 (2.2); 0.8850 (2.9); 0.8701 (2.2); 0.5976 (1.0); 0.5791 (2.1); 0.5708 (2.2); 0.5641 (2.4); 0.5562 (2.6); 0.5375 (2.0); 0.4125 (1.1); 0.3951 (2.1); 0.3849 (2.4); 0.3800 (2.3); 0.3683 (2.7); 0.3529 (1.9)

Ib-10: $^1$H-NMR (400.1 MHz, d$_6$-DMSO):
δ=8.9897 (16.0); 7.3764 (0.7); 7.3715 (0.8); 7.3548 (2.2); 7.3356 (2.7); 7.3202 (1.4); 7.3156 (1.4); 7.2964 (1.6); 7.2758 (2.8); 7.2531 (2.5); 7.2302 (0.9); 5.5829 (13.7); 5.1917 (6.0); 5.1564 (7.4); 4.8661 (7.1); 4.8307 (5.9); 3.3271 (196.4); 3.2826 (6.3); 3.0815 (4.7); 3.0460 (3.5); 2.8984 (0.5); 2.7390 (0.5); 2.5090 (15.8); 2.5050 (12.4); 0.6145 (0.4); 0.6006 (2.0); 0.5922 (2.5); 0.5801 (3.3); 0.5726 (5.2); 0.5683 (4.9); 0.5533 (4.8); 0.5354 (1.4); 0.4693 (1.8); 0.4557 (2.7); 0.4475 (2.4); 0.4327 (3.0); 0.4168 (2.7); 0.3991 (2.8); 0.3902 (2.3); 0.3842 (2.0); 0.3770 (1.7); 0.3721 (2.0); 0.3580 (1.0)

Ib-11: $^1$H-NMR (400.1 MHz, d$_6$-DMSO):
δ=8.9945 (16.0); 7.4713 (0.8); 7.4634 (1.0); 7.4560 (1.1); 7.4486 (1.8); 7.4433 (1.8); 7.4356 (1.9); 7.4272 (1.8); 7.4230 (1.9); 7.4154 (1.2); 7.4076 (1.1); 7.3999 (1.0); 7.1951 (2.1); 7.1833 (2.2); 7.1783 (2.0); 7.1716 (2.2); 5.6560 (14.0); 5.2038 (5.8); 5.1684 (7.1); 4.8643 (6.9); 4.8289 (5.8); 3.3544 (4.0); 3.3243 (151.4); 3.1121 (4.5); 3.0763 (3.4); 2.8990 (0.6); 2.7391 (0.5); 2.5137 (15.2); 2.5095 (20.7); 2.5054 (16.2); 0.6562 (0.7); 0.6423 (1.8); 0.6378 (1.5); 0.6292 (1.5); 0.6234 (2.5); 0.6158 (4.0); 0.5970 (4.7); 0.5914 (3.3); 0.5839 (1.6); 0.5726 (3.0); 0.5589 (1.7); 0.4902 (1.7); 0.4763 (2.6); 0.4655 (1.6); 0.4574 (2.5); 0.4515 (2.4); 0.4339 (3.1); 0.4169 (2.6); 0.4080 (2.3); 0.4029 (1.9); 0.3899 (2.0); 0.3757 (1.0)

Ib-12: $^1$H-NMR (400.1 MHz, d$_6$-DMSO):
δ=8.9912 (16.0); 7.5573 (1.5); 7.5366 (3.3); 7.5199 (3.4); 7.4992 (1.9); 7.2978 (2.6); 7.2791 (4.5); 7.2760 (4.7); 7.2570 (2.2); 7.2540 (2.2); 5.5833 (13.8); 5.1964 (6.0); 5.1611 (7.3); 4.8596 (7.1); 4.8243 (6.0); 3.3258 (150.7); 3.2907 (6.4); 3.0911 (4.8); 3.0553 (3.6); 2.8986 (0.3); 2.5136 (15.7); 2.5095 (20.8); 2.5057 (16.3); 0.6081 (0.4); 0.5945 (2.0); 0.5839 (2.5); 0.5743 (3.2); 0.5643 (4.9); 0.5611 (4.8); 0.5472 (4.5); 0.5418 (4.1); 0.5280 (1.4); 0.4707 (2.0); 0.4572 (2.7); 0.4490 (2.3); 0.4340 (3.0); 0.4180 (2.9); 0.4006 (2.9); 0.3915 (2.4); 0.3858 (2.0); 0.3779 (1.8); 0.3734 (2.0); 0.3593 (1.1)

Ib-13: $^1$H-NMR (400.1 MHz, d$_6$-DMSO):
δ=8.7509 (1.2); 6.7528 (0.3); 5.2319 (0.9); 4.9482 (0.4); 4.9130 (0.5); 4.5737 (0.5); 4.5385 (0.5); 3.6415 (3.5); 3.1023 (16.0); 3.0040 (0.3); 2.9685 (0.5); 2.8390 (0.4); 2.2822 (1.4)

Ib-14: $^1$H-NMR (400.1 MHz, d$_6$-DMSO):
δ=8.9778 (6.6); 7.2464 (0.6); 7.2254 (1.2); 7.2091 (1.3); 7.1895 (0.8); 7.1022 (1.0); 7.0991 (1.1); 7.0762 (1.8); 7.0536 (0.8); 7.0506 (0.8); 5.4744 (5.6); 5.1834 (2.4); 5.1482 (2.9); 4.8056 (2.8); 4.7704 (2.4); 3.9010 (16.0);

3.3263 (97.1); 3.2411 (1.6); 3.2058 (2.2); 3.0758 (2.0); 3.0403 (1.4); 2.5089 (8.1); 0.6602 (0.3); 0.6451 (0.8); 0.6324 (0.7); 0.6269 (1.0); 0.6186 (1.0); 0.6011 (1.2); 0.5859 (1.0); 0.5787 (1.1); 0.5720 (0.7); 0.5604 (1.2); 0.5465 (0.8); 0.4606 (0.7); 0.4463 (1.1); 0.4353 (0.7); 0.4279 (1.0); 0.4213 (1.0); 0.4016 (1.4); 0.3830 (1.1); 0.3738 (1.0); 0.3576 (0.9); 0.3419 (0.4)

Ib-15: $^1$H-NMR (400.1 MHz, d$_6$-DMSO):
δ=8.9724 (5.6); 6.7210 (3.6); 6.6970 (3.6); 6.6802 (0.4); 5.2015 (5.6); 5.1622 (2.4); 4.7769 (2.2); 4.7418 (2.0); 3.7846 (16.0); 3.3225 (46.1); 3.1759 (0.3); 3.1353 (3.5); 3.0967 (0.4); 2.5090 (6.2); 0.8848 (0.4); 0.8703 (0.6); 0.8597 (0.7); 0.8513 (0.7); 0.8438 (0.8); 0.8252 (0.7); 0.7263 (0.5); 0.7061 (0.8); 0.6905 (0.9); 0.6820 (0.8); 0.6678 (0.6); 0.4593 (1.5); 0.4371 (2.2); 0.4168 (1.2); 0.4119 (1.1)

Ib-16: $^1$H-NMR (400.1 MHz, d$_6$-DMSO):
δ=8.9867 (16.0); 7.5541 (1.5); 7.5320 (3.4); 7.5255 (2.4); 7.5144 (3.8); 7.5080 (4.6); 7.4874 (3.5); 7.4642 (1.8); 5.5938 (14.3); 5.1881 (6.0); 5.1528 (7.2); 4.8189 (6.8); 4.7836 (5.8); 3.3228 (121.0); 3.2727 (4.7); 3.2373 (5.7); 3.0433 (4.8); 3.0078 (3.7); 2.8987 (1.1); 2.7395 (1.0); 2.5092 (17.1); 0.6486 (0.7); 0.6341 (1.8); 0.6155 (2.4); 0.6070 (4.0); 0.5883 (4.7); 0.5813 (3.1); 0.5740 (1.7); 0.5628 (3.1); 0.5489 (1.8); 0.4778 (1.8); 0.4638 (2.6); 0.4529 (1.7); 0.4449 (2.5); 0.4390 (2.4); 0.4181 (3.0); 0.3990 (2.6); 0.3894 (2.4); 0.3724 (2.1); 0.3576 (1.1)

Ib-17: $^1$H-NMR (400.1 MHz, d$_6$-DMSO):
δ=8.9824 (16.0); 7.5766 (1.6); 7.5554 (3.6); 7.5377 (3.7); 7.5164 (1.8); 7.2055 (1.8); 7.1992 (2.0); 7.1805 (3.3); 7.1747 (3.6); 7.1563 (2.0); 7.1499 (2.1); 7.0676 (1.8); 7.0623 (1.8); 7.0465 (3.6); 7.0406 (3.4); 7.0253 (1.9); 7.0193 (1.7); 5.5064 (13.4); 5.1843 (5.9); 5.1491 (7.0); 4.7979 (6.7); 4.7627 (5.8); 3.3316 (128.6); 3.2537 (4.2); 3.2184 (5.7); 3.0667 (5.2); 3.0312 (3.7); 2.8981 (0.4); 2.7389 (0.4); 2.5131 (13.8); 2.5092 (18.2); 2.5054 (14.3); 0.6254 (0.8); 0.6107 (1.8); 0.5980 (1.7); 0.5924 (2.4); 0.5839 (2.7); 0.5785 (2.9); 0.5651 (3.0); 0.5578 (2.8); 0.5509 (2.8); 0.5440 (1.7); 0.5326 (3.1); 0.5187 (1.8); 0.4520 (1.8); 0.4379 (2.7); 0.4268 (1.7); 0.4192 (2.6); 0.4129 (2.4); 0.3922 (3.0); 0.3737 (2.6); 0.3641 (2.4); 0.3464 (2.1); 0.3324 (1.1)

Ib-18: $^1$H-NMR (400.1 MHz, d$_6$-DMSO):
δ=8.9901 (16.0); 7.5619 (4.1); 7.5581 (4.4); 7.5436 (4.3); 7.5395 (4.4); 7.4078 (1.2); 7.4034 (1.2); 7.3950 (1.7); 7.3866 (3.7); 7.3821 (3.6); 7.3738 (3.6); 7.3690 (3.6); 7.3629 (6.2); 7.3400 (6.7); 7.3184 (2.5); 5.6206 (14.1); 5.1597 (6.1); 5.1244 (7.4); 4.8072 (7.0); 4.7720 (5.9); 3.3672 (0.4); 3.3263 (270.2); 3.2453 (5.7); 3.2106 (6.8); 2.9675 (6.0); 2.9326 (4.9); 2.8981 (1.4); 2.7390 (1.2); 2.5088 (22.2); 0.4627 (0.4); 0.4269 (12.1); 0.4213 (12.9); 0.3934 (1.4); 0.3617 (0.9); 0.3249 (4.1); 0.3050 (2.5); 0.2956 (1.8)

Ib-19: $^1$H-NMR (400.1 MHz, d$_6$-DMSO):
δ=8.9923 (16.0); 7.9598 (0.4); 7.4656 (0.8); 7.4528 (0.9); 7.4421 (2.2); 7.4295 (2.3); 7.4180 (2.4); 7.4056 (2.3); 7.3947 (1.1); 7.3821 (0.9); 7.1325 (1.1); 7.1276 (1.4); 7.1233 (1.4); 7.1182 (1.4); 7.1099 (2.2); 7.1047 (2.6); 7.1009 (2.6); 7.0957 (2.4); 7.0874 (1.3); 7.0821 (1.4); 7.0782 (1.3); 7.0730 (1.1); 5.4275 (13.9); 5.2243 (6.1); 5.1890 (7.3); 4.8686 (6.9); 4.8334 (5.9); 3.3299 (150.1); 3.2965 (7.0); 3.2346 (5.6); 3.1995 (2.8); 2.8984 (2.2); 2.7392 (2.0); 2.5134 (9.2); 2.5093 (12.4); 2.5052 (9.6); 0.8238 (1.1); 0.8097 (1.8); 0.8019 (2.3); 0.7869 (3.7); 0.7781 (2.1); 0.7641 (2.2); 0.7374 (1.6); 0.7230 (1.5); 0.7139 (2.9); 0.7046 (1.8); 0.6931 (2.8); 0.6790 (1.8); 0.5101 (0.4); 0.4957 (6.4); 0.4727 (8.3); 0.4501 (3.9)

Ib-20: $^1$H-NMR (400.1 MHz, d$_6$-DMSO):
δ=8.9753 (5.6); 7.1259 (0.5); 7.1158 (1.1); 7.1028 (1.2); 7.0927 (0.8); 7.0797 (1.5); 7.0251 (0.9); 7.0217 (1.0); 7.0023 (1.4); 6.9988 (1.5); 6.9760 (0.7); 5.2620 (4.8); 5.2155 (2.0); 5.1804 (2.3); 4.7815 (2.2); 4.7464 (1.9); 3.8246 (16.0); 3.3253 (39.5); 3.2279 (5.1); 2.8992 (0.3); 2.5139 (4.4); 2.5099 (6.1); 2.5059 (4.9); 0.8954 (0.4); 0.8811 (0.6); 0.8752 (0.7); 0.8703 (0.8); 0.8621 (0.8); 0.8548 (0.9); 0.8505 (0.8); 0.8358 (0.7); 0.7380 (0.5); 0.7180 (0.8); 0.7136 (0.8); 0.7019 (0.9); 0.6934 (0.9); 0.6793 (0.6); 0.4699 (1.5); 0.4497 (2.2); 0.4298 (1.2); 0.4238 (1.1)

Ib-21: $^1$H-NMR (400.1 MHz, d$_6$-DMSO):
δ=8.9788 (11.6); 7.2307 (1.4); 7.2132 (3.0); 7.1954 (1.8); 7.0431 (1.7); 7.0245 (3.0); 7.0055 (1.5); 5.4859 (9.7); 5.1791 (4.3); 5.1439 (5.2); 4.8193 (5.0); 4.7841 (4.2); 3.3277 (116.8); 3.2682 (3.0); 3.2329 (4.0); 3.0929 (3.7); 3.0575 (2.6); 2.8979 (0.4); 2.7388 (0.4); 2.5088 (9.1); 2.5049 (7.0); 2.2704 (15.9); 2.2673 (16.0); 0.6694 (0.7); 0.6548 (1.3); 0.6422 (1.4); 0.6370 (1.6); 0.6282 (1.8); 0.6103 (1.5); 0.5939 (1.0); 0.5752 (1.6); 0.5683 (1.8); 0.5613 (1.2); 0.5498 (2.0); 0.5359 (1.4); 0.4657 (1.2); 0.4516 (2.0); 0.4402 (1.1); 0.4332 (1.9); 0.4264 (1.8); 0.4159 (1.8); 0.4073 (1.6); 0.3979 (1.9); 0.3891 (1.8); 0.3711 (1.5); 0.3565 (0.7)

Ib-22: $^1$H-NMR (400.0 MHz, CD$_3$CN):
δ=8.6529 (15.1); 8.5685 (16.0); 8.4194 (9.6); 8.4069 (9.7); 7.5499 (9.0); 7.5374 (8.6); 5.3631 (10.8); 5.3274 (12.1); 4.7419 (12.1); 4.7063 (10.8); 3.6335 (7.8); 3.5160 (7.2); 3.4810 (12.3); 3.3867 (12.4); 3.3517 (7.3); 2.4745 (0.4); 2.4699 (0.7); 2.4652 (0.9); 2.4606 (0.6); 2.1797 (217.2); 2.1205 (0.8); 2.1143 (1.1); 2.1082 (1.2); 2.1021 (0.9); 2.0958 (0.5); 2.0869 (0.7); 1.9650 (8.6); 1.9586 (19.3); 1.9530 (76.1); 1.9470 (132.4); 1.9408 (168.8); 1.9346 (113.8); 1.9285 (56.5); 1.7815 (0.4); 1.7753 (0.8); 1.7693 (1.0); 1.7631 (0.7); 1.7569 (0.3); 1.2037 (0.4); 0.8658 (2.0); 0.8509 (4.1); 0.8467 (2.9); 0.8385 (2.7); 0.8318 (4.3); 0.8237 (4.8); 0.8194 (3.2); 0.8104 (4.0); 0.8045 (4.7); 0.7955 (3.0); 0.7921 (4.3); 0.7842 (4.3); 0.7773 (2.3); 0.7692 (3.8); 0.7659 (4.8); 0.7510 (2.7); 0.5685 (3.3); 0.5535 (4.7); 0.5494 (3.4); 0.5422 (3.0); 0.5343 (3.9); 0.5272 (4.0); 0.5231 (2.6); 0.5080 (2.9); 0.4412 (3.7); 0.4260 (4.2); 0.4229 (4.1); 0.4138 (3.6); 0.4077 (3.1); 0.3988 (3.7); 0.3956 (3.5); 0.3805 (2.4); 0.1459 (0.6); −0.0004 (132.8); −0.0087 (4.8); −0.1497 (0.6)

Ib-23: $^1$H-NMR (300.2 MHz, CDCl$_3$):
δ=8.6512 (16.0); 8.4527 (8.8); 8.4387 (8.7); 8.4295 (8.5); 7.5423 (2.6); 7.5342 (3.2); 7.5277 (2.5); 7.5110 (2.6); 7.5035 (3.2); 7.4963 (2.5); 7.2989 (14.8); 5.3808 (8.5); 5.3340 (10.0); 4.8482 (10.8); 4.8014 (9.2); 3.6834 (13.4); 3.4203 (6.2); 3.3736 (7.7); 2.9896 (7.6); 2.9429 (6.2); 2.0425 (13.7); 1.6764 (4.4); 1.2887 (0.6); 0.7345 (0.6); 0.7151 (3.1); 0.7087 (1.5); 0.7002 (3.7); 0.6897 (3.5); 0.6793 (6.7); 0.6761 (6.8); 0.6655 (4.3); 0.6534 (5.6); 0.6423 (5.5); 0.6234 (2.0); 0.5763 (3.8); 0.5573 (4.2); 0.5534 (3.2); 0.5399 (2.2); 0.5330 (3.4); 0.5217 (2.8); 0.5170 (1.8); 0.4972 (2.0); 0.3875 (3.3); 0.3685 (3.0); 0.3614 (3.0); 0.3544 (3.2); 0.3431 (2.6); 0.3341 (2.7); 0.3278 (2.7); 0.3082 (1.9); 0.0446 (0.6); 0.0337 (18.9); 0.0228 (0.8)

Ib-24: $^1$H-NMR (400.1 MHz, d$_6$-DMSO):
δ=8.7578 (5.6); 7.1772 (0.6); 7.1726 (0.7); 7.1575 (1.2); 7.1525 (0.9); 7.1470 (0.8); 7.1416 (0.9); 7.1364 (1.4); 7.1299 (1.0); 7.1221 (0.8); 7.1149 (0.9); 7.1091 (1.3); 7.0877 (0.7); 7.0109 (0.8); 7.0003 (0.9); 6.9797 (0.6);

5.3780 (5.5); 4.9295 (2.1); 4.8942 (2.5); 4.5816 (2.5); 4.5464 (2.1); 3.0898 (16.0); 3.0144 (1.7); 2.9797 (2.1); 2.7373 (2.0); 2.7026 (1.6); 2.2854 (1.7); 2.2812 (2.3); 2.2770 (1.7); 0.2259 (0.7); 0.2154 (1.6); 0.2107 (1.8); 0.1989 (7.4); 0.1865 (0.8); 0.1760 (0.4); 0.1000 (1.4); 0.0829 (0.8); 0.0724 (0.5); 0.0649 (0.4)

Ib-25: $^1$H-NMR (300.2 MHz, CDCl$_3$):

δ=8.6392 (9.3); 8.4076 (0.4); 8.1985 (2.4); 8.1878 (2.0); 8.1829 (2.4); 7.9444 (1.4); 7.9380 (1.3); 7.9197 (1.6); 7.9129 (2.6); 7.9061 (1.4); 7.8878 (1.5); 7.8814 (1.4); 7.2988 (12.4); 7.2412 (1.7); 7.2350 (1.8); 7.2251 (1.7); 7.2179 (2.6); 7.2105 (1.7); 7.2005 (1.6); 7.1944 (1.5); 5.4464 (4.8); 5.39% (5.5); 5.3249 (0.4); 5.2655 (0.4); 4.7919 (5.7); 4.7451 (5.0); 3.5383 (6.7); 3.2430 (16.0); 2.0435 (0.7); 1.6264 (9.0); 1.3191 (0.3); 1.2897 (2.9); 1.2691 (0.4); 1.1386 (0.4); 0.8823 (0.9); 0.8632 (2.0); 0.8566 (1.4); 0.8460 (1.1); 0.8371 (2.8); 0.8342 (2.5); 0.8271 (2.6); 0.8199 (1.6); 0.8144 (1.2); 0.8095 (2.6); 0.8002 (4.4); 0.7905 (0.9); 0.7799 (1.6); 0.7757 (2.7); 0.7566 (1.3); 0.6218 (1.8); 0.6022 (2.2); 0.5956 (1.6); 0.5880 (1.5); 0.5764 (2.0); 0.5680 (1.9); 0.5619 (1.2); 0.5421 (1.4); 0.4705 (1.9); 0.4507 (1.9); 0.4469 (2.2); 0.4339 (1.8); 0.4267 (1.6); 0.4146 (1.6); 0.4102 (1.7); 0.3904 (1.1); 0.1048 (0.4); 0.0456 (0.4); 0.0348 (10.7); 0.0239 (0.4)

Ia-en-01: $^1$H-NMR (300.2 MHz, CDCl$_3$):

δ=8.8949 (11.8); 7.2983 (5.0); 7.1351 (0.9); 7.1313 (1.0); 7.1228 (2.1); 7.1166 (1.1); 7.1104 (2.6); 7.1034 (3.0); 7.0947 (6.2); 7.0855 (2.7); 7.0790 (5.2); 7.0743 (7.3); 7.0682 (4.3); 7.0540 (5.3); 7.0453 (1.5); 7.0329 (0.4); 5.9069 (15.5); 5.5023 (16.0); 5.3327 (2.7); 5.2811 (6.0); 5.2334 (7.8); 4.9165 (7.3); 4.8688 (5.7); 3.3473 (1.0); 2.0748 (0.9); 1.2891 (0.5); 0.9095 (2.8); 0.9027 (3.4); 0.8821 (3.7); 0.8757 (7.7); 0.8685 (4.0); 0.8463 (5.6); 0.8232 (0.7); 0.6798 (2.2); 0.6601 (2.8); 0.6549 (2.3); 0.6442 (1.6); 0.6332 (2.5); 0.6263 (2.2); 0.6193 (1.5); 0.5994 (1.7); 0.5206 (2.3); 0.5009 (2.0); 0.4889 (2.8); 0.4736 (1.8); 0.4670 (2.0); 0.4595 (1.9); 0.4396 (1.4); 0.0298 (6.2)

Ia-en-02: $^1$H-NMR (300.2 MHz, CDCl$_3$):

δ=8.8741 (10.4); 7.4257 (0.7); 7.41% (0.9); 7.4077 (0.9); 7.4012 (2.0); 7.3949 (1.7); 7.3925 (1.5); 7.3830 (1.4); 7.3800 (1.5); 7.3737 (2.9); 7.3677 (2.6); 7.3560 (1.4); 7.3461 (4.1); 7.3401 (3.2); 7.3210 (2.5); 7.3150 (1.9); 7.2984 (7.1); 7.2310 (2.9); 7.2272 (3.2); 7.2061 (4.0); 7.2025 (4.0); 7.1811 (1.7); 7.1774 (1.7); 7.1552 (2.3); 7.1519 (2.0); 7.1276 (2.1); 7.1225 (3.1); 7.1184 (2.2); 7.0941 (1.9); 7.0910 (1.7); 5.9075 (14.9); 5.4932 (16.0); 5.2678 (5.8); 5.2201 (7.5); 4.9133 (7.0); 4.8657 (5.4); 3.1080 (1.5); 2.0771 (0.4); 2.0418 (1.0); 1.6734 (0.3); 0.9083 (0.4); 0.8879 (2.4); 0.8817 (1.2); 0.8756 (2.5); 0.8613 (2.7); 0.8522 (5.0); 0.8411 (3.0); 0.8255 (3.6); 0.8166 (3.6); 0.7962 (1.0); 0.6804 (2.1); 0.6610 (2.7); 0.6562 (2.1); 0.6446 (1.6); 0.6355 (2.4); 0.6261 (2.0); 0.6202 (1.4); 0.6006 (1.6); 0.5278 (2.2); 0.5084 (1.9); 0.5004 (2.0); 0.4944 (2.2); 0.4819 (1.7); 0.4738 (1.8); 0.4669 (1.8); 0.4472 (1.3); 0.0329 (7.4

Ia-en-03: $^1$H-NMR (300.2 MHz, CDCl$_3$):

δ=8.8620 (10.7); 7.4051 (1.5); 7.3969 (6.2); 7.3845 (9.8); 7.3750 (14.2); 7.3640 (3.7); 7.3585 (2.9); 7.3501 (4.1); 7.3462 (7.6); 7.3362 (5.0); 7.3263 (2.7); 7.3230 (3.4); 7.3132 (2.5); 7.2983 (5.1); 5.7061 (15.0); 5.3896 (16.0); 5.3322 (2.4); 5.0613 (2.9); 5.0136 (10.2); 4.9806 (9.6); 4.9329 (2.7); 2.9895 (0.8); 2.9075 (0.4); 1.2882 (3.3); 1.2723 (0.6); 1.2490 (0.4); 1.0048 (0.9); 0.9835 (2.0); 0.9797 (1.6); 0.9688 (1.6); 0.9585 (2.2); 0.9476 (2.9); 0.9437 (2.3); 0.9304 (2.1); 0.9226 (3.0); 0.9061 (3.0); 0.8942 (2.7); 0.8850 (1.9); 0.8701 (3.4); 0.8491 (2.0); 0.7697 (2.3); 0.7498 (2.8); 0.7458 (2.2); 0.7338 (1.8); 0.7256 (2.4); 0.7139 (2.2); 0.7099 (1.6); 0.6896 (1.6); 0.5850 (2.2); 0.5651 (2.1); 0.5600 (2.3); 0.5492 (2.2); 0.5401 (1.9); 0.5291 (1.9); 0.5240 (2.0); 0.5039 (1.4); 0.1048 (7.7); 0.0324 (5.4); 0.0215 (0.3)

Ia-en-04: $^1$H-NMR (499.9 MHz, CDCl$_3$):

δ=8.8291 (6.8); 8.7802 (0.3); 7.3153 (1.0); 7.3117 (1.0); 7.3046 (1.1); 7.3006 (2.0); 7.2968 (1.6); 7.2893 (1.5); 7.2879 (1.6); 7.2844 (2.0); 7.2804 (1.3); 7.2734 (1.2); 7.2696 (1.5); 7.2651 (6.8); 7.2216 (0.6); 7.2086 (1.2); 7.2070 (1.2); 7.1990 (1.3); 7.1966 (1.3); 7.1883 (1.0); 7.1854 (1.0); 7.1726 (0.4); 7.1692 (0.4); 7.1236 (2.5); 7.1217 (2.4); 7.1086 (3.7); 7.1068 (3.6); 7.0985 (0.5); 7.0937 (1.6); 7.0917 (1.5); 7.0501 (2.1); 7.0484 (1.9); 7.0333 (2.2); 7.0308 (3.0); 7.0136 (1.8); 5.8214 (1.5); 5.8062 (4.7); 5.7910 (4.7); 5.7759 (1.5); 5.2219 (0.4); 5.1933 (1.1); 5.1623 (1.0); 5.0770 (0.3); 5.0480 (1.0); 5.0417 (1.0); 5.0139 (0.7); 4.8760 (0.4); 2.9792 (1.0); 2.0536 (16.0); 2.0430 (2.9); 2.0384 (15.7); 2.0075 (1.1); 1.9499 (0.8); 1.9356 (0.7); 1.6321 (0.9); 1.5054 (2.0); 1.4919 (2.0); 1.2729 (0.3); 1.2586 (0.7); 1.2443 (0.3); 0.9932 (0.4); 0.9867 (0.5); 0.9804 (0.4); 0.9745 (0.4); 0.9674 (0.5); 0.9533 (0.6); 0.9403 (0.6); 0.9334 (0.6); 0.9186 (1.0); 0.9041 (1.2); 0.8911 (1.1); 0.8844 (1.2); 0.8733 (0.7); 0.7032 (0.3); 0.6953 (0.8); 0.6826 (1.3); 0.6672 (1.2); 0.6623 (1.2); 0.6437 (1.9); 0.6310 (1.7); 0.6288 (1.7); 0.6215 (1.6); 0.6164 (1.1); 0.6065 (1.7); 0.5942 (0.8); 0.0062 (0.3); −0.0002 (5.8)

Ia-en-05: $^1$H-NMR (300.2 MHz, CDCl$_3$):

δ=8.8801 (6.3); 7.4117 (1.2); 7.4053 (1.0); 7.3880 (1.7); 7.3794 (2.0); 7.3636 (0.9); 7.3558 (1.4); 7.2983 (5.6); 7.1310 (0.8); 7.1002 (2.9); 7.0746 (2.7); 7.0483 (0.9); 5.8812 (1.1); 5.8558 (3.7); 5.8306 (3.8); 5.8054 (1.1); 5.2647 (0.9); 5.2168 (1.4); 5.0664 (1.0); 5.0183 (0.6); 3.1478 (0.5); 2.1035 (13.8); 2.0782 (13.7); 2.0517 (0.3); 2.0500 (0.4); 2.0427 (16.0); 2.0350 (0.4); 0.9891 (0.3); 0.9572 (0.7); 0.9290 (1.1); 0.9075 (0.9); 0.8981 (1.0); 0.8780 (0.6); 0.6970 (2.0); 0.6688 (2.1); 0.6611 (1.8); 0.6407 (1.0); 0.6336 (1.2); 0.0324 (6.9)

Ia-en-06: $^1$H-NMR (300.2 MHz, CDCl$_3$):

δ=8.8798 (8.0); 7.2983 (5.3); 7.1980 (0.6); 7.1918 (0.6); 7.1708 (1.1); 7.1649 (1.5); 7.1584 (0.6); 7.1459 (1.1); 7.1396 (1.7); 7.1317 (1.1); 7.1137 (0.9); 7.1070 (1.1); 7.1023 (0.9); 7.0985 (0.8); 7.0853 (0.9); 7.0822 (0.8); 7.0766 (1.4); 7.0725 (1.5); 7.0599 (1.5); 7.0566 (1.5); 7.0492 (0.8); 7.0454 (0.9); 7.0324 (0.9); 7.0299 (0.9); 7.0087 (1.0); 6.9886 (1.1); 6.9646 (0.5); 5.8930 (1.2); 5.8676 (4.2); 5.8424 (4.2); 5.8172 (1.3); 5.2593 (1.7); 5.2113 (2.9); 5.0790 (2.2); 5.0310 (1.3); 3.1565 (1.7); 2.1087 (16.0); 2.0835 (15.8); 2.0429 (0.6); 1.6642 (1.7); 1.2880 (0.4); 0.9692 (1.2); 0.9420 (1.5); 0.9194 (1.1); 0.9099 (1.5); 0.8891 (0.9); 0.7326 (0.4); 0.7118 (1.7); 0.7066 (2.7); 0.6859 (2.1); 0.6796 (2.8); 0.6699 (1.9); 0.6535 (1.2); 0.6432 (1.6); 0.0323 (6.7)

Ia-en-07: $^1$H-NMR (300.2 MHz, CDCl$_3$):

δ=8.8914 (7.9); 8.8455 (4.2); 8.6702 (0.3); 7.2981 (5.8); 7.2667 (0.4); 7.2618 (0.4); 7.2533 (0.5); 7.2363 (1.3); 7.2288 (1.3); 7.2121 (2.2); 7.2040 (2.7); 7.1952 (1.6); 7.1841 (2.8); 7.1792 (2.8); 7.1731 (2.6); 7.1629 (4.1); 7.1534 (3.2); 7.1432 (3.1); 7.1275 (1.8); 7.1187 (0.9); 7.1110 (0.6); 7.1034 (0.5); 6.9178 (0.8); 6.8976 (1.1); 6.8927 (1.1); 6.8789 (0.4); 6.8733 (0.6); 6.5314 (0.6); 6.5087 (1.7); 6.4860 (1.7); 6.4634 (0.6); 6.3933 (1.0); 6.3707 (2.9); 6.3482 (2.9); 6.3258 (0.9); 5.8609 (0.4); 5.8357 (0.4); 5.2712 (3.5); 5.2236 (4.4); 5.1648 (2.0); 5.1173 (2.5); 4.8870 (4.1); 4.8395 (3.3); 4.7728 (2.4); 4.7252 (1.9); 3.0857 (3.9); 3.0748 (3.9); 2.9721 (2.6);

2.9678 (2.7); 2.2117 (0.7); 2.2074 (0.7); 2.1026 (1.5); 2.0773 (1.5); 2.0402 (6.4); 1.5549 (15.8); 1.5325 (16.0); 1.4720 (0.4); 1.4497 (0.3); 1.3105 (0.5); 1.2849 (1.1); 1.1011 (0.4); 1.0286 (0.4); 1.0073 (0.9); 0.9927 (0.6); 0.9825 (0.9); 0.9703 (1.7); 0.9461 (1.8); 0.9337 (1.2); 0.9241 (0.7); 0.9091 (1.4); 0.8857 (1.8); 0.8639 (1.5); 0.8486 (0.9); 0.8384 (1.8); 0.8340 (1.8); 0.8282 (2.1); 0.8089 (2.1); 0.8026 (2.2); 0.7989 (2.0); 0.7887 (0.8); 0.7738 (1.9); 0.7533 (0.9); 0.6733 (0.9); 0.6642 (0.3); 0.6531 (1.1); 0.6370 (1.0); 0.6308 (1.9); 0.6119 (2.1); 0.5947 (1.5); 0.5870 (1.5); 0.5757 (1.3); 0.5712 (1.0); 0.5554 (1.0); 0.5514 (1.1); 0.5358 (0.8); 0.5309 (0.9); 0.5202 (0.8); 0.5110 (0.7); 0.4998 (0.7); 0.4950 (0.8); 0.4750 (0.4); 0.4233 (1.2); 0.4036 (1.3); 0.3982 (1.3); 0.3880 (1.3); 0.3786 (1.1); 0.3679 (1.2); 0.3627 (1.2); 0.3428 (0.8); 0.0284 (6.9)

Ia-en-08: $^1$H-NMR (499.9 MHz, CDCl$_3$):
δ=8.8950 (13.5); 7.2701 (3.2); 7.1954 (0.9); 7.1854 (1.5); 7.1803 (1.2); 7.1755 (2.7); 7.1688 (1.5); 7.1654 (1.6); 7.1608 (2.4); 7.1556 (1.5); 7.1525 (1.1); 7.1490 (1.0); 7.1406 (1.2); 7.1335 (0.4); 7.1165 (1.1); 7.1006 (5.2); 7.0963 (5.6); 7.0896 (8.0); 7.0820 (5.3); 7.0736 (0.7); 7.0672 (0.4); 5.8827 (15.2); 5.4694 (16.0); 5.3025 (0.7); 5.2582 (6.8); 5.22% (7.9); 4.9026 (7.6); 4.8740 (6.5); 3.4180 (2.5); 0.8768 (0.4); 0.8640 (4.2); 0.8627 (4.2); 0.8451 (8.3); 0.8267 (6.7); 0.8137 (0.4); 0.6333 (2.1); 0.6212 (2.7); 0.6176 (2.4); 0.6124 (2.0); 0.6041 (2.7); 0.6019 (2.4); 0.5967 (1.7); 0.5846 (1.7); 0.4882 (2.1); 0.4828 (0.6); 0.4761 (2.2); 0.4698 (3.4); 0.4595 (2.0); 0.4560 (2.2); 0.4515 (2.0); 0.4395 (1.5); −0.0002 (3.8)

Ia-en-09: $^1$H-NMR (300.2 MHz, CDCl$_3$):
δ=8.8523 (9.2); 7.4688 (2.2); 7.4596 (1.9); 7.4529 (2.4); 7.4446 (2.6); 7.4373 (4.6); 7.4250 (1.9); 7.4192 (2.0); 7.4038 (1.9); 7.3805 (0.7); 7.3706 (1.7); 7.3558 (5.9); 7.3514 (6.5); 7.3461 (4.4); 7.3385 (6.6); 7.3300 (3.4); 7.3225 (5.5); 7.2984 (28.0); 5.9813 (2.3); 5.4793 (16.0); 5.2571 (2.8); 5.2092 (3.8); 4.9221 (1.0); 4.8784 (0.8); 2.9630 (8.8); 2.0445 (2.0); 1.6030 (7.3); 1.2912 (1.2); 0.9791 (1.2); 0.9426 (2.0); 0.9193 (2.0); 0.7109 (2.0); 0.6914 (2.7); 0.6864 (2.0); 0.6751 (1.6); 0.6665 (2.1); 0.6560 (1.9); 0.6505 (1.6); 0.6310 (1.6); 0.5392 (2.1); 0.5198 (2.1); 0.5135 (1.9); 0.5042 (2.1); 0.4945 (1.6); 0.4844 (1.7); 0.4783 (2.0); 0.4587 (1.3); 0.0471 (0.9); 0.0364 (29.4); 0.0255 (1.2)

Ia-en-10: $^1$H-NMR (300.2 MHz, CDCl$_3$):
δ=8.9078 (4.9); 7.4593 (0.7); 7.4534 (0.8); 7.4328 (1.2); 7.4301 (1.2); 7.4275 (1.2); 7.4092 (0.8); 7.4033 (0.9); 7.2988 (1.8); 7.2821 (0.6); 7.2763 (0.7); 7.2608 (0.7); 7.2559 (1.4); 7.2507 (1.0); 7.2353 (1.0); 7.2294 (0.9); 7.1580 (1.3); 7.1558 (1.4); 7.1296 (2.0); 7.1058 (0.7); 7.1032 (0.8); 5.9069 (5.7); 5.4875 (5.9); 5.2872 (2.3); 5.2395 (3.0); 4.9157 (2.8); 4.8680 (2.2); 3.3541 (0.4); 2.0477 (0.4); 2.0405 (16.0); 0.9064 (1.1); 0.9001 (1.3); 0.8787 (1.4); 0.8730 (2.8); 0.8666 (1.5); 0.8422 (2.4); 0.6740 (0.8); 0.6543 (1.0); 0.6491 (0.8); 0.6386 (0.6); 0.6272 (0.9); 0.6208 (0.8); 0.6135 (0.5); 0.5936 (0.6); 0.5254 (0.8); 0.5057 (0.8); 0.4942 (1.2); 0.4782 (0.6); 0.4722 (0.7); 0.4643 (0.7); 0.4445 (0.5); 0.0284 (1.7)

Ia-en-11: $^1$H-NMR (499.9 MHz, CDCl$_3$):
δ=8.8522 (0.4); 8.8186 (16.0); 8.7289 (6.1); 8.7109 (1.3); 8.0178 (0.7); 8.0033 (0.8); 8.0007 (0.6); 7.6984 (0.5); 7.6835 (0.3); 7.5806 (0.7); 7.5651 (1.0); 7.5493 (0.6); 7.4706 (0.5); 7.4568 (0.5); 7.4532 (0.5); 7.4427 (0.7); 7.4259 (1.0); 7.4109 (4.2); 7.4078 (4.7); 7.3955 (11.5); 7.3794 (10.0); 7.3677 (4.5); 7.3649 (7.1); 7.3621 (4.5); 7.3553 (2.7); 7.3507 (6.8); 7.3444 (1.8); 7.3385 (2.0); 7.3358 (2.4); 7.3301 (1.3); 7.3217 (1.3); 7.3178 (1.4);

7.2923 (6.7); 7.2857 (7.4); 7.2796 (7.5); 7.2715 (1.7); 7.2640 (20.8); 7.2302 (0.5); 7.2127 (0.5); 7.1434 (4.3); 7.1053 (1.4); 7.0969 (3.9); 7.0938 (2.9); 7.0905 (3.8); 7.0864 (2.9); 7.0834 (3.2); 7.0780 (2.9); 7.0698 (0.5); 6.1672 (2.7); 6.1538 (8.1); 6.1403 (8.0); 6.1268 (2.5); 5.7372 (1.3); 5.7281 (1.2); 5.7129 (3.4); 5.6977 (3.4); 5.6825 (1.1); 5.1379 (2.7); 5.1221 (0.6); 5.1096 (3.3); 5.0152 (0.8); 4.9866 (0.9); 4.9718 (0.5); 4.9559 (2.6); 4.9388 (1.8); 4.9274 (14.8); 4.9177 (15.7); 4.8890 (2.9); 4.8836 (4.4); 4.8552 (3.4); 4.4802 (0.7); 4.4545 (0.7); 4.4518 (0.6); 4.3187 (0.4); 4.3042 (0.4); 2.9573 (0.3); 2.8808 (0.4); 2.7094 (3.9); 2.4860 (10.0); 2.0414 (14.0); 2.0262 (13.7); 1.9761 (0.4); 1.9741 (0.4); 1.6047 (0.7); 1.5642 (0.7); 1.5508 (0.6); 1.4928 (0.6); 1.4814 (0.9); 1.4672 (2.6); 1.4526 (3.1); 1.4387 (35.8); 1.4252 (35.1); 1.3515 (0.4); 1.3399 (0.4); 1.3363 (0.4); 1.3294 (0.4); 1.3250 (0.4); 1.3179 (0.5); 1.3144 (0.5); 1.3095 (0.5); 1.3029 (0.5); 1.2963 (0.5); 1.2886 (0.5); 1.2836 (0.4); 1.2729 (0.6); 1.2582 (1.5); 1.2559 (1.4); 1.2442 (0.5); 1.2394 (0.4); 1.2273 (0.3); 1.1065 (0.4); 1.0970 (1.0); 1.0921 (0.4); 1.0838 (1.6); 1.0754 (1.4); 1.0689 (1.6); 1.0623 (2.0); 1.0475 (1.7); 1.0319 (1.3); 1.0175 (1.9); 1.0098 (1.6); 1.0044 (1.3); 0.9956 (2.0); 0.9826 (1.5); 0.9710 (0.5); 0.9677 (0.5); 0.9609 (0.5); 0.9562 (0.5); 0.9494 (0.6); 0.9459 (0.6); 0.9321 (1.9); 0.9245 (2.8); 0.9194 (3.0); 0.9121 (3.8); 0.9049 (5.0); 0.8975 (4.9); 0.8911 (4.5); 0.8890 (4.2); 0.8808 (3.0); 0.8672 (1.4); 0.8548 (0.4); 0.8387 (0.3); 0.8090 (0.3); 0.8003 (0.3); 0.7940 (0.3); 0.7872 (0.4); 0.7587 (2.6); 0.7439 (4.8); 0.7373 (3.2); 0.7315 (4.9); 0.7274 (2.8); 0.7225 (5.6); 0.7152 (12.0); 0.7085 (6.1); 0.6990 (4.2); 0.6937 (3.6); 0.6876 (3.8); 06847 (2.1); 0.6729 (2.2); 0.6596 (0.3); 0.5780 (0.3); 0.5660 (0.4); 0.5630 (0.4); 0 5563 (0.4); 0.5510 (0.4); 0.5443 (0.4); 0.5413 (0.4); 0.5291 (0.5); 0.5225 (1.2); 0.5089 (2.6); 0.5016 (3.6); 0.4984 (3.7); 0.4918 (3.4); 0.4867 (3.7); 0.4770 (2.8); 0.4711 (1.0); 0.4656 (2.3); 0.0062 (1.2); −0.0002 (20.8); −0.0067 (0.9)

Ib-en-01: $^1$H-NMR (300.2 MHz, CDCl$_3$):
δ=8.6325 (11.0); 8.5864 (1.4); 7.4097 (0.4); 7.4044 (0.4); 7.3848 (0.3); 7.3788 (0.4); 7.3698 (0.9); 7.3636 (1.4); 7.3521 (1.0); 7.3454 (2.5); 7.3395 (4.4); 7.3276 (1.4); 7.3184 (5.5); 7.3146 (5.6); 7.2981 (19.1); 7.2918 (3.3); 7.2877 (1.6); 7.2800 (0.4); 7.2523 (0.3); 7.1771 (3.0); 7.1732 (3.2); 7.1520 (4.5); 7.1468 (2.8); 7.1272 (2.1); 7.1234 (2.2); 7.0939 (2.3); 7.0901 (2.0); 7.0651 (2.4); 7.0608 (3.3); 7.0324 (1.9); 6.9378 (0.6); 6.8844 (0.7); 6.5812 (0.9); 6.5278 (0.7); 5.9281 (0.7); 5.7171 (15.7); 5.4783 (5.1); 5.4311 (7.9); 5.3574 (16.0); 5.3365 (0.5); 5.2709 (8.8); 5.2238 (6.2); 4.0859 (6.9); 4.0746 (6.9); 3.6646 (1.4); 1.6370 (0.3); 1.6043 (7.6); 1.2912 (0.6); 1.0447 (0.4); 1.0324 (0.6); 1.0227 (0.4); 1.0127 (0.4); 1.0062 (0.8); 0.9869 (1.1); 0.9686 (1.6); 0.9591 (1.4); 0.9517 (1.5); 0.9413 (2.5); 0.9345 (2.5); 0.9252 (2.2); 0.9083 (4.0); 0.8849 (2.3); 0.8715 (2.7); 0.8500 (3.4); 0.8334 (3.5); 0.8270 (3.0); 0.8112 (3.6); 0.7898 (5.5); 0.7770 (3.5); 0.7733 (2.8); 0.7631 (3.3); 0.7548 (3.9); 0.7460 (1.2); 0.7385 (1.0); 0.7282 (1.8); 0.7105 (0.6); 0.0471 (0.5); 0.0363 (17.0); 0.0286 (0.6); 0.0271 (0.6); 0.0254 (0.6)

XVIa-01: $^1$H-NMR (499.9 MHz, d$_6$-DMSO):
δ=9.2718 (7.3); 6.0189 (16.0); 3.3267 (4.2); 2.5059 (2.4); 2.5026 (3.2); 2.4993 (2.4); 1.8135 (2.0); 1.8022 (5.5);

1.7953 (5.7); 1.7853 (2.7); 1.6384 (2.7); 1.6284 (5.6); 1.6216 (5.6); 1.6102 (2.0)

XVIa-02: $^1$H-NMR (499.9 MHz, CDCl$_3$):

δ=8.7454 (4.9); 7.2666 (4.0); 5.4668 (16.0); 1.6069 (2.5); 1.5219 (19.1); 1.4422 (1.4); 1.4337 (4.6) 1.4279 (4.7); 1.4198 (1.4); 0.9815 (1.6); 0.9738 (6.2); 0.9678 (6.1); 0.9598 (1.4); −0.0002 (3.7)

XVIa-03: $^1$H-NMR (499.9 MHz, CDCl$_3$):

δ=8.7514 (8.8); 7.2646 (10.1); 5.8175 (15.7); 5.8130 (16.0); 1.6993 (0.3); 1.6688 (1.7); 1.6592 (2.3); 1.6548 (3.4); 1.6484 (4.3); 1.6385 (3.1); 1.6336 (1.9); 1.6261 (2.0); 1.6189 (3.4); 1.6139 (3.7); 1.6125 (4.3); 1.6063 (1.8); 1.6034 (3.9); 1.5850 (10.3); 1.5711 (3.5); 1.5616 (4.4); 1.5606 (4.2); 1.5544 (5.9); 1.5508 (2.9); 1.5454 (4.4); 1.5440 (4.0); 1.5391 (3.5); 1.5318 (1.8); 1.5241 (1.5); 0.0063 (0.6); −0.0002 (9.8); −0.0068 (0.6)

XVIb-01: $^1$H-NMR (400.1 MHz, d$_6$-DMSO):

δ=9.0517 (73); 6.2906 (16.0); 3.3356 (8.4); 2.5136 (1.6); 2.5096 (2.2); 2.5054 (1.7); 1.8770 (1.8); 1.8626 (5.1); 1.8543 (5.4); 1.8414 (2.8); 1.7996 (0.4); 1.6608 (2.5); 1.6479 (5.1); 1.6395 (5.5); 1.6251 (2.0)

XVIb-02: $^1$H-NMR (300.2 MHz, CDCl$_3$):

δ=8.6112 (3.9); 7.2986 (14.9); 5.7117 (14.1); 1.5870 (1.8); 1.5545 (16.0); 1.4828 (1.2); 1.4688 (3.8); 1.4590 (3.9); 1.4457 (1.3); 0.9877 (1.4); 0.9753 (5.2); 0.9653 (5.0); 0.9521 (1.2); 0.0483 (0.8); 0.0375 (16.8); 0.0266 (0.7)

XVIb-03: $^1$H-NMR (300.2 MHz, CDCl$_3$):

δ=8.6414 (8.7); 7.2982 (4.4); 6.0367 (15.9); 6.0289 (16.0); 1.6948 (1.3); 1.6703 (2.6); 1.6688 (2.6); 1.6612 (3.2); 1.6580 (4.0); 1.6445 (4.1); 1.6347 (2.4); 1.6105 (2.5); 1.6090 (2.6); 1.5983 (8.2); 1.5876 (6.3); 1.5818 (3.5); 1.5742 (3.2); 1.5724 (3.0); 1.5678 (4.0); 1.5602 (5.2); 1.5535 (3.2); 1.5473 (3.6); 1.5172 (0.7); 0.0316 (4.7)

BIOLOGICAL EXAMPLES

Example A

In Vivo Preventive Test on *Alternaria brassicae* (Leaf Spot on Radish or Cabbage)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone/Tween® 80 and then diluted in water to the desired concentration.

The young plants of radish or cabbage were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Alternaria brassicae* spores. The contaminated radish or cabbage plants were incubated for 6 days at 20° C. and at 100% relative humidity.

The test was evaluated 6 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: Ia-06; Ia-36; Ia-46; Ia-48; Ia-52; Ia-55; Ia-57; Ia-58; Ia-61; Ia-en-05; Ia-en-11; Ib-09; Ib-10; Ib-18.

In this test the following compounds according to the invention showed efficacy between 80% and 89% at a concentration of 500 ppm of active ingredient: Ia-44; Ia-50; Ia-63; Ia-en-06; Ib-25.

In this test the following compounds according to the invention showed efficacy between 90% and 100% at a concentration of 500 ppm of active ingredient: Ia-18; Ia-22; Ia-24; Ia-41; Ia-66; Ia-en-01; Ia-en-02; Ia-en-07; Ia-en-09.

Example B

In Vivo Preventive Test on *Botrytis cinerea* (Grey Mould)

Solvent: 5% by volume of Dimethyl sulfoxide
10% by volume of Acetone
Emulsifier: 1 µl of Tween®80 per mg of active ingredient The active ingredients were made soluble and homogenized in a mixture of Dimethyl sulfoxide/Acetone/Tween® 80 and then diluted in water to the desired concentration.

The young plants of gherkin were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Botrytis* cinerea spores. The contaminated gherkin plants were incubated for 4 to 5 days at 17° C. and at 90% relative humidity.

The test was evaluated 4 to 5 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: Ia-37; Ia-en-01.

In this test the following compounds according to the invention showed efficacy between 80% and 89% at a concentration of 500 ppm of active ingredient: Ia-03; Ia-06; Ia-24; Ia-69; Ia-en-03.

In this test the following compounds according to the invention showed efficacy between 90% and 100% at a concentration of 500 ppm of active ingredient: Ia-01; Ia-15; Ia-18; Ia-22; Ia-66; Ia-en-02; Ia-en-09; Ib-03.

Example C

In Vivo Preventive Test on *Puccinia recondita* (Brown Rust on Wheat)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone/Tween®80 and then diluted in water to the desired concentration.

The young plants of wheat were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Puccinia recondita* spores. The contaminated wheat plants were incubated for 24 hours at 20° C. and at 100% relative humidity and then for 10 days at 20° C. and at 70-80% relative humidity.

The test was evaluated 11 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: Ia-17; Ia-29; Ia-55; Ia-62; Ia-69; Ib-02; Ib-03.

In this test the following compounds according to the invention showed efficacy between 80% and 89% at a concentration of 500 ppm of active ingredient: Ia-01; Ia-03; Ia-04; Ia-07; Ia-08; Ia-42; Ia-58; Ia-68; Ia-71; Ia-en-04; Ia-en-06; Ib-06.

In this test the following compounds according to the invention showed efficacy between 90% and 100% at a concentration of 500 ppm of active ingredient: Ia-02; Ia-05; Ia-06; Ia-09; Ia-15; Ia-16; Ia-18; Ia-20; Ia-21; Ia-22; Ia-24; Ia-25; Ia-32; Ia-37; Ia-39; Ia-41; Ia-44; Ia-53; Ia-66; Ia-67; Ia-72; Ia-73; Ia-en-01; Ia-en-02; Ia-en-03; Ia-en-05; Ia-en-07; Ia-en-08; Ia-en-09; Ia-en-10; Ia-en-11.

Example D

In Vivo Preventive Test on *Septoria tritici* (Leaf Spot on Wheat)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone/Tween® 80 and then diluted in water to the desired concentration.

The young plants of wheat were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Septoria tritici* spores. The contaminated wheat plants were incubated for 72 hours at 17° C. and at 100% relative humidity and then for 15 days at 20° C. and at 90% relative humidity.

The test was evaluated 19 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: Ia-01; Ia-07; Ia-18; Ib-13.

In this test the following compounds according to the invention showed efficacy between 80% and 89% at a concentration of 500 ppm of active ingredient: Ia-08; Ia-13; Ia-14; Ia-31; Ia-42; Ia-48; Ia-55; Ia-en-04.

In this test the following compounds according to the invention showed efficacy between 90% and 100% at a concentration of 500 ppm of active ingredient: Ia-02; Ia-03; Ia-04; Ia-05; Ia-06; Ia-09; Ia-15; Ia-17; Ia-20; Ia-21; Ia-22; Ia-24; Ia-29; Ia-39; Ia-41; Ia-44; Ia-53; Ia-66; Ia-72; Ia-73; Ia-en-02; Ia-en-03; Ia-en-07; Ia-en-08; Ia-en-11; Ib-01; Ib-02; Ib-05; Ib-06.

Example E

In Vivo Preventive Test on *Sphaerotheca fulikinea* (Powdery Mildew on Cucurbits)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone/Tween® 80 and then diluted in water to the desired concentration.

The young plants of gherkin were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Sphaerotheca fuliginea* spores. The contaminated gherkin plants were incubated for 8 days at 20° C. and at 70-80% relative humidity.

The test was evaluated 8 days after the inoculation. 0% means an efficacy which corresponds to that of the control plants while an efficacy of 100% means that no disease was observed.

In this test the following compounds according to the invention showed efficacy between 80% and 89% at a concentration of 500 ppm of active ingredient: Ia-30; Ib-19.

In this test the following compounds according to the invention showed efficacy between 90% and 100% at a concentration of 500 ppm of active ingredient: Ia-01; Ia-02; Ia-03; Ia-04; Ia-05; Ia-06; Ia-07; Ia-08; Ia-09; Ia-13; Ia-14; Ia-15; Ia-16; Ia-17; Ia-18; Ia-20; Ia-21; Ia-22; Ia-24; Ia-25; Ia-26; Ia-27; Ia-28; Ia-29; Ia-31; Ia-32; Ia-33; Ia-34; Ia-36; Ia-37; Ia-39; Ia-41; Ia-42; Ia-44; Ia-46; Ia-48; Ia-50; Ia-52; Ia-53; Ia-54; Ia-55; Ia-56; Ia-57; Ia-58; Ia-59; Ia-60; Ia-61; Ia-62; Ia-63; Ia-64; Ia-65; Ia-66; Ia-67; Ia-68; Ia-69; Ia-71; Ia-72; Ia-73; Ia-76; Ia-en-01; Ia-en-02; Ia-en-03; Ia-en-04; Ia-en-06; Ia-en-07; Ia-en-08; Ia-en-09; Ia-en-10; Ia-en-11; Ib-02; Ib-03; Ib-05; Ib-06; Ib-09; Ib-10; Ib-13; Ib-14; Ib-21; Ib-22.

Example F

In Vivo Preventive Test on *Uromyces appendiculatus* (Bean Rust)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone/Tween® 80 and then diluted in water to the desired concentration.

The young plants of bean were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Uromyces appendiculatus* spores. The contaminated bean plants were incubated for 24 hours at 20° C. and at 100% relative humidity and then for 10 days at 20° C. and at 70-80% relative humidity.

The test was evaluated 11 days after the inoculation. 0% means an efficacy which corresponds to that of the control plants while an efficacy of 100% means that no disease was observed.

In this test the following compounds according to the invention showed efficacy between 70% and 79% at a concentration of 500 ppm of active ingredient: Ia-69; Ib-05

In this test the following compounds according to the invention showed efficacy between 80% and 89% at a concentration of 500 ppm of active ingredient: Ia-17; Ia-68; Ia-en-03.

In this test the following compounds according to the invention showed efficacy between 90% and 100% at a concentration of 500 ppm of active ingredient: Ia-01; Ia-02; Ia-03; Ia-04; Ia-05; Ia-06; Ia-08; Ia-09; Ia-15; Ia-18; Ia-20; Ia-21; Ia-22; Ia-24; Ia-25; Ia-32; Ia-37; Ia-39; Ia-41; Ia-42; Ia-44; Ia-53; Ia-67; Ia-73; Ia-en-01; Ia-en-02; Ia-en-04; Ia-en-05; Ia-en-06; Ia-en-07; Ia-en-08; Ia-en-09; Ia-en-10; Ia-en-11; Ib-02; Ib-06.

Example G

In Vivo Preventive Test on *Colletotrichum lindemuthianum* (leaf spot on bean)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone/Tween®80 and then diluted in water to the desired concentration.

The young plants of bean were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Colletotrichum lindemuthianum* spores. The contaminated bean plants were incubated for 24 hours at 20° C. and at 100% relative humidity and then for 6 days at 20° C. and at 90% relative humidity.

The test was evaluated 7 days after the inoculation. 0% means an efficacy which corresponds to that of the control plants while an efficacy of 100% means that no disease was observed.

In this test the following compounds according to the invention showed efficacy between 80% and 89% at a concentration of 500 ppm of active ingredient: Ia-01; Ia-08; Ia-en-05.

In this test the following compounds according to the invention showed efficacy between 90% and 100% at a concentration of 500 ppm of active ingredient: Ia-02; Ia-03; Ia-04; Ia-05; Ia-06; Ia-09; Ia-15; Ia-18; Ia-21; Ia-22; Ia-24; Ia-25; Ia-27; Ia-32; Ia-39; Ia-42; Ia-44; Ia-53; Ia-62; Ia-64; Ia-en-01; Ia-en-02; Ia-en-03; Ia-en-07; Ia-en-08; Ia-en-09; Ia-en-10; Ia-en-11.

Example H

In Vivo Preventive Test on *Phakospora pachyrhizi* (Soybean Rust)

Solvent: 5% by volume of Dimethyl sulfoxide
10% by volume of Acetone
Emulsifier: 1 µl of Tween® 80 per mg of active ingredient The active ingredients were made soluble and homogenized in a mixture of Dimethyl sulfoxide/Acetone/Tween® 80 and then diluted in water to the desired concentration.

The young plants of soybean were treated by spraying the active ingredient prepared as described above. Control plants were treated only with an aqueous solution of Acetone/Dimethyl sulfoxide/Tween® 80.

After 24 hours, the plants were contaminated by spraying the leaves with an aqueous suspension of *Phakospora pachyrhizi* spores. The contaminated soybean plants were incubated for 24 hours at 24° C. and at 100% relative humidity and then for 11 days at 24° C. and at 70-80% relative humidity.

The test was evaluated 12 days after the inoculation. 0% means an efficacy which corresponds to that of the control plants while an efficacy of 100% means that no disease was observed.

hi this test the following compounds according to the invention showed efficacy between 70% and 79% at a concentration of 500 ppm of active ingredient: Ia-32.

In this test the following compounds according to the invention showed efficacy between 80% and 89% at a concentration of 500 ppm of active ingredient: Ia-69.

hi this test the following compounds according to the invention showed efficacy between 90% and 100% at a concentration of 500 ppm of active ingredient: Ia-37.

Example I

In Vivo Preventive Test on *Phakopsora* Test (Soybeans)

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for preventive activity, young plants were sprayed with the preparation of active compound at the stated rate of application. After the spray coating had dried on, the plants were inoculated with an aqueous spore suspension of the causal agent of soybean rust (*Phakopsora pachyrhizi*) and stay for 24 h without light in an incubation cabinet at approximately 24° C. and a relative atmospheric humidity of 95%.

The plants remained in the incubation cabinet at approximately 24° C. and a relative atmospheric humidity of approximately 80% and a day/night interval of 12 h.

The test was evaluated 7 days after the inoculation. 0% means an efficacy which corresponds to that of the untreated control, while an efficacy of 100% means that no disease is observed.

In this test the following compounds according to the invention showed efficacy between 80% and 89% at a concentration of 50 ppm of active ingredient: Ia-22; Ia-en-07.

In this test the following compounds according to the invention showed efficacy between 90% and 100% at a concentration of 50 ppm of active ingredient: Ia-06; Ia-15; Ia-18; Ia-24; Ia-39; Ia-en-01; Ia-en-02; Ia-en-04; Ia-en-08; Ia-en-09; Ia-en-10; Ia-en-11.

Example J

In Vivo Preventive *Blumeria* Test (Barley)

Solvent: 49 parts by weight of N,N-dimethylacetamide
Emulsifier: 1 part by weight of alkylaryl polyglycol ether To produce a suitable preparation of active compound, 1 part by weight of active compound or active compound combination was mixed with the stated amounts of solvent and emulsifier, and the concentrate was diluted with water to the desired concentration.

To test for preventive activity, young plants were sprayed with the preparation of active compound or active compound combination at the stated rate of application.

After the spray coating had been dried, the plants were dusted with spores of *Blumeria graminis f.* sp. *hordei*.

The plants were placed in the greenhouse at a temperature of approximately 18° C. and a relative atmospheric humidity of approximately 80% to promote the development of mildew pustules.

The test was evaluated 7 days after the inoculation. 0% means an efficacy which corresponds to that of the untreated control, while an efficacy of 100% means that no disease is observed.

In this test the following compounds according to the invention showed efficacy between 90% and 100% at a concentration of 500 ppm of active ingredient: Ia-03; Ia-04; Ia-05; Ia-06; Ia-24; Ia-53; Ia-73; Ia-en-02; Ia-en-08; Ib-04.

Example K

In Vivo Preventive *Fusarium culmorum* Test
(Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination was mixed with the stated amounts of solvent and emulsifier, and the concentrate was diluted with water to the desired concentration.

To test for preventive activity, young plants were sprayed with the preparation of active compound or active compound combination at the stated rate of application. After the spray coating had been dried, the plants were slightly injured by using a sandblast and afterwards they were sprayed with a conidia suspension of *Fusarium culmorum*.

The plants were placed in the greenhouse under a translucent incubation cabinet at a temperature of approximately 22° C. and a relative atmospheric humidity of approximately 100%.

The test was evaluated 5 days after the inoculation. 0% means an efficacy which corresponds to that of the untreated control, while an efficacy of 100% means that no disease is observed.

In this test the following compounds according to the invention showed efficacy between 90% and 100% at a concentration of 500 ppm of active ingredient: Ia-05.

Example L

In Vivo Preventive *Leptosphaeria nodorum* Test
(Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination was mixed with the stated amounts of solvent and emulsifier, and the concentrate was diluted with water to the desired concentration.

To test for preventive activity, young plants were sprayed with the preparation of active compound or active compound combination at the stated rate of application.

After the spray coating had been dried, the plants were sprayed with a spore suspension of *Leptosphaeria nodorum*.

The plants remained for 48 hours in an incubation cabinet at approximately 20° C. and a relative atmospheric humidity of approximately 100%.

The plants were placed in the greenhouse at a temperature of approximately 25° C. and a relative atmospheric humidity of approximately 80%.

The test was evaluated 8 days after the inoculation. 0% means an efficacy which corresponds to that of the untreated control, while an efficacy of 100% means that no disease is observed.

In this test the following compounds according to the invention showed efficacy between 70% and 79% at a concentration of 500 ppm of active ingredient: Ib-04.

In this test the following compounds according to the invention showed efficacy between 90% and 100% at a concentration of 500 ppm of active ingredient: Ia-05.

The invention claimed is:

1. Compound of formula (I)

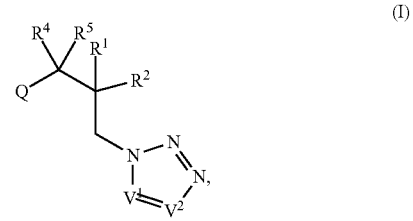

wherein $R^1$ represents hydrogen, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, phenyl-$C_2$-$C_8$-alkynyl, [tri($C_1$-$C_8$-alkyl)silyl]phenyl-$C_2$-$C_8$-alkynyl, $C_3$-$C_7$-cycloalkyl, bicycloalkyl, $C_3$-$C_7$-cycloalkyl-$C_1$-$C_4$-alkyl, $C_3$-$C_7$-cycloalkyl-$C_3$-$C_7$-cycloalkyl, $C_3$-$C_7$-cycloalkenyl, tri($C_1$-$C_8$-alkyl)silyl-$C_1$-$C_4$-alkyl, or tri($C_1$-$C_8$-alkyl)silyl-$C_3$-$C_7$-cycloalkyl, wherein the phenyl-$C_2$-$C_8$-alkynyl, [tri($C_1$-$C_8$-alkyl)silyl]phenyl-$C_2$-$C_8$-alkynyl, $C_3$-$C_7$-cycloalkyl, bicycloalkyl, $C_3$-$C_7$-cycloalkyl-$C_1$-$C_4$-alkyl, $C_3$-$C_7$-cycloalkyl-$C_3$-$C_7$-cycloalkyl, $C_3$-$C_7$-cycloalkenyl, tri($C_1$-$C_8$-alkyl)silyl-$C_1$-$C_4$-alkyl, and tri($C_1$-$C_8$-alkyl)silyl-$C_3$-$C_7$-cycloalkyl is non-substituted or substituted by one or more group(s) selected from halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

$R^2$ represents hydrogen, halogen, cyano or —$OR^{2a}$, wherein $R^{2a}$ represents hydrogen, $C_1$-$C_8$-alkyl, —Si($R^{6a}$)($R^{6b}$)($R^{6c}$), —P(O)(OH)$_2$, —CH$_2$—O—P(O)(OH)$_2$, —C(O)—$C_1$-$C_8$-alkyl, —C(O)—$C_3$-$C_7$-cycloalkyl, —C(O)NH—$C_1$-$C_8$-alkyl, —C(O)N-di-$C_1$-$C_8$-alkyl, or —C(O)O—$C_1$-$C_8$-alkyl, wherein the —C(O)—$C_1$-$C_8$-alkyl, —C(O)—$C_3$-$C_7$-cycloalkyl, —C(O)NH—$C_1$-$C_8$-alkyl, —C(O)N-di-$C_1$-$C_8$-alkyl and —C(O)O—$C_1$-$C_8$-alkyl is non-substituted or substituted by one or more group(s) selected from halogen and $C_1$-$C_8$-alkoxy, wherein $R^{6a}$, $R^{6b}$, $R^{6c}$ represent independently from each other phenyl or $C_1$-$C_8$-alkyl;

one of $V^1$ and $V^2$ represents $CR^3$ and the other one of $V^1$ and $V^2$ represents N, $R^3$ represents hydrogen, halogen, hydroxyl, cyano, sulfanyl, $C_1$-$C_8$-alkyl, or $C_1$-$C_8$-haloalkyl;

$R^4$ represents hydrogen, fluorine, $C_1$-$C_8$-alkyl, $C_1$-$C_8$-haloalkyl or $C_1$-$C_8$-alkyloxy;

$R^5$ represents hydrogen, fluorine, $C_1$-$C_8$-alkyl, $C_1$-$C_8$-haloalkyl or $C_1$-$C_8$-alkyloxy;

or $R^4$ and $R^5$ form together with the carbon atom to which they are attached $C_3$-$C_7$-cycloalkyl, wherein the $C_3$-$C_7$-cycloalkyl ring is non-substituted or substituted by one or more substituent(s) selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

or $R^4$ and $R^5$ form together with the carbon atom to which they are attached $C_2$-alkenyl, wherein the $C_2$-alkenyl is non-substituted or substituted by one or more substituent(s) selected from halogen, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

and

Q represents a 6-membered aromatic cycle of formula (Q-I)

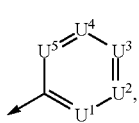

(Q-1)

wherein $U^1$ represents $CX^1$ or N;
$U^2$ represents $CX^2$ or N;
$U^3$ represents $CX^3$ or N;
$U^4$ represents $CX^4$ or N;
$U^5$ represents $CX^5$ or N;

wherein $X^1$, $X^2$, $X^3$, $X^4$, and $X^5$ independently from each other represent hydrogen, halogen, nitro, cyano, sulfanyl, pentafluoro-$\lambda^6$-sulfanyl, $C_1$-$C_8$-alkyl, $C_1$-$C_8$-haloalkyl having 1 to 5 halogen atoms, $C_3$-$C_8$-cycloalkyl, $C_3$-$C_8$-halocycloalkyl having 1 to 5 halogen atoms, $C_1$-$C_8$-haloalkyl-$C_3$-$C_7$-cycloalkyl, $C_3$-$C_7$-cycloalkenyl, $C_2$-$C_8$-alkenyl, $C_2$-$C_8$-alkynyl, $C_6$-$C_{12}$-bicycloalkyl, $C_3$-$C_8$-cycloalkyl-$C_2$-$C_8$-alkenyl, $C_3$-$C_8$-cycloalkyl-$C_2$-$C_8$-alkynyl, $C_1$-$C_8$-alkoxy, $C_1$-$C_8$-haloalkoxy having 1 to 5 halogen atoms, $C_1$-$C_8$-alkoxycarbonyl, $C_1$-$C_8$-haloalkoxycarbonyl, $C_1$-$C_8$-alkylsulfenyl, $C_2$-$C_8$-alkenyloxy, $C_3$-$C_8$-alkynyloxy, $C_3$-$C_6$-cycloalkoxy, $C_1$-$C_8$-alkylsulfinyl, $C_1$-$C_8$-alkylsulfonyl, tri($C_1$-$C_8$-alkyl)-silyloxy, tri($C_1$-$C_8$-alkyl)-silyl, tri($C_1$-$C_8$-alkyl)-silyl-$C_2$-$C_8$-alkynyl, tri($C_1$-$C_8$-alkyl)-silyl-$C_2$-$C_8$-alkynyloxy, $C_6$-$C_{14}$-aryl, $C_6$-$C_{14}$-aryloxy, $C_6$-$C_{14}$-arylsulfenyl, 5- or 6-membered heteroaryl, 5- or 6-membered heteroaryloxy, wherein the $C_6$-$C_{14}$-aryl, $C_6$-$C_{14}$-aryloxy, $C_6$-$C_{14}$-arylsulfenyl, 5- or 6-membered heteroaryl, 5- or 6-membered heteroaryloxy is non-substituted or substituted by one or more group(s) selected from halogen, cyanosulfanyl, pentafluoro-$\lambda^6$-sulfanyl, $C_1$-$C_8$-alkyl, $C_1$-$C_8$-haloalkyl, $C_1$-$C_8$-cyanoalkyl, $C_1$-$C_8$-alkyloxy, $C_1$-$C_8$-haloalkyloxy, tri($C_1$-$C_8$-alkyl)silyl, tri($C_1$-$C_8$-alkyl)silyl-$C_1$-$C_8$-alkyl, $C_3$-$C_7$-cycloalkyl, $C_3$-$C_7$-halocycloalkyl, $C_3$-$C_7$-cycloalkenyl, $C_3$-$C_7$-halocycloalkenyl, $C_4$-$C_{10}$-cycloalkylalkyl, $C_4$-$C_{10}$-halocycloalkylalkyl, $C_6$-$C_{12}$-cycloalkylcycloalkyl, $C_1$-$C_8$-alkyl-$C_3$-$C_7$-cycloalkyl, $C_1$-$C_8$-alkoxy-$C_3$-$C_7$-cycloalkyl, tri($C_1$-$C_8$-alkyl)silyl-$C_3$-$C_7$-cycloalkyl, $C_2$-$C_8$-alkenyl, $C_2$-$C_8$-alkynyl, $C_2$-$C_8$-alkenyloxy, $C_2$-$C_8$-haloalkenyloxy, $C_3$-$C_8$-alkynyloxy, $C_3$-$C_8$-haloalkynyloxy, $C_1$-$C_8$-cyanoalkoxy, $C_4$-$C_8$-cycloalkylalkoxy, $C_3$-$C_6$-cycloalkoxy, $C_1$-$C_8$-alkylsulfanyl, $C_1$-$C_8$-haloalkylsulfanyl, $C_1$-$C_8$-alkylsulfinyl, $C_1$-$C_8$-haloalkylsulfinyl, $C_1$-$C_8$-alkylsulfonyl, $C_1$-$C_8$-haloalkylsulfonyl, $C_1$-$C_8$-alkylsulfonyloxy, $C_1$-$C_8$-haloalkylsulfonyloxy, $C_1$-$C_8$-alkoxyalkyl, $C_1$-$C_8$-alkylthioalkyl, $C_1$-$C_8$-alkoxyalkoxyalkyl, $C_1$-$C_8$-haloalkoxyalkyl, benzyl, phenyl, 5-membered heteroaryl, 6-membered heteroaryl, 6-membered heteroaryloxy, benzyloxy, phenyloxy, benzylsulfanyl, and phenylsulfanyl, wherein the benzyl, phenyl, 5-membered heteroaryl, 6-membered heteroaryl, 6-membered heteroaryloxy, benzyloxy, phenyloxy, benzylsulfanyl and phenylsulfanyl is non-substituted or substituted by one or more group(s) selected from halogen, CN, nitro, $C_1$-$C_8$-alkyl, $C_1$-$C_4$-haloalkyl, $C_1$-$C_4$-alkoxy, $C_1$-$C_4$-haloalkoxy and pentafluoro-$\lambda^6$-sulfanyl;

and wherein at most two of $U^1$, $U^2$, $U^3$, $U^4$ and $U^5$ represent N;

or $U^1$ and $U^2$ or $U^2$ and $U^3$ or $U^3$ and $U^4$ form together an additional saturated or unsaturated 4 to 6-membered halogen- or $C_1$-$C_8$-alkyl-substituted or non-substituted ring;

and/or a salt and/or N-oxide thereof.

2. The compound according to claim 1, wherein $R^1$ represents $C_1$-$C_8$-alkyl, $C_1$-$C_8$-haloalkyl, or optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio- or $C_1$-$C_4$-haloalkylthio-substituted $C_3$-$C_7$-cycloalkyl.

3. The compound according to claim 1, wherein $R^2$ represents —$OR^{2a}$, and wherein $R^{2a}$ represents hydrogen or $C_1$-$C_8$-alkyl.

4. The compound according to claim 1, wherein $R^3$ represents hydrogen, fluorine, chlorine, bromine, or iodine.

5. The compound according to claim 1, wherein $R^4$ represents hydrogen, fluorine or methyl and $R^5$ represents hydrogen or fluorine, or $R^4$ and $R^5$ form together with the carbon atom to which they are attached $C_2$-alkenyl, wherein the $C_2$-alkenyl is non-substituted or substituted by one or more substituent(s) selected from halogen, $C_1$-$C_4$-alkyl, and $C_1$-$C_4$-haloalkyl.

6. The compound according to claim 1, wherein

Q represents a 6-membered aromatic cycle selected from the group consisting of formula (Q-I-1) to (Q-I-10)

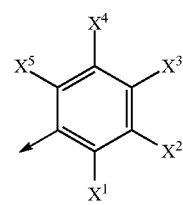

(Q-I-1)

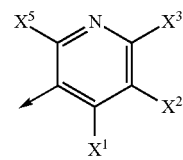

(Q-I-2)

-continued

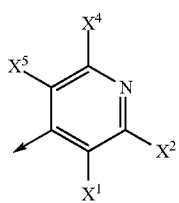
(Q-I-3)

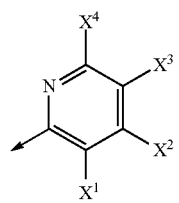
(Q-I-4)

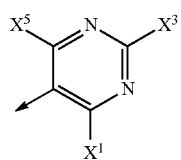
(Q-I-5)

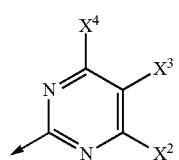
(Q-I-6)

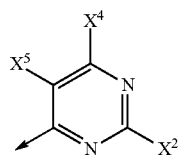
(Q-I-7)

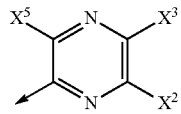
(Q-I-8)

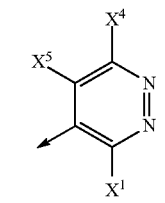
(Q-I-9)

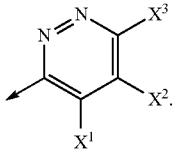
(Q-I-10)

7. The compound according to claim 1, wherein
Q represents a 6-membered aromatic cycle of formula (Q-I-1) or (Q-I-2)

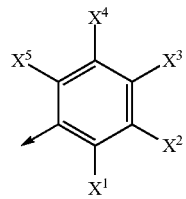
(Q-I-1)

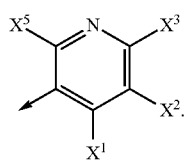
(Q-I-2)

8. The compound according to claim 1, wherein $X^1$, $X^2$, $X^3$, $X^4$ and $X^5$ independently from each other represent hydrogen, halogen, cyano, $C_1$-$C_8$-alkyl, $C_1$-$C_8$-haloalkyl having 1 to 5 halogen atoms, $C_2$-$C_8$-alkenyl, $C_2$-$C_8$-alkynyl, $C_3$-$C_8$-cycloalkyl-$C_2$-$C_8$-alkenyl, $C_3$-$C_8$-cycloalkyl-$C_2$-$C_8$-alkynyl, $C_1$-$C_8$-alkoxy, $C_1$-$C_8$-haloalkoxy having 1 to 5 halogen atoms, $C_6$-$C_{14}$-aryl, or $C_6$-$C_{14}$-aryloxy, wherein the $C_6$-$C_{14}$-aryl and $C_6$-$C_{14}$-aryloxy is non-substituted or substituted by one or more group(s) selected from halogen, $C_1$-$C_8$-alkyl, $C_1$-$C_8$-haloalkyl, $C_1$-$C_8$-alkyloxy, and $C_1$-$C_8$-haloalkyloxy.

9. The compound according to claim 1, wherein
$R^1$ represents $C_1$-$C_8$-alkyl, or optionally halogen-, or $C_1$-$C_4$-alkyl-substituted $C_3$-$C_7$-cycloalkyl;
$R^2$ represents —OH;
one of $V^1$ and $V^2$ represents CH and the other one of $V^1$ and $V^2$ represents N;
$R^4$ represents hydrogen, fluorine or methyl;
$R^5$ represents hydrogen or fluorine;
or $R^4$ and $R^5$ form together with the carbon atom to which they are attached $C_2$-alkenyl, wherein the $C_2$-alkenyl is substituted by methyl non-substituted;
and
Q represents a 6-membered aromatic cycle of formula (Q-I-1) or (Q-I-2)

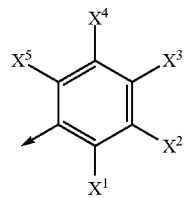
(Q-I-1)

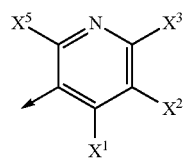
(Q-I-2)

wherein
$X^1$, $X^2$, $X^3$, $X^4$, and $X^5$ independently from each other represent hydrogen, halogen, cyano, $C_1$-$C_8$-alkyl, $C_1$-$C_8$-haloalkyl having 1 to 5 halogen atoms, $C_2$-$C_8$-alkenyl, $C_2$-$C_8$-alkynyl, $C_3$-$C_8$-cycloalkyl-$C_2$-$C_8$-alkenyl, $C_3$-$C_8$-cycloalkyl-$C_2$-$C_8$-alkynyl, $C_1$-$C_8$-alkoxy, $C_1$-$C_8$-haloalkoxy having 1 to 5 halogen atoms, $C_6$-$C_{14}$-aryl, or $C_6$-$C_{14}$-aryloxy, wherein the $C_6$-$C_{14}$-aryl and $C_6$-$C_{14}$-aryloxy is non-substituted or substituted by one or more group(s) selected from halogen, $C_1$-$C_8$-alkyl, $C_1$-$C_8$-haloalkyl, $C_1$-$C_8$-alkyloxy, and $C_1$-$C_8$-haloalkyloxy;

and/or a salt and/or N-oxide thereof.

10. A composition for controlling one or more harmful microorganisms, optionally for controlling phytopathogenic harmful fungi, comprising at least one compound according to claim 1, and at least one carrier and/or surfactant.

11. A method for controlling one or more harmful microorganisms, optionally phytopathogenic harmful fungi, in crop protection and/or in protection of materials, comprising applying at least one compound according to claim 1 to the harmful microorganisms and/or a habitat thereof.

12. A product comprising at least one compound according to claim 1 for control of one or more harmful microorganisms, optionally phytopathogenic harmful fungi, in crop protection and/or in protection of materials.

13. A product comprising at least one compound of formula (I) according to claim 1 for treatment of a transgenic plant or for treatment of seed, optionally seed of a transgenic plant.

14. Ketone of formula (XVI)

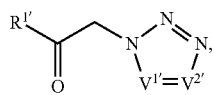

(XVI)

wherein $R^{1'}$ represents $C_3$-$C_7$-cycloalkyl, wherein the $C_3$-$C_7$-cycloalkyl is non-substituted or substituted by one or more group(s) selected from halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio; and one of $V^{1'}$ and $V^{2'}$ represents CH and the other one of $V^{1'}$ and $V^{2'}$ represents N;

and/or a salt and/or N-oxide thereof.

15. Epoxide of formula (XVII)

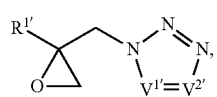

(XVII)

wherein $R^{1'}$ represents $C_3$-$C_7$-cycloalkyl, wherein the $C_3$-$C_7$-cycloalkyl is non-substituted or substituted by one or more group(s) selected from halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio; and one of $V^{1'}$ and $V^{2'}$ represents CH and the other one of $V^{1'}$ and $V^{2'}$ represents N;

and/or a salt and/or N-oxide thereof.

* * * * *